(12) United States Patent
Topczewski et al.

(10) Patent No.: US 11,987,572 B2
(45) Date of Patent: May 21, 2024

(54) THERAPEUTIC COMPOUNDS AND METHODS OF USE THEREOF

(71) Applicant: REGENTS OF THE UNIVERSITY OF MINNESOTA, Minneapolis, MN (US)

(72) Inventors: Joseph J. Topczewski, Minneapolis, MN (US); William C. K. Pomerantz, Minneapolis, MN (US); Angela S. Carlson, Minneapolis, MN (US); Huarui Cui, Minneapolis, MN (US); Anand Divakaran, Minneapolis, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 624 days.

(21) Appl. No.: 16/892,072

(22) Filed: Jun. 3, 2020

(65) Prior Publication Data
US 2020/0377474 A1    Dec. 3, 2020

Related U.S. Application Data

(60) Provisional application No. 62/856,617, filed on Jun. 3, 2019.

(51) Int. Cl.
C07D 401/14    (2006.01)
C07D 403/14    (2006.01)

(52) U.S. Cl.
CPC ......... C07D 401/14 (2013.01); C07D 403/14 (2013.01)

(58) Field of Classification Search
CPC .................................................. C07D 401/14
See application file for complete search history.

(56) References Cited

U.S. PATENT DOCUMENTS 6,727,364 B2 *    4/2004    Tullis ...................... A61P 29/00
546/268.4

OTHER PUBLICATIONS

Andrieu, G., et al., "Clinical trials for BET inhibitors run ahead of the science", Drug Discovery Today Technology 19, 45-50 (2016).
Ayaz, M, et al., "Potent dual BET bromodomain-kinase inhibitors as value added multi-targeted chemical probes and cancer therapeutics", Mol. Cancer Ther. 16(6), 1054-1067 (2017).
Bhattacharya, S., et al., "Bromodomain Inhibitors: What Does the Future Hold?", Clinical Advances in Hematology & Oncology 16 (7), 504-515 (2018).
Boehm, J, et al., "Phenoxypyrimidine inhibitors of p38α kinase: synthesis and statistical evaluation of the p38 inhibitory potencies of a series of 1-(piperidin-4-yl)-4-(4-fluorophenyl)-5-(2-phenoxypyrimidin-4-yl) imidazoles", Bioorganic & Medicinal Chemistry Letters 11(9), 1123-1126 (2001).
Carlino, L, et al., "Dual Kinase-Bromodomain Inhibitors in Anticancer Drug Discovery: A Structural and Pharmacological Perspective", J. Med. Chem. 59(20), 9305-9320 (2016).
Carlson, A, "Achieving Selective Bromodomain Inhibition", Graduate Student Research Symposium, Presented at the University of Minnesota, Dept of Chemistry, 58 pages, Jun. 4, 2019.
Carlson, A, et al., "Systematically Mitigating the p38α Activity of Triazole-based BET Inhibitors", ACS Med Chem Lett 10 (9), 1296-1301 (2019).
Chen, L, et al., "BRD4 Structure-Activity Relationships of Dual PLK1 Kinase/BRD4 Bromodomain Inhibitor BI-2536", ACS Med. Chem. Lett.6, 764-769 (2015).
Ciceri, P., et al., "Dual kinase-bromodomain inhibitors for rationally designed polypharmacology", Nat. Chem. Ciol. 10, 305-312 (2014).
Cui, H, "Development of small molecule chemical probes for BRD4", Graduate Student Research Symposium, Presented at the University of Minnesota, Dept of Chemistry, 25 pages, Jun. 4, 2019.
Cui, H, et al., "Selective N-Terminal BET Bromodomain Inhibitors by Targeting Non-Conserved Residues and Structured Water Displacement", Angewandte Chemie 60 (3), 1220-1226 (2021).
Delmore, J, et al., "BET bromodomain inhibition as a therapeutic strategy to target c-Myc", Cell 146(6), 904-917 (2011).
Divakaran, A, et al., "Molecular Basis for the N-Terminal Bromodomain-and-Extra-Terminal-Family Selectivity of a Dual Kinase-Bromodomain Inhibitor", J. Med. Chem. 61(20), 9316-9334 (2018).
Ember, S, et al., "Acetyl-lysine Binding Site of Bromodomain-Containing Protein 4 (BRD4) Interacts with Diverse Kinase Inhibitors", ACS Chem Biol 9, 1160-1171 (2014).
Filippakopoulos, P., et al., "The bromodomain interaction module", FEBS Letters 586, 2691-2704 (2012).
Gallagher, T, et al., "Regulation of stress-induced cytokine production by pyridinylimidazoles; inhibition of CSBP kinase", Bioorganic & Medicinal Chemistry 5 (1), 49-64 (1997).
Gallinari, P., et al., "HDACs, histone deacetylation and gene transcription: from molecular biology to cancer therapeutics", Cell Research 17, 195-211 (2007).

(Continued)

Primary Examiner — Brian E McDowell
(74) Attorney, Agent, or Firm — Viksnins Harris Padys Malen LLP

(57) ABSTRACT

The invention provides a compound of formula I:

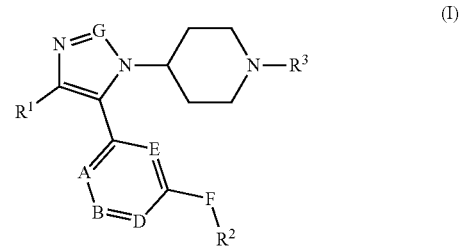

(I)

or a salt thereof, wherein $R^1$, $R^2$, $R^3$, A, B, D, E, F and G have any of the values described in the specification, as well as compositions comprising a compound of formula I. The compounds are useful as bromodomain inhibitors.

3 Claims, 10 Drawing Sheets

(56) References Cited

OTHER PUBLICATIONS

Hajmirza, A., et al., "BET Family Protein BRD4: An Emerging Actor in NFKB Signaling in Inflammation and Cancer", Biomedicines 6 (16), 1-9 ; doi:10.3390/biomedicines6010016 (2018).
Huang, B., et al., "Brd4 Coactivates Transcriptional Activation of NF-κB via Specific Binding to Acetylated RelA", Molecular and Cellular Biology 29(5), 1375-1387 (2009).
Liu, M, et al., "Super enhancer regulation of cytokine-induced chemokine production in alcoholic hepatitis", Nature Communications 12 (4560), 1-14 (2021).
Martin, P, et al., "The cyclin-dependent kinase inhibitor dinaciclib interacts with the acetyl-lysine recognition site of promodomains", ACS Chem Biol. 8(11), 2360-2365 (2013).
Pervaiz, M., et al., "Bromodomain Drug Discovery—the Past, the Present, and the Future", Chem. Rec. 18 (12), 1808-1817 (2018).
Sabat, M, et al., "The development of novel C-2, C-8, and N-9 trisubstituted purines as inhibitors of TNF—a production", Bioorganic & Medicinal Chemistry Letters 16 (16), 4360-4365 (2006).
Urick, A. K., et al., "Dual Screening of BPTF and Brd4 Using Protein-Observed Fluorine NMR Uncovers New Bromodomain Probe Molecules", ACS Chem. Biol. 10, 2246-2256 (2015).
Watts, E, et al., "Designing Dual Inhibitors of Anaplastic Lymphoma Kinase (ALK) and Bromodomain-4 (BRD4) by Tuning Kinase Selectivity", J. Med. Chem 62, 2618-2637 (2019).

\* cited by examiner

A.

B.

| Example | X | Y | p38α $K_d$ (nM)$^a$ |
|---|---|---|---|
| 76 | N | NH | 2.2 ± 0.63 |
| 14 | N | O | 120 ± 51 |
| 15 | CH | NH | 6500 ± 6300 |
| 16 | CH | O | 5000 ± 6100 |

| Example | R | X | BRD4-D1 IC$_{50}$ (μM)$^a$ |
|---|---|---|---|
| 14 | 4-F-C$_6$H$_4$ | H | >100$^b$ |
| 5 | c-hexyl | H | >100 |
| 6 | c-pentyl | H | >100 |
| 7 | t-Bu | H | >100 |
| 17 | i-Pr | C(NH)NH$_2$ | >100 |
| 18 | n-Pr | C(NH)NH$_2$ | >100 |
| 19 | c-Pr | C(NH)NH$_2$ | 61 ± 8.1 |
| 20 | Me | C(NH)NH$_2$ | 9.7 ± 1.8 |

| Compound | N Atom | BRD4-D1 IC$_{50}$ (µM)[a] |
|---|---|---|
| 20 | 1,2 | 9.7 ± 1.8 |
| 21 | none | 12 ± 1.1 |
| 22 | 1 | 3.6 ± 0.05 |
| 23 | 2 | 97 ± 2.6 |
| 24 | 3 | >100 |
| 25 | 4 | >100 |

| Protein Target | X = O | X = NH |
|---|---|---|
| BRD4-D1 IC$_{50}$ | 3.6 ± 0.05 | 4.5 ± 0.35 |
| BRD4-D1 $K_d$ | 1.1 ± 0.63 | 1.2 ± 0.62 |
| BRD4-D2 $K_d$ | 0.94 ± | 2.1 ± 1.1 |
| SMARCA2 $K_d$ | >100 | >100 |
| p38α $K_d$ (μM)[c] | >200 | >25 |

Compound 22   Compound 26

| Compound | R | X | Y | BRD4-D1 IC$_{50}$ (µM)$^a$ | MM.1S EC$_{50}$ (µM)$^b$ |
|---|---|---|---|---|---|
| 20 | C(NH)NH$_2$ | O | N | 9.7 ± 1.8 | >50 |
| 22 | C(NH)NH$_2$ | O | CH | 3.6 ± 0.05 | >50 |
| 26 | C(NH)NH$_2$ | N | CH | 4.5 ± 0.35 | >50 |
| 4 | H | O | N | 11 ± 2.5 | 6.6 ± 1.9 |
| 10 | H | O | CH | 2.9 ± 0.07 | 2.9 ± 0.6 |
| 13 | H | N | CH | 3.9 ± 0.35 | 6.3 ± 1.1 |

| | | 27 ALPHAscreen IC50 (µM) | 27 Selectivity vs BRD4(1) | 34 ALPHAscreen IC50 (µM) | 34 Selectivity vs BRD4(1) | 35 ALPHAscreen IC50 (µM) | 35 Selectivity vs BRD4(1) |
|---|---|---|---|---|---|---|---|
| BRD4 | D1 | 1.79 | | 0.58 | | 0.94 | |
| | D2 | >100 | >55 | 6.71 | 12 | 25.8 | 27 |
| BRDT | D1 | 5.33 | 3 | 1.79 | 3 | 9.04 | 10 |
| | D2 | ND | - | ND | - | ND | - |
| BRD2 | D1 | 29 | 16 | 3.1 | 5 | 8.69 | 9 |
| | D2 | 67.1 | 37 | 4.66 | 8 | 23 | 24 |
| BRD3 | D1 | 11.2 | 6 | 3.95 | 7 | 18 | 19 |
| | D2 | >100 | >55 | 9.57 | 17 | 30.6 | 32 |

THERAPEUTIC COMPOUNDS AND METHODS OF USE THEREOF

PRIORITY

This application claims priority to U.S. Provisional Patent Application No. 62/856,617, filed 3 Jun. 2019. The entire content of this United States Provisional Patent Applications is hereby incorporated by reference herein.

STATEMENT REGARDING FEDERALLY SPONSORED RESEARCH

This invention was made with government support under GM124718 awarded by the National Institutes of Health. Kathryn Schwertfeger PhD was supported by an Institutional Research Grant, IRG-16-189-58 from the American Cancer Society. The government has certain rights in the invention.

BACKGROUND OF THE INVENTION

Bromodomains act as "readers" for epigenetic modifications. Specifically, they bind N-ε-acetylated lysine residues on histones and transcription factors through protein-protein interactions to regulate cellular processes including the cell cycle, proliferation, and cellular differentiation (Filippakopoulos, P. et al. *FEBS Lett.* 2012, 586, 2692-2704). The 61 human bromodomains, which are contained in 46 proteins, have been subdivided into eight classes based on structural or sequence similarities (Pervaiz, M. et al. *Chem. Rec.* 2018, 18, 1-11). The Bromodomain and Extra Terminal (BET) family, which includes BRD2, BRD3, BRD4 and BRDT, has a similar domain architecture, including two tandem bromodomains and an extra-terminal domain.

Inhibiting the protein-protein interactions between BET bromodomains and N-ε-acetylated lysine residues is a key target for potential treatment of BET related diseases, including cancer, inflammation and heart diseases (Pervaiz, M. et al. *Chem. Rec.* 2018, 18, 1-11; Gallinari, P. et al. *Cell Res.* 2007, 17, 195; Andrieu, G. et al. *Drug Discov. Today Technol.* 2016, 19, 45-50 and Bhattacharya, S. et al. *Clin. Adv. Hematol. Oncol.* 2018, 16, 504-515). For example, BRD4 can recognize N-ε-acetylated Lys310 in the RelA subunit of NF-κB, which is important for the activation of NF-κB, following inflammatory signaling (Huang, B. et al. *Mol. Cell. Biol.* 2008, 29, 1375-1387). Additionally, the bromodomains of BRD4 and BRDT can recognize N-ε-acetylated lysine residues on histones and recruit transcription factors to super-enhancer regions. Inhibition of BRD4 at super-enhancer regions can reduce c-Myc expression, which could be a therapeutic strategy for treating cancer (Delmore, J. E. et al. *Cell* 2011, 146, 904-917). Given the significant roles that BET bromodomains play in oncogene expression and in inflammation, 19 clinical trials are underway to assess the therapeutic effects of BET inhibition.

Several dual kinase-bromodomain inhibitors were discovered by screening kinase inhibitor libraries against BRD4-D1 (Ember, S. W. J. et al. *ACS Chem. Biol.* 2014, 9, 1160-1171; Carlino, L. et al. *J. Med. Chem.* 2016, 59, 9305-9320; Boehm, J. C. et al. *Bioorg. Med. Chem. Lett.* 2001, 11, 1123-1126; Ciceri, P. et al. *Nat. Chem. Biol.* 2014, 10, 305-312; Martin, M. P. et al. *ACS Chem. Biol.* 2013, 8, 2360-2365 and Urick, A. K. et al. *ACS Chem. Biol.* 2015, 10, 2246-2256). In 2014, both Ciceri et al. and Ember et al. identified several dual kinase-bromodomain inhibitors including BI-2536, a PLK1 inhibitor with high affinity against BRD4-D1 (Ember, S. W. J. et al. *ACS Chem. Biol.* 2014, 9, 1160-1171 and Ciceri, P. et al. *Nat. Chem. Biol.* 2014, 10, 305-312) The dihydropteridinone carbonyl and the methylamino group function as the N-ε-acetylated lysine mimic. P38-BET inhibitors including SB-202190 and SB-203580 were also identified. Similarly, the CDK inhibitor Dinaciclib functions as a BRDT inhibitor (Martin, M. P. et al. *ACS Chem. Biol.* 2013, 8, 2360-2365). The pyridine oxide serves as the N ε-acetylated lysine mimic and is recognized by Asn109 on BRDT. Although modest in affinity, the molecule is of historical note, as the first dual kinase-bromodomain inhibitor reported. Since these reports, developing bromodomain inhibitors by kinase library screening has attracted more attention (Ember, S. W. J. et al. *ACS Chem. Biol.* 2014, 9, 1160-1171; Ciceri, P. et al. *Nat. Chem. Biol.* 2014, 10, 305-312; Urick, A. K. et al. *ACS Chem. Biol.* 2015, 10, 2246-2256 and Ayaz, M. et al. *Mol. Cancer Ther.* 2017, 16, 1054-1067). Urick et al. screened a library of 229 small molecules by protein-observed fluorine NMR and subsequently developed a dual p38α-BRD4-D1inhibitor named V (Urick, A. K. et al. *ACS Chem. Biol.* 2015, 10, 2246-2256 and Divakaran, A. et al. *J. Med. Chem.* 2018, 61, 9316-9334). While BI-2536 and Dinaciclib are pan-BET inhibitors, V was shown to selectively inhibit the N-terminal BET bromodomains with highest affinity for BRD4. Although, dual kinase-bromodomain inhibitors may produce synergistic effects in some cases (Carlino, L. et al. *J. Med. Chem.* 2016, 59, 9305-9320; Ciceri, P. et al. Nat. *Chem. Biol.* 2014, 10, 305-312; Ayaz, M. et al. *Mol. Cancer Ther.* 2017, 16, 1054-1067 and Watts, E. et al. *J. Med. Chem.* 2019, 62, 2618-2637), selective inhibition is ideal for understanding the physiological and pharmacological effect of BET inhibition as well as minimizing potential side effects (Chen, L. et al. *ACS Med. Chem. Lett.* 2015, 6, 764-769).

Currently there is a need for additional agents that are bromodomain (BRD) inhibitors. In particular, there is a need for compounds with improved properties, such as, for example, improved activity, potency, solubility, selectivity, or toxicity. Such agents would be useful for treating bromodomain mediated conditions, such as cancer, heart disease, or an inflammatory condition.

SUMMARY OF THE INVENTION

In one aspect the present invention provides compounds having bromodomain/BET activity that are useful for treating cancer, inflammatory and/or heart disease.

Accordingly, the invention provides a compound of formula (I):

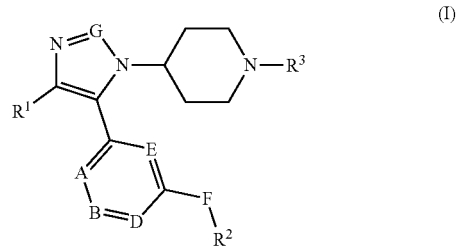

or a pharmaceutically acceptable salt thereof, wherein:
R$^1$ is selected from H, halo, aryl, (C$_1$-C$_6$)alkyl, (C$_3$-C$_6$) cycloalkyl, (C$_1$-C$_6$)alkoxy, (C$_2$-C$_6$)alkenyl, and (C$_2$-C$_6$)alkynyl, wherein any (C$_1$-C$_6$)alkyl, (C$_3$-C$_6$)cycloalkyl, (C$_1$-C$_6$)alkoxy, (C$_2$-C$_6$)alkenyl, and (C$_2$-C$_6$)

alkynyl, is optionally substituted with one or more groups independently selected from the group consisting of halo, oxo, —OH, cyano, $(C_3-C_6)$cycloalkyl, and $(C_1-C_6)$alkoxy; and wherein any aryl is optionally substituted with one or more groups independently selected from the group consisting of halo, —OH, cyano, $(C_1-C_6)$alkyl, $(C_3-C_6)$cycloalkyl, $(C_1-C_6)$alkoxy, $(C_2-C_6)$alkenyl, $(C_2-C_6)$alkynyl, $(C_1-C_6)$alkanoyl, $(C_1-C_6)$alkoxycarbonyl, $(C_1-C_6)$alkylthio and $(C_2-C_6)$alkanoyloxy, wherein any $(C_1-C_6)$alkyl, $(C_3-C_6)$cycloalkyl, $(C_1-C_6)$alkoxy, $(C_2-C_6)$alkenyl, $(C_2-C_6)$alkynyl, $(C_1-C_6)$alkanoyl, $(C_1-C_6)$alkoxycarbonyl, $(C_1-C_6)$alkylthio and $(C_2-C_6)$alkanoyloxy is optionally substituted with one or more groups independently selected from the group consisting of halo and —OH;

$R^2$ is aryl that is optionally substituted with one or more groups independently selected from the group consisting of selected from halo, —OH, cyano, $(C_1-C_6)$alkyl, $(C_3-C_6)$cycloalkyl, and $(C_1-C_6)$alkoxy, wherein any $(C_1-C_6)$alkyl, $(C_3-C_6)$cycloalkyl, and $(C_1-C_6)$alkoxy is optionally substituted with one or more groups independently selected from the group consisting of halo, and $(C_1-C_6)$alkoxy;

$R^3$ is selected from the group consisting of H, —C(=N($R^a$))$NR^aR^b$, and $(C_1-C_6)$alkyl that is optionally substituted with one or more groups independently selected from the group consisting of halo, —OH, cyano, $(C_3-C_6)$cycloalkyl, $(C_1-C_6)$alkoxy, —C(=N($R^a$))$NR^aR^b$, and —$NR^aR^b$;

each $R^a$ and $R^b$ is independently selected from the group consisting of H, $(C_1-C_6)$alkyl, $(C_1-C_6)$alkanoyl, and $(C_3-C_6)$cycloalkyl; or $R^a$ and $R^b$ together with the nitrogen to which they are attached form a 4-6 membered ring heterocycle;

A, B, D and E are each independently selected from CH or N; provided that no more than two of A, B, D and E are N;

F is O, S, or $NR^c$;

G is CH or N; and $R^c$ is H or $(C_1-C_6)$alkyl.

The invention also provides a pharmaceutical composition comprising a compound of formula I or a pharmaceutically acceptable salt thereof, and a pharmaceutically acceptable excipient.

The invention also provides a method for treating cancer, heart disease, or an inflammatory condition in an animal (e.g., a mammal such as a human) comprising administering a compound of formula I or a pharmaceutically acceptable salt thereof to the animal.

The invention also provides a compound of formula I or a pharmaceutically acceptable salt thereof for use in medical therapy.

The invention also provides a compound of formula I or a pharmaceutically acceptable salt thereof for the prophylactic or therapeutic treatment of cancer, heart disease, or an inflammatory condition.

The invention also provides the use of a compound of formula I or a pharmaceutically acceptable salt thereof to prepare a medicament for treating cancer, heart disease, or an inflammatory condition in an animal (e.g. a mammal such as a human).

The invention also provides processes and intermediates disclosed herein that are useful for preparing a compound of formula I or a salt thereof.

Certain compounds of formula I have improved BET vs p38α selectivity.

DETAILED DESCRIPTION OF THE INVENTION

Figure 1A:
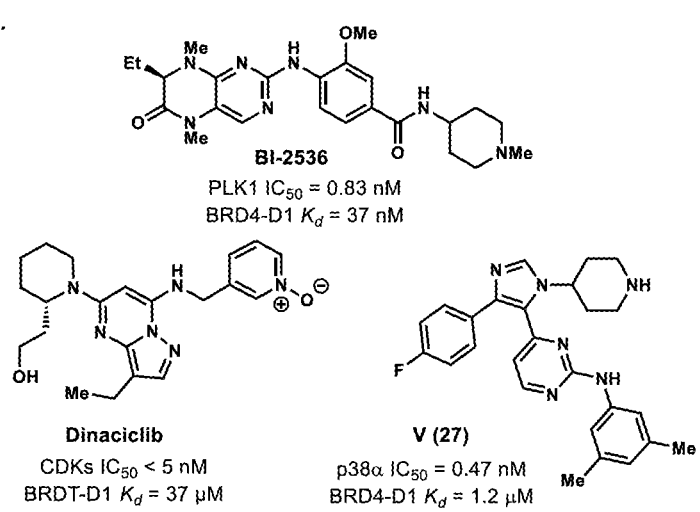
FIGS. 1A-1B shows Dual kinase-bromodomain inhibitors A) Examples of bromodomain inhibitors in kinase screen B) Improving BET vs p38α selectivity.
Figure 1B:
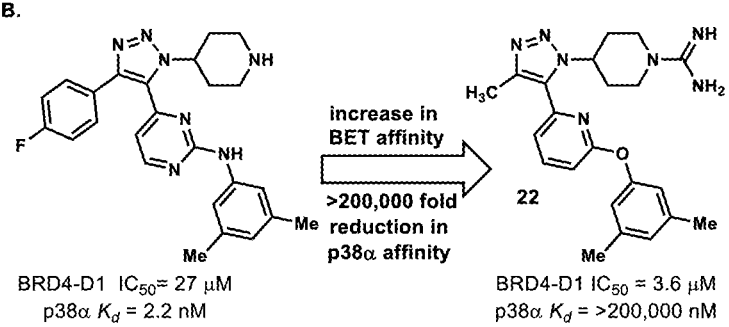
Figure 2:
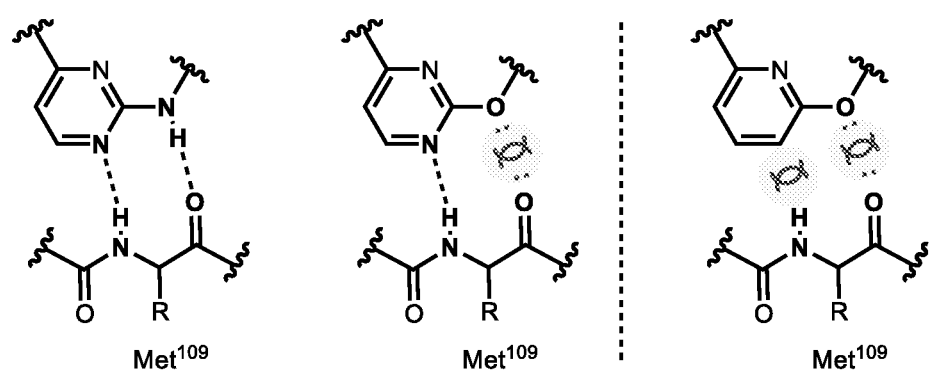
FIG. 2 shows Hydrogen Bonding Interactions in p38α Co-Crystal Structure and Proposed Analogues.
Figure 3:
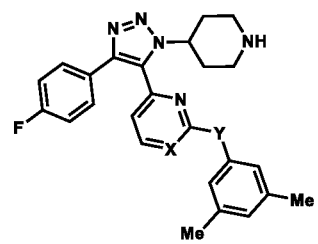
FIG. 3 shows Systematically Minimizing Binding to Met-109 in p38α. $^a K_d$ values were determined by KINOMEscan™. Data represents the mean and standard error from two independent trials.
Figure 4:
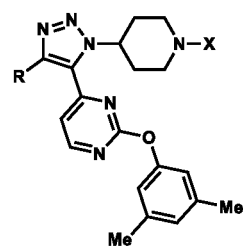
FIG. 4 shows the significance of R Group to BRD4-D1 Binding Affinity. $^a IC_{50}$ values were determined by fluorescence anisotropy. Data represents the mean and standard deviation of three independent trials. $^b$The $IC_{50}$ value could not be determined by fluorescence anisotropy. The $IC_{50}$ value was determined to be 27 μM by AlphaScreen by Reaction Biology.
Figure 5:
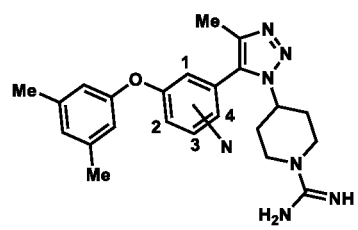
FIG. 5 shows the effect of Nitrogen Atom(s) to BRD4-D1 Affinity. $^a IC_{50}$ values were determined by fluorescence anisotropy. Data represents the mean and standard deviation of three independent trials.
Figure 6:
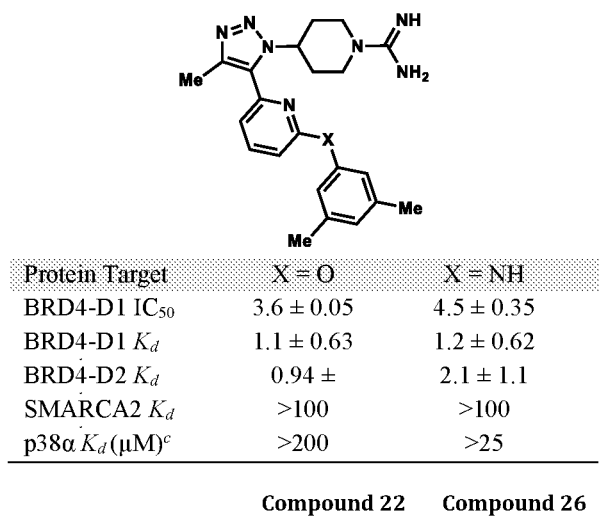
FIG. 6 shows selectivities for Compound 22 and Compound 26. $^a IC_{50}$ values were determined by fluorescence anisotropy. Data represents the mean and standard deviation of three independent trials. $^b K_d$ values were determined by BROMOscan™. Data represents the mean and standard error from two independent trials. $^c K_d$ values were determined by KINOMEscan™. Data represents the mean and standard error from two independent trials.
Figure 7:
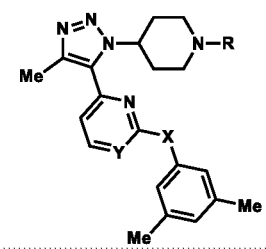
FIG. 7 shows viability of MM.1S cells treated with compounds. $^a IC_{50}$ values were determined by fluorescence anisotropy. Data represents the mean and standard deviation of three independent trials. $^b$Data reported are mean±SEM of 3 biological replicates, with 3 technical replicates each. $EC_{50}$ values were determined using the Non-linear fit algorithm on GraphPad Prism.
Figure 8:
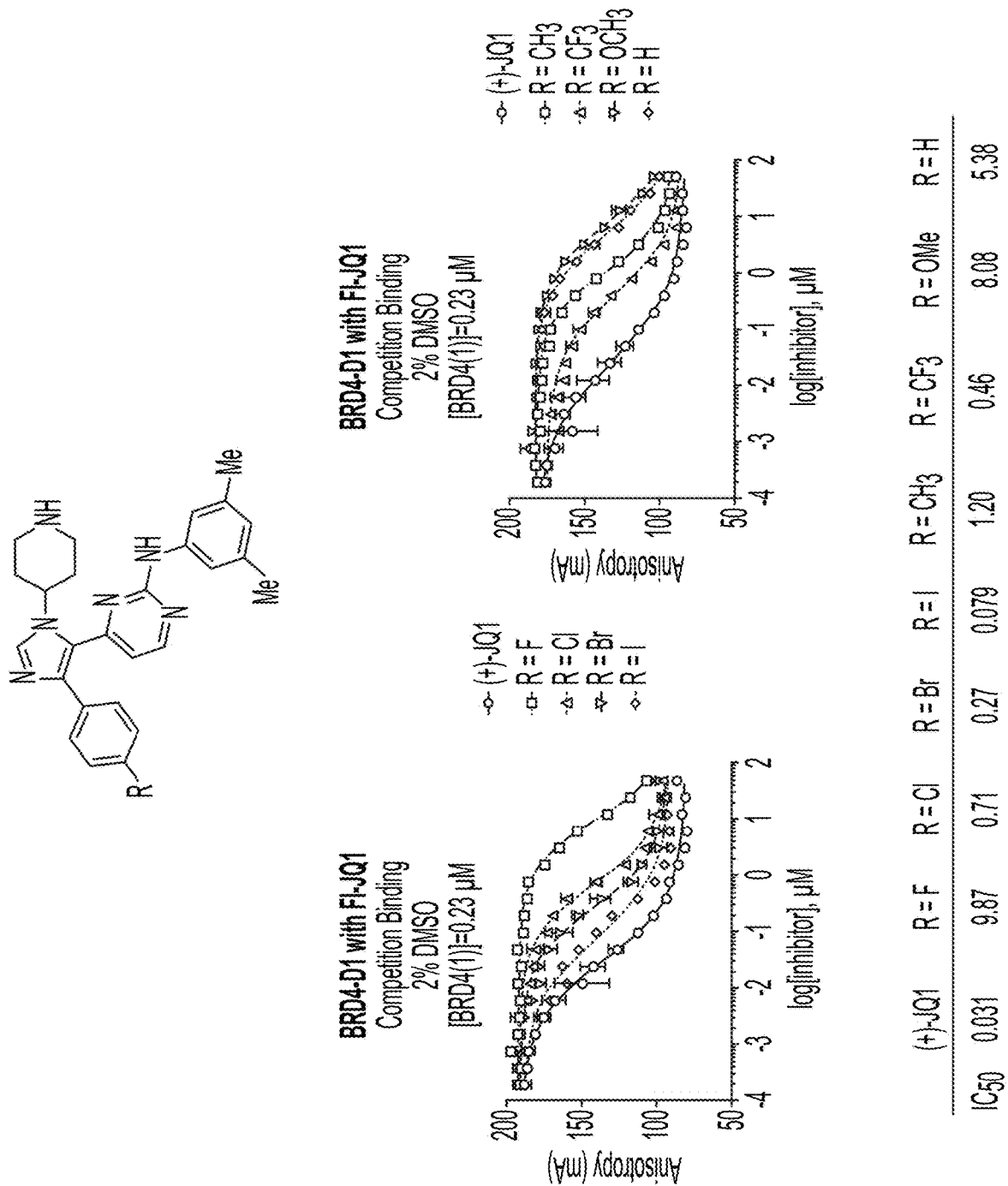
FIG. 8 shows affinity data of different R group. Affinity: F<OMe<H<Me<Cl<CF_3<Br<I.
Figure 9:
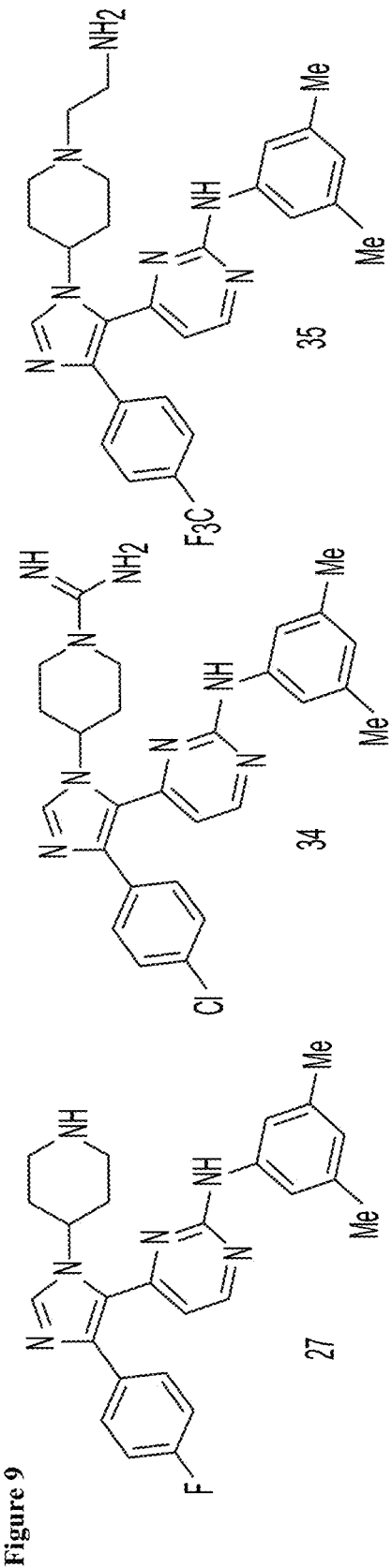
FIG. 9 shows selectivity in BET family by ALPHAScreen.
Figure 10:
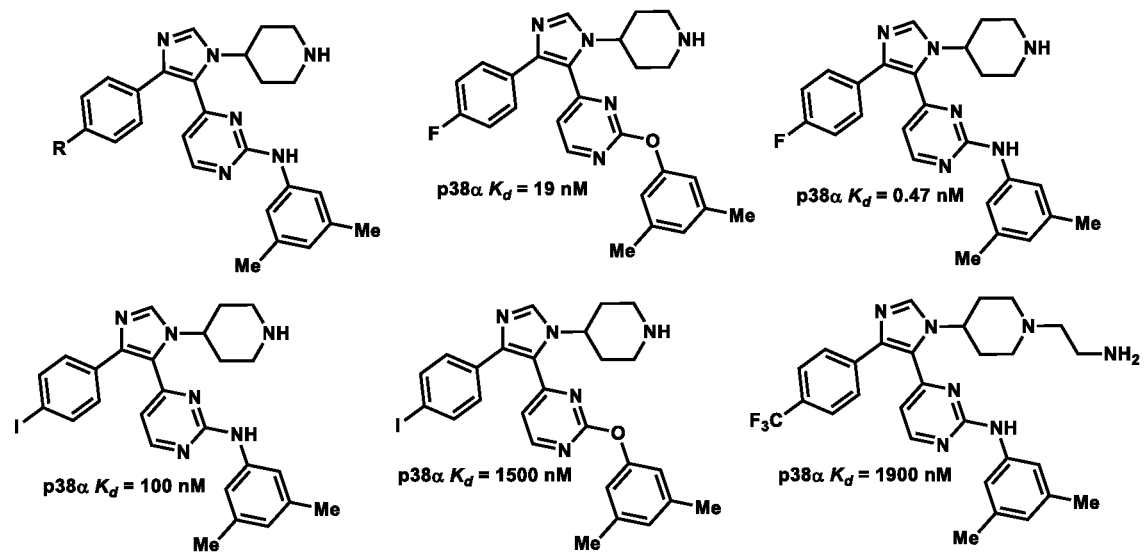
FIG. 10 shows p38α kinase activity is reduced by increasing the size of R group.

The following definitions are used, unless otherwise described: halo or halogen is fluoro, chloro, bromo, or iodo. Alkyl, alkoxy, alkenyl, alkynyl, etc. denote both straight and branched groups; but reference to an individual radical such as propyl embraces only the straight chain radical, a branched chain isomer such as isopropyl being specifically referred to.

The term "alkyl", by itself or as part of another substituent, means, unless otherwise stated, a straight or branched chain hydrocarbon radical, having the number of carbon atoms designated (i.e., $C_{1-8}$ means one to eight carbons). Examples include $(C_1-C_8)$alkyl, $(C_2-C_8)$alkyl, $C_1-C_6)$alkyl, $(C_2-C_6)$alkyl and $(C_3-C_6)$alkyl. Examples of alkyl groups include methyl, ethyl, n-propyl, iso-propyl, n-butyl, t-butyl, iso-butyl, sec-butyl, n-pentyl, n-hexyl, n-heptyl, n-octyl, and and higher homologs and isomers.

The term "alkenyl" refers to an unsaturated alkyl radical having one or more double bonds. Examples of such unsaturated alkyl groups include vinyl, 2-propenyl, crotyl, 2-isopentenyl, 2-(butadienyl), 2,4-pentadienyl, 3-(1,4-pentadienyl) and the higher homologs and isomers.

The term "alkynyl" refers to an unsaturated alkyl radical having one or more triple bonds. Examples of such unsaturated alkyl groups ethynyl, 1- and 3-propynyl, 3-butynyl, and higher homologs and isomers.

The term "alkoxy" refers to an alkyl groups attached to the remainder of the molecule via an oxygen atom ("oxy").

The term "alkylthio" refers to an alkyl groups attached to the remainder of the molecule via a thio group.

The term "cycloalkyl" refers to a saturated or partially unsaturated (non-aromatic) all carbon ring having 3 to 8 carbon atoms (i.e., ($C_3$-$C_8$)carbocycle). The term also includes multiple condensed, saturated all carbon ring systems (e.g., ring systems comprising 2, 3 or 4 carbocyclic rings). Accordingly, carbocycle includes multicyclic carbocyles such as a bicyclic carbocycles (e.g., bicyclic carbocycles having about 3 to 15 carbon atoms, about 6 to 15 carbon atoms, or 6 to 12 carbon atoms such as bicyclo[3.1.0]hexane and bicyclo[2.1.1]hexane), and polycyclic carbocycles (e.g tricyclic and tetracyclic carbocycles with up to about 20 carbon atoms). The rings of the multiple condensed ring system can be connected to each other via fused, spiro and bridged bonds when allowed by valency requirements. For example, multicyclic carbocyles can be connected to each other via a single carbon atom to form a spiro connection (e.g., spiropentane, spiro[4,5]decane, etc), via two adjacent carbon atoms to form a fused connection (e.g., carbocycles such as decahydronaphthalene, norsabinane, norcarane) or via two non-adjacent carbon atoms to form a bridged connection (e.g., norbornane, bicyclo[2.2.2]octane, etc). Non-limiting examples of cycloalkyls include cyclopropyl, cyclobutyl, cyclopentyl, cyclohexyl, bicyclo[2.2.1]heptane, pinane, and adamantane.

The term "aryl" as used herein refers to a single all carbon aromatic ring or a multiple condensed all carbon ring system wherein at least one of the rings is aromatic. For example, in certain embodiments, an aryl group has 6 to 20 carbon atoms, 6 to 14 carbon atoms, 6 to 12 carbon atoms, or 6 to 10 carbon atoms. Aryl includes a phenyl radical. Aryl also includes multiple condensed carbon ring systems (e.g., ring systems comprising 2, 3 or 4 rings) having about 9 to 20 carbon atoms in which at least one ring is aromatic and wherein the other rings may be aromatic or not aromatic (i.e., cycloalkyl. The rings of the multiple condensed ring system can be connected to each other via fused, spiro and bridged bonds when allowed by valency requirements. It is to be understood that the point of attachment of a multiple condensed ring system, as defined above, can be at any position of the ring system including an aromatic or a carbocycle portion of the ring. Non-limiting examples of aryl groups include, but are not limited to, phenyl, indenyl, indanyl, naphthyl, 1, 2, 3, 4-tetrahydronaphthyl, anthracenyl, and the like.

The term "heterocycle" refers to a single saturated or partially unsaturated ring that has at least one atom other than carbon in the ring, wherein the atom is selected from the group consisting of oxygen, nitrogen and sulfur; the term also includes multiple condensed ring systems that have at least one such saturated or partially unsaturated ring, which multiple condensed ring systems are further described below. Thus, the term includes single saturated or partially unsaturated rings (e.g., 3, 4, 5, 6 or 7-membered rings) from about 1 to 6 carbon atoms and from about 1 to 3 heteroatoms selected from the group consisting of oxygen, nitrogen and sulfur in the ring. The sulfur and nitrogen atoms may also be present in their oxidized forms. Exemplary heterocycles include but are not limited to azetidinyl, tetrahydrofuranyl and piperidinyl. The term "heterocycle" also includes multiple condensed ring systems (e.g., ring systems comprising 2, 3 or 4 rings) wherein a single heterocycle ring (as defined above) can be condensed with one or more groups selected from cycloalkyl, aryl, and heterocycle to form the multiple condensed ring system. The rings of the multiple condensed ring system can be connected to each other via fused, spiro and bridged bonds when allowed by valency requirements. It is to be understood that the individual rings of the multiple condensed ring system may be connected in any order relative to one another. It is also to be understood that the point of attachment of a multiple condensed ring system (as defined above for a heterocycle) can be at any position of the multiple condensed ring system including a heterocycle, aryl and carbocycle portion of the ring. In one embodiment the term heterocycle includes a 3-15 membered heterocycle. In one embodiment the term heterocycle includes a 3-10 membered heterocycle. In one embodiment the term heterocycle includes a 3-8 membered heterocycle. In one embodiment the term heterocycle includes a 3-7 membered heterocycle. In one embodiment the term heterocycle includes a 3-6 membered heterocycle. In one embodiment the term heterocycle includes a 4-6 membered heterocycle. In one embodiment the term heterocycle includes a 3-10 membered monocyclic or bicyclic heterocycle comprising 1 to 4 heteroatoms. In one embodiment the term heterocycle includes a 3-8 membered monocyclic or bicyclic heterocycle heterocycle comprising 1 to 3 heteroatoms. In one embodiment the term heterocycle includes a 3-6 membered monocyclic heterocycle comprising 1 to 2 heteroatoms. In one embodiment the term heterocycle includes a 4-6 membered monocyclic heterocycle comprising 1 to 2 heteroatoms. Exemplary heterocycles include, but are not limited to aziridinyl, azetidinyl, pyrrolidinyl, piperidinyl, homopiperidinyl, morpholinyl, thiomorpholinyl, piperazinyl, tetrahydrofuranyl, dihydrooxazolyl, tetrahydropyranyl, tetrahydrothiopyranyl, 1,2,3,4 tetrahydroquinolyl, benzoxazinyl, dihydrooxazolyl, chromanyl, 1,2-dihydropyridinyl, 2,3-dihydrobenzofuranyl, 1,3-benzodioxolyl, 1,4-benzodioxanyl, spiro[cyclopropane-1,1'-isoindolinyl]-3'-one, isoindolinyl-1-one, 2-oxa-6-azaspiro[3.3]heptanyl, imidazolidin-2-one imidazolidine, pyrazolidine, butyrolactam, valerolactam, imidazolidinone, hydantoin, dioxolane, phthalimide, and 1,4-dioxane.

The term "heteroaryl" as used herein refers to a single aromatic ring that has at least one atom other than carbon in the ring, wherein the atom is selected from the group consisting of oxygen, nitrogen and sulfur; "heteroaryl" also includes multiple condensed ring systems that have at least one such aromatic ring, which multiple condensed ring systems are further described below. Thus, "heteroaryl" includes single aromatic rings of from about 1 to 6 carbon atoms and about 1-4 heteroatoms selected from the group consisting of oxygen, nitrogen and sulfur. The sulfur and nitrogen atoms may also be present in an oxidized form provided the ring is aromatic. Exemplary heteroaryl ring systems include but are not limited to pyridyl, pyrimidinyl, oxazolyl or furyl. "Heteroaryl" also includes multiple condensed ring systems (e.g., ring systems comprising 2, 3 or 4 rings) wherein a heteroaryl group, as defined above, is condensed with one or more rings selected from cycloalkyl, aryl, heterocycle, and heteroaryl. It is to be understood that the point of attachment for a heteroaryl or heteroaryl multiple condensed ring system can be at any suitable atom of the heteroaryl or heteroaryl multiple condensed ring system including a carbon atom and a heteroatom (e.g., a nitrogen). Exemplary heteroaryls include but are not limited to pyridyl, pyrrolyl, pyrazinyl, pyrimidinyl, pyridazinyl, pyrazolyl, thienyl, indolyl, imidazolyl, triazolyl, tetrazolyl, oxazolyl, isoxazolyl, thiazolyl, furyl, oxadiazolyl, thiadiazolyl, quinolyl, isoquinolyl, benzothiazolyl, benzoxazolyl, indazolyl, quinoxalyl, and quinazolyl.

The term "alkoxycarbonyl" as used herein refers to a group (alkyl)-O—C(=O)—, wherein the term alkyl has the meaning defined herein.

The term "alkanoyloxy" as used herein refers to a group (alkyl)-C(=O)—O—, wherein the term alkyl has the meaning defined herein.

As used herein, the term "heteroatom" is meant to include oxygen (O), nitrogen (N), sulfur (S) and silicon (Si).

As used herein, the term "protecting group" refers to a substituent that is commonly employed to block or protect a particular functional group on a compound. For example, an "amino-protecting group" is a substituent attached to an amino group that blocks or protects the amino functionality in the compound. Suitable amino-protecting groups include acetyl, trifluoroacetyl, t-butoxycarbonyl (BOC), benzyloxycarbonyl (CBZ) and 9-fluorenylmethylenoxycarbonyl (Fmoc). Similarly, a "hydroxy-protecting group" refers to a substituent of a hydroxy group that blocks or protects the hydroxy functionality. Suitable protecting groups include acetyl and silyl. A "carboxy-protecting group" refers to a substituent of the carboxy group that blocks or protects the carboxy functionality. Common carboxy-protecting groups include phenylsulfonylethyl, cyanoethyl, 2-(trimethylsilyl)ethyl, 2-(trimethylsilyl)ethoxymethyl, 2-(p-toluenesulfonyl)ethyl, 2-(p-nitrophenylsulfenyl)ethyl, 2-(diphenylphosphino)-ethyl, nitroethyl and the like. For a general description of protecting groups and their use, see P. G. M. Wuts and T. W. Greene, Greene's Protective Groups in Organic Synthesis 4$^{th}$ edition, Wiley-Interscience, New York, 2006.

As used herein a wavy line "⁓" that intersects a bond in a chemical structure indicates the point of attachment of the bond that the wavy bond intersects in the chemical structure to the remainder of a molecule.

The terms "treat", "treatment", or "treating" to the extent it relates to a disease or condition includes inhibiting the disease or condition, eliminating the disease or condition, and/or relieving one or more symptoms of the disease or condition. The terms "treat", "treatment", or "treating" also refer to both therapeutic treatment and/or prophylactic treatment or preventative measures, wherein the object is to prevent or slow down (lessen) an undesired physiological change or disorder, such as, for example, the development or spread of cancer. For example, beneficial or desired clinical results include, but are not limited to, alleviation of symptoms, diminishment of extent of disease or disorder, stabilized (i.e., not worsening) state of disease or disorder, delay or slowing of disease progression, amelioration or palliation of the disease state or disorder, and remission (whether partial or total), whether detectable or undetectable. "Treat", "treatment", or "treating," can also mean prolonging survival as compared to expected survival if not receiving treatment. Those in need of treatment include those already with the disease or disorder as well as those prone to have the disease or disorder or those in which the disease or disorder is to be prevented. In one embodiment "treat", "treatment", or "treating" does not include preventing or prevention, The phrase "therapeutically effective amount" or "effective amount" includes but is not limited to an amount of a compound of the that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The term "mammal" as used herein refers to humans, higher non-human primates, rodents, domestic, cows, horses, pigs, sheep, dogs and cats. In one embodiment, the mammal is a human. The term "patient" as used herein refers to any animal including mammals. In one embodiment, the patient is a mammalian patient. In one embodiment, the patient is a human patient.

The compounds disclosed herein can also exist as tautomeric isomers in certain cases. Although only one delocalized resonance structure may be depicted, all such forms are contemplated within the scope of the invention.

It is understood by one skilled in the art that this invention also includes any compound claimed that may be enriched at any or all atoms above naturally occurring isotopic ratios with one or more isotopes such as, but not limited to, deuterium ($^2$H or D). As a non-limiting example, a —CH$_3$ group may be substituted with —CD$_3$.

The pharmaceutical compositions of the invention can comprise one or more excipients. When used in combination with the pharmaceutical compositions of the invention the term "excipients" refers generally to an additional ingredient that is combined with the compound of formula (I) or the pharmaceutically acceptable salt thereof to provide a corresponding composition. For example, when used in combination with the pharmaceutical compositions of the invention the term "excipients" includes, but is not limited to: carriers, binders, disintegrating agents, lubricants, sweetening agents, flavoring agents, coatings, preservatives, and dyes.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. The compounds of the invention can contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer can also be referred to as an enantiomer, and a mixture of such isomers is often called an enantiomeric mixture. A 50:50 mixture of enantiomers is referred to as a racemic mixture or a racemate, which can occur where there has been no stereoselection or stereospecificity in a chemical reaction or process.

The terms "racemic mixture" and "racemate" refer to an equimolar mixture of two enantiomeric species, devoid of optical activity.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

When a bond in a compound formula herein is drawn in a non-stereochemical manner (e.g. flat), the atom to which the bond is attached includes all stereochemical possibilities. When a bond in a compound formula herein is drawn in a defined stereochemical manner (e.g. bold, bold-wedge, dashed or dashed-wedge), it is to be understood that the atom to which the stereochemical bond is attached is enriched in the absolute stereoisomer depicted unless otherwise noted. In one embodiment, the compound may be at least 51% the absolute stereoisomer depicted. In another embodiment, the compound may be at least 60% the absolute stereoisomer depicted. In another embodiment, the compound may be at least 80% the absolute stereoisomer depicted. In another embodiment, the compound may be at least 90% the absolute stereoisomer depicted. In another embodiment, the compound may be at least 95 the absolute stereoisomer depicted. In another embodiment, the compound may be at least 99% the absolute stereoisomer depicted.

The term "residue" as it applies to the residue of a compound refers to a compound that has been modified in any manner which results in the creation of an open valence wherein the site of the open valence. The open valence can be created by the removal of 1 or more atoms from the compound (e.g., removal of a single atom such as hydrogen or removal of more than one atom such as a group of atoms including but not limited to an amine, hydroxyl, methyl, amide (e.g., —C(=O)NH$_2$) or acetyl group). The open valence can also be created by the chemical conversion of a first function group of the compound to a second functional group of the compound (e.g., reduction of a carbonyl group, replacement of a carbonyl group with an amine,) followed by the removal of 1 or more atoms from the second functional group to create the open valence.

Specific values listed below for radicals, substituents, and ranges, are for illustration only; they do not exclude other defined values or other values within defined ranges for the radicals and substituents. It is to be understood that two or more values may be combined. It is also to be understood that the values listed herein below (or subsets thereof) can be excluded.

Specifically, $(C_1-C_6)$alkyl can be methyl, ethyl, propyl, isopropyl, butyl, iso-butyl, sec-butyl, pentyl, 3-pentyl, or hexyl; $(C_3-C_6)$cycloalkyl can be cyclopropyl, cyclobutyl, cyclopentyl, or cyclohexyl; $(C_3-C_6)$cycloalkyl$(C_1-C_6)$alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; $(C_1-C_6)$alkoxy can be methoxy, ethoxy, propoxy, isopropoxy, butoxy, iso-butoxy, sec-butoxy, pentoxy, 3-pentoxy, or hexyloxy; $(C_2-C_6)$alkenyl can be vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, or 5-hexenyl; $(C_2-C_6)$alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; $(C_1-C_6)$alkanoyl can be acetyl, propanoyl or butanoyl; $(C_1-C_6)$alkoxycarbonyl can be methoxycarbonyl, ethoxycarbonyl, propoxycarbonyl, isopropoxycarbonyl, butoxycarbonyl, pentoxycarbonyl, or hexyloxycarbonyl; $(C_1-C_6)$alkylthio can be methylthio, ethylthio, propylthio, isopropylthio, butylthio, isobutylthio, pentylthio, or hexylthio; $(C_2-C_6)$alkanoyloxy can be acetoxy, propanoyloxy, butanoyloxy, isobutanoyloxy, pentanoyloxy, or hexanoyloxy; aryl can be phenyl, indenyl, or naphthyl; and heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

In one embodiment, the invention provides, a compound of formula (Ia):

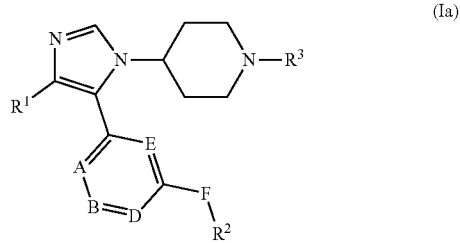

(Ia)

or a pharmaceutically acceptable salt thereof.

In one embodiment, the invention provides, a compound of formula (Ib):

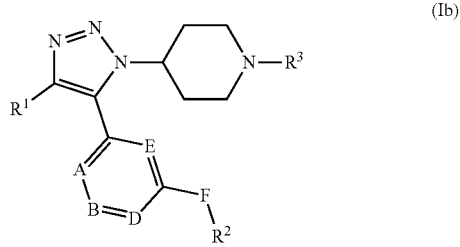

(Ib)

or a pharmaceutically acceptable salt thereof.

In one embodiment, the invention provides, a compound of formula (Ic):

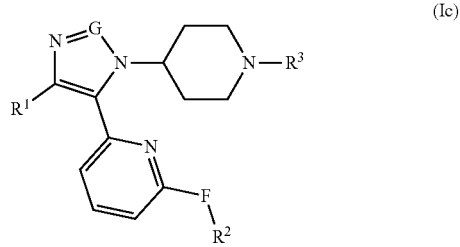

(Ic)

or a pharmaceutically acceptable salt thereof.

In one embodiment, the invention provides, a compound of formula (Id):

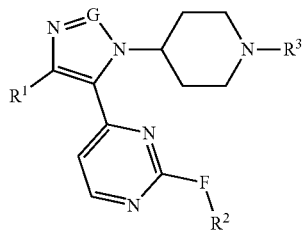

(Id)

or a pharmaceutically acceptable salt thereof.

In one embodiment, the invention provides, a compound of formula (Ie):

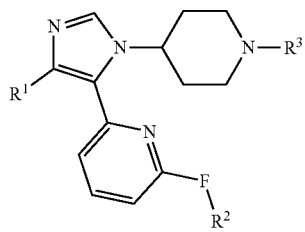

(Ie)

or a pharmaceutically acceptable salt thereof.

In one embodiment, the invention provides, a compound of formula (If):

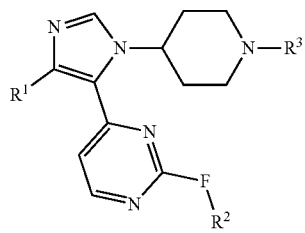

(If)

or a pharmaceutically acceptable salt thereof.

In one embodiment, the invention provides, a compound of formula (Ig):

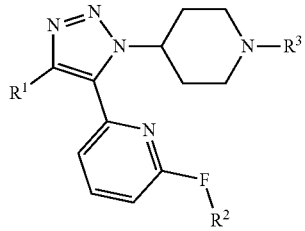

(Ig)

or a pharmaceutically acceptable salt thereof.

In one embodiment, the invention provides, a compound of formula (Ih):

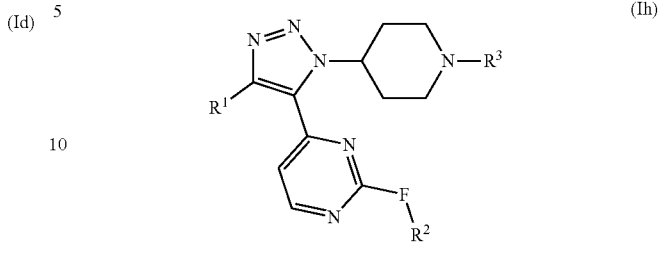

(Ih)

or a pharmaceutically acceptable salt thereof.

A specific value for $R^1$ is aryl, $(C_1-C_6)$alkyl, or $(C_3-C_6)$cycloalkyl, wherein any $(C_1-C_6)$alkyl and $(C_3-C_6)$cycloalkyl is optionally substituted with one or more groups independently selected from the group consisting of halo, oxo, —OH, cyano, $(C_3-C_6)$cycloalkyl, and $(C_1-C_6)$alkoxy; and wherein any aryl is optionally substituted with one or more groups independently selected from the group consisting of halo, —OH, cyano, $(C_1-C_6)$alkyl, $(C_3-C_6)$cycloalkyl, $(C_1-C_6)$alkoxy, $(C_2-C_6)$alkenyl, $(C_2-C_6)$alkynyl, $(C_1-C_6)$alkanoyl, $(C_1-C_6)$alkoxycarbonyl, $(C_1-C_6)$alkylthio and $(C_2-C_6)$alkanoyloxy, wherein any $(C_1-C_6)$alkyl, $(C_3-C_6)$cycloalkyl, $(C_1-C_6)$alkoxy, $(C_2-C_6)$alkenyl, $(C_2-C_6)$alkynyl, $(C_1-C_6)$alkanoyl, $(C_1-C_6)$alkoxycarbonyl, $(C_1-C_6)$alkylthio and $(C_2-C_6)$alkanoyloxy is optionally substituted with one or more groups independently selected from the group consisting of halo and —OH.

A specific value for $R^1$ is phenyl, $(C_1-C_6)$alkyl, or $(C_3-C_6)$cycloalkyl, wherein any $(C_1-C_6)$alkyl and $(C_3-C_6)$cycloalkyl is optionally substituted with one or more groups independently selected from the group consisting of halo, oxo, —OH, cyano, $(C_3-C_6)$cycloalkyl, and $(C_1-C_6)$alkoxy; and wherein any phenyl is optionally substituted with one or more groups independently selected from the group consisting of halo, —OH, cyano, $(C_1-C_6)$alkyl, $(C_3-C_6)$cycloalkyl, $(C_1-C_6)$alkoxy, $(C_2-C_6)$alkenyl, $(C_2-C_6)$alkynyl, $(C_1-C_6)$alkanoyl, $(C_1-C_6)$alkoxycarbonyl, $(C_1-C_6)$alkylthio and $(C_2-C_6)$alkanoyloxy, wherein any $(C_1-C_6)$alkyl, $(C_3-C_6)$cycloalkyl, $(C_1-C_6)$alkoxy, $(C_2-C_6)$alkenyl, $(C_2-C_6)$alkynyl, $(C_1-C_6)$alkanoyl, $(C_1-C_6)$alkoxycarbonyl, $(C_1-C_6)$alkylthio and $(C_2-C_6)$alkanoyloxy is optionally substituted with one or more groups independently selected from the group consisting of halo and —OH.

A specific value for $R^1$ is phenyl, $(C_1-C_6)$alkyl, or $(C_3-C_6)$cycloalkyl, wherein any $(C_1-C_6)$alkyl and $(C_3-C_6)$cycloalkyl is optionally substituted with one or more groups independently selected from the group consisting of halo, and —OH; and wherein any phenyl is optionally substituted with one or more groups independently selected from the group consisting of halo, $(C_1-C_6)$alkyl and $(C_1-C_6)$alkoxy, wherein any $(C_1-C_6)$alkyl and $(C_1-C_6)$alkoxy is optionally substituted with one or more groups independently selected from the group consisting of halo and —OH.

A specific value for $R^1$ is 4-fluorophenyl, 4-iodophenyl, 4-chlorophenyl, 4-bromophenyl, 4-(trifluoromethyl)phenyl and 4-(methoxy)phenyl.

A specific value for $R^1$ is phenyl.

A specific value for $R^1$ is $(C_1-C_6)$alkyl optionally substituted with —OH.

A specific value for $R^1$ is hydroxymethyl.

A specific value for $R^1$ is $(C_1-C_6)$alkyl.

A specific value for $R^1$ is methyl, ethyl, n-propyl, i-propyl, n-butyl, t-butyl, i-pentyl, n-pentyl, n-hexyl, n-octyl, n-nonyl, n-undecyl, n-tridecyl, n-pentadecyl or n-heptadecyl.

A specific value for $R^1$ is $(C_3-C_6)$cycloalkyl.

A specific value for $R^1$ is cyclopropyl, cyclopentyl, or cyclohexyl.

A specific value for $R^2$ is phenyl that is optionally substituted with one or more groups independently selected from the group consisting of selected from halo, —OH, cyano, $(C_1-C_6)$alkyl, $(C_3-C_6)$cycloalkyl, and $(C_1-C_6)$alkoxy, wherein any $(C_1-C_6)$alkyl, $(C_3-C_6)$cycloalkyl, and $(C_1-C_6)$alkoxy is optionally substituted with one or more groups independently selected from the group consisting of halo, and $(C_1-C_6)$alkoxy.

A specific value for $R^2$ is phenyl that is optionally substituted with one or more groups independently selected from the group consisting of selected from halo, $(C_1-C_6)$alkyl, and $(C_1-C_6)$alkoxy, wherein any $(C_1-C_6)$alkyl and $(C_1-C_6)$alkoxy is optionally substituted with one or more groups independently selected from the group consisting of halo and $(C_1-C_6)$alkoxy.

A specific value for $R^2$ is phenyl that is optionally substituted with one or more groups independently selected from the group consisting of $C_1-C_6$)alkyl.

A specific value for $R^2$ is phenyl that is optionally substituted with one or more methyl groups.

A specific value for $R^2$ is 3,5-dimethylphenyl.

A specific value for $R^2$ is 4-methoxy-3,5-dimethylphenyl.

A specific value for $R^3$ is H.

A specific value for $R^3$ is —C(=N($R^a$))$NR^aR^b$.

A specific value for $R^3$ is guanidinyl.

A specific value for $R^3$ is $(C_1-C_6)$alkyl substituted with —$NR^aR^b$, wherein $R^a$ and $R^b$ are H.

A specific value for $R^3$ is $(C_1-C_6)$alkyl substituted with —$NH_2$.

A specific value for $R^3$ is 2-aminoethyl.

A specific value for F is O.

A specific value for F is S.

A specific value for F is $NR^c$.

A specific value for F is NH.

Processes for preparing compounds of formula I are provided as further embodiments of the invention and are illustrated by the following procedures in which the meanings of the generic radicals are as given above unless otherwise qualified.

In cases where compounds are sufficiently basic or acidic, a salt of a compound of formula I can be useful as an intermediate for isolating or purifying a compound of formula I. Additionally, administration of a compound of formula I as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The invention will now be illustrated by the following non-limiting Examples.

EXAMPLES

Preparative Example 1. Synthesis of Compound 11c Using the General Procedure I: Copper-Catalyzed Azide-Alkyne Cycloaddition Products

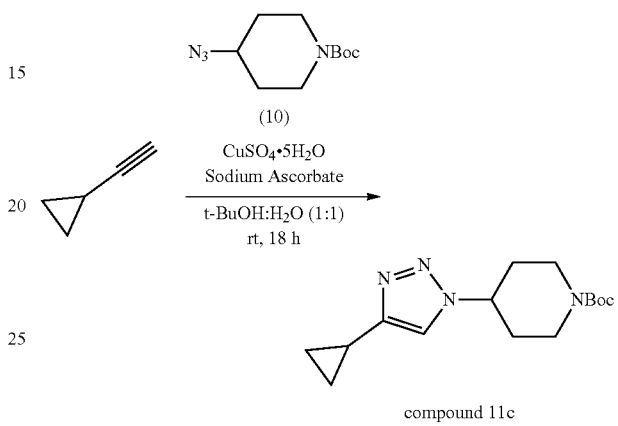

compound 11c

General Procedure I—

Compound 10 was synthesized using a known procedure (Divakaran, A. et al. *J. Med. Chem.* 2018, 61, 9316-9334). To a solution of azide 10 (250 mg, 1.11 mmol) and ethynylcyclopropane (0.12 mL, 1.4 mmol) in t-BuOH/$H_2O$ (5 mL, 1:1) at rt, sodium ascorbate (55.6 mg, 0.281 mmol) was added followed by copper sulfate pentahydrate (19.1 mg, 76.5 µmol). After 18 h, the reaction mixture was diluted with $H_2O$ and extracted with EtOAc. The combined organic phases were washed with brine, dried ($Na_2SO_4$), filtered, and concentrated under reduced pressure to afford triazole 11c (305 mg, 94%) as a white solid. $^1$H NMR (500 MHz, $CDCl_3$) δ 7.23 (s, 1H), 4.52 (tt, J=11.5, 4.1 Hz, 1H), 4.21 (br, 2H), 2.90 (br, 2H), 2.17-2.06 (m, 2H), 1.96-1.82 (m, 3H), 1.45 (s, 9H), 0.95-0.88 (m, 2H), 0.85-0.77 (m, 2H). $^{13}$C NMR (126 MHz, $CDCl_3$) δ 154.5, 150.0, 117.4, 80.1, 57.9, 42.5 (br), 32.4, 28.4, 7.7, 6.7. IR (NaCl, thin film, cm$^{-1}$): 2976, 2864, 1690, 1425, 1366, 1247, 1168, 1017. HRMS (ESI-TOF) m/z [M+Na]$^+$ calcd for $C_{15}H_{24}N_4NaO_2^+$ 315.1791, found 315.1791.

Preparative Example 2. Synthesis of

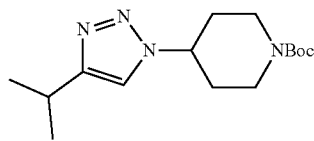 [SMILES: CC(C)c1cn(C2CCN(C(=O)OC(C)(C)C)CC2)nn1]

General Procedure I was used and the triazole (291 mg, 88%) was isolated as a white solid. $^1$H NMR (500 MHz, $CDCl_3$) δ 7.24 (s, 1H), 4.54 (tt, J=11.6, 4.0 Hz, 1H), 4.22 (br, 2H), 3.05 (hept, J=7.0 Hz, 1H), 2.92-2.86 (m, 2H), 2.16-2.11 (m, 2H), 1.97-1.83 (m, 2H), 1.44 (s, 9H), 1.27 (d, J=7.0 Hz, 6H). $^{13}$C NMR (126 MHz, $CDCl_3$) δ 154.5, 154.4, 116.8, 80.0, 57.9, 42.6 (br), 32.4, 28.4, 25.9, 22.5. IR (NaCl, thin film, cm$^{-1}$): 3132, 2966, 2933, 2871, 1692, 1424, 1167. HRMS (ESI-TOF) m/z [M+Na]$^+$ calcd for $C_{15}H_{26}N_4NaO_2^+$ 317.1948, found 317.1941.

Preparative Example 3. Synthesis of

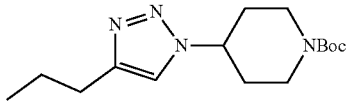 [SMILES: CCCc1cn(C2CCN(C(=O)OC(C)(C)C)CC2)nn1]

General Procedure I was used and the triazole (315 mg, 96%) was isolated as a white solid. $^1$H NMR (400 MHz, CDCl$_3$) δ 7.28 (s, 1H), 4.64-4.48 (m, 1H), 4.26 (br, 2H), 2.93 (apparent t, J=12.1 Hz, 2H), 2.68 (t, J=7.6 Hz, 2H), 2.17 (apparent d, J=12.4 Hz, 2H), 1.93 (apparent qd, J=12.3, 4.2 Hz, 2H), 1.74-1.65 (m, 2H), 1.48 (s, 9H), 0.96 (t, J=7.3 Hz, 3H). $^{13}$C NMR (101 MHz, CDCl$_3$) δ 154.5, 148.1, 118.3, 80.1, 57.9, 42.5 (br), 32.4, 28.4, 27.7, 22.7, 13.8. IR (NaCl, thin film, cm$^{-1}$): 3133, 2963, 2933, 2871, 1693, 1424, 1170, 1004. HRMS (ESI-TOF) m/z [M+Na]$^+$ calcd for $C_{15}H_{26}N_4NaO_2^+$ 317.1948, found 317.1954.

Preparative Example 4. Synthesis of

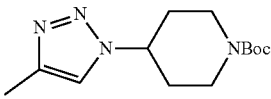 [SMILES: Cc1cn(C2CCN(C(=O)OC(C)(C)C)CC2)nn1]

This compound was synthesized though a known procedure (Divakaran, A. et al. *J. Med. Chem.* 2018, 61, 9316-9334).

Preparative Example 5. Synthesis of

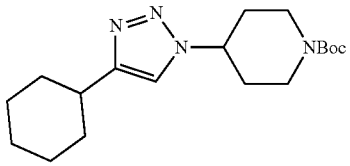 [SMILES: CC(C)(C)OC(=O)N1CCC(n2cc(C3CCCCC3)nn2)CC1]

General Procedure I was used and the triazole (279 mg, 77%) was isolated as a white solid. $^1$H NMR (500 MHz, CDCl$_3$) δ 7.24 (s, 1H), 4.56 (tt, J=11.6, 4.2 Hz, 1H), 4.25 (br, 2H), 3.05-2.81 (m, 2H), 2.75 (br, 1H), 2.16 (apparent d, J=12.3 Hz, 2H), 2.10-2.01 (m, 2H), 1.92 (apparent qd, J=12.2, 4.2 Hz, 2H), 1.85-1.76 (m, 2H), 1.72 (d, J=12.7 Hz, 1H), 1.47 (s, 9H), 1.39 (apparent t, J=9.9 Hz, 4H), 1.31-1.20 (m, 1H). $^{13}$C NMR (126 MHz, CDCl$_3$) δ 154.7, 153.8, 117.0, 80.2, 58.1, 42.8 (br), 35.5, 33.2, 32.6, 28.6, 26.3, 26.2. IR (NaCl, thin film, cm$^{-1}$): 3117, 3059, 2976, 2924, 2851, 1686, 1425, 1249, 1174, 1157, 1009. HRMS (ESI-TOF) m/z [M+Na]$^+$ calcd for $C_{18}H_{30}N_4NaO_2^+$ 357.2261, found 357.2257.

Preparative Example 6. Synthesis of

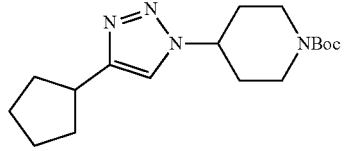 [SMILES: CC(C)(C)OC(=O)N1CCC(n2cc(C3CCCC3)nn2)CC1]

General Procedure I was used and the triazole (325 mg, 92%) was isolated as a white solid. $^1$H NMR (500 MHz, CDCl$_3$) δ 7.27 (s, 1H), 4.57 (tt, J=11.6, 4.1 Hz, 1H), 4.25 (br, 2H), 3.17 (p, J=7.9 Hz, 1H), 3.01-2.84 (m, 2H), 2.21-2.13 (m, 2H), 2.13-2.05 (m, 2H), 1.92 (apparent qd, J=12.2, 4.4 Hz, 2H), 1.83-1.72 (m, 2H), 1.71-1.62 (m, 4H), 1.47 (s, 9H). $^{13}$C NMR (126 MHz, CDCl$_3$) δ 154.5, 152.6, 117.2, 80.1, 57.9, 42.6 (br), 36.8, 33.2, 32.5, 28.4, 25.2. IR (NaCl, thin film, cm$^{-1}$): 3109, 3061, 2957, 2866, 1686, 1430, 1365, 1245, 1180, 1159, 1007. HRMS (ESI-TOF) m/z [M+Na]$^+$ calcd for $C_{17}H_{28}N_4NaO_2^+$ 343.2104, found 343.2111.

Preparative Example 7. Synthesis of

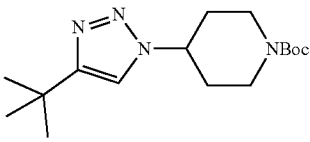 [SMILES: CC(C)(C)OC(=O)N1CCC(n2cc(C(C)(C)C)nn2)CC1]

General Procedure I was used and the triazole (300 mg, 88%) was isolated as a white solid. $^1$H NMR (500 MHz, CDCl$_3$) δ 7.24 (s, 1H), 4.55 (tt, J=11.6, 4.1 Hz, 1H), 4.23 (br, 2H), 2.93-2.86 (m, 2H), 2.19-2.09 (m, 2H), 1.97-1.85 (m, 2H), 1.44 (s, 9H), 1.32 (s, 9H). $^{13}$C NMR (126 MHz, CDCl$_3$) δ 157.6, 154.5, 116.2, 80.0, 57.8, 42.6 (br), 32.4, 30.8, 30.4, 28.4. IR (NaCl, thin film, cm$^{-1}$): 3132, 2964, 2867, 1694, 1424, 1366, 1168. HRMS (ESI-TOF) m/z [M+Na]$^+$ calcd for $C_{16}H_{28}N_4NaO_2^+$ 331.2104, found 331.2109.

Preparative Example 8. Synthesis of

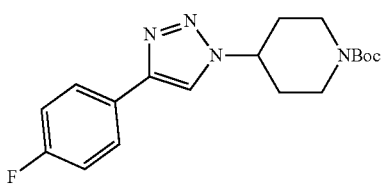 [SMILES: CC(C)(C)OC(=O)N1CCC(n2cc(-c3ccc(F)cc3)nn2)CC1]

General Procedure I was used and the triazole (1.10 mg, 77%) was isolated as a white solid. Characterization data for this compound has been reported (Divakaran, A. et al. *J. Med. Chem.* 2018, 61, 9316-9334).

Preparative Example 9. Synthesis of Compound S2

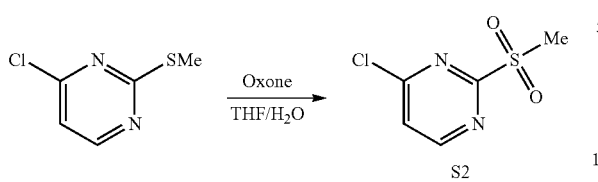

To a solution of 4-chloro-2-(methylthio)pyrimidine (1.0 mL, 8.6 mmol) in THF (40 mL) and cooled in an ice bath, a solution of Oxone (10.8 g, 35.2 mmol) in H$_2$O (40 mL) was added. After 15 min, the reaction was warmed to rt. After 18 h, the reaction was diluted with water and extracted with EtOAc. The combined organic phases were washed with brine, dried (Na$_2$SO$_4$), filtered, and concentrated under reduced pressure to afford sulfone S2 (1.34 g, 81%) in quantitative yield as a yellow oil. Characterization data for this compound has been reported (Serrano, C. M. et al. *Org. Lett.* 2011, 13, 5000-5003).

Preparative Example 10. Synthesis of Compound 12

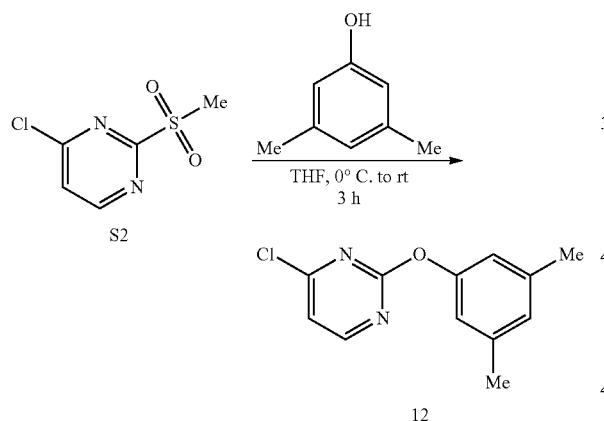

To a suspension of NaH (642 mg, 60% in mineral oil, 16.0 mmol) in THF (15 mL) in an ice bath, was added 3,5-dimethylphenol (1.14 g, 9.36 mmol). The reaction mixture was warmed to rt. After 10 min, the reaction was cooled in an ice bath. A solution of sulfone S2 (1.89 g, 9.82 mmol) in THF (30 mL) was added over 10 min. After 10 minutes, the reaction was removed from the ice bath. After 3 h, the reaction was quenched by the addition of saturated aqueous NH$_4$Cl. The resulting mixture was extracted with EtOAc. The combined organic phases were washed with brine, dried (Na$_2$SO$_4$), filtered, and concentrated under reduced pressure to afford the ether (2.40 g) in quantitative yield as a yellow oil. $^1$H NMR (500 MHz, CDCl$_3$) δ 8.38 (d, J=5.4 Hz, 1H), 7.05 (d, J=5.3 Hz, 1H), 6.91 (s, 1H), 6.81 (s, 2H), 2.35 (s, 6H). $^{13}$C NMR (126 MHz, CDCl$_3$) δ 165.2, 163.1, 160.2, 152.5, 139.6, 127.7, 119.1, 116.2, 21.4. IR (NaCl, thin film, cm$^{-1}$): 2920, 1548, 1418, 1373, 1315, 1292, 1136, 1030. HRMS (ESI-TOF) m/z [M+Na]$^+$ calcd for C$_{12}$H$_{11}$C$_1$N$_2$NaO$^+$ 257.0452, found 257.0450.

Preparative Example 11. Synthesis of Compound S3

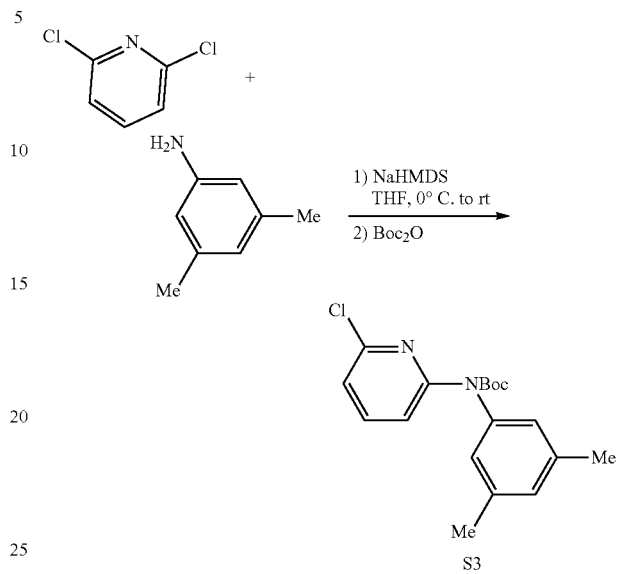

To a flask containing 3,5-dimethylaniline (0.50 mL, 4.0 mmol) pre-cooled in an ice bath, NaHMDS (10 mL, 1M in THF, 10 mmol) was added. After 5 min, 2,6-dichloropyridine (1.18 g, 7.98 mmol) was added as a solution in THF (5 mL). After 2.5 h, Boc$_2$O (2.09 g, 9.56 mmol) was added as a solution in THF (2 mL) and the reaction was removed from the ice bath. After 16 h at rt, the reaction was quenched by the addition of H$_2$O. The resulting mixture was extracted with EtOAc. The combined organic phases were washed with brine, dried (Na$_2$SO$_4$), filtered, and concentrated under reduced pressure. Final purification by column chromatography (0-60% EtOAc in hexanes) afforded the product (994 mg, 75%) as a yellow solid. $^1$H NMR (500 MHz, CDCl$_3$) δ 7.63 (apparent t, J=7.8 Hz, 1H), 7.29 (d, J=7.8 Hz, 1H), 7.12 (d, J=7.8 Hz, 1H), 6.89 (s, 1H), 6.85 (s, 2H), 2.31 (s, 6H), 1.48 (s, 9H). $^{13}$C NMR (126 MHz, CDCl$_3$) δ 155.3, 153.5, 149.5, 140.9, 139.7, 138.4, 128.4, 125.3, 121.0, 119.4, 81.8, 28.2, 21.3. IR (NaCl, thin film, cm$^{-1}$): 2979, 2921, 1715, 1580, 1433, 1368, 1309, 1256, 1157. HRMS (ESI-TOF) m/z [M+Na]$^+$ calcd for C$_{18}$H$_{21}$ClN$_2$NaO$_2^+$ 355.1184, found 355.1185.

Preparative Example 12. Synthesis of Compound S4

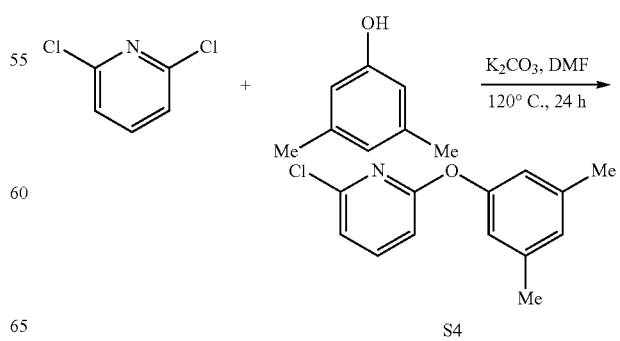

To a solution of 2,6-dichloropyridine (586 mg, 3.96 mmol) and 3,5-dimethylphenol (484 mg, 3.96 mmol) in DMF (10 mL) at rt, solid $K_2CO_3$ (844 mg, 6.10 mmol) was added. The reaction was sealed under air and heated to 120° C. After 24 h, the reaction was cooled to rt and quenched by the addition of $H_2O$. The resulting mixture was extracted with EtOAc. The combined organic phases were washed with KOH (1 M), brine, dried ($Na_2SO_4$), and concentrated under reduced pressure. This afforded product S4 (777 mg, 84%) as a white solid. Characterization data for this compound has been reported (Damkaci, F. et al. *Tetrahedron Lett.* 2017, 58, 3559-3564).

Preparative Example 13. Synthesis of Compound S5

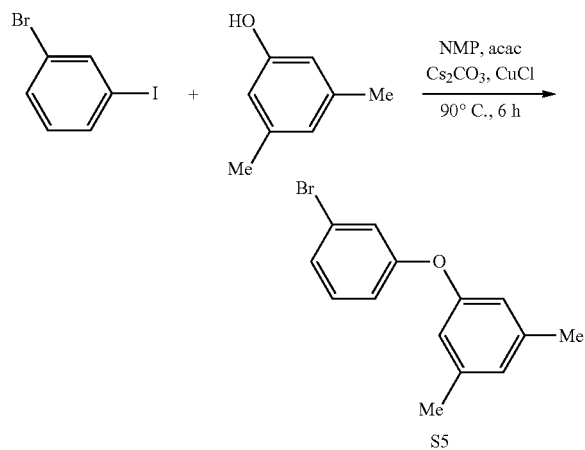

To a flask containing 3,5-dimethylphenol (580 mg, 4.75 mmol), $Cs_2CO_3$ (1.43 g, 4.39 mmol), and CuCl (46.8 mg, 0.473 mmol) at rt was added N-methyl-2-pyrrolidone (5 mL), acetylacetone (40 μL, 0.4 mmol), and 3-bromoiodobenzene (0.50 mL, 3.9 mmol). The reaction was heated to 90° C. After 6 h, the reaction was cooled to rt and quenched by the addition of $H_2O$. The resulting mixture was extracted with hexanes. The combined organic phases were washed with brine, dried ($Na_2SO_4$), filtered, and concentrated under reduced pressure. Final purification by column chromatography (0-20% DCM in hexanes) afforded the product (538 mg, 50%) as a colorless oil. $^1$H NMR (400 MHz, $CDCl_3$) δ 7.34-7.18 (m, 3H), 7.05-6.98 (m, 1H), 6.88 (s, 1H), 6.75 (s, 2H), 2.40 (s, 6H). $^{13}$C NMR (101 MHz, $CDCl_3$) δ 158.8, 156.3, 139.9, 130.8, 125.9, 122.9, 121.7, 117.3, 117.3, 117.2, 21.4. IR (NaCl, thin film, $cm^{-1}$): 3015, 2917, 2860, 1580, 1468, 1425, 1298, 1221, 1157, 1134, 1061. HRMS (EI) m/z $[M]^+$ calcd for $C_{14}H_{13}BrO^+$ 276.0144, found 276.0141.

Preparative Example 14. Synthesis of Compound S6

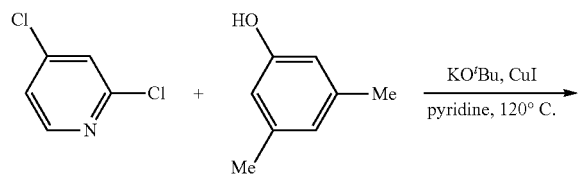

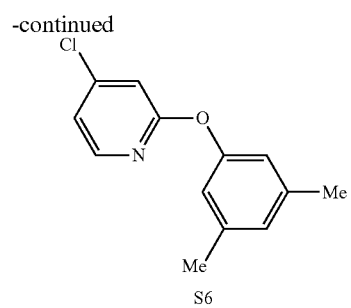

2,4-dichloropyridine (505 mg, 3.41 mmol), 3,5-dimethylphenol (455 mg, 3.73 mmol), and pyridine (2.7 mL) were added to a vial containing CuI (141 mg, 0.740 mmol) and KOtBu (423 mg, 3.77 mmol). The vial was sealed and heated to 120° C. After 2 h, the reaction was cooled to rt and quenched by the addition of 1M NaOH. The resulting mixture was extracted with hexanes. The combined organic phases were washed with 1M NaOH, 1M HCl, $H_2O$, brine, dried ($Na_2SO_4$), filtered, and concentrated under reduced pressure. Initial purification by column chromatography (0-60% EtOAc in hexanes) afforded semi-pure material. Final purification by recrystallization (MeOH) afforded the product (338 mg, 42%) as a white solid. $^1$H NMR (400 MHz, $CDCl_3$) δ 8.14 (d, J=5.5 Hz, 1H), 7.01 (dd, J=5.5, 1.7 Hz, 1H), 6.93 (d, J=1.8 Hz, 1H), 6.91 (s, 1H), 6.79 (s, 2H), 2.37 (s, 6H). $^{13}$C NMR (101 MHz, $CDCl_3$) δ 164.9, 153.6, 148.5, 146.2, 139.6, 127.1, 119.0, 118.8, 111.5, 21.4. IR (NaCl, thin film, $cm^{-1}$): 2918, 1616, 1574, 1560, 1467, 1389, 1295, 1222, 1136, 1088, 1025. HRMS (ESI-TOF) m/z $[M+Na]^+$ calcd for $C_{13}H_{12}ClNNaO^+$ 256.0500, found 256.0502.

Preparative Example 15. Synthesis of Compound S7

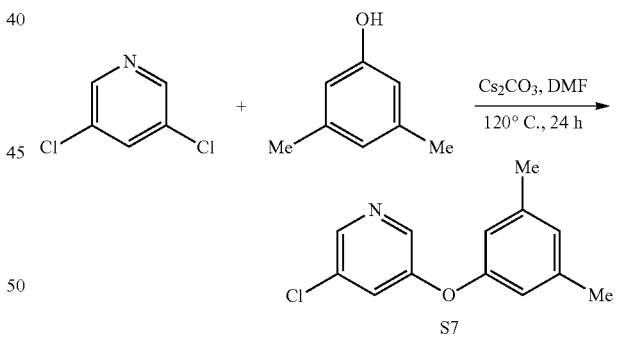

To solution of 3,5-dichloropyridine (655 mg, 4.42 mmol) and 3,5-dimethylphenol (494 mg, 4.04 mmol) in DMF (10 mL) at rt was added $Cs_2CO_3$ (2.11 g, 6.48 mmol). The reaction was sealed under air and heated to 120° C. After 24 h, the reaction was cooled to rt and quenched by the addition of $H_2O$. The reaction mixture was extracted with $Et_2O$. The combined organic layers were washed with several portions of 1M KOH, brine, dried ($MgSO_4$), and concentrated under reduced pressure. Final purification by column chromatography (0-20% EtOAc in hexanes) afforded product YY (540 mg, 57%) as a clear oil. $^1$H NMR (500 MHz, $CDCl_3$) δ 8.31 (d, J=2.0 Hz, 1H), 8.29 (d, J=2.4 Hz, 1H), 7.26 (dd, J=2.3, 2.2 Hz, 1H), 6.87 (s, 1H), 6.68 (s, 2H), 2.34 (s, 6H). $^{13}$C NMR (126 MHz, $CDCl_3$) δ 155.3, 154.7, 142.6, 140.2, 138.8, 132.0, 126.6, 124.7, 117.2, 21.3. IR (NaCl, thin film, cm$^{-1}$): 3047, 2919, 2863, 1568, 1417, 1293, 1240, 1142, 1090, 1015, 956, 901, 847, 692. HRMS (ESI-TOF) m/z [M+Na]$^+$ calcd for C$_{13}$H$_{12}$ClNNaO$^+$ 256.0500, found 256.0504.

Preparative Example 16. Synthesis of Compound S8

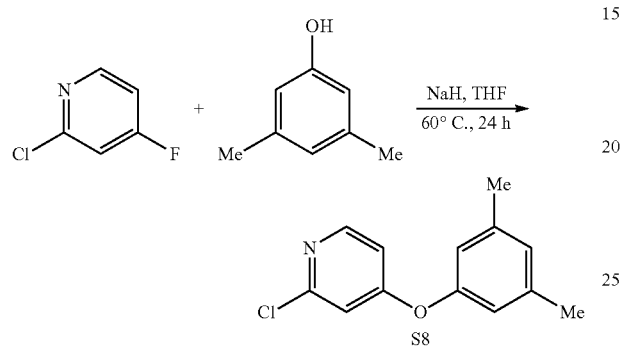

To a suspension of NaH (190 mg, 60% in mineral oil, 4.75 mmol) in THF (5 mL) was added a solution of 3,5-dimethylphenol (503 mg, 4.12 mmol) in THF (10 mL) at rt. After 10 min, 2-chloro-4-fluoropyridine (0.35 mL, 3.5 mmol) was added neat and the reaction was heated to 60° C. After 24 h, the reaction was cooled to rt and quenched by the addition of H$_2$O. The resulting mixture was extracted with Et$_2$O. The combined organic layers were washed with three separate portions of 1 M KOH, brine, dried (MgSO$_4$), and concentrated under reduced pressure. Purification by column chromatography (0-25% EtOAc in hexanes) afforded product XX (218 mg, 26%) as a clear oil. $^1$H NMR (500 MHz, CDCl$_3$) δ 8.23 (d, J=5.7 Hz, 1H), 6.94 (s, 1H), 6.83-6.79 (m, 2H), 6.72 (s, 2H), 2.36 (s, 6H). $^{13}$C NMR (126 MHz, CDCl$_3$) δ 166.7, 153.4, 152.7, 150.6, 140.4, 127.6, 118.4, 111.8, 111.4, 21.3. IR (NaCl, thin film, cm$^{-1}$): 2920, 1574, 1466, 1297, 1136, 1068, 1025, 958, 848. HRMS (ESI-TOF) m/z [M+Na]$^+$ calcd for C$_{13}$H$_{12}$ClNNaO$^+$ 256.0500, found 256.0507.

Preparative Example 17. Synthesis of Compound 13e

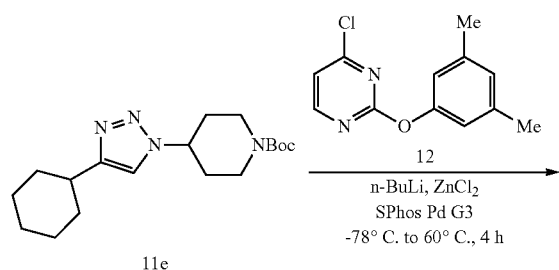

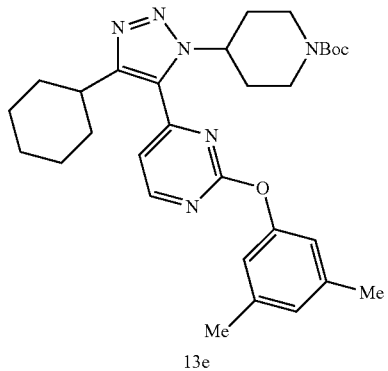

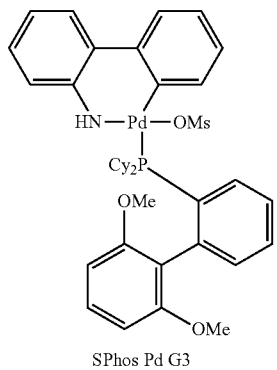

SPhos Pd G3

General Procedure II—

A solution of triazole 11e (103 mg, 0.311 mmol) in THF (10 mL) was cooled in a dry ice/acetone bath. Then n-BuLi (0.16 mL, 2.5 M in hexanes, 0.40 mmol) was added dropwise. After 10 min, a freshly prepared solution of ZnCl$_2$ (109 mg, 0.804 mmol) in THF (3 mL) was added dropwise. The reaction was warmed to rt. After 10 min, a freshly prepared solution of chloride 12 (96.5 mg, 0.412 mmol) in THF (3 mL) was added followed by SPhos Pd G3 (16.0 mg, 20.5 μmol) in THF (3 mL). The reaction was heated to 60° C. After 4 h, the reaction was cooled to rt and quenched by the addition of saturated aqueous NH$_4$Cl. The resulting mixture was extracted with EtOAc. The combined organic phases were washed with brine, dried (Na$_2$SO$_4$), filtered, and concentrated under reduced pressure. Final purification by column chromatography (0-40% IPA in hexanes) yielded the product 13e as a white solid (131 mg, 79%). $^1$H NMR (500 MHz, CDCl$_3$) δ 8.74 (d, J=5.0 Hz, 1H), 7.12 (d, J=5.1 Hz, 1H), 6.91 (s, 1H), 6.81 (s, 2H), 4.83-4.65 (m, 1H), 4.06 (br, 2H), 2.83-2.65 (m, 1H), 2.56 (br, 2H), 2.33 (s, 6H), 2.15-2.00 (m, 2H), 1.94-1.70 (m, 9H), 1.47 (s, 9H), 1.42-1.31 (m, 3H). $^{13}$C NMR (126 MHz, CDCl$_3$) δ 165.7, 161.3, 157.5, 154.7, 152.7, 152.6, 139.7, 128.4, 127.6, 119.4, 115.0, 79.9, 57.3, 42.9 (br), 35.4, 32.9, 32.0, 28.5, 26.6, 25.9, 21.4. IR (NaCl, thin film, cm$^{-1}$): 2928, 2852, 1694, 1578, 1555, 1448, 1386, 1319, 1293, 1142. HRMS (ESI-TOF) m/z [M+Na]$^+$ calcd for C$_{29}$H$_{38}$N$_6$NaO$_3^+$ 455.2530, found 455.2518.

Preparative Example 18. Synthesis of

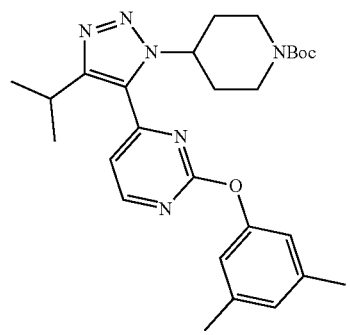 [SMILES: Cc1cc(C)cc(Oc2nccc(-c3c(C(C)C)nnn3C3CCN(C(=O)OC(C)(C)C)CC3)n2)c1]

A variation of general procedure II was used. Final purification by column chromatography (0-100% MTBE in hexanes) afforded the product as a white solid (142 mg, 74%). $^1$H NMR (500 MHz, CDCl$_3$) δ 8.73 (d, J=5.0 Hz, 1H), 7.15 (d, J=5.0 Hz, 1H), 6.90 (s, 1H), 6.80 (s, 2H), 4.72 (tt, J=11.1, 4.0 Hz, 1H), 4.06 (br, 2H), 3.13 (hept, J=6.8 Hz, 1H), 2.56 (br, 2H), 2.33 (s, 6H), 2.16-1.98 (m, 2H), 1.85-1.76 (m, 2H), 1.47 (s, 9H), 1.38 (d, J=7.0 Hz, 6H). $^{13}$C NMR (126 MHz, CDCl$_3$) δ 165.6, 161.1, 157.4, 154.6, 153.1, 152.6, 139.6, 128.2, 127.5, 119.3, 115.0, 79.8, 57.2, 43.0 (br), 31.9, 28.4, 25.5, 22.6, 21.3. IR (NaCl, thin film, cm$^{-1}$): 2972, 2931, 2869, 1693, 1578, 1556, 1425, 1386, 1315, 1163, 1142, 1003. HRMS (ESI-TOF) m/z [M+Na]$^+$ calcd for C$_{27}$H$_{36}$N$_6$NaO$_3^+$ 515.2741, found 515.2751.

Preparative Example 19. Synthesis of

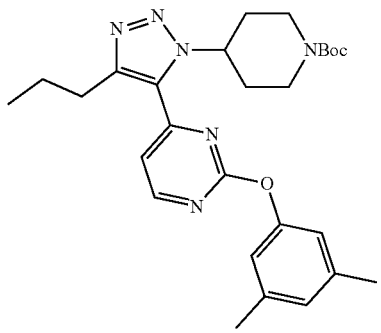

A variation of general procedure II was used. Final purification by column chromatography (0-100% MTBE in hexanes) afforded the product (187.4 mg) in quantitative yield. $^1$H NMR (500 MHz, CDCl$_3$) δ 8.74 (d, J=5.1 Hz, 1H), 7.17 (d, J=5.0 Hz, 1H), 6.92 (s, 1H), 6.82 (s, 2H), 4.94-4.72 (m, 1H), 4.07 (br, 2H), 2.80 (t, J=7.8 Hz, 2H), 2.55 (br, 2H), 2.34 (s, 6H), 2.16-2.01 (m, 2H), 1.90-1.71 (m, 4H), 1.48 (s, 9H), 1.02 (t, J=7.4 Hz, 3H). $^{13}$C NMR (126 MHz, CDCl$_3$) δ 165.6, 161.1, 157.3, 154.6, 152.7, 148.1, 139.7, 129.1, 127.5, 119.3, 114.7, 79.8, 57.5, 43.1 (br), 32.0, 28.4, 28.2, 22.4, 21.3, 14.1. IR (NaCl, thin film, cm$^{-1}$): 2965, 2932, 2871, 1694, 1578, 1557, 1453, 1425, 1376, 1319, 1164, 1143, 1004. HRMS (ESI-TOF) m/z [M+Na]$^+$ calcd for C$_{27}$H$_{36}$N$_6$NaO$_3^+$ 515.2741, found 515.2754.

Preparative Example 20. Synthesis of

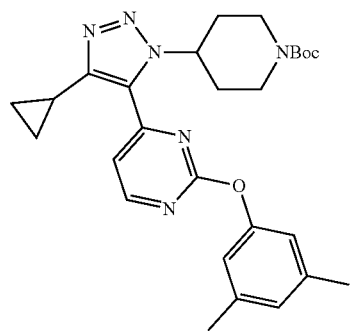 [SMILES: Cc1cc(C)cc(Oc2nccc(-c3c(C4CC4)nnn3C3CCN(C(=O)OC(C)(C)C)CC3)n2)c1]

A variation of general procedure II was used. RuPhos Pd G3 was used in place of SPhos Pd G3. Initial purification by column chromatography (0-80% EtOAc in hexanes) resulted in semi-pure material. Final purification by column chromatography (0-40% IPA in hexanes) yielded the product as a white solid (132 mg, 77%). $^1$H NMR (500 MHz, CDCl$_3$) δ 8.74 (d, J=5.0 Hz, 1H), 7.52 (d, J=5.0 Hz, 1H), 6.92 (s, 1H), 6.82 (s, 2H), 4.89 (tt, J=11.0, 4.0 Hz, 1H), 4.04 (br, 2H), 2.51 (br, 2H), 2.34 (s, 6H), 2.13-2.00 (m, 2H), 1.92 (tt, J=8.8, 5.3 Hz, 1H), 1.79 (apparent d, J=12.1 Hz, 2H), 1.48 (s, 9H), 1.19-1.14 (m, 2H), 1.06 (apparent d, J=7.8 Hz, 2H). $^{13}$C NMR (126 MHz, CDCl$_3$) δ 165.5, 161.0, 157.1, 154.6, 152.8, 149.4, 139.7, 129.6, 127.5, 119.3, 114.8, 79.8, 57.5, 42.6 (br), 31.9, 28.4, 21.3, 7.9, 7.4. IR (NaCl, thin film, cm$^{-1}$): 2975, 2863, 1692, 1578, 1424, 1388, 1315, 1163, 1143. HRMS (ESI-TOF) m/z [M+Na]$^+$ calcd for C$_{27}$H$_{34}$N$_6$NaO$_3^+$ 513.2585, found 513.2598.

Preparative Example 21. Synthesis of Compound 13d

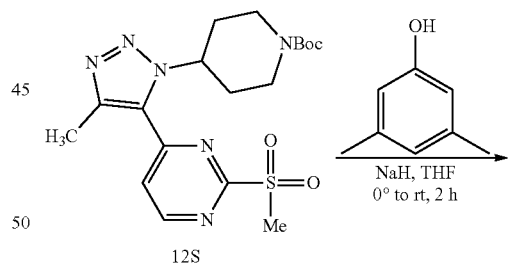

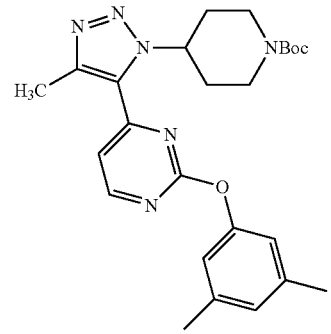

Compound 12S was obtained through a known procedure (Divakaran, A. et al. *J. Med. Chem.* 2018, 61, 9316-9334). To a slurry of NaH (37.8 mg, 0.945 mmol) in THF (5 mL), cooled in an ice bath, a solution of 3,5-dimethylphenol (55.5 mg, 0.455 mmol) in THF (5 mL) was added. The reaction was warmed to room temperature. After 10 minutes, the reaction was cooled cooled in an ice bath and a solution of compound 12S (170 mg, 0.403 mmol) in THF (5 mL) was added. The reaction was warmed to room temperature. After 2 hours, the reaction was quenched by the addition of $H_2O$. The resulting mixture was extracted with EtOAc. The combined organic phases were washed with brine, dried ($Na_2SO_4$), filtered, and concentrated under reduced pressure. Final purification by column chromatography (0-60% IPA in Hexanes) afforded ether 13d as a white solid. $^1$H NMR (500 MHz, $CDCl_3$) δ 8.74 (d, J=5.1 Hz, 1H), 7.19 (d, J=5.1 Hz, 1H), 6.91 (s, 1H), 6.80 (s, 2H), 4.88 (tt, J=11.2, 4.0 Hz, 1H), 4.05 (br, 2H), 2.52 (s, 3H), 2.50-2.43 (m, 2H), 2.32 (s, 6H), 2.12-2.02 (m, 2H), 1.85-1.76 (m, 2H), 1.47 (s, 9H). $^{13}$C NMR (126 MHz, $CDCl_3$) δ 165.5, 161.2, 157.0, 154.6, 152.7, 144.1, 139.7, 129.3, 127.5, 119.3, 114.5, 79.8, 57.6, 42.2, 31.9, 28.4, 21.3, 12.5. IR (NaCl, thin film, $cm^{-1}$): 2978, 2930, 2865, 1693, 1578, 1557, 1452, 1424, 1372, 1318, 1164, 1143. HRMS (ESI-TOF) m/z [M+Na]$^+$ calcd for $C_{25}H_{32}N_6NaO_3^+$ 487.2428, found 487.2439.

Preparative Example 22. Synthesis of

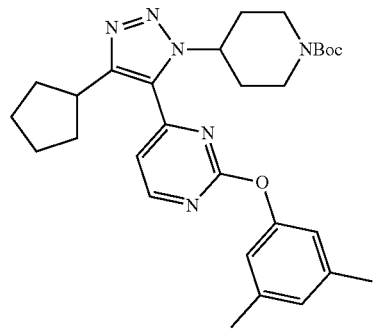 [SMILES: Cc1cc(C)cc(Oc2nccc(-c3c(C4CCCC4)nnn3C3CCN(C(=O)OC(C)(C)C)CC3)n2)c1]

A variation of general procedure II was used. XPhos Pd G3 was used in place of SPhos Pd G3. Final purification by column chromatography (0-40% IPA in hexanes) yielded the product as a white solid (137 mg, 82%). $^1$H NMR (500 MHz, $CDCl_3$) δ 8.70 (d, J=5.3 Hz, 1H), 7.16 (d, J=5.0 Hz, 1H), 6.88 (s, 1H), 6.78 (s, 2H), 4.76-4.65 (m, 1H), 4.02 (br, 2H), 3.13 (p, J=8.1 Hz, 1H), 2.52 (br, 2H), 2.30 (s, 6H), 2.10-1.83 (m, 8H), 1.77 (apparent d, J=12.3 Hz, 2H), 1.70-1.62 (m, 2H), 1.44 (s, 9H). $^{13}$C NMR (126 MHz, $CDCl_3$) δ 165.6, 161.1, 157.3, 154.6, 152.6, 151.8, 139.6, 128.8, 127.5, 119.3, 115.1, 79.8, 57.2, 43.0 (br), 36.2, 33.4, 31.9, 28.4, 25.7, 21.3. IR (NaCl, thin film, $cm^{-1}$): 2963, 2868, 1693, 1578, 1556, 1425, 1387, 1317, 1294, 1164, 1143. HRMS (ESI-TOF) m/z [M+Na]$^+$ calcd for $C_{29}H_{38}N_6NaO_3^+$ 541.2898, found 541.2897.

Preparative Example 23. Synthesis of

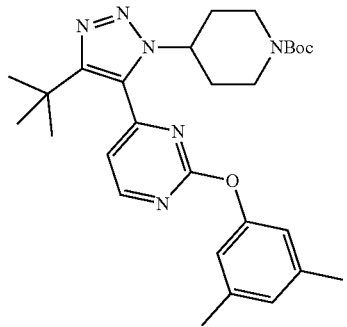 [SMILES: Cc1cc(C)cc(Oc2nccc(-c3c(C(C)(C)C)nnn3C3CCN(C(=O)OC(C)(C)C)CC3)n2)c1]

A variation of general procedure II was used. Purification by column chromatography (0-100% MTBE in hexanes) afforded semi-pure material. Final purification by column chromatography (0-20% IPA in hexanes) afforded the product as a white solid (61.7 mg, 32%). $^1$H NMR (500 MHz, $CDCl_3$) δ 8.72 (d, J=4.9 Hz, 1H), 7.15 (d, J=4.9 Hz, 1H), 6.92 (s, 1H), 6.81 (s, 2H), 4.16 (br, 2H), 4.04 (tt, J=11.2, 4.1 Hz, 1H), 2.72 (br, 2H), 2.35 (s, 6H), 2.23-2.11 (m, 2H), 1.94-1.81 (m, 2H), 1.48 (s, 9H), 1.31 (s, 9H). $^{13}$C NMR (126 MHz, $CDCl_3$) δ165.6, 160.5, 160.4, 154.5, 153.9, 152.5, 139.6, 129.2, 127.7, 119.1, 118.1, 80.0, 56.7, 42.8 (br), 32.1, 32.0, 30.7, 28.4, 21.3. IR (NaCl, thin film, $cm^{-1}$): 2971, 2868, 1692, 1583, 1560, 1424, 1370, 1389, 1316, 1164, 1141, 1003. HRMS (ESI-TOF) m/z [M+Na]$^+$ calcd for $C_{28}H_{38}N_6NaO_3^+$ 529.2898, found 529.2904.

Preparative Example 24. Synthesis of

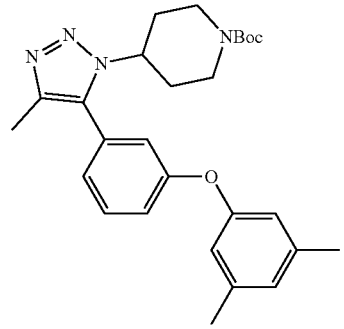

A variation of general procedure III was used. Final purification by column chromatography (0-100% EtOAc in hexanes) afforded the product (177 mg, 72%) as a white solid. $^1$H NMR (500 MHz, $CDCl_3$) δ 7.47 (apparent t, J=7.9 Hz, 1H), 7.11 (d, J=8.3 Hz, 1H), 6.96 (d, J=7.5 Hz, 1H), 6.84 (s, 1H), 6.82 (s, 1H), 6.69 (s, 2H), 4.33-4.09 (m, 3H), 2.76 (br, 2H), 2.31 (s, 6H), 2.28 (s, 3H), 2.26-2.16 (m, 2H), 1.87 (apparent d, J=12.5 Hz, 2H), 1.48 (s, 9H). $^{13}$C NMR (126 MHz, $CDCl_3$) δ 158.6, 156.0, 154.5, 141.1, 139.9, 133.3, 130.6, 129.1, 126.1, 123.5, 118.8, 118.8, 117.3, 79.9, 56.2, 43.0, 32.3, 28.4, 21.3, 10.5. IR (NaCl, thin film, $cm^{-1}$): 2931, 1693, 1613, 1579, 1453, 1424, 1366, 1287, 1248, 1155. HRMS (ESI-TOF) m/z [M+Na]$^+$ calcd for $C_{27}H_{34}N_4NaO_3^+$ 485.2523, found 485.2526.

Preparative Example 25. Synthesis of

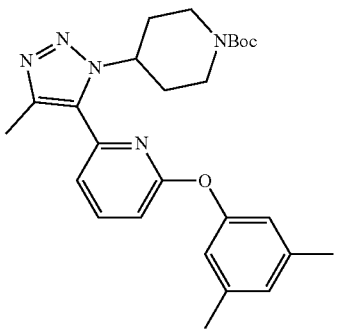

A variation of general procedure III was used. Initial purification by column chromatography (0-45% IPA in hexanes) afforded semi-pure material. Final purification by recrystallization (DCM/hexanes, ca. 2:10) afforded the product (101 mg, 41%) as a white solid. $^1$H NMR (500 MHz, CDCl$_3$) δ 7.83 (apparent t, J=7.9 Hz, 1H), 7.15 (d, J=7.4 Hz, 1H), 6.97 (d, J=8.3 Hz, 1H), 6.85 (s, 1H), 6.74 (s, 2H), 4.69 (tt, J=11.3, 4.0 Hz, 1H), 4.00 (br, 2H), 2.49-2.39 (m, 5H), 2.31 (s, 6H), 2.11-1.96 (m, 2H), 1.78-1.66 (m, 2H), 1.47 (s, 9H). $^{13}$C NMR (126 MHz, CDCl$_3$) δ 163.6, 154.6, 153.6, 145.3, 141.9, 140.2, 139.5, 131.4, 126.8, 119.3, 118.4, 111.2, 79.6, 56.7, 43.1, 31.9, 28.4, 21.3, 12.0. IR (NaCl, thin film, cm$^{-1}$): 2973, 2864, 1692, 1572, 1426, 1301, 1246, 1166. HRMS (ESI-TOF) m/z [M+Na]$^+$ calcd for C$_{26}$H$_{33}$N$_5$NaO$_3^+$ 486.2476, found 486.2471.

Preparative Example 26. Synthesis of

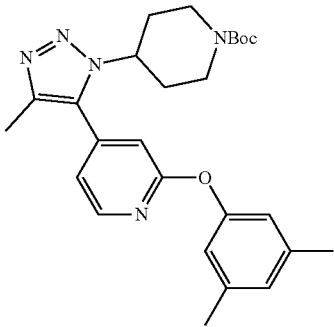

A variation of general procedure III was used. Final purification by column chromatography (0-100% EtOAc in hexanes) afforded the product (162 mg, 71%) as a white solid. $^1$H NMR (500 MHz, CDCl$_3$) δ 8.34 (d, J=5.2 Hz, 1H), 6.92-6.87 (m, 2H), 6.80 (s, 2H), 6.77 (s, 1H), 4.34-4.14 (m, 3H), 2.80 (br, 2H), 2.34 (s, 6H), 2.32 (s, 3H), 2.29-2.18 (m, 2H), 1.92 (apparent d, J=12.3 Hz, 2H), 1.47 (s, 9H). $^{13}$C NMR (101 MHz, CDCl$_3$) δ 164.8, 154.4, 153.4, 148.9, 141.7, 139.7, 139.3, 131.2, 127.2, 119.0, 118.2, 111.3, 80.0, 56.6, 43.0 (br), 32.4, 28.4, 21.4, 10.6. IR (NaCl, thin film, cm$^{-1}$): 2974, 2929, 2865, 1693, 1615, 1545, 1454, 1425, 1397, 1295, 1248, 1211, 1174, 1155, 1003. HRMS (ESI-TOF) m/z [M+Na]$^+$ calcd for C$_{26}$H$_{33}$N$_5$NaO$_3^+$ 486.2476, found 486.2477.

Preparative Example 27. Synthesis of Compound 13k

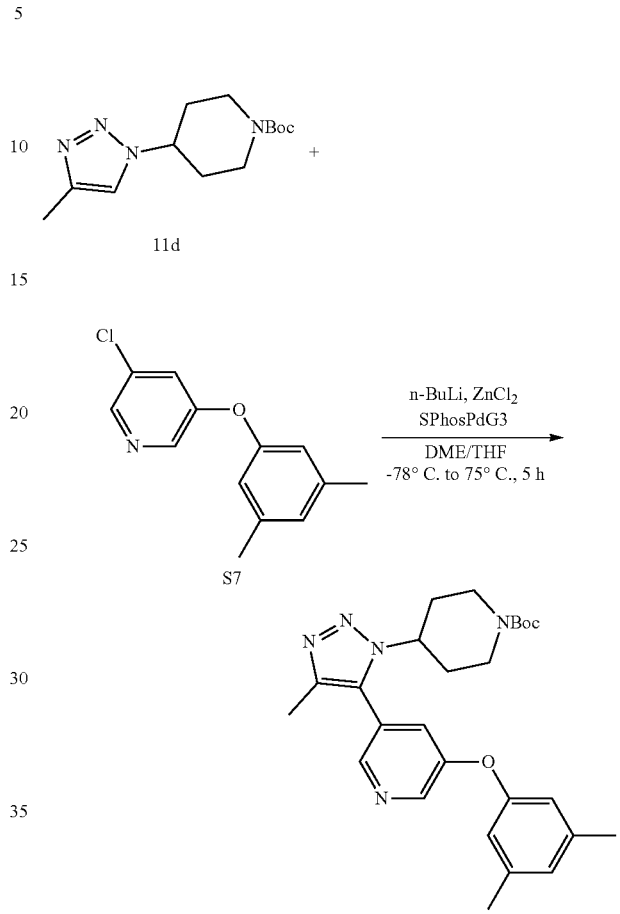

General Procedure III—

A solution of triazole 11d (134 mg, 0.590 mmol) in DME (5 mL) was cooled in a dry ice/acetone bath. Then n-BuLi (0.31 mL, 2.5 M in hexanes, 0.78 mmol) was added dropwise. After 10 min, a freshly prepared solution of ZnCl$_2$ (203 mg, 1.49 mmol) in THF (2 mL) was added dropwise. The reaction was warmed to rt. After 10 min, a freshly prepared solution chloride S7 (178 mg, 0.763 mmol) in DME (3 mL) was added followed by SPhos Pd G3 (15.1 mg, 19.4 µmol) in DME (2 mL). The reaction was heated to 75° C. After 5 h, the reaction mixture was quenched with saturated aqueous NH$_4$Cl and extracted with EtOAc. The combined organic phases were washed with brine, dried (Na$_2$SO$_4$), filtered, and concentrated under reduced pressure. Final purification by column chromatography (0-60% IPA in hexanes) yielded the product 13k as a white solid (218 mg, 87%). $^1$H NMR (500 MHz, CDCl$_3$) δ 8.47 (br, 1H), 8.23 (br, 1H), 7.11 (s, 1H), 6.85 (s, 1H), 6.69 (s, 2H), 4.35-3.98 (m, 3H), 2.74 (br, 2H), 2.30 (s, 6H), 2.27-2.13 (m, 5H), 1.89-1.81 (m, 2H), 1.45 (s, 9H). $^{13}$C NMR (126 MHz, CDCl$_3$) δ 155.0, 154.8 (br), 154.4, 143.3, 141.9, 141.2, 140.3, 130.0, 126.9, 124.8, 124.6 (br), 117.3, 80.0, 56.5, 42.8 (br), 32.4, 28.4, 21.3, 10.5. IR (NaCl, thin film, cm$^{-1}$): 2974, 1693, 1417, 1292, 1152. HRMS (ESI-TOF) m/z [M+Na]$^+$ calcd for C$_{26}$H$_{33}$N$_5$NaO$_3^+$ 486.2476, found 486.2474.

Preparative Example 28. Synthesis of

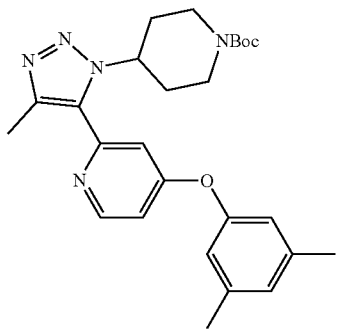

A variation of general procedure III was used. Final purification by column chromatography (0-45% IPA in hexanes) afforded the product (127 mg, 62%) as a white solid. $^1$H NMR (500 MHz, CDCl$_3$) δ 8.54 (d, J=5.8 Hz, 1H), 6.94 (d, J=2.4 Hz, 1H), 6.92 (s, 1H), 6.85 (dd, J=5.8, 2.4 Hz, 1H), 6.75 (s, 2H), 4.99 (tt, J=11.3, 4.0 Hz, 1H), 4.23 (br, 2H), 2.83 (br, 2H), 2.35 (s, 3H), 2.34 (s, 6H), 2.28-2.14 (m, 2H), 2.05 (apparent d, J=10.6 Hz, 2H), 1.47 (s, 9H). $^{13}$C NMR (101 MHz, CDCl$_3$) δ 165.8, 154.6, 153.5, 151.6, 149.4, 141.8, 140.4, 132.1, 127.6, 118.4, 112.7, 111.2, 79.8, 56.9, 43.3, 32.1, 28.4, 21.3, 11.4. IR (NaCl, thin film, cm$^{-1}$): 2972, 2930, 1692, 1572, 1464, 1423, 1365, 1295, 1247, 1213, 1157, 1133. HRMS (ESI-TOF) m/z [M+Na]$^+$ calcd for C$_{26}$H$_{33}$N$_5$NaO$_3$$^+$ 486.2476, found 486.2475.

Preparative Example 29. Synthesis of

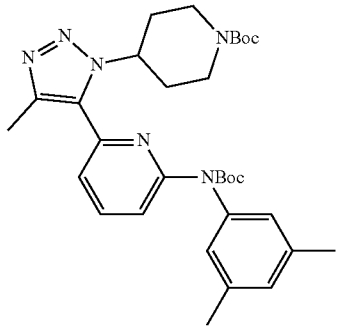

General procedure III was used. This afforded the product (162 mg, 66%) as a white solid. $^1$H NMR (500 MHz, CDCl$_3$) δ 7.82 (apparent t, J=8.4 Hz, 1H), 7.51 (d, J=8.2 Hz, 1H), 7.20 (d, J=7.6 Hz, 1H), 6.87 (s, 1H), 6.78 (s, 2H), 4.69-4.50 (m, 1H), 3.99 (br, 2H), 2.52 (br, 2H), 2.40 (s, 3H), 2.27 (s, 6H), 2.05-1.94 (m, 2H), 1.70 (apparent d, J=11.5 Hz, 2H), 1.45 (s, 9H), 1.44 (s, 9H). $^{13}$C NMR (126 MHz, CDCl$_3$) δ 155.7, 154.7, 153.8, 146.3, 141.9, 141.4, 138.5, 138.4, 131.6, 128.6, 125.8, 120.6, 120.0, 82.0, 79.7, 56.2, 42.8, 31.8, 28.5, 28.3, 21.3, 11.8. IR (NaCl, thin film, cm$^{-1}$): 2976, 2930, 2866, 1694, 1590, 1574, 1472, 1367, 1329, 1276, 1249, 1158, 1109. HRMS (ESI-TOF) m/z [M+Na]$^+$ calcd for C$_{31}$H$_{42}$N$_6$NaO$_4$$^+$ 585.3160, found 585.3162.

Preparative Example 30. Synthesis of

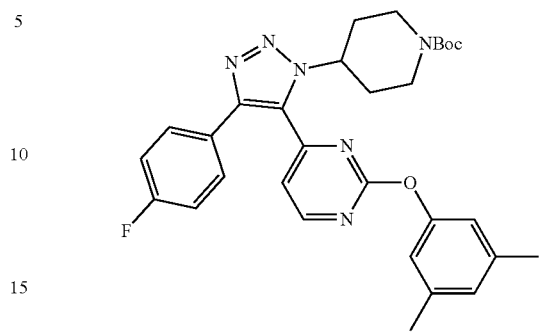

A variation of general procedure II was used. Final purification by recrystallization (DCM in hexanes) afforded the product (140 mg, 73%) as a white solid. $^1$H NMR (500 MHz, CDCl$_3$) δ 8.55 (d, J=5.1 Hz, 1H), 7.51 (dd, J=8.6, 5.5 Hz, 2H), 7.11 (apparent t, J=8.7 Hz, 2H), 6.94 (s, 1H), 6.92 (d, J=5.0 Hz, 1H), 6.85 (s, 2H), 4.82 (tt, J=11.3, 4.0 Hz, 1H), 4.12 (br, 2H), 2.59 (br, 2H), 2.36 (s, 6H), 2.24-2.09 (m, 2H), 1.87 (apparent d, J=12.8 Hz, 2H), 1.49 (s, 9H). $^{13}$C NMR (126 MHz, CDCl$_3$) δ 165.8, 163.1 (d, J$_{C-F}$=249.0 Hz), 161.0, 157.3, 154.6, 152.6, 146.7, 139.7, 130.5 (d, J$_{C-F}$=8.3 Hz), 129.0, 127.7, 126.5, 126.5, 119.3, 116.0 (d, J$_{C-F}$=21.6 Hz), 79.9, 57.7, 42.9 (br), 32.0, 28.4, 21.3. $^{19}$F NMR (376 MHz, CDCl$_3$) δ −112.0. IR (NaCl, thin film, cm$^{-1}$): 2924, 2853, 1691, 1579, 1508, 1375, 1317, 1161. HRMS (ESI-TOF) m/z [M+Na]$^+$ calcd for C$_{30}$H$_{33}$FN$_6$NaO$_3$$^+$ 567.2490, found 567.2492.

Preparative Example 31. Synthesis of

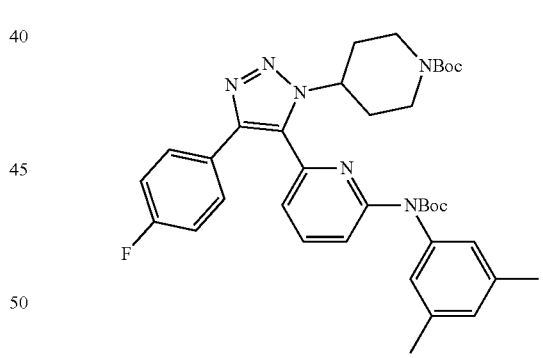

A variation of general procedure III was used. Final purification by column chromatography (0-100% EtOAc in Hexanes) afforded the product (352 mg, 82%) as a white solid. $^1$H NMR (400 MHz, CDCl$_3$) δ 7.66 (apparent t, J=7.9 Hz, 1H), 7.56 (d, J=8.1 Hz, 1H), 7.45 (dd, J=8.6, 5.5 Hz, 2H), 7.04-6.93 (m, 3H), 6.90 (s, 1H), 6.83 (s, 2H), 4.49 (tt, J=10.9, 4.1 Hz, 1H), 4.02 (br, 2H), 2.64-2.41 (m, 2H), 2.29 (s, 6H), 2.13-1.91 (m, 2H), 1.79-1.67 (m, 2H), 1.46 (s, 9H), 1.44 (s, 9H). $^{13}$C NMR (101 MHz, CDCl$_3$) δ 162.7 (d, J$_{C-F}$=247.7 Hz), 155.8, 154.6, 153.6, 146.1, 144.7, 141.2, 138.5, 138.4, 131.2, 129.9 (d, J$_{C-F}$=8.1 Hz), 128.6, 127.1 (d, J$_{C-F}$=3.3 Hz), 125.9, 121.9, 120.5, 115.6 (d, J$_{C-F}$=21.6 Hz), 81.9, 79.7, 56.1, 42.5, 31.8, 28.4, 28.2, 21.2. $^{19}$F NMR (376 MHz, CDCl$_3$) δ −113.4. IR (NaCl, thin film, cm$^{-1}$): 2976, 2930, 1696, 1509, 1456, 1420, 1367, 1328, 1277, 1242, 1157. HRMS (ESI-TOF) m/z [M+Na]$^+$ calcd for $C_{36}H_{43}FN_6NaO_4^+$ 665.3222, found 665.3225.

Preparative Example 32. Synthesis of

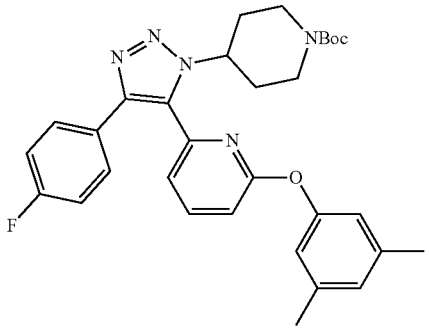 [SMILES: Cc1cc(C)cc(Oc2cccc(-c3c(-c4ccc(F)cc4)nnn3C3CCN(C(=O)OC(C)(C)C)CC3)n2)c1]

A variation of general procedure III was used. Final purification by recrystallization (Toluene/Hexanes, ca. 1:5) afforded the product (214 mg, 83%) as a white solid. $^1$H NMR (500 MHz, CDCl$_3$) δ 7.68 (apparent t, J=7.8 Hz, 1H), 7.55-7.49 (m, 2H), 7.07 (apparent t, J=8.5 Hz, 2H), 6.99 (d, J=8.2 Hz, 1H), 6.96 (d, J=7.4 Hz, 1H), 6.90 (s, 1H), 6.80 (s, 2H), 4.64-4.55 (m, 1H), 4.07 (br, 2H), 2.53 (br, 2H), 2.35 (s, 6H), 2.20-2.03 (m, 2H), 1.80 (apparent d, J=12.4 Hz, 2H), 1.50 (s, 9H). $^{13}$C NMR (126 MHz, CDCl$_3$) δ 164.1, 162.9 (d, $J_{C-F}$=247.8 Hz), 154.8, 153.6, 145.3, 144.8, 140.3, 139.7, 131.4, 130.2 (d, $J_{C-F}$=8.1 Hz), 127.3 (d, $J_{C-F}$=3.2 Hz), 127.1, 120.0, 119.5, 115.8 (d, $J_{C-F}$=21.5 Hz), 111.9, 80.0, 57.0, 43.1 (br), 32.0, 28.6, 21.5. $^{19}$F NMR (376 MHz, CDCl$_3$) δ −113.4. IR (NaCl, thin film, cm$^{-1}$): 2940, 1708, 1691, 1572, 1504, 1451, 1403, 1365, 1335, 1153. HRMS (ESI-TOF) m/z [M+Na]$^+$ calcd for $C_{31}H_{34}FN_5NaO_3^+$ 566.2538, found 566.2527.

Preparative Example 33. Synthesis of

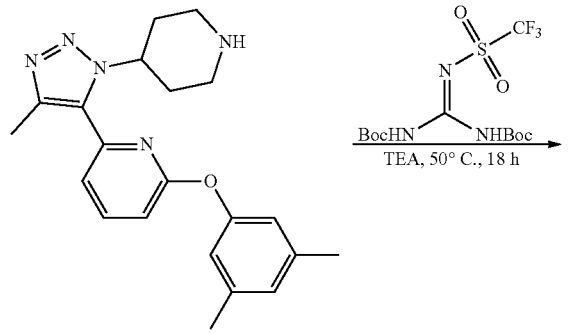

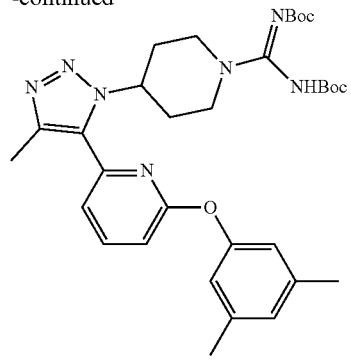

General procedure VI (Guanidine Formation) To a solution of compound 14i (48.2 mg, 0.133 mmol) and N,N'-di-Boc-N"-triflylguanidine (82.6 mg, 0.211 mmol) in Dioxane/H$_2$O (2.5 mL, 4:1), was added TEA (0.07 mL, 0.5 mmol). The reaction was heated to 50° C. After 18 h, the reaction was cooled to rt and the solvent was evaporated under reduced pressure. Final purification by column chromatography (0-60% EtOAc in hexanes with 1% TEA) afforded the product 15i (37.5 mg, 47%) as a white solid. $^1$H NMR (500 MHz, CDCl$_3$) δ 10.21 (br, 1H), 7.84 (apparent t, J=7.8 Hz, 1H), 7.16 (d, J=7.4 Hz, 1H), 6.98 (d, J=8.3 Hz, 1H), 6.87 (s, 1H), 6.76 (s, 2H), 4.97-4.76 (m, 1H), 4.06 (br, 2H), 2.75 (apparent t, J=12.0 Hz, 2H), 2.48 (s, 3H), 2.33 (s, 6H), 2.26-2.13 (m, 2H), 1.86-1.75 (m, 2H), 1.51 (s, 18H). $^{13}$C NMR (126 MHz, CDCl$_3$) δ163.7, 154.9, 153.6, 145.3, 141.9, 140.2, 139.6, 131.4, 126.9, 119.3, 118.3, 111.1, 56.1, 45.7, 31.6, 28.2, 21.3, 12.1. Note: The Boc group carbons (expected ~160 and ~80 ppm) were generally not observed in the $^{13}$C NMR. IR (NaCl, thin film, cm$^{-1}$): 2976, 2923, 1748, 1607, 1572, 1453, 1427, 1367, 1299, 1247, 1146, 1123, 1097. HRMS (ESI-TOF) m/z [M+Na]$^+$ calcd for $C_{32}H_{43}N_7NaO_5^+$ 628.3218, found 628.3199.

Preparative Example 34. Synthesis of

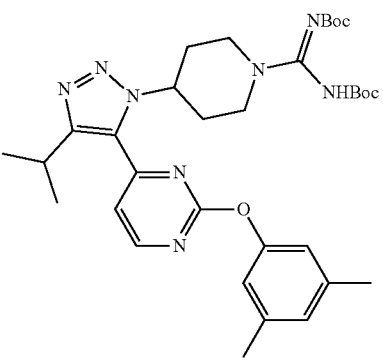

General procedure VI was used. This afforded the product (11.1 mg, 39%) as a white solid. $^1$H NMR (500 MHz, CDCl$_3$) δ 10.23 (br, 1H), 8.74 (d, J=5.0 Hz, 1H), 7.16 (d, J=5.0 Hz, 1H), 6.94 (s, 1H), 6.83 (s, 2H), 4.99-4.80 (m, 1H), 4.14 (br, 2H), 3.15 (hept, J=6.9 Hz, 1H), 2.98-2.86 (m, 2H), 2.36 (s, 6H), 2.34-2.24 (m, 2H), 1.93 (apparent d, J=12.1 Hz, 2H), 1.52 (s, 18H), 1.41 (d, J=6.9 Hz, 6H). $^{13}$C NMR (126 MHz, CDCl$_3$) δ 165.7, 161.1, 157.4, 155.0, 153.2, 152.6, 139.7, 128.1, 127.7, 119.3, 114.9, 56.5, 45.5, 31.7, 28.1, 25.5, 22.6, 21.3. IR (NaCl, thin film, cm$^{-1}$): 2975, 2931, 1748, 1608, 1578, 1555, 1479, 1377, 1298, 1251, 1232, 1145, 1125, 1098, 1000. HRMS (ESI-TOF) m/z [M+Na]$^+$ calcd for C$_{33}$H$_{46}$N$_8$NaO$_5^+$ 657.3483, found 657.3484.

Preparative Example 35. Synthesis of

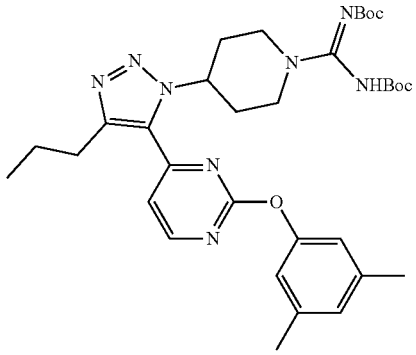

General procedure VI was used. This afforded the product (37.2 mg, 52%) as a white solid. $^1$H NMR (500 MHz, CDCl$_3$) δ 8.74 (d, J=5.0 Hz, 1H), 7.18 (d, J=5.0 Hz, 1H), 6.93 (s, 1H), 6.82 (s, 2H), 5.09-4.85 (m, 1H), 4.12 (br, 2H), 2.86 (apparent t, J=12.5 Hz, 2H), 2.81 (t, J=7.8 Hz, 2H), 2.35 (s, 6H), 2.26 (apparent q, J=11.1 Hz, 2H), 1.90 (apparent d, J=11.4 Hz, 2H), 1.85-1.76 (m, 2H), 1.51 (s, 18H), 1.02 (t, J=7.3 Hz, 3H). $^{13}$C NMR (126 MHz, CDCl$_3$) δ 165.6, 161.1, 157.2, 155.0, 152.6, 148.2, 139.8, 129.1, 127.7, 119.3, 114.6, 56.8, 45.7, 31.7, 28.2, 28.1, 22.4, 21.3, 14.1. IR (NaCl, thin film, cm$^{-1}$): 2976, 1747, 1607, 1579, 1482, 1452, 1389, 1299, 1252, 1145, 1125, 1098, 1000. HRMS (ESI-TOF) m/z [M+Na]$^+$ calcd for C$_{33}$H$_{46}$N$_8$NaO$_5^+$ 657.3483, found 657.3472.

Preparative Example 36. Synthesis of

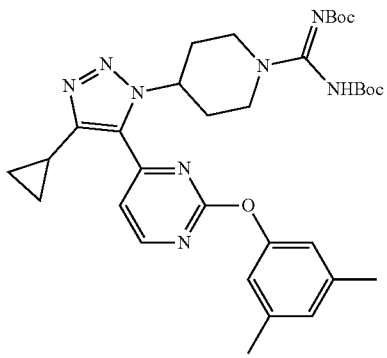

General procedure VI was used. This afforded the product (17.2 mg, 48%) as a white solid. $^1$H NMR (500 MHz, CDCl$_3$) δ 10.22 (br, 1H), 8.75 (d, J=5.1 Hz, 1H), 7.53 (d, J=5.0 Hz, 1H), 6.94 (s, 1H), 6.84 (s, 2H), 5.15-4.96 (m, 1H), 4.11 (br, 2H), 2.84 (apparent t, J=11.9 Hz, 2H), 2.36 (s, 6H), 2.30-2.18 (m, 2H), 1.99-1.86 (m, 3H), 1.52 (s, 18H), 1.18 (d, J=4.8 Hz, 2H), 1.07 (d, J=6.9 Hz, 2H). $^{13}$C NMR (126 MHz, CDCl$_3$) δ 165.6, 161.0, 157.1, 155.0, 152.7, 149.4, 139.8, 129.6, 127.6, 119.3, 114.7, 56.8, 45.6, 31.6, 28.2, 21.3, 7.9, 7.5. IR (NaCl, thin film, cm$^{-1}$): 2976, 2930, 1748, 1607, 1578, 1556, 1483, 1453, 1389, 1366, 1298, 1251, 1145, 1125, 1099. HRMS (ESI-TOF) m/z [M+Na]$^+$ calcd for C$_{33}$H$_{44}$N$_8$NaO$_5^+$ 655.3327, found 655.3329.

Preparative Example 37. Synthesis of

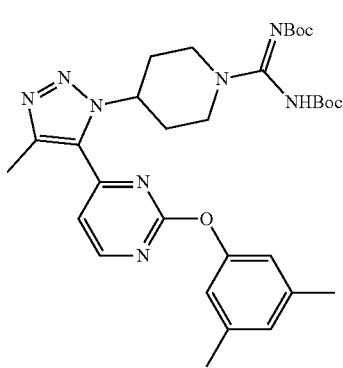

General procedure VI was used. This afforded the product (36 mg, 51%) as a white solid. $^1$H NMR (500 MHz, CDCl$_3$) δ 8.73 (d, J=5.1 Hz, 1H), 7.18 (d, J=5.1 Hz, 1H), 6.92 (s, 1H), 6.80 (s, 2H), 5.04 (tt, J=10.7, 4.1 Hz, 1H), 2.86-2.75 (m, 2H), 2.53 (s, 3H), 2.34 (s, 6H), 2.28-2.18 (m, 2H), 1.91-1.83 (m, 2H), 1.50 (s, 18H). HRMS (ESI-TOF) m/z [M+H]$^+$ calcd for C$_{31}$H$_{43}$N$_8$O$_5^+$ 607.7280, found 607.4007.

Preparative Example 38. Synthesis of

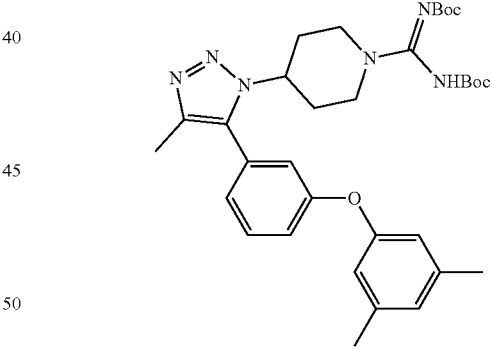

General procedure VI was used. This afforded the product (91.6 mg, 65%) as a white solid. $^1$H NMR (500 MHz, CDCl$_3$) δ 10.05 (br, 1H), 7.46 (apparent t, J=7.9 Hz, 1H), 7.11 (d, J=8.3 Hz, 1H), 6.96 (d, J=7.5 Hz, 1H), 6.84 (s, 1H), 6.82 (s, 1H), 6.70 (s, 2H), 4.39-4.31 (m, 1H), 4.25 (br, 2H), 3.06 (apparent t, J=12.3 Hz, 2H), 2.45-2.35 (m, 2H), 2.32 (s, 6H), 2.28 (s, 3H), 1.97 (apparent d, J=11.7 Hz, 2H), 1.50 (s, 18H). $^{13}$C NMR (126 MHz, CDCl$_3$) δ 158.7, 155.9, 155.1, 141.1, 140.0, 133.3, 130.6, 129.0, 126.1, 123.4, 118.8, 118.8, 117.4, 55.5, 45.7, 32.0, 28.1, 21.3, 10.5. IR (NaCl, thin film, cm$^{-1}$): 2978, 2930, 1748, 1633, 1608, 1580, 1485, 1423, 1366, 1297, 1251, 1147, 1118. HRMS (ESI-TOF) m/z [M+Na]$^+$ calcd for C$_{33}$H$_{44}$N$_6$NaO$_5^+$ 627.3265, found 627.3265.

Preparative Example 39. Synthesis of

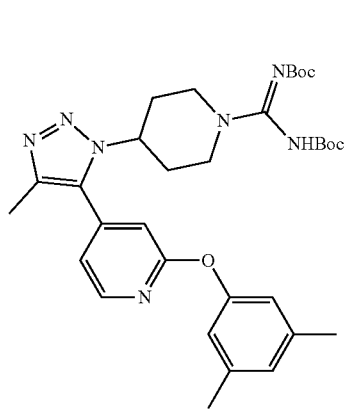

General procedure VI was used. This afforded the product (44.7 mg, 52%) as a white solid. $^1$H NMR (500 MHz, CDCl$_3$) δ 10.17 (br, 1H), 8.35 (d, J=5.1 Hz, 1H), 6.90 (s, 1H), 6.88 (d, J=5.0 Hz, 1H), 6.81 (s, 2H), 6.78 (s, 1H), 4.42-4.34 (m, 1H), 4.28 (br, 2H), 3.10 (apparent t, 2H), 2.44 (apparent q, J=12.3 Hz, 2H), 2.35 (s, 6H), 2.33 (s, 3H), 2.01 (apparent d, J=12.0 Hz, 2H), 1.50 (s, 18H). $^{13}$C NMR (126 MHz, CDCl$_3$) δ 164.8, 155.2, 153.3, 149.0, 141.8, 139.8, 139.2, 131.2, 127.3, 119.0, 118.1, 111.3, 55.9, 45.7, 32.0, 28.1, 21.4, 10.6. IR (NaCl, thin film, cm$^{-1}$): 2978, 2930, 1747, 1607, 1483, 1453, 1396, 1366, 1298, 1250, 1147, 1119. HRMS (ESI-TOF) m/z [M+Na]$^+$ calcd for C$_{32}$H$_{43}$N$_7$NaO$_5$$^+$ 628.3218, found 628.3230.

Preparative Example 40. Synthesis of

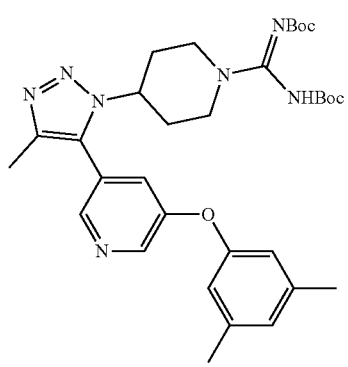

General procedure VI was used. This afforded the product (113 mg, 55%) as a white solid. $^1$H NMR (500 MHz, CDCl$_3$) δ 10.23 (br, 1H), 8.48 (s, 1H), 8.24 (s, 1H), 7.13 (s, 1H), 6.87 (s, 1H), 6.71 (s, 2H), 4.34-4.13 (m, 3H), 3.04 (apparent t, J=12.2 Hz, 2H), 2.49-2.35 (m, 2H), 2.32 (s, 6H), 2.28 (s, 3H), 1.96 (apparent d, J=11.3 Hz, 2H), 1.49 (s, 18H). $^{13}$C NMR (126 MHz, CDCl$_3$) δ 155.1, 155.0, 154.8, 143.3, 142.0, 141.2, 140.4, 130.1, 126.9, 124.8, 124.6, 117.3, 55.9, 45.7, 32.0, 28.1, 21.3, 10.5. IR (NaCl, thin film, cm$^{-1}$): 2976, 2930, 1748, 1607, 1572, 1479, 1417, 1366, 1296, 1252, 1146, 1118. HRMS (ESI-TOF) m/z [M+Na]$^+$ calcd for C$_{32}$H$_{43}$N$_7$NaO$_5$$^+$ 628.3218, found 628.3230.

Preparative Example 41. Synthesis of

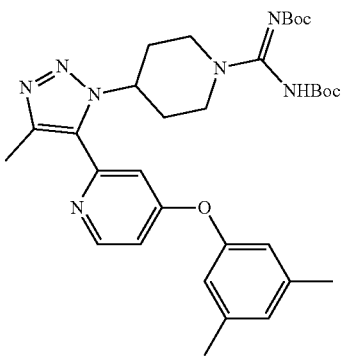

General procedure VI was used. This afforded the product (60.4 mg, 50%) as a white solid. $^1$H NMR (500 MHz, CDCl$_3$) δ 10.20 (br, 1H), 8.53 (d, J=5.7 Hz, 1H), 6.94 (d, J=2.4 Hz, 1H), 6.92 (s, 1H), 6.84 (dd, J=5.9, 2.3 Hz, 1H), 6.75 (s, 2H), 5.12 (tt, J=11.0, 4.1 Hz, 1H), 4.27 (br, 2H), 3.11 (apparent t, J=12.2 Hz, 2H), 2.43-2.36 (m, 2H), 2.35 (s, 3H), 2.34 (s, 6H), 2.12 (apparent d, J=11.3 Hz, 2H), 1.48 (s, 18H). $^{13}$C NMR (126 MHz, CDCl$_3$) δ 165.9, 155.2, 153.6, 151.7, 149.5, 142.0, 140.5, 132.1, 127.7, 118.5, 112.8, 111.3, 56.5, 46.2, 32.0, 28.3, 21.4, 11.6. IR (NaCl, thin film, cm$^{-1}$): 2977, 2929, 1748, 1605, 1464, 1415, 1366, 1298, 1251, 1230, 1214, 1147, 1122. HRMS (ESI-TOF) m/z [M+Na]$^+$ calcd for C$_{32}$H$_{43}$N$_7$NaO$_5$$^+$ 628.3218, found 628.3235.

Preparative Example 42. Synthesis of

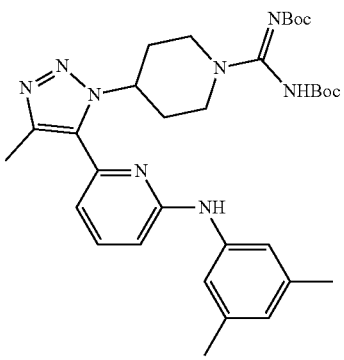

General procedure VI was used. Final purification by column chromatography (0-60% IPA in hexanes) afforded the product (49.7 mg, 53%) as a white solid. $^1$H NMR (500 MHz, CDCl$_3$) δ 10.22 (br, 1H), 7.61 (apparent t, J=7.8 Hz, 1H), 6.97 (s, 1H), 6.87-6.80 (m, 2H), 6.75 (s, 2H), 6.55 (br, 1H), 5.22-5.02 (m, 1H), 4.20 (br, 2H), 2.97 (apparent t, J=12.1 Hz, 2H), 2.45 (s, 3H), 2.44-2.36 (m, 2H), 2.31 (s, 6H), 2.10 (apparent d, J=12.1 Hz, 2H), 1.49 (s, 18H). $^{13}$C NMR (126 MHz, CDCl$_3$) δ 156.3, 155.1, 145.9, 141.7, 139.4, 139.0, 138.5, 132.3, 125.5, 119.0, 115.4, 108.3, 56.1, 46.0, 31.7, 28.2, 21.4, 11.6. IR (NaCl, thin film, cm$^{-1}$): 2978, 2933, 1748, 1595, 1466, 1453, 1367, 1299, 1246, 1152, 1124, 1101. HRMS (ESI-TOF) m/z [M+Na]$^+$ calcd for C$_{32}$H$_{44}$N$_8$NaO$_4$$^+$ 627.3378, found 627.3375.

Example 1. Synthesis of Compound 1

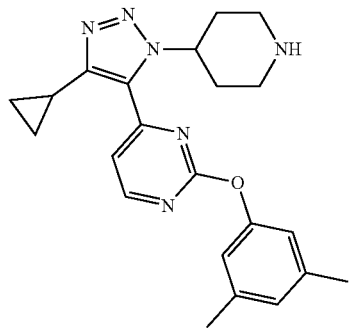 [SMILES: Cc1cc(C)cc(Oc2nccc(-c3c(C4CC4)nnn3C3CCNCC3)n2)c1]

General Procedure IV (Boc Deprotection)—

To a solution of the Boc protected amine (66.3 mg, 0.135) in DCM (1 mL) was added TFA (1 mL). After 2 h, the reaction was concentrated under reduced pressure. The crude material was dissolved in EtOAc and washed with NaOH (2 M). The combined organic phases were washed with brine, dried ($Na_2SO_4$), filtered, and concentrated under reduced pressure. This afforded the title compound (46.9 mg, 89%) as a white solid. $^1$H NMR (500 MHz, $CDCl_3$) δ 8.74 (d, J=5.1 Hz, 1H), 7.48 (d, J=5.1 Hz, 1H), 6.92 (s, 1H), 6.84 (s, 2H), 4.96-4.80 (m, 1H), 3.10 (d, J=12.7 Hz, 2H), 2.40 (t, J=12.6 Hz, 2H), 2.35 (s, 6H), 2.13-2.00 (m, 2H), 1.92 (tt, J=8.9, 5.2 Hz, 1H), 1.84 (d, J=12.8 Hz, 2H), 1.19-1.13 (m, 2H), 1.08-1.00 (m, 2H). $^{13}$C NMR (126 MHz, $CDCl_3$) δ 165.5, 160.9, 157.3, 152.7, 149.2, 139.6, 129.6, 127.4, 119.3, 114.9, 57.8, 45.4, 33.5, 21.3, 7.9, 7.3. IR (NaCl, thin film, $cm^{-1}$): 2949, 1577, 1558, 1388, 1315, 1293, 1140. HRMS (ESI-TOF) m/z [M+Na]$^+$ calcd for $C_{22}H_{26}N_6NaO^+$ 413.2060, found 413.2060.

Example 2. Synthesis of Compound 2

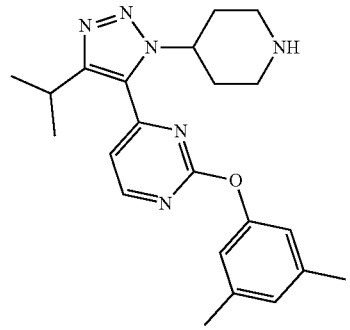 [SMILES: Cc1cc(C)cc(Oc2nccc(-c3c(C(C)C)nnn3C3CCNCC3)n2)c1]

A variation of general procedure IV was used. Final purification by preparatory TLC (20% TEA in IPA) afforded the amine (28.6 mg, 37%) as a white solid. $^1$H NMR (500 MHz, $CDCl_3$) δ 8.75 (d, J=5.0 Hz, 1H), 7.16 (d, J=5.0 Hz, 1H), 6.96 (s, 1H), 6.83 (s, 2H), 4.85 (tt, J=9.3, 4.1 Hz, 1H), 3.35 (d, J=11.7 Hz, 2H), 3.15 (p, J=6.9 Hz, 1H), 2.70 (t, J=11.6 Hz, 2H), 2.38 (s, 6H), 2.31-2.21 (m, 2H), 2.08-2.00 (m, 2H), 1.41 (d, J=6.9 Hz, 6H). $^{13}$C NMR (126 MHz, $CDCl_3$) δ 165.7, 161.2, 157.3, 153.2, 152.6, 139.8, 128.2, 127.6, 119.3, 114.9, 55.6, 43.8, 31.3, 25.5, 22.6, 21.4. IR (NaCl, thin film, $cm^{-1}$): 2965, 1577, 1541, 1386, 1317, 1293, 1140. HRMS (ESI-TOF) m/z [M+Na]$^+$ calcd for $C_{22}H_{28}N_6NaO^+$ 415.2217, found 415.2222.

Example 3. Synthesis of Compound 3

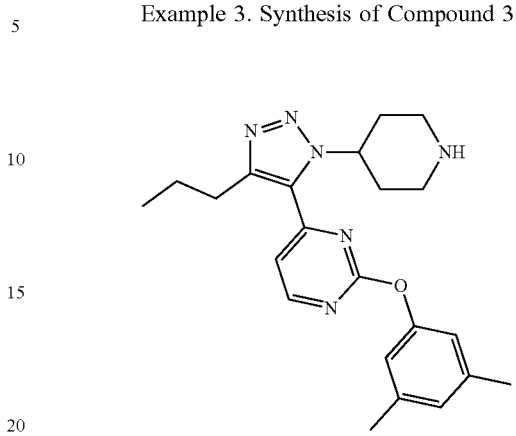

General procedure IV was used and the amine (49.6 mg, 75%) was isolated as a white solid. $^1$H NMR (500 MHz, $CDCl_3$) δ 8.73 (d, J=5.1 Hz, 1H), 7.15 (d, J=5.0 Hz, 1H), 6.91 (s, 1H), 6.82 (s, 2H), 4.77 (tt, J=11.3, 4.2 Hz, 1H), 3.11 (d, J=12.8 Hz, 2H), 2.78 (t, J=7.8 Hz, 2H), 2.44 (t, J=12.6 Hz, 2H), 2.34 (s, 6H), 2.19-2.01 (m, 3H), 1.90-1.84 (m, 2H), 1.83-1.75 (m, 2H), 1.00 (t, J=7.4 Hz, 3H). $^{13}$C NMR (126 MHz, $CDCl_3$) δ 165.6, 161.0, 157.5, 152.7, 148.0, 139.6, 129.1, 127.5, 119.3, 114.8, 57.7, 45.4, 33.6, 28.0, 22.5, 21.3, 14.1. IR (NaCl, thin film, $cm^{-1}$): 2959, 2865, 1577, 1556, 1384, 1318, 1293, 1140. HRMS (ESI-TOF) m/z [M+Na]$^+$ calcd for $C_{22}H_{28}N_6NaO^+$ 415.2217, found 415.2219.

Example 4. Synthesis of Compound 4

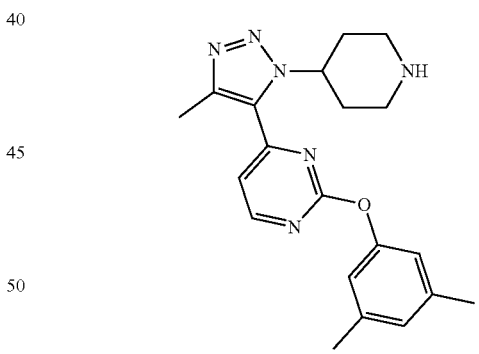

General procedure IV was used and the amine (133 mg) was isolated as a white solid in quantitative yield. $^1$H NMR (400 MHz, $CDCl_3$) δ 8.71 (d, J=5.0 Hz, 1H), 7.16 (d, J=5.1 Hz, 1H), 6.89 (s, 1H), 6.80 (s, 2H), 4.82 (tt, J=11.3, 4.1 Hz, 1H), 3.08 (apparent d, J=12.7 Hz, 2H), 2.49 (s, 3H), 2.45-2.34 (m, 2H), 2.32 (s, 6H), 2.04 (apparent qd, J=12.1, 3.9 Hz, 2H), 1.82 (apparent d, J=11.2 Hz, 2H). $^{13}$C NMR (101 MHz, $CDCl_3$) δ 165.5, 161.0, 157.2, 152.7, 143.9, 139.6, 129.3, 127.4, 119.2, 114.6, 57.8, 45.3, 33.5, 21.3, 12.3. IR (NaCl, thin film, $cm^{-1}$): 2948, 2860, 1617, 1578, 1557, 1451, 1372, 1318, 1294, 1142. HRMS (ESI-TOF) m/z [M+Na]$^+$ calcd for $C_{20}H_{24}N_6NaO^+$ 387.1904, found 387.1903.

Example 5. Synthesis of Compound 5

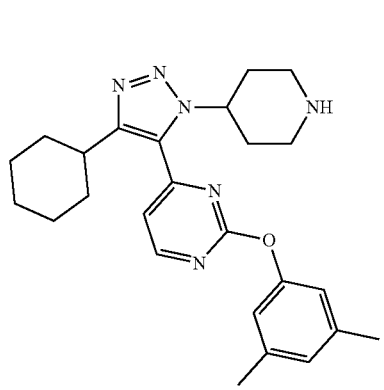 [SMILES: Cc1cc(C)cc(Oc2nccc(-c3c(C4CCCCC4)nnn3C3CCNCC3)n2)c1]

General procedure IV was used and the amine (37.1 mg 96%) was isolated as a white solid. $^1$H NMR (500 MHz, CDCl$_3$) δ 8.72 (d, J=5.0 Hz, 1H), 7.09 (d, J=5.0 Hz, 1H), 6.90 (s, 1H), 6.82 (s, 2H), 4.75-4.63 (m, 1H), 3.11 (d, J=12.8 Hz, 2H), 2.76-2.63 (m, 1H), 2.45 (t, J=12.4 Hz, 2H), 2.33 (s, 6H), 2.19 (br, 1H), 2.09 (qd, J=12.2, 3.9 Hz, 2H), 1.91-1.79 (m, 8H), 1.74 (m, 1H), 1.39-1.29 (m, 2H). $^{13}$C NMR (126 MHz, CDCl$_3$) δ 165.6, 161.0, 157.7, 152.6, 152.3, 139.6, 128.3, 127.5, 119.3, 115.1, 57.4, 45.4, 35.3, 33.6, 32.8, 26.5, 25.8, 21.4. IR (NaCl, thin film, cm$^{-1}$): 2928, 2852, 1578, 1555, 1448, 1386, 1293, 1142. HRMS (ESI-TOF) m/z [M+Na]$^+$ calcd for C$_{25}$H$_{32}$N$_6$NaO$^+$ 455.2530, found 455.2518.

Example 6. Synthesis of Compound 6

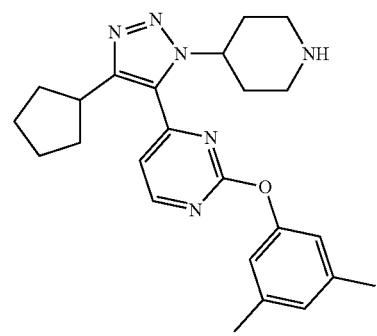 [SMILES: Cc1cc(C)cc(Oc2nccc(-c3c(C4CCCC4)nnn3C3CCNCC3)n2)c1]

General procedure IV was used and the amine (33.6 mg, 38%) was isolated as a white solid. $^1$H NMR (500 MHz, CDCl$_3$) δ 8.72 (d, J=5.0 Hz, 1H), 7.16 (d, J=5.0 Hz, 1H), 6.91 (s, 1H), 6.82 (s, 2H), 4.93 (br, 2H), 4.75 (t, J=10.7 Hz, 1H), 3.28-3.09 (m, 3H), 2.51 (apparent t, J=11.1 Hz, 2H), 2.34 (s, 6H), 2.16 (apparent q, J=10.7 Hz, 2H), 2.07-1.84 (m, 8H). $^{13}$C NMR (126 MHz, CDCl$_3$) δ 165.8, 161.1, 157.6, 152.8, 151.9, 139.8, 129.0, 127.7, 119.4, 115.3, 56.7, 44.5, 36.3, 33.6, 32.4, 25.9, 21.5. IR (NaCl, thin film, cm$^{-1}$): 2953, 2868, 1577, 1558, 1386, 1319, 1293, 1141. HRMS (ESI-TOF) m/z [M+Na]$^+$ calcd for C$_{24}$H$_{30}$N$_6$NaO$^+$ 441.2373, found 441.2369.

Example 7. Synthesis of Compound 7

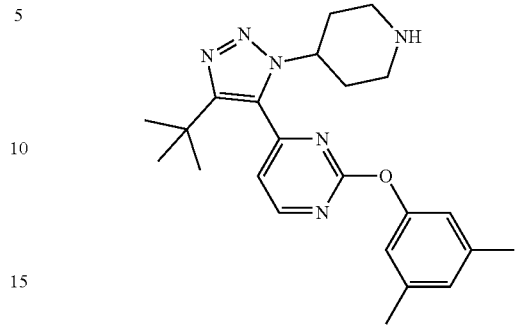

General procedure IV was used and the amine (26.2 mg) was isolated as a white solid in quantitative yield. $^1$H NMR (500 MHz, CDCl$_3$) δ 8.71 (d, J=4.9 Hz, 1H), 7.14 (d, J=4.8 Hz, 1H), 6.91 (s, 1H), 6.82 (s, 2H), 4.05 (tt, J=10.9, 4.1 Hz, 1H), 3.34-3.20 (m, 2H), 2.96 (br, 1H), 2.72-2.58 (m, 2H), 2.34 (s, 6H), 2.20 (apparent qd, J=11.4, 3.7 Hz, 2H), 1.96 (apparent d, J=13.0 Hz, 2H), 1.30 (s, 9H). $^{13}$C NMR (126 MHz, CDCl$_3$) δ 165.6, 160.6, 160.3, 153.9, 152.5, 139.6, 129.2, 127.6, 119.1, 118.1, 56.5, 45.1, 33.0, 32.1, 30.7, 21.3. IR (NaCl, thin film, cm$^{-1}$): 2957, 2865, 1584, 1560, 1387, 1372, 1318, 1293, 1275, 1201, 1140. HRMS (ESI-TOF) m/z [M+Na]$^+$ calcd for C$_{23}$H$_{30}$N$_6$NaO$^+$ 429.2373, found 429.2378.

Example 8. Synthesis of Compound 8

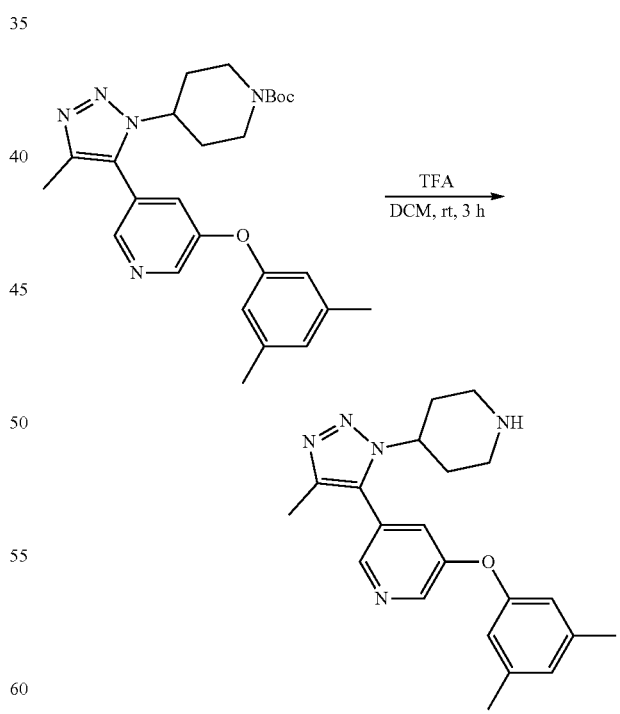

General Procedure V—

To a solution of the Boc protected amine (218 mg, 0.515) in DCM (1 mL) was added TFA (1 mL). After 3 h, the reaction was concentrated under reduced pressure. This afforded the title compound (204 mg, 91%) as a white solid.

¹H NMR (500 MHz, MeOD) δ 8.74-8.44 (m, 2H), 7.91 (d, J=1.8 Hz, 1H), 6.97 (s, 1H), 6.85 (s, 2H), 4.71 (tt, J=10.5, 4.1 Hz, 1H), 3.59 (apparent d, J=13.3 Hz, 2H), 3.25-3.15 (m, 2H), 2.57-2.45 (m, 2H), 2.33 (s, 6H), 2.35-2.28 (m, 2H), 2.29 (s, 3H). ¹³C NMR (126 MHz, MeOD) δ 157.1, 154.2, 142.4, 140.8, 138.6, 135.4, 130.8, 129.4, 127.4, 126.4, 117.2, 53.1, 42.4, 28.7, 19.8, 8.6. IR (NaCl, thin film, cm⁻¹): 3000, 1678, 1421, 1293, 1201, 1135. HRMS (ESI-TOF) m/z [M+Na]⁺ calcd for $C_{20}H_{25}N_5NaO^+$ 386.1951, found 386.1951.

Example 9. Synthesis of Compound 9

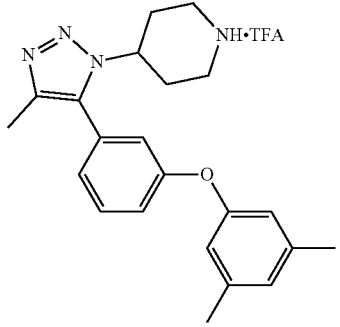

General procedure V was used. This afforded the title compound (144 mg) as a white solid in quantitative yield. ¹H NMR (500 MHz, MeOD) δ 7.54 (apparent t, J=8.0 Hz, 1H), 7.16-7.08 (m, 2H), 6.98 (s, 1H), 6.84 (s, 1H), 6.69 (s, 2H), 4.69 (tt, J=10.0, 4.1 Hz, 1H), 3.58 (apparent d, J=13.3 Hz, 2H), 3.24-3.11 (m, 2H), 2.54-2.42 (m, 2H), 2.28 (s, 9H), 2.27-2.24 (m, 2H). ¹³C NMR (126 MHz, MeOD) δ 158.8, 156.1, 140.5, 139.9, 134.6, 130.7, 127.5, 125.6, 123.5, 119.0, 118.7, 117.0, 52.9, 42.3, 28.7, 19.9, 8.6. IR (NaCl, thin film, cm⁻¹): 2991, 2747, 1678, 1614, 1580, 1462, 1425, 1294, 1203, 1135. HRMS (ESI-TOF) m/z [M+H]⁺ calcd for $C_{22}H_{27}N_4O^+$ 363.2179, found 363.2175.

Example 10. Synthesis of Compound 10

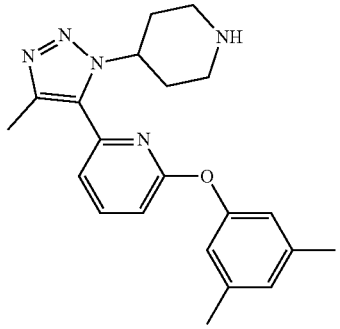

General procedure V was used. This afforded the title compound (97.4 mg, 95%) as a white solid. ¹H NMR (500 MHz, MeOD) δ 8.00 (apparent t, J=7.9 Hz, 1H), 7.37 (d, J=7.4 Hz, 1H), 7.10 (d, J=8.3 Hz, 1H), 6.92 (s, 1H), 6.80 (s, 2H), 4.90 (tt, J=10.7, 4.1 Hz, 1H), 3.41-3.29 (m, 2H), 2.70 (apparent td, J=12.8, 2.6 Hz, 2H), 2.45 (s, 3H), 2.32 (s, 6H), 2.30-2.22 (m, 2H), 2.02 (apparent dd, J=14.3, 4.0 Hz, 2H). ¹³C NMR (126 MHz, MeOD) δ 163.7, 153.9, 144.0, 141.4, 140.9, 139.6, 132.2, 126.3, 119.0, 118.9, 111.8, 53.7, 42.6, 28.5, 19.9, 10.1. IR (NaCl, thin film, cm⁻¹): 2992, 1776, 1677, 1574, 1454, 1433, 1201, 1139. HRMS (ESI-TOF) m/z [M+H]⁺ calcd for $C_{21}H_{26}N_5O^+$ 364.2132, found 364.2133.

Example 11. Synthesis of Compound 11

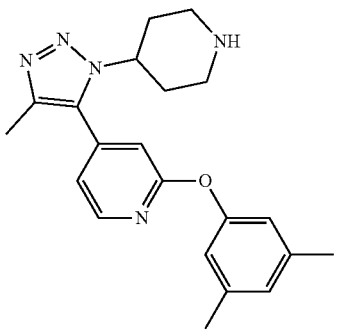

General procedure V was used. This afforded the title compound (190 mg, 98%) as a white solid. ¹H NMR (500 MHz, MeOD) δ 8.33 (d, J=5.3 Hz, 1H), 7.20 (d, J=5.3 Hz, 1H), 6.94 (s, 1H), 6.91 (s, 1H), 6.78 (s, 2H), 4.74 (tt, J=10.0, 4.1 Hz, 1H), 3.60 (apparent d, J=13.3 Hz, 2H), 3.29-3.16 (m, 2H), 2.51 (apparent q, J=14.5 Hz, 2H), 2.35-2.26 (m, 2H), 2.30 (s, 9H). ¹³C NMR (126 MHz, MeOD) δ 164.3, 153.4, 147.8, 141.5, 140.0, 139.2, 131.9, 126.8, 118.7, 118.3, 111.6, 53.2, 42.3, 28.7, 19.9, 8.7. IR (NaCl, thin film, cm⁻¹): 2991, 2845, 1678, 1615, 1592, 1398, 1295, 1202, 1180, 1139. HRMS (ESI-TOF) m/z [M+Na]⁺ calcd for $C_{21}H_{25}N_5NaO^+$ 386.1951, found 386.1963.

Example 12. Synthesis of Compound 12

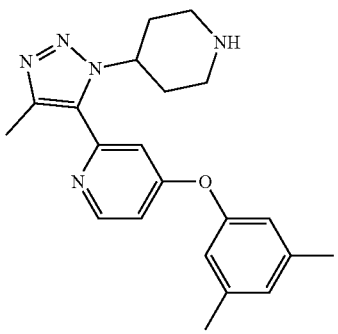

General procedure V was used. This afforded the title compound (114 mg, 90%) as a white solid. ¹H NMR (500 MHz, MeOD) δ 8.72 (d, J=6.3 Hz, 1H), 7.38 (d, J=2.6 Hz, 1H), 7.19 (dd, J=6.4, 2.5 Hz, 1H), 7.04 (s, 1H), 6.87 (s, 2H), 5.03 (tt, J=10.4, 4.2 Hz, 1H), 3.60 (apparent d, J=13.3 Hz, 2H), 3.22 (apparent td, J=12.5, 3.4 Hz, 2H), 2.56-2.45 (m, 2H), 2.40 (apparent dd, J=14.4, 3.9 Hz, 2H), 2.36 (s, 6H), 2.35 (s, 3H). ¹³C NMR (126 MHz, MeOD) δ168.9, 153.0, 149.0, 145.0, 142.7, 140.8, 129.8, 128.0, 117.9, 114.9, 112.4, 53.8, 42.5, 28.7, 19.9, 9.1. IR (NaCl, thin film, cm⁻¹): 3018, 1776, 1674, 1620, 1588, 1468, 1319, 1290, 1200, 1140, 1000. HRMS (ESI-TOF) m/z [M+H]+ calcd for C21H26N5O+ 386.1951, found 386.1947.

Example 13. Synthesis of Compound 13

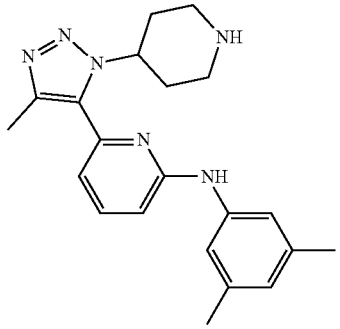

General procedure V was used. This afforded the title compound (55.8 mg, 53%) as a white solid. 1H NMR (400 MHz, CDCl3) δ 7.61 (dd, J=8.5, 7.3 Hz, 1H), 7.02 (s, 1H), 6.85 (d, J=8.4 Hz, 1H), 6.83 (d, J=7.2 Hz, 1H), 6.81 (s, 1H), 6.73 (s, 2H), 4.94 (tt, J=11.4, 4.1 Hz, 1H), 3.21-3.10 (m, 2H), 2.54 (apparent t, J=11.8 Hz, 2H), 2.45 (s, 3H), 2.30 (s, 6H), 2.19 (apparent qd, J=12.0, 3.7 Hz, 2H), 2.09-2.02 (m, 2H). 13C NMR (101 MHz, CDCl3) δ 156.3, 146.0, 141.5, 139.7, 138.8, 138.2, 132.5, 125.1, 118.7, 115.3, 108.5, 56.9, 45.7, 33.7, 21.4, 11.5. IR (NaCl, thin film, cm−1): 3307, 2930, 1588, 1537, 1453, 1331. HRMS (ESI-TOF) m/z [M+H]+ calcd for C21H27N6O6+ 363.2292, found 363.2289.

Example 14. Synthesis of Compound 14

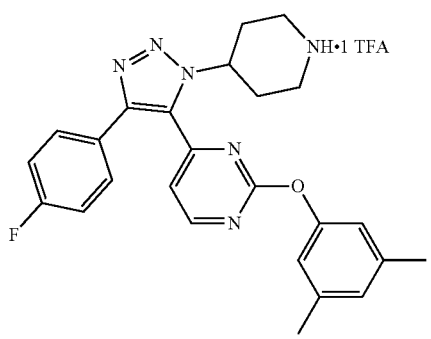

General procedure IV was used and the amine (20.2 mg, 24%) was isolated as a white solid. 1H NMR (500 MHz, MeOD) δ 8.65 (d, J=5.1 Hz, 1H), 7.55 (dd, J=8.7, 5.3 Hz, 2H), 7.23 (t, J=8.7 Hz, 2H), 7.09 (d, J=5.1 Hz, 1H), 7.00 (s, 1H), 6.94 (s, 2H), 5.00-4.93 (m, 1H), 3.44 (apparent dt, J=13.3, 4.2 Hz, 2H), 2.82 (apparent td, J=12.7, 3.2 Hz, 2H), 2.44-2.30 (m, 8H), 2.16 (apparent dd, J=14.6, 3.9 Hz, 2H). 13C NMR (126 MHz, MeOD) δ 165.4, 163.4 (d, J$_{C-F}$=248.0 Hz), 161.2, 156.5, 152.9, 146.2, 139.8, 130.4 (d, J$_{C-F}$=8.5 Hz), 129.9, 127.1, 126.0, 119.0, 116.3, 115.7 (d, J$_{C-F}$=22.2 Hz), 54.2, 42.6, 28.6, 19.9. 19F NMR (471 MHz, MeOD) δ 76.9 (s, 3H), −113.9--113.9 (m, 1H). IR (NaCl, thin film, cm−1): 2996, 2850, 2742, 2532, 1777, 1677, 1583, 1562, 1510, 1380, 1322, 1292, 1203, 1159, 1141, 1031, 1001. HRMS (ESI-TOF) m/z [M+H]+ calcd for C25H26FN6O+ 445.2147, found 445.2158.

Example 15. Synthesis of Compound 15

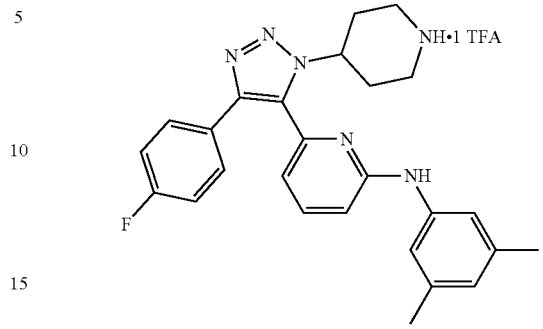

A variation of general procedure V was used. The product was purified by recrystallization (Toluene/THF/Hexanes, ca. 5:2:10) and the resulting solid was rinsed with MeCN. This afforded the title compound (201 mg, 83%) as a white solid. 1H NMR (500 MHz, MeOD) δ 7.62-7.54 (m, 3H), 7.16 (apparent t, J=8.5 Hz, 2H), 7.12 (s, 2H), 6.88 (d, J=8.4 Hz, 1H), 6.71 (d, J=7.3 Hz, 1H), 6.70 (s, 1H), 5.11-5.00 (m, 1H), 3.45 (apparent d, J=13.1 Hz, 2H), 2.96-2.77 (m, 2H), 2.53-2.43 (m, 2H), 2.39 (apparent d, J=11.8 Hz, 2H), 2.25 (s, 6H). 13C NMR (126 MHz, MeOD) δ 162.9 (d, J$_{C-F}$=246.9 Hz), 157.2, 144.0, 143.8, 140.4, 138.1, 138.0, 133.1, 129.6 (d, J$_{C-F}$=8.3 Hz), 126.8 (d, J$_{C-F}$=3.3 Hz), 123.9, 118.1, 115.7, 115.3 (d, J$_{C-F}$=22.0 Hz), 110.8, 53.4, 42.6, 28.8, 20.1. 19F NMR (471 MHz, MeOD) δ −76.89 (s, 3H), 115.09--115.17 (m, 1H). IR (NaCl, thin film, cm−1): 3001, 2838, 1673, 1591, 1462, 1454, 1201, 1178, 1131. HRMS (ESI-TOF) m/z [M+H]+ calcd for C26H28FN6+ 443.2354, found 443.2357.

Example 16. Synthesis of Compound 16

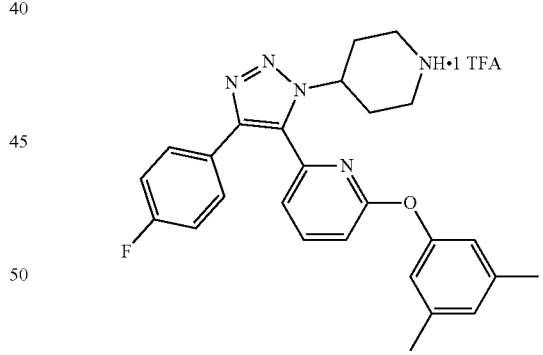

A variation of general procedure V was used. The product was purified by recrystallization (Toluene/THF/Hexanes, ca. 5:2:10) and the resulting solid was rinsed with MeCN. This afforded the title compound (109 mg, 67%) as a white solid. 1H NMR (500 MHz, MeOD) δ 7.84 (apparent t, J=7.9 Hz, 1H), 7.53-7.47 (m, 2H), 7.17 (apparent t, J=8.4 Hz, 2H), 7.11 (d, J=8.3 Hz, 1H), 7.06 (d, J=7.4 Hz, 1H), 6.94 (s, 1H), 6.86 (s, 2H), 4.84-4.73 (m, 1H), 3.42 (apparent d, J=13.3 Hz, 2H), 2.87-2.78 (m, 2H), 2.40-2.31 (m, 2H), 2.34 (s, 6H), 2.16-2.09 (m, 2H). 13C NMR (126 MHz, MeOD) δ 164.1, 163.1 (d, J$_{C-F}$=247.3 Hz), 153.8, 144.4, 144.0, 140.8, 139.6, 132.0, 130.0 (d, J$_{C-F}$=8.4 Hz), 126.6 (d, J$_{C-F}$=3.4 Hz), 126.4, 120.1, 119.1, 115.4 (d, J$_{C-F}$=21.9 Hz), 112.2, 53.6, 42.6, 28.6, 19.9.

¹⁹F NMR (471 MHz, MeOD) δ −76.9 (s, 3H), −114.7-−114.7 (m, 1H). IR (NaCl, thin film, cm⁻¹): 2973, 2737, 1676, 1573, 1509, 1456, 1431, 1296, 1202, 1137. HRMS (ESI-TOF) m/z [M+H]⁺ calcd for $C_{26}H_{27}FN_{50}^+$ 444.2194, found 444.2182.

Example 17. Synthesis of Compound 17

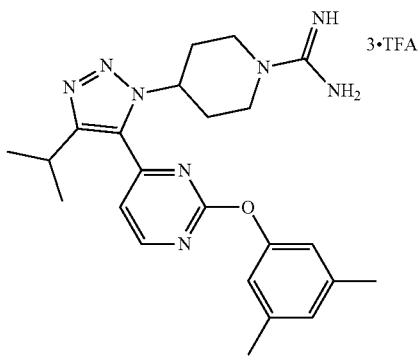 [SMILES: Cc1cc(C)cc(Oc2nccc(-c3c(C(C)C)nnn3C3CCN(C(=N)N)CC3)n2)c1]

Guanidine Deprotection:

General procedure V was used. This afforded the title compound (7.9 mg, 72%) as a white solid. Analysis by ¹⁹F NMR with 2,2,2-trifluoroethanol as the standard indicated the formation of a tris-TFA salt. ¹H NMR (500 MHz, MeOD) δ 8.83 (d, J=5.0 Hz, 1H), 7.43 (d, J=5.1 Hz, 1H), 7.00 (s, 1H), 6.89 (s, 2H), 5.00-4.93 (m, 1H), 3.88 (apparent d, J=13.8 Hz, 2H), 3.24 (hept, J=6.8 Hz, 1H), 2.95 (apparent t, J=12.2 Hz, 2H), 2.36 (s, 6H), 2.19-2.08 (m, 2H), 1.95 (apparent d, J=13.0 Hz, 2H), 1.35 (d, J=6.9 Hz, 6H). 13C NMR (126 MHz, MeOD) δ 165.4, 161.5, 156.5, 156.5, 152.9, 152.8, 139.7, 128.9, 127.1, 119.0, 115.5, 55.7, 44.4, 31.1, 25.0, 21.4, 19.9. IR (NaCl, thin film, cm⁻¹): 3349, 3140, 2967, 1688, 1666, 1612, 1580, 1562, 1554, 1388, 1320, 1295, 1203, 1182, 1160, 1141, 1102. HRMS (ESI-TOF) m/z [M+H]⁺ calcd for $C_{23}H_{31}N_8O^+$ 435.2615, found 435.2607.

Example 18. Synthesis of Compound 18

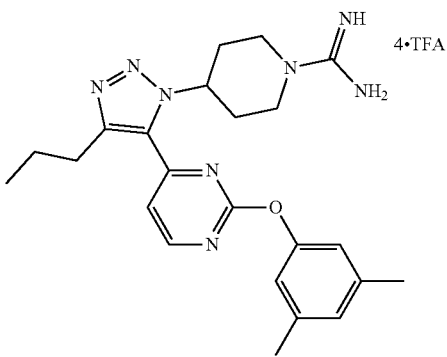 [SMILES: CCCc1nnn(C2CCN(C(=N)N)CC2)c1-c1ccnc(Oc2cc(C)cc(C)c2)n1]

General procedure V was used. This afforded the title compound (32.3 mg, 88%) as a white solid. Analysis by ¹⁹F NMR with 2,2,2-trifluoroethanol as the standard indicated the formation of a tetrakis-TFA salt. ¹H NMR (500 MHz, MeOD) δ 8.83 (d, J=5.1 Hz, 1H), 7.45 (d, J=5.1 Hz, 1H), 6.99 (s, 1H), 6.88 (s, 2H), 5.17 (tt, J=9.8, 4.3 Hz, 1H), 3.93-3.80 (m, 2H), 2.90 (apparent t, J=12.2 Hz, 2H), 2.84 (t, J=7.7 Hz, 2H), 2.35 (s, 6H), 2.18-2.06 (m, 2H), 1.97-1.90 (m, 2H), 1.75 (qt, J=7.5 Hz, 7.5 Hz, 2H), 0.99 (t, J=7.3 Hz, 3H). ¹³C NMR (126 MHz, MeOD) (Two of the peaks in the aryl region of the ¹³C NMR appear to be overlapping.) δ 165.2, 161.5, 156.5, 153.0, 147.8, 139.8, 129.8, 127.1, 119.0, 115.2, 55.9, 44.3, 31.0, 27.2, 21.9, 19.9, 12.7. IR (NaCl, thin film, cm⁻¹): 3349, 3141, 2963, 1688, 1666, 1612, 1581, 1562, 1554, 1388, 1201, 1171, 1157. HRMS (ESI-TOF) m/z [M+H]⁺ calcd for $C_{23}H_{31}N_8O^+$ 435.2615, found 435.2620.

Example 19. Synthesis of Compound 19

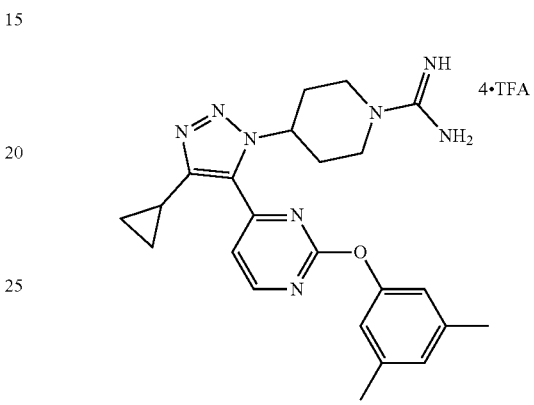

General procedure V was used. This afforded the title compound (15.5 mg, 91%) as a white solid. Analysis by ¹⁹F NMR with 2,2,2-trifluoroethanol as the standard indicated the formation of a tetrakis-TFA salt. ¹H NMR (500 MHz, MeOD) δ 8.84 (d, J=5.2 Hz, 1H), 7.73 (d, J=5.1 Hz, 1H), 7.00 (s, 1H), 6.90 (s, 2H), 5.13 (tt, J=10.3, 4.5 Hz, 1H), 3.85 (d, J=13.9 Hz, 2H), 2.84 (apparent t, J=12.7 Hz, 2H), 2.36 (s, 6H), 2.16-2.03 (m, 3H), 1.92 (d, J=13.3 Hz, 2H), 1.14-1.08 (m, 2H), 1.04-0.99 (m, 2H). ¹³C NMR (126 MHz, MeOD) δ 165.2, 161.3, 156.5, 156.4, 153.1, 149.3, 139.8, 130.1, 127.1, 119.1, 115.2, 56.0, 44.3, 30.9, 19.9, 6.9, 6.5. IR (NaCl, thin film, cm⁻¹): 3334, 3167, 1679, 1650, 1598, 1469, 1452, 1203, 1131. HRMS (ESI-TOF) m/z [M+H]⁺ calcd for $C_{23}H_{29}N_8O^+$ 433.2459, found 433.2451.

Example 20. Synthesis of Compound 20

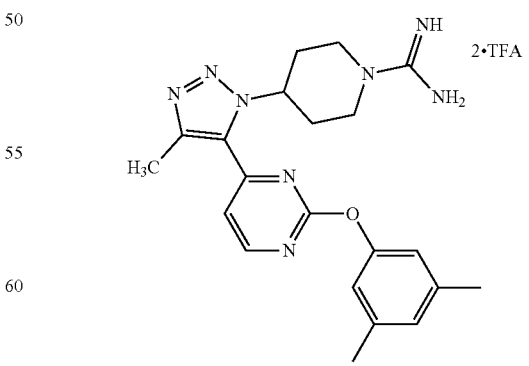

General procedure V was used and the title compound was isolated (30.0 mg, 70%) as a white solid. Analysis by ¹⁹F NMR with 2,2,2-trifluoroethanol as the standard indicated the formation of a bis-TFA salt. ¹H NMR (500 MHz, MeOD) δ 8.82 (d, J=5.1 Hz, 1H), 7.49 (d, J=5.2 Hz, 1H), 6.99 (s, 1H), 6.89 (s, 2H), 5.12 (tt, J=10.3, 4.3 Hz, 1H), 3.87-3.80 (m, 2H), 2.89-2.81 (m, 2H), 2.53 (s, 3H), 2.35 (s, 6H), 2.12-2.07 (m, 2H), 1.92 (apparent dd, J=13.4, 3.7 Hz, 2H). ¹³C NMR (500 MHz, MeOD) δ 166.6, 162.8, 157.8, 154.5, 145.4, 141.2, 131.1, 128.5, 120.4, 116.4, 57.5, 45.7, 32.3, 21.3, 12.0. HRMS (ESI-TOF) m/z [M+H]⁺ calcd for $C_{21}H_{27}N_8O^+$ 407.2302, found 407.1844.

Example 21. Synthesis of Compound 21

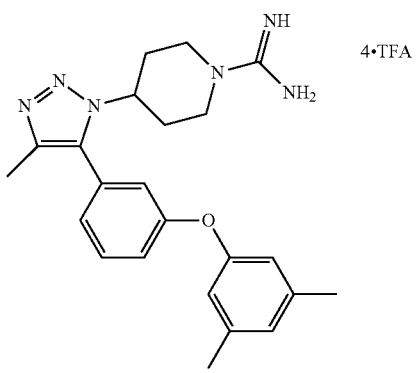

4·TFA

General procedure V was used. This afforded the title compound (123 mg) as a white solid in quantitative yield. Analysis by ¹⁹F NMR with 2,2,2-trifluoroethanol as the standard indicated the formation of a tetrakis-TFA salt. ¹H NMR (500 MHz, MeOD) δ 7.55 (apparent t, J=8.0 Hz, 1H), 7.17-7.11 (m, 2H), 6.97 (s, 1H), 6.85 (s, 1H), 6.70 (s, 2H), 4.64 (tt, J=10.7, 4.8 Hz, 1H), 4.06-3.97 (m, 2H), 3.29-3.18 (m, 2H), 2.30 (s, 6H), 2.27 (s, 3H), 2.24 (apparent d, J=11.4 Hz, 2H), 2.16-2.08 (m, 2H). ¹³C NMR (126 MHz, MeOD) δ 158.8, 156.6, 156.1, 140.4, 139.9, 134.6, 130.7, 127.7, 125.6, 123.5, 119.1, 118.7, 117.0, 55.0, 44.2, 31.1, 20.0, 8.6. IR (NaCl, thin film, cm⁻¹): 3350, 3174, 1666, 1613, 1295, 1201, 1140. HRMS (ESI-TOF) m/z [M+H]⁺ calcd for $C_{23}H_{29}N_6O^+$ 405.2397, found 405.2393.

Example 22. Synthesis of Compound 22

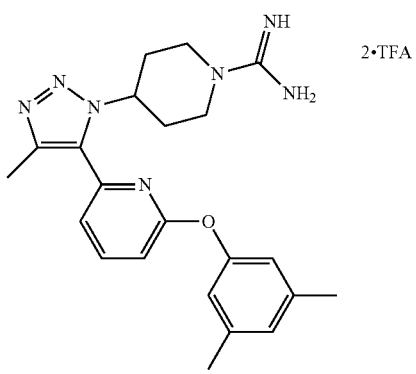

2·TFA

General procedure V was used. This afforded the title compound (64.7 mg) as a white solid in quantitative yield. Analysis by ¹⁹F NMR with 2,2,2-trifluoroethanol as the standard indicated the formation of a bis-TFA salt. ¹H NMR (500 MHz, MeOD) δ 8.01 (apparent t, J=7.9 Hz, 1H), 7.38 (d, J=7.5 Hz, 1H), 7.10 (d, J=8.3 Hz, 1H), 6.94 (s, 1H), 6.81 (s, 2H), 5.00 (tt, J=10.4, 4.1 Hz, 1H), 3.83 (apparent d, J=13.8 Hz, 2H), 2.83 (apparent t, J=12.8 Hz, 2H), 2.45 (s, 3H), 2.33 (s, 6H), 2.14-2.00 (m, 2H), 1.87 (apparent d, J=12.9 Hz, 2H). ¹³C NMR (126 MHz, MeOD) δ 163.7, 156.5, 154.0, 144.3, 141.5, 140.9, 139.5, 131.8, 126.4, 119.1, 118.7, 111.5, 55.4, 44.4, 30.9, 19.9, 10.3. IR (NaCl, thin film, cm⁻¹): 3353, 3160, 2922, 2853, 1703, 1680, 1666, 1614, 1573, 1466, 1453, 1431, 1394, 1302, 1248, 1201, 1181, 1135. HRMS (ESI-TOF) m/z [M+Na]⁺ calcd for $C_{22}H_{27}N_7NaO^+$ 428.2169, found 428.2171.

Example 23. Synthesis of Compound 23

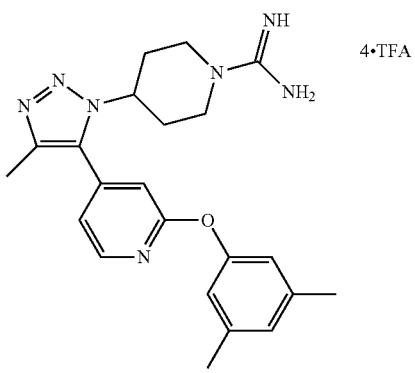

4·TFA

General procedure V was used. This afforded the title compound (50.7 mg) as a white solid in quantitative yield. Analysis by ¹⁹F NMR with 2,2,2-trifluoroethanol as the standard indicated the formation of a tetrakis-TFA salt. ¹H NMR (500 MHz, MeOD) δ 8.33 (d, J=5.0 Hz, 1H), 7.19 (d, J=5.1 Hz, 1H), 6.99 (s, 1H), 6.94 (s, 1H), 6.81 (s, 2H), 4.67 (tt, J=10.0, 4.3 Hz, 1H), 4.02 (apparent d, J=14.0 Hz, 2H), 3.28 (apparent t, J=12.7 Hz, 2H), 2.34 (s, 6H), 2.31 (s, 3H), 2.29-2.23 (m, 2H), 2.16 (apparent d, J=11.6 Hz, 2H). ¹³C NMR (126 MHz, MeOD) δ 164.6, 156.6, 153.7, 148.3, 141.4, 139.8, 139.1, 131.8, 126.6, 118.7, 118.4, 111.6, 55.0, 44.2, 31.3, 19.9, 8.9. IR (NaCl, thin film, cm⁻¹): 3353, 3180, 1679, 1659, 1613, 1201, 1139. HRMS (ESI-TOF) m/z [M+H]⁺ calcd for $C_{22}H_{28}N_7O^+$ 406.2350, found 406.2350.

Example 24. Synthesis of Compound 24

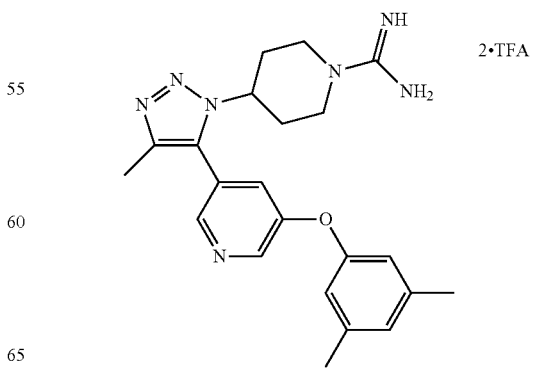

2·TFA

General procedure V was used. This afforded the title compound (128 mg) as a white solid in quantitative yield. Analysis by $^{19}$F NMR with 2,2,2-trifluoroethanol as the standard indicated the formation of a bis-TFA salt. $^{1}$H NMR (500 MHz, MeOD) δ 8.57 (br, 2H), 7.84 (s, 1H), 6.98 (s, 1H), 6.85 (s, 2H), 4.63 (tt, J=10.6, 4.6 Hz, 1H), 4.03 (apparent d, J=14.0 Hz, 2H), 3.26 (apparent t, J=12.4 Hz, 2H), 2.34 (s, 6H), 2.29 (s, 3H), 2.32-2.23 (m, 2H), 2.20-2.12 (m, 2H). $^{13}$C NMR (126 MHz, MeOD) δ 156.7, 156.6, 154.4, 142.1, 140.8, 139.3, 136.3, 130.0, 129.5, 127.3, 126.2, 117.2, 55.1, 44.1, 31.2, 19.9, 8.6. IR (NaCl, thin film, cm$^{-1}$): 3349, 3167, 1688, 1672, 1612, 1422, 1293, 1202, 1137. HRMS (ESI-TOF) m/z [M+H]$^{+}$ calcd for $C_{22}H_{28}H_{7}O^{+}$ 406.2350, found 406.2342.

Example 25. Synthesis of Compound 25

General procedure V was used. This afforded the title compound (20.0 mg, 68%) as a white solid. Analysis by $^{19}$F NMR with 2,2,2-trifluoroethanol as the standard indicated the formation of a tetrakis-TFA salt. $^{1}$H NMR (500 MHz, MeOD) δ 7.71 (apparent t, J=7.9 Hz, 1H), 7.15 (s, 2H), 6.96 (d, J=7.3 Hz, 1H), 6.87 (d, J=8.5 Hz, 1H), 6.72 (s, 1H), 5.40-5.28 (m, 1H), 3.89 (apparent d, J=13.8 Hz, 2H), 2.88 (apparent t, J=11.8 Hz, 2H), 2.46 (s, 3H), 2.29 (s, 6H), 2.24-2.10 (m, 4H). $^{13}$C NMR (126 MHz, MeOD) δ 156.7, 156.5, 143.8, 141.0, 140.4, 138.2, 138.1, 133.0, 124.0, 118.2, 114.7, 110.4, 55.3, 44.4, 31.1, 20.2, 9.9. IR (NaCl, thin film, cm$^{-1}$): 3328, 3166, 1680, 1650, 1603, 1468, 1202, 1184, 1139. HRMS (ESI-TOF) m/z [M+H]$^{+}$ calcd for $C_{22}H_{29}N_{8}^{+}$ 405.2510, found 405.2507.

Example 27. Synthesis of Compound 27

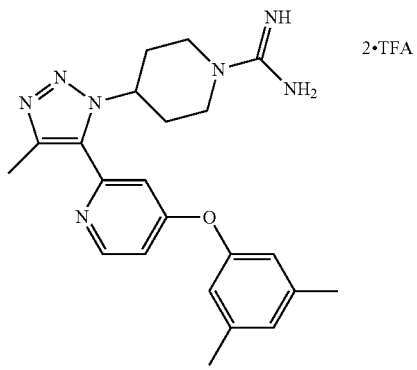

General procedure V was used. This afforded the title compound (128 mg) as a white solid in quantitative yield. Analysis by $^{19}$F NMR with 2,2,2-trifluoroethanol as the standard indicated the formation of a bis-TFA salt. $^{1}$H NMR (500 MHz, MeOD) δ 8.63 (d, J=6.0 Hz, 1H), 7.18 (d, J=2.5 Hz, 1H), 7.03 (dd, J=6.0, 2.4 Hz, 1H), 7.01 (s, 1H), 6.84 (s, 2H), 5.19-5.06 (m, 1H), 4.04 (apparent d, J=13.7 Hz, 2H), 3.32-3.24 (m, 2H), 2.36 (s, 6H), 2.34 (s, 3H), 2.31-2.23 (m, 4H). $^{13}$C NMR (126 MHz, MeOD) δ 166.8, 156.6, 153.5, 151.1, 147.7, 141.8, 140.6, 132.0, 127.4, 118.0, 113.5, 111.7, 55.6, 44.4, 31.2, 19.9, 9.5. IR (NaCl, thin film, cm$^{-1}$): 3359, 3170, 2925, 1671, 1617, 1468, 1296, 1201, 1134. HRMS (ESI-TOF) m/z [M+Na]$^{+}$ calcd for $C_{22}H_{27}N_{7}NaO^{+}$ 428.2169, found 428.2166.

Example 26. Synthesis of Compound 26

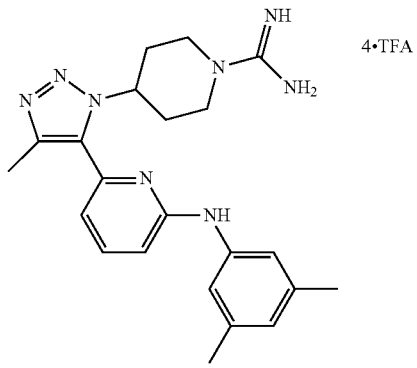

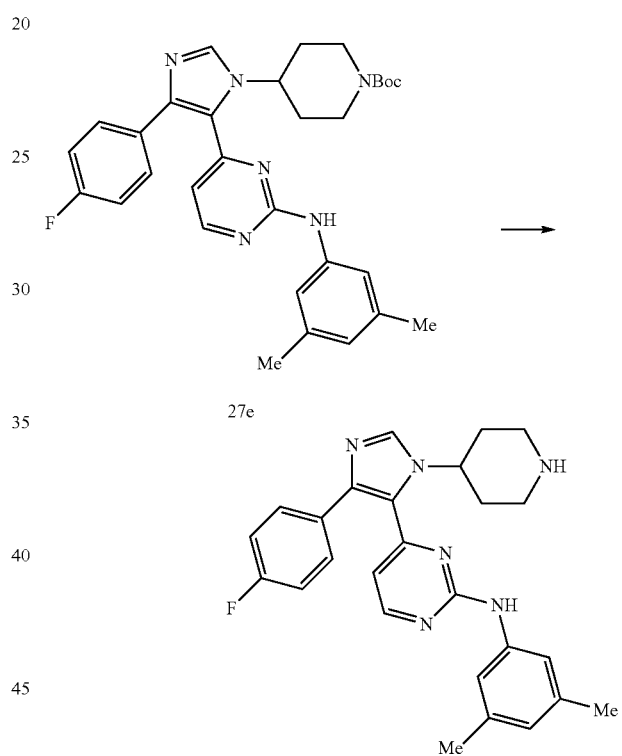

Trifluoroacetic acid (TFA) (0.50 mL) was added to a solution of compound 27e (0.13 mmol) in DCM (0.50 mL). After 16 hours, the reaction was concentrated under reduced pressure. Cold ether (4.0 mL) was used to precipitate compound 27 (53 mg, 0.12 mmol, 96%) as a white solid. $^{1}$H NMR (500 MHz, CDCl$_{3}$) δ 8.29 (d, J=5.1 Hz, 1H), 7.80 (s, 1H), 7.51 (dd, J=8.4, 5.4 Hz, 2H), 7.24 (s, 2H), 7.19 (s, 1H), 7.04 (t, J=8.6 Hz, 2H), 6.76 (s, 1H), 6.58 (d, J=5.1 Hz, 1H), 4.78 (tt, J=12.0, 3.9 Hz, 1H), 3.15-3.08 (m, 2H), 2.49-2.40 (m, 2H), 2.34 (s, 6H), 2.12—2.05 (m, 2H), 1.84 (qd, J=12.2, 3.9 Hz, 2H). $^{13}C$ NMR (125 MHz, methanol-d4) δ 164.4, (d, J=247.6 Hz) 162.4, 160.7, 158.8, 156.0, 152.6, 148.2, 139.1, 138.2, 135.4, 130.7, (d, J=8.4 Hz) 130.6, 124.8, 119.0, 115.8, (d, J=22.1 Hz) 115.6, 112.6, 52.3, 48.1, 43.0, 29.5, 20.1. HRMS (ESI-TOF) m/z [M+H]$^{+}$ calcd for $C_{26}H_{28}FN_{6}^{+}$ 443.2359, found: 443.2388.

Example 28. Synthesis of Compound 28

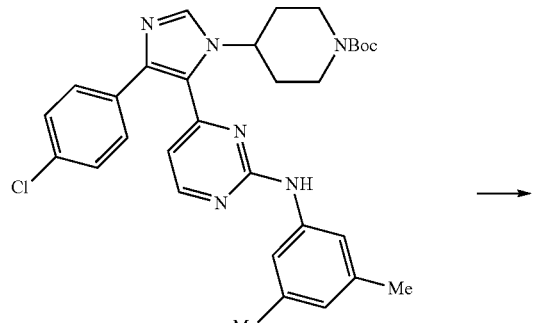

28e

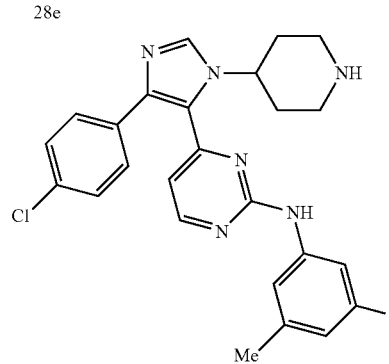

28

Trifluoroacetic acid (TFA) (0.50 mL) was added to a solution of compound 28e (0.13 mmol) in DCM (0.50 mL). After 16 hours, the reaction was concentrated under reduced pressure. Cold ether (4.0 mL) was used to precipitate compound 28 (55 mg, 0.12 mmol, 96%) as a yellow solid. $^1$H NMR (500 MHz, MeOD) δ 8.70 (s, 1H), 8.37 (d, J=5.0 Hz, 1H), 7.49 (s, 4H), 7.23 (s, 2H), 6.80 (s, 1H), 6.59 (d, J=5.0 Hz, 1H), 5.01 (ddt, J=12.5, 7.9, 3.9 Hz, 1H), 3.44-3.37 (m, 2H), 2.78 (t, J=13.6 Hz, 2H), 2.50-2.44 (m, 2H), 2.32 (s, 6H), 2.21 (td, J=13.0, 4.1 Hz, 2H).

Example 29. Synthesis of Compound 29

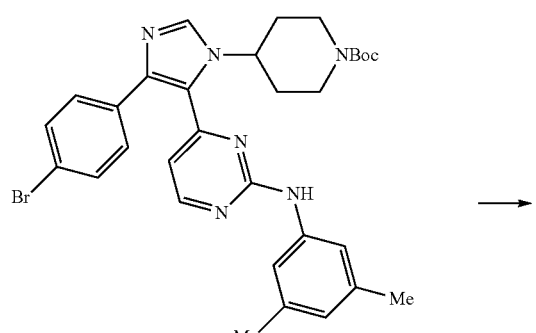

29e

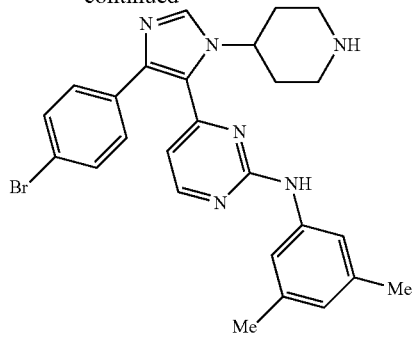

29

Trifluoroacetic acid (TFA) (0.50 mL) was added to a solution of compound 29e (0.13 mmol) in DCM (0.50 mL). After 16 hours, the reaction was concentrated under reduced pressure. Cold ether (4.0 mL) was used to precipitate compound 29 (60 mg, 0.12 mmol, 96%) as a yellow solid. $^1$H NMR (400 MHz, MeOD) δ 9.03 (s, 1H), 8.39 (d, J=5.1 Hz, 1H), 7.69-7.65 (m, 2H), 7.47-7.42 (m, 2H), 7.23 (d, J=1.5 Hz, 2H), 6.80 (s, 1H), 6.61 (d, J=5.1 Hz, 1H), 5.05 (it, J=12.1, 3.8 Hz, 1H), 3.42 (d, J=13.1 Hz, 2H), 2.78 (t, J=13.0 Hz, 2H), 2.47 (d, J=13.3 Hz, 2H), 2.31 (s, 6H), 2.25 (dd, J=12.7, 4.1 Hz, 2H). $^{13}$C NMR (101 MHz, MeOD) δ 162.00, 160.21, 156.73, 140.26, 139.63, 136.84, 133.52, 131.70, 129.04, 126.43, 125.21, 120.49, 114.03, 54.26, 44.28, 30.79, 21.47.

Example 30. Synthesis of Compound 30

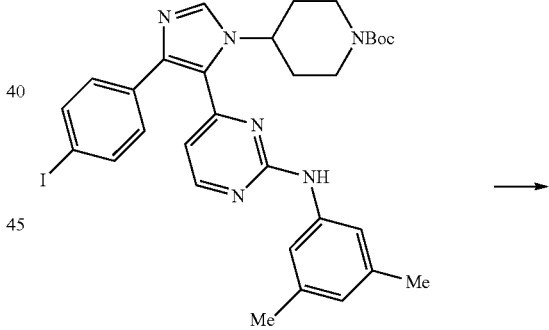

30e

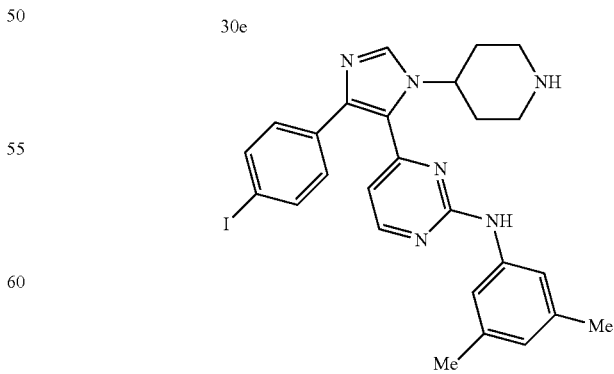

30

Trifluoroacetic acid (TFA) (0.50 mL) was added to a solution of compound 30e (0.113 mmol) in DCM (0.50 mL). After 16 hours, the reaction was concentrated under reduced pressure. Cold ether (4.0 mL) was used to precipitate compound 30 (60 mg, 0.12 mmol, 96%) as a yellow solid. $^1$H NMR (500 MHz, MeOD) δ 8.77 (d, J=4.5 Hz, 1H), 8.38 (d, J=5.0 Hz, 1H), 7.86-7.83 (m, 2H), 7.30-7.26 (m, 2H), 7.23 (s, 2H), 6.80 (s, 1H), 6.60 (d, J=5.0 Hz, 1H), 5.01 (ddd, J=12.2, 8.4, 3.8 Hz, 1H), 3.41 (d, J=13.0 Hz, 2H), 2.78 (t, J=13.2 Hz, 2H), 2.46 (d, J=13.7 Hz, 2H), 2.31 (s, 6H), 2.20 (qd, J=13.0, 4.1 Hz, 2H).

Example 31. Synthesis of Compound 31

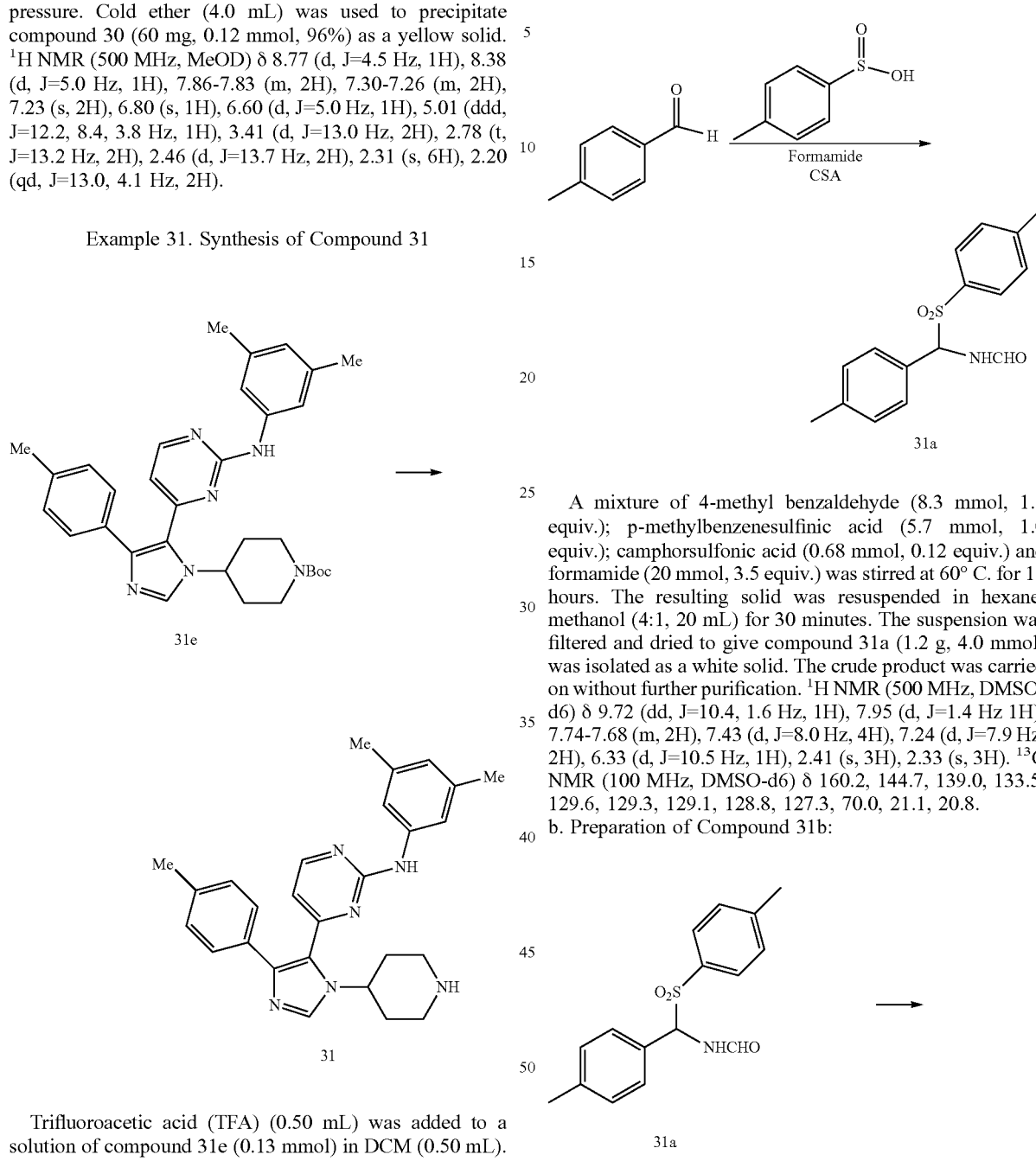

Trifluoroacetic acid (TFA) (0.50 mL) was added to a solution of compound 31e (0.13 mmol) in DCM (0.50 mL). After 16 hours, the reaction was concentrated under reduced pressure. Cold ether (4.0 mL) was used to precipitate compound 31 (94 mg, 0.12 mmol, 96%) as a white solid. $^1$H NMR (500 MHz, MeOD) δ 9.17 (d, J=5.0 Hz, 1H), 8.35 (d, J=5.0 Hz, 1H), 7.38 (d, J=8.1 Hz, 3H), 7.32 (d, J=8.0 Hz, 3H), 7.21 (s, 2H), 6.78 (s, 1H), 6.57 (d, J=5.1 Hz, 1H), 5.08 (tt, J=12.3, 3.8 Hz, 1H), 3.42-3.37 (m, 2H), 2.75 (t, J=13.0 Hz, 2H), 2.47 (dt, J=14.0, 2.8 Hz, 2H), 2.40 (s, 3H), 2.29 (s, 6H), 2.27-2.19 (m, 2H). $^{13}$C NMR (125 MHz, MeOD) δ 162.2, 160.5, 156.3, 142.1, 140.4, 139.6, 136.2, 131.1, 129.9, 126.4, 120.5, 114.1, 54.8 (d, J=40.0 Hz), 44.3, 30.7, 21.5, 21.4. HRMS (ESI-TOF) m/z [M+Na]+ calcd. for $C_{27}H_{31}N_6^+$ 439.2605, found 439.2605.

The intermediate compound 31e was prepared as follows.

a. Preparation of Compound 31a:

A mixture of 4-methyl benzaldehyde (8.3 mmol, 1.5 equiv.); p-methylbenzenesulfinic acid (5.7 mmol, 1.0 equiv.); camphorsulfonic acid (0.68 mmol, 0.12 equiv.) and formamide (20 mmol, 3.5 equiv.) was stirred at 60° C. for 18 hours. The resulting solid was resuspended in hexane/methanol (4:1, 20 mL) for 30 minutes. The suspension was filtered and dried to give compound 31a (1.2 g, 4.0 mmol) was isolated as a white solid. The crude product was carried on without further purification. $^1$H NMR (500 MHz, DMSO-d6) δ 9.72 (dd, J=10.4, 1.6 Hz, 1H), 7.95 (d, J=1.4 Hz 1H), 7.74-7.68 (m, 2H), 7.43 (d, J=8.0 Hz, 4H), 7.24 (d, J=7.9 Hz, 2H), 6.33 (d, J=10.5 Hz, 1H), 2.41 (s, 3H), 2.33 (s, 3H). $^{13}$C NMR (100 MHz, DMSO-d6) δ 160.2, 144.7, 139.0, 133.5, 129.6, 129.3, 129.1, 128.8, 127.3, 70.0, 21.1, 20.8.

b. Preparation of Compound 31b:

POCl₃ (6.6 mmol, 2.0 equiv.) was added drop-wise to a solution of compound 31a (3.3 mmol, 1.0 equiv.) in anhydrous THF at −10° C., followed by 2,6-lutidine (20 mmol, 6.0 equiv.). The reaction was warmed to room temperature and stirred for 16 hours. The reaction was quenched by saturated NH₄Cl. The aqueous phase was extracted with ethyl acetate (3×40 mL), dried over anhydrous magnesium sulfate and concentrated under reduced pressure to give the crude product. The crude product was purified by silica gel chromatography using hexane and ethyl acetate (0-100%) as eluent to give compound 31b (0.76 g, 2.7 mmol, 81%) as a brown solid. ¹H NMR (400 MHz, Chloroform-d) δ 7.68-7.56 (m, 2H), 7.33 (d, J=8.1 Hz, 2H), 7.23-7.16 (m, 4H), 5.56 (s, 1H), 2.47 (s, 3H), 2.39 (s, 3H). ¹³C NMR (100 MHz, Chloroform-d) δ 165.9, 146.6, 141.2, 130.7, 130.3, 129.9, 129.6, 128.5, 123.6, 76.5, 21.9, 21.5.

c. Preparation of Compound 31c:

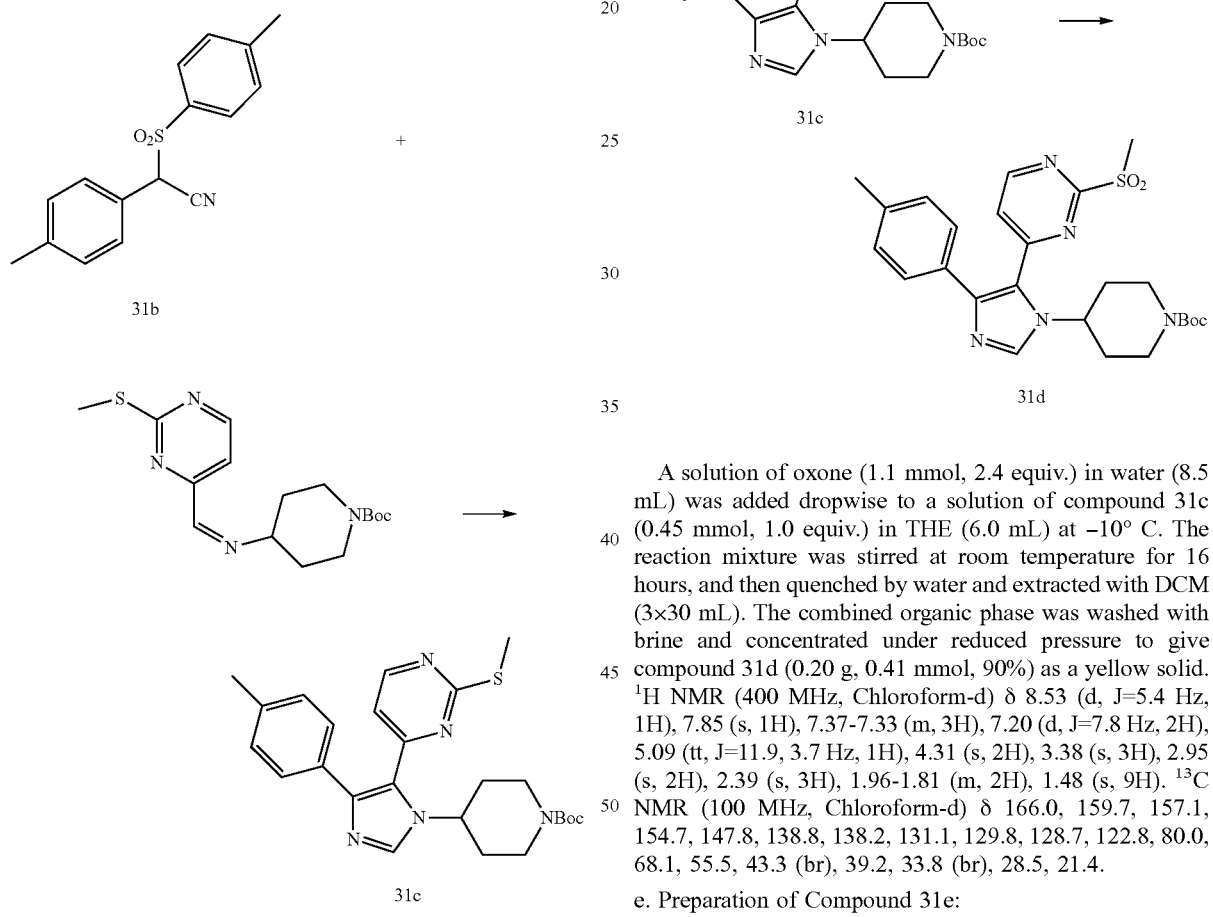

A mixture of compound 31b (1.2 mmol, 1.0 equiv.), tert-butyl 4-(((2-(methylthio)pyrimidin-4-yl)methylene)-amino)piperidine-1-carboxylate (1.2 mmol, 1.0 equiv.) and potassium carbonate (4.8 mmol, 4.0 equiv.) in acetonitrile (3.9 mL) was stirred at 40° C. for 16 hours. The reaction mixture was quenched by addition of brine and extracted with ethyl acetate (3×20 mL). The combined organic phase was dried over anhydrous magnesium sulfate and concentrated under reduced pressure to give the crude product. The crude product was purified by silica gel chromatography using hexane and ethyl acetate (0-100%) as eluent to give compound 31c (0.22 g, 0.48 mmol, 40%) as a yellow solid.

¹H NMR (400 MHz, Chloroform-d) δ 8.31 (d, J=5.2 Hz, 1H), 7.75 (s, 1H), 7.37-7.32 (m, 2H), 7.14 (d, J=7.8 Hz, 2H), 6.84 (d, J=5.2 Hz, 1H), 4.88 (tt, J=12.0, 3.7 Hz, 1H), 4.30 (s, 2H), 2.85-2.73 (m, 1H), 2.59 (s, 3H), 2.36 (s, 3H), 2.17 (dt, J=12.5, 2.6 Hz, 2H), 1.86 (qd, J=12.3, 4.3 Hz, 2H), 1.48 (s, 9H). ¹³C NMR (125 MHz, Chloroform-d) δ 172.7, 158.1, 157.0, 154.7, 144.9, 137.9, 136.5, 131.4, 129.4, 128.6, 117.1, 80.2, 54.4, 43.4, 33.6, 28.5, 21.4, 14.2. HRMS (ESI-TOF) m/z [M+Na]+ calcd. for C₂₅H₃₁N₅NaO₂S⁺ 488.2091, found 488.2102.

d. Preparation of Compound 31d:

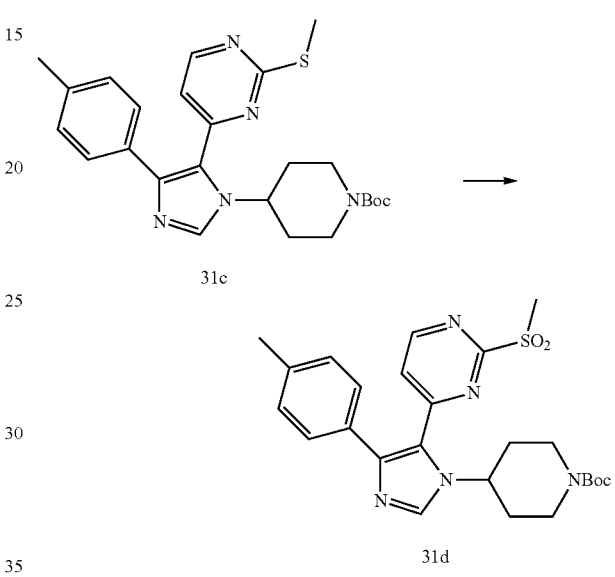

A solution of oxone (1.1 mmol, 2.4 equiv.) in water (8.5 mL) was added dropwise to a solution of compound 31c (0.45 mmol, 1.0 equiv.) in THF (6.0 mL) at −10° C. The reaction mixture was stirred at room temperature for 16 hours, and then quenched by water and extracted with DCM (3×30 mL). The combined organic phase was washed with brine and concentrated under reduced pressure to give compound 31d (0.20 g, 0.41 mmol, 90%) as a yellow solid. ¹H NMR (400 MHz, Chloroform-d) δ 8.53 (d, J=5.4 Hz, 1H), 7.85 (s, 1H), 7.37-7.33 (m, 3H), 7.20 (d, J=7.8 Hz, 2H), 5.09 (tt, J=11.9, 3.7 Hz, 1H), 4.31 (s, 2H), 3.38 (s, 3H), 2.95 (s, 2H), 2.39 (s, 3H), 1.96-1.81 (m, 2H), 1.48 (s, 9H). ¹³C NMR (100 MHz, Chloroform-d) δ 166.0, 159.7, 157.1, 154.7, 147.8, 138.8, 138.2, 131.1, 129.8, 128.7, 122.8, 80.0, 68.1, 55.5, 43.3 (br), 39.2, 33.8 (br), 28.5, 21.4.

e. Preparation of Compound 31e:

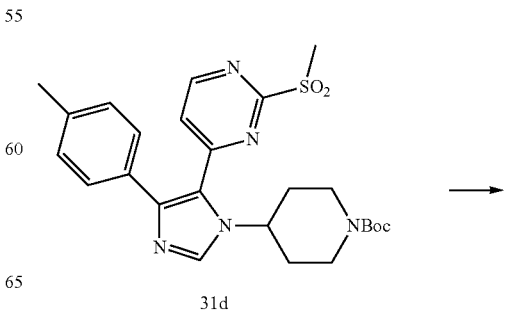

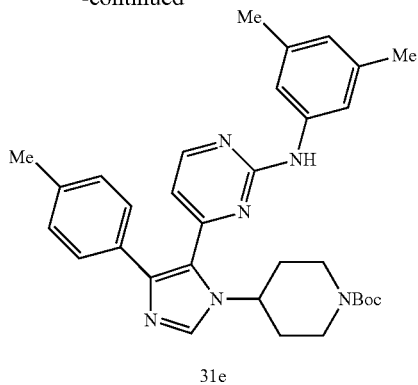

31e

A mixture of compound 31d (0.26 mmol, 1.0 equiv.) and 3,5-dimethylaniline (1.3 mmol, 5.0 equiv.) were heated in a sealed tube at 130° C. for 16 hours behind a blast shield. The crude product was obtained as a brown oil, which was purified by silica gel chromatography using hexane and ethyl acetate (0-100%) as eluent to give compound 31e (64 mg, 0.12 mmol, 46%) as a yellow solid. $^1$H NMR (400 MHz, Chloroform-d) δ 8.23 (d, J=5.1 Hz, 1H), 7.72 (s, 1H), 7.43-7.39 (m, 2H), 7.31 (s, 1H), 7.21-7.18 (m, 2H), 7.15-7.11 (m, 2H), 6.75-6.72 (m, 1H), 6.60 (d, J=5.1 Hz, 1H), 4.84 (tt, J=12.0, 3.7 Hz, 1H), 2.48-2.38 (m, 2H), 2.36 (s, 3H), 2.31 (s, 6H), 2.03 (d, J=6.6 Hz, 2H), 1.78 (td, J=12.3, 4.3 Hz, 2H), 1.45 (s, 9H). $^{13}$C NMR (100 MHz, Chloroform-d) δ 160.5, 158.8, 158.2, 154.6, 143.7, 139.0, 138.7, 137.6, 135.9, 131.5, 129.3, 128.5, 125.3, 118.4, 113.7, 80.1, 53.8, 43.1(br), 33.5, 28.5, 21.6, 21.4.

Example 32. Synthesis of Compound 32

Trifluoroacetic acid (TFA) (0.50 mL) was added to a solution of compound 32e (0.13 mmol) in DCM (0.50 mL). After 16 hours, the reaction was concentrated under reduced pressure. Cold ether (4.0 mL) was used to precipitate compound 32 (86 mg, 0.12 mmol, 96%) as a white solid. $^1$H NMR (500 MHz, MeOD) δ 8.87 (s, 1H), 8.36 (d, J=5.1 Hz, 1H), 7.77 (d, J=8.3 Hz, 2H), 7.71 (d, J=8.2 Hz, 2H), 7.22 (d, J=1.6 Hz, 2H), 6.78 (s, 1H), 6.60 (d, J=5.1 Hz, 1H), 4.99 (ddt, J=12.1, 8.3, 3.8 Hz, 1H), 3.44-3.37 (m, 2H), 2.82-2.74 (m, 2H), 2.49-2.41 (m, 2H), 2.29 (s, 6H), 2.24 (td, J=13.0, 3.9 Hz, 2H). $^{13}$C NMR (125 MHz, MeOD) δ 161.9, 160.0, 157.2, 140.2, 139.6, 137.6, 137.4, 130.5, 127.1, 127.1, 127.0, 127.0, 126.4, 120.5, 114.1, 54.0, 44.3, 30.9, 30.8, 21.5. $^{19}$F NMR (376 MHz, MeOD) δ −64.28, −77.09. HRMS (ESI-TOF) m/z [M+Na]+ calcd. for $C_{27}H_{28}F_3N_6^+$ 493.2322, found 493.2348.

The intermediate compound 31e was prepared as follows.

a. Preparation of Compound 32a:

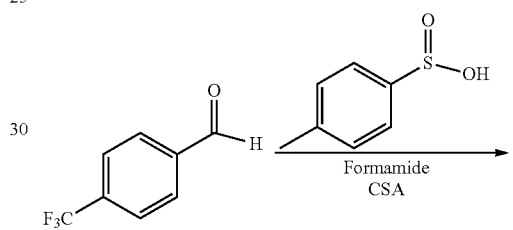

32a

A mixture of 4-trifluoromethyl benzaldehyde (8.3 mmol, 1.5 equiv.); p-methylbenzene-sulfinic acid (5.7 mmol, 1.0 equiv.); camphorsulfonic acid (0.68 mmol, 0.12 equiv.) and formamide (20 mmol, 3.5 equiv.) was stirred at 60° C. for 18 hours. The resulting solid was resuspended in hexane/methanol (4:1, 20 mL) for 30 minutes. The suspension was filtered and dried to give compound 32a (0.79 g, 2.2 mmol) as a white solid. The crude product was carried on without further purification. $^1$H NMR (500 MHz, DMSO-d6) δ 9.89 (dd, J=10.4, 1.5 Hz, 1H), 8.03-7.94 (m, 2H), 7.84 (s, 4H), 7.79-7.76 (m, 2H), 7.46 (d, J=8.0 Hz, 3H), 6.61 (d, J=10.5 Hz, 1H), 2.43 (s, 3H). $^{13}$C NMR (100 MHz, DMSO-d6) δ 162.9, 160.4, 145.1, 135.0, 133.2, 130.4, 129.7, 129.3, 125.4-125.1 (m), 69.6, 21.2. $^{19}$F NMR (470 MHz, DMSO-d60) δ −61.18.

b. Preparation of Compound 32b:

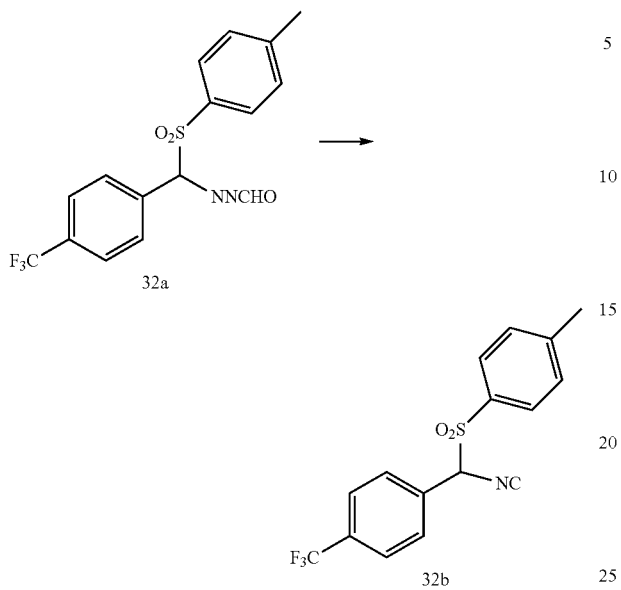

POCl$_3$ (6.6 mmol, 2.0 equiv.) was added drop-wise to a solution of compound 32a (3. GP 123'C$_1$ mmol, 1.0 equiv.) in anhydrous THF at −10° C., followed by 2,6-lutidine (20 mmol, 6.0 equiv.). The reaction was warmed to room temperature and stirred for 16 hours. The reaction was quenched by saturated NH$_4$Cl. The aqueous phase was extracted with ethyl acetate (3×40 mL), dried over anhydrous magnesium sulfate and concentrated under reduced pressure to give the crude product. The crude product was purified by silica gel chromatography using hexane and ethyl acetate (0-100%) as eluent to give compound 32b (0.89 g, 2.6 mmol, 79%) as a yellow solid. $^1$H NMR (400 MHz, Chloroform-d) δ 7.73-7.65 (m, 4H), 7.53 (d, J=8.1 Hz, 2H), 7.39 (d, J=8.1 Hz, 2H), 5.68 (s, 1H), 2.51 (s, 3H). $^{13}$C NMR (125 MHz, Chloroform-d) δ 167.2, 147.3, 130.6, 130.1, 129.9, 129.1, 125.9 (q, J=3.7 Hz), 75.9, 22.0. $^{19}$F NMR (470 MHz, CDCl$_3$) δ −62.95.

c. Preparation of Compound 32c:

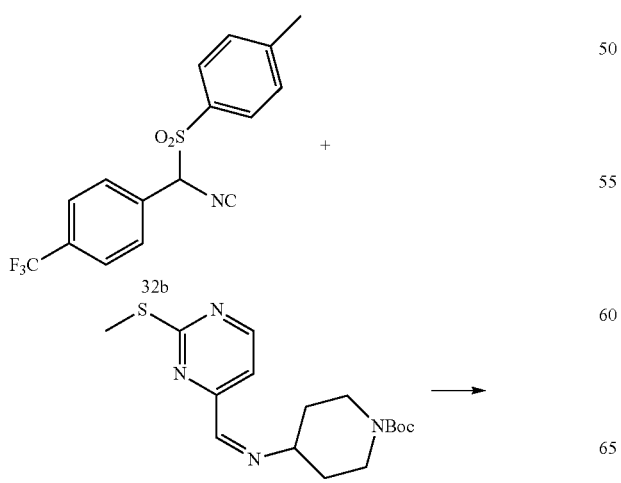

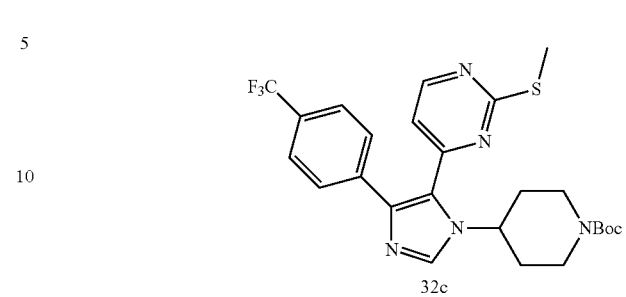

A mixture of compound 32b (1.2 mmol, 1.0 equiv.), tert-butyl 4-(((2-(methylthio)-pyrimidin-4-yl)methylene)-amino)piperidine-1-carboxylate (1.2 mmol, 1.0 equiv.) and potassium carbonate (4.8 mmol, 4.0 equiv.) in acetonitrile (3.9 mL) was stirred at 40° C. for 16 hours. The reaction mixture was quenched by addition of brine and extracted with ethyl acetate (3×20 mL). The combined organic phase was dried over anhydrous magnesium sulfate and concentrated under reduced pressure to give the crude product. The crude product was purified by silica gel chromatography using hexane and ethyl acetate (0-100%) as eluent to give compound 32c (0.49 g, 0.94 mmol, 79%) as a yellow solid. $^1$H NMR (500 MHz, Chloroform-d) δ 8.34 (d, J=5.3 Hz, 1H), 7.80 (s, 1H), 7.50-7.46 (m, 2H), 7.37-7.33 (m, 3H), 6.84 (d, J=5.2 Hz, 1H), 4.95-4.84 (m, 1H), 4.33 (s, 2H), 2.89-2.78 (m, 2H), 2.62 (s, 3H), 2.20 (dq, J=12.0, 2.3 Hz, 2H), 1.90 (tt, J=12.3, 6.1 Hz, 2H), 1.51 (s, 10H). $^{13}$C NMR (125 MHz, Chloroform-d) δ 172.8, 158.0, 157.1, 154.6, 144.7, 136.6, 134.3, 128.7, 128.7, 128.1, 124.1, 117.2, 80.2, 54.4, 43.4(br), 33.6, 28.5, 14.2. $^{19}$F NMR (470 MHz, CDCl$_3$) δ −62.52. HRMS (ESI-TOF) m/z [M+Na]+ calcd. for C$_{25}$H$_{28}$F$_3$N$_5$NaO$_2$S$^+$ 542.1808, found 542.1818.

d. Preparation of Compound 32d:

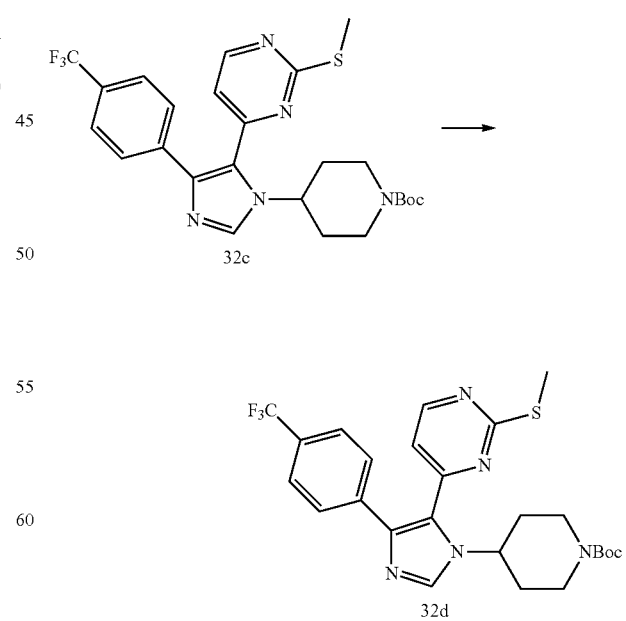

A solution of oxone (1.1 mmol, 2.4 equiv.) in water (8.5 mL) was added dropwise to a solution of compound 32c (0.45 mmol, 1.0 equiv.) in THF (6.0 mL) at −10° C. The reaction mixture was stirred at room temperature for 16 hours, and then quenched by water and extracted with DCM (3×30 mL). The combined organic phase was washed with brine and concentrated under reduced pressure to give compound 32d (0.24 g, 0.44 mmol, 98%) as a yellow solid. $^1$H NMR (400 MHz, Chloroform-d) δ 8.63 (d, J=5.4 Hz, 1H), 7.89 (s, 1H), 7.63 (q, J=8.4 Hz, 5H), 7.31 (d, J=5.4 Hz, 1H), 5.02 (tt, J=12.2, 3.7 Hz, 1H), 3.40 (s, 3H), 2.94 (s, 2H), 2.25 (s, 2H) 1.87 (d, J=13.4 Hz, 2H), 1.48 (s, 9H). $^{13}$C NMR (125 MHz, Chloroform-d) δ 166.4, 159.3, 157.7, 154.7, 145.4, 138.4, 137.6, 129.1, 126.0 (q, J=3.7 Hz), 123.0, 80.1, 55.6, 43.1(br), 39.1, 33.9(br), 28.5. $^{19}$F NMR (470 MHz, CDCl$_3$) δ −62.63.

e. Preparation of Compound 31e:

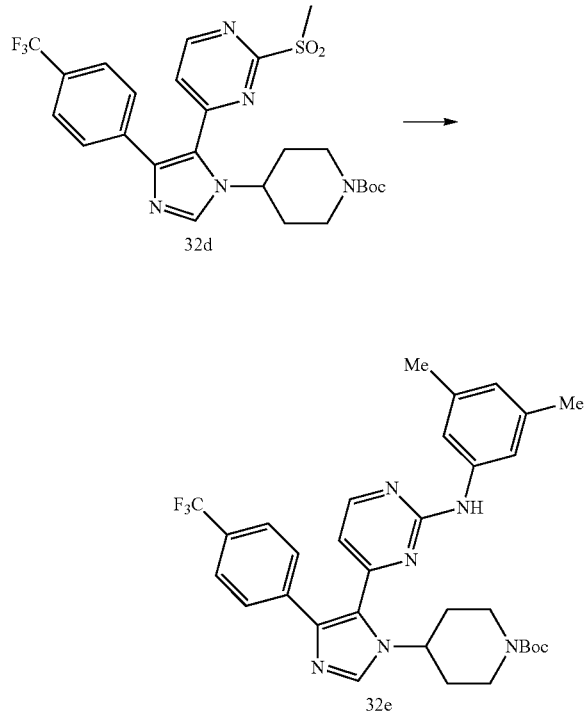

A mixture of compound 32d (0.26 mmol, 1.0 equiv.) and 3,5-dimethylaniline (1.3 mmol, 5.0 equiv.) were heated in a sealed tube at 130° C. for 16 hours behind a blast shield. The crude product was obtained as a brown oil, which was purified by silica gel chromatography using hexane and ethyl acetate (0-100%) as eluent to give compound 32e (69 mg, 0.12 mmol, 45%) as a yellow solid. $^1$H NMR (500 MHz, CDCl$_3$) δ 8.31 (d, J=5.0 Hz, 1H), 7.75 (s, 1H), 7.68-7.63 (m, 2H), 7.57 (d, J=8.3 Hz, 2H), 7.22-7.18 (m, 2H), 7.09 (s, 1H), 6.78-6.74 (m, 1H), 6.58 (d, J=5.0 Hz, 1H), 4.75 (tt, J=12.1, 3.8 Hz, 1H), 2.45 (d, J=9.2 Hz, 2H), 2.32 (s, 5H), 2.07 (s, 1H), 1.87-1.71 (m, 2H), 1.46 (s, 9H). $^{13}$C NMR (125 MHz, Chloroform-d) δ160.7, 158.8, 158.3, 154.6, 141.5, 138.8, 138.7, 138.0, 136.2, 128.6, 125.5 (q, J=4.5 Hz), 118.5, 113.7, 80.2, 53.9, 43.1(br), 33.5, 28.50, 21.54. $^{19}$F NMR (470 MHz, CDCl$_3$) δ −62.46.

Example 33. Synthesis of Compound 33

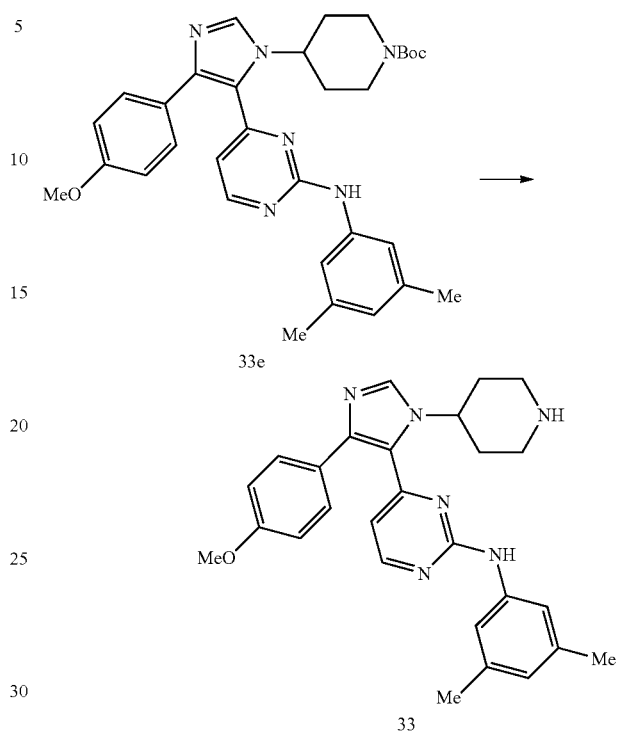

Trifluoroacetic acid (TFA) (0.50 mL) was added to a solution of compound 33e (0.13 mmol) in DCM (0.50 mL). After 16 hours, the reaction was concentrated under reduced pressure. Cold ether (4.0 mL) was used to precipitate compound 33 (mg, 0.12 mmol, 96%) as a yellowsolid. $^1$H NMR (400 MHz, MeOD) δ 9.25-9.21 (m, 1H), 8.37 (d, J=5.1 Hz, 1H), 7.47-7.40 (m, 2H), 7.21 (d, J=1.5 Hz, 2H), 7.09-7.03 (m, 2H), 6.79 (s, 1H), 6.59 (d, J=5.1 Hz, 1H), 5.11 (tt, J=12.0, 3.7 Hz, 1H), 3.85 (s, 3H), 3.41 (d, J=13.1 Hz, 2H), 2.76 (t, J=12.6 Hz, 2H), 2.48 (d, J=13.4 Hz, 2H), 2.30 (s, 6H), 2.22 (td, J=13.2, 4.2 Hz, 2H). $^{13}$C NMR (101 MHz, MeOD) δ 162.94, 160.51, 156.25, 140.35, 139.63, 135.91, 131.49, 126.39, 120.48, 115.91, 114.00, 55.99, 54.72, 44.23, 30.69, 21.47.

Example 34. Synthesis of Compound 34

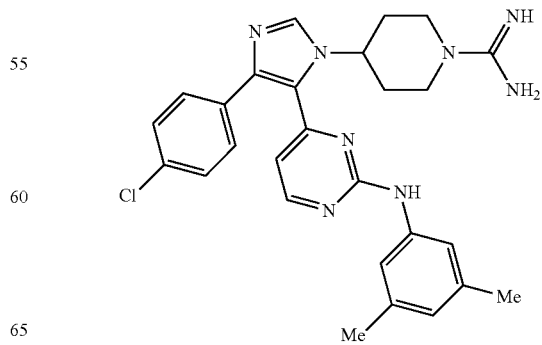

Compound 34 was prepared using procedures similar to those described herein for the preparation of other Examples.

The intermediate compound 35a was prepared as follows.

a. Preparation of Compound 35a:

Example 35. Synthesis of Compound 35

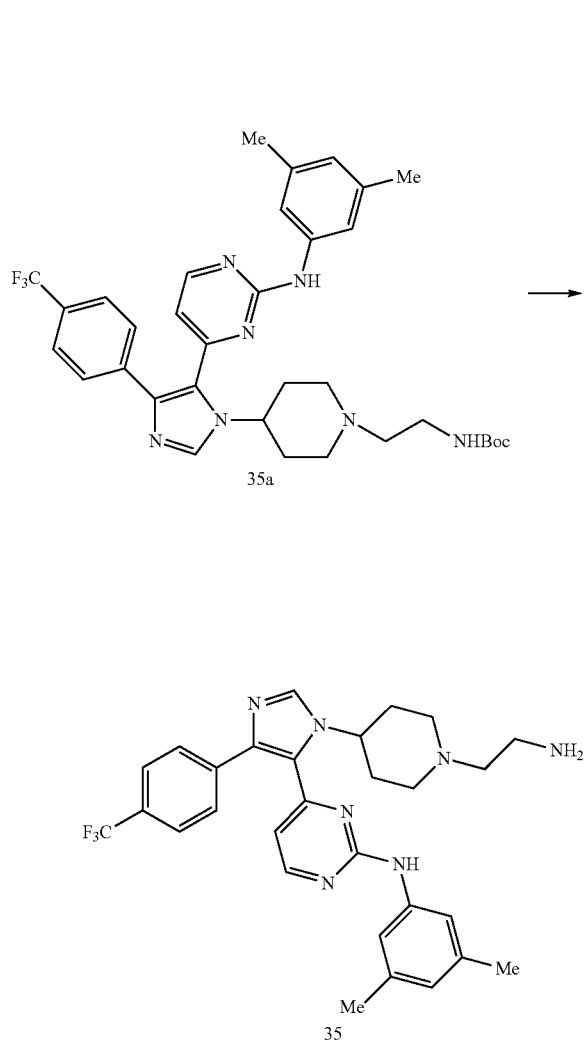

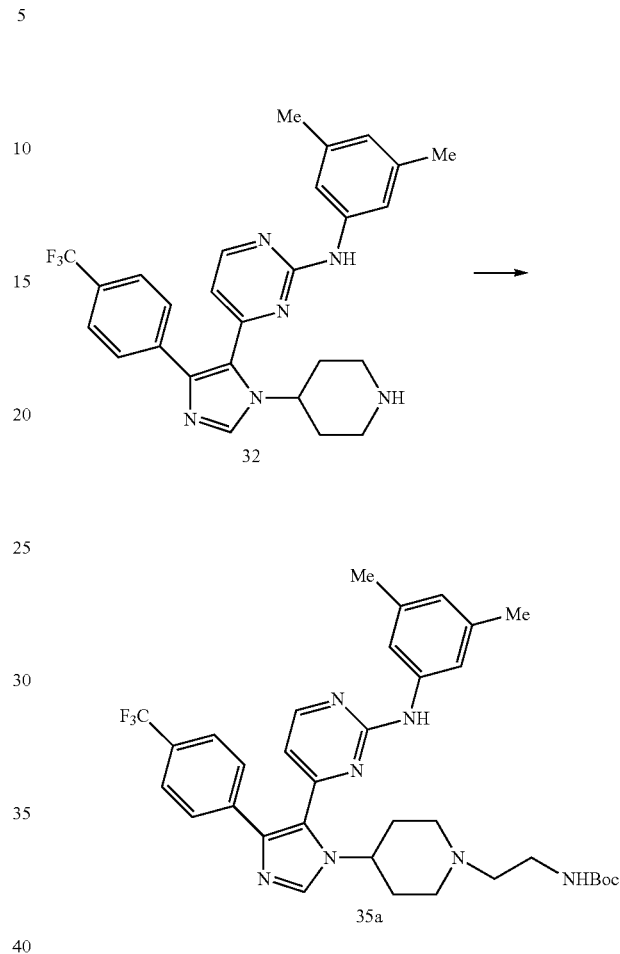

Compound 32 (0.11 mmol, 1.0 equiv.), 2-(Boc-amino)ethyl bromide (0.14 mmol, 1.3 equiv.), NaI (0.14 mmol, 1.3 equiv.) and $K_2CO_3$ (0.77 mmol, 7.0 equiv.) were dissolved in methyl ethyl ketone (0.37 mL). The reaction was stirred at room temperature for 16 h then quenched by water and extracted with ethyl acetate (3×20 mL). The combined organic phase was dried over anhydrous magnesium sulfate and concentrated under reduced pressure to give the crude product, which was purified by silica gel chromatography using DCM and methanol (0-20%) as eluent to give the desired product 35a (47 mg, 0.074 mmol, 67%). $^1$H NMR (500 MHz, CDCl$_3$) δ 8.31 (d, J=5.3 Hz, 1H), 7.80 (s, 1H), 7.65 (d, J=8.0 Hz, 2H), 7.57 (d, J=8.1 Hz, 2H), 7.21 (s, 2H), 7.07 (s, 1H), 6.75 (s, 1H), 6.58 (d, J=5.0 Hz, 1H), 4.90 (s, 1H), 4.59 (tt, J=11.9, 4.1 Hz, 1H), 3.19 (q, J=5.9 Hz, 2H), 2.89 (d, J=11.3 Hz, 2H), 2.38 (t, J=6.1 Hz, 2H), 2.32 (s, 6H), 2.04 (d, J=10.9 Hz, 2H), 1.95 (qd, J=12.0, 3.6 Hz, 2H), 1.80 (t, J=11.6 Hz, 2H), 1.46 (s, 9H). $^{13}$C NMR (100 MHz, CDCl$_3$) δ 160.7, 158.7, 158.5, 156.1, 141.3, 138.9, 138.7, 138.0, 136.3, 128.5, 125.5-125.3 (m), 118.4, 113.7, 57.1, 53.9, 52.6, 37.5, 33.6, 28.6, 21.6. $^{19}$F NMR (470 MHz, CDCl$_3$) δ −62.45.

TFA (0.30 mL) was added to a solution of Compound 35a (0.074 mmol) in DCM (0.30 mL). After 16 hours, the reaction was concentrated under reduced pressure. Cold ether (3 mL) was used to precipitate compound 35 (70 mg, 0.071 mmol, 96%). $^1$H NMR (400 MHz, CDCl$_3$) δ 8.31 (d, J=5.1 Hz, 1H), 7.80 (s, 1H), 7.65 (d, J=8.1 Hz, 2H), 7.56 (d, J=8.2 Hz, 2H), 7.22 (s, 1H), 7.20 (s, 2H), 6.75 (s, 1H), 6.57 (d, J=5.0 Hz, 1H), 5.95 (s, 1H), 4.60 (tt, J=11.8, 4.0 Hz, 1H), 3.30 (q, J=5.6 Hz, 2H), 2.88 (d, J=11.2 Hz, 2H), 2.39 (t, J=6.0 Hz, 2H), 2.31 (s, 6H), 2.09-2.03 (m, 2H), 2.00 (s, 3H), 1.93 (qd, J=12.2, 3.5 Hz, 2H), 1.79 (td, J=11.8, 2.2 Hz, 2H). $^{13}$C NMR (100 MHz, MeOD) δ 161.8, 160.0, 156.7, 140.2, 139.7, 137.2, 130.6, 127.2 (d, J=3.8 Hz), 126.5, 120.3, 114.0, 54.3, 54.1, 53.2, 35.4, 31.0, 21.5. $^{19}$F NMR (376 MHz, MeOD) δ −64.33, −77.27. HRMS (ESI-TOF) m/z [M+H]+ calcd. for $C_{29}H_{33}F_3N_7^+$ 536.2744, found 536.2749.

Example 36. Synthesis of Compound 36

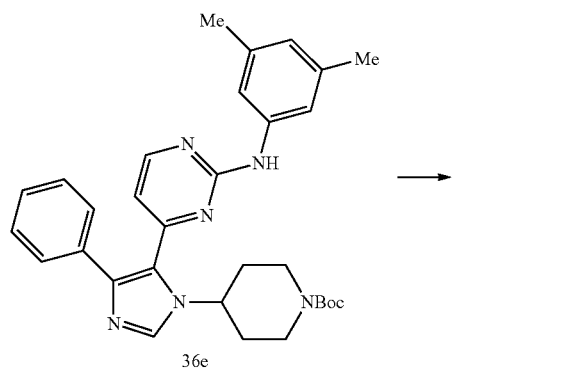

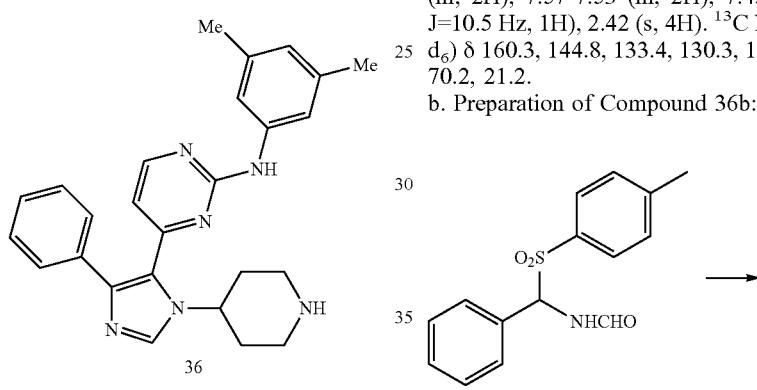

Trifluoroacetic acid (TFA) (0.50 mL) was added to a solution of compound 36e (0.13 mmol) in DCM (0.50 mL). After 16 hours, the reaction was concentrated under reduced pressure. Cold ether (4.0 mL) was used to precipitate compound 32 (92 mg, 0.12 mmol, 95%) as a white solid. $^1$H NMR (400 MHz, MeOD) δ 8.97 (s, 1H), 8.35 (d, J=5.1 Hz, 1H), 7.50 (s, 5H), 7.27-7.19 (m, 2H), 6.79 (tt, J=1.5, 0.8 Hz, 1H), 6.57 (d, J=5.1 Hz, 1H), 5.08 (ddt, J=12.2, 8.5, 3.8 Hz, 1H), 3.46-3.38 (m, 2H), 2.77 (t, J=13.0 Hz, 2H), 2.48 (d, J=13.3 Hz, 2H), 2.34-2.29 (m, 6H), 2.27-2.18 (m, 2H). $^{13}$C NMR (125 MHz, MeOD) δ 162.1, 160.3, 156.5, 140.3, 139.6, 137.3, 136.4, 131.2, 130.4, 130.0, 129.3, 126.4, 120.5, 114.1, 54.5, 44.3, 30.7, 21.5. HRMS (ESI-TOF) m/z [M+Na]+ calcd. for $C_{26}H_{29}N_6^+$ 425.2448, found 425.2449.

The intermediate compound 36e was prepared as follows.

a. Preparation of Compound 36a:

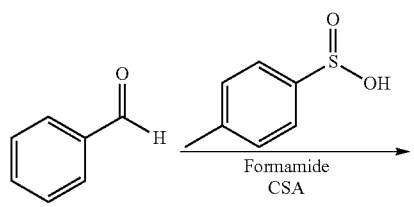

A mixture of benzaldehyde (8.3 mmol, 1.5 equiv.); p-methylbenzenesulfinic acid (5.7 mmol, 1.0 equiv.); camphorsulfonic acid (0.68 mmol, 0.12 equiv.) and formamide (20 mmol, 3.5 equiv.) was stirred at 60° C. for 18 hours. The resulting solid was resuspended in hexane/methanol (4:1, 20 mL) for 30 minutes. The suspension was filtered and dried to give compound 36a (0.60 g, 2.1 mmol) was isolated as a white solid. The crude product was carried on without further purification. $^1$H NMR (500 MHz, DMSO-$d_6$) δ 9.77 (dd, J=10.5, 1.5 Hz, 1H), 7.97 (d, J=1.4 Hz, 1H), 7.77-7.68 (m, 2H), 7.57-7.53 (m, 2H), 7.45-7.42 (m, 5H), 6.39 (d, J=10.5 Hz, 1H), 2.42 (s, 4H). $^{13}$C NMR (125 MHz, DMSO-$d_6$) δ 160.3, 144.8, 133.4, 130.3, 129.6, 129.5, 129.2, 128.3, 70.2, 21.2.

b. Preparation of Compound 36b:

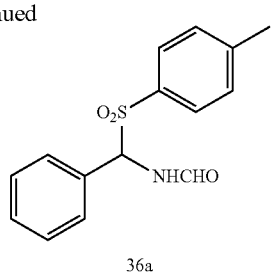

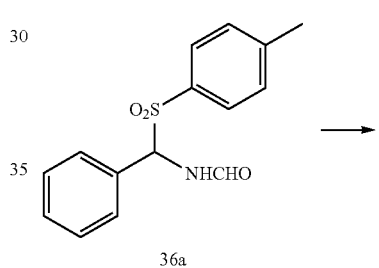

POCl$_3$ (6.6 mmol, 2.0 equiv.) was added drop-wise to a solution of compound 36a (3.3 mmol, 1.0 equiv.) in anhydrous THF at −10° C., followed by 2,6-lutidine (20 mmol, 6.0 equiv.). The reaction was warmed to room temperature and stirred for 16 hours. The reaction was quenched by saturated NH$_4$Cl. The aqueous phase was extracted with ethyl acetate (3×40 mL), dried over anhydrous magnesium sulfate and concentrated under reduced pressure to give the crude product. The crude product was purified by silica gel chromatography using hexane and ethyl acetate (0-100%) as eluent to give compound 36b (0.75 g, 2.8 mmol, 85%) as a brown solid. $^1$H NMR (400 MHz, Chloroform-d) δ 7.68-7.56 (m, 2H), 7.33 (d, J=8.1 Hz, 2H), 7.23-7.16 (m, 4H), 5.56 (s, 1H), 2.47 (s, 3H), 2.39 (s, 3H). $^{13}$C NMR (100 MHz, Chloroform-d) δ165.9, 146.6, 141.2, 130.7, 130.3, 129.88, 129.6, 128.5, 123.6, 76.5, 21.9, 21.5.

c. Preparation of Compound 36c:

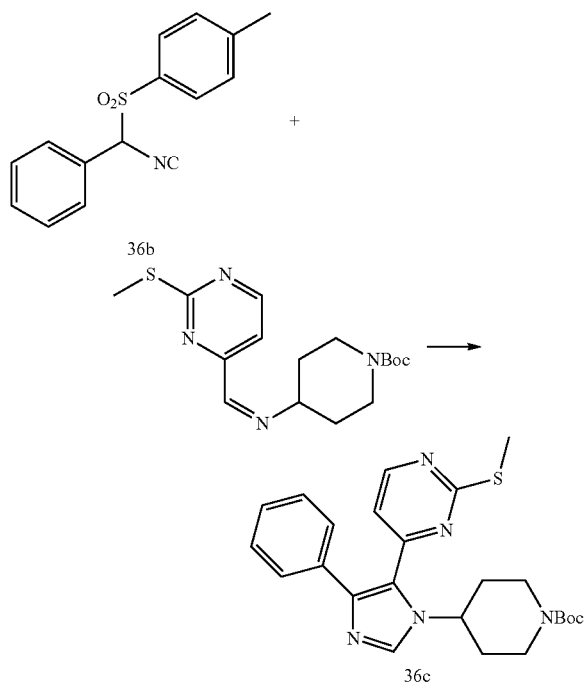

A mixture of compound 36b (1.2 mmol, 1.0 equiv.), tert-butyl 4-(((2-(methylthio)pyrimidin-4-yl)methylene)-amino)piperidine-1-carboxylate (1.2 mmol, 1.0 equiv.) and potassium carbonate (4.8 mmol, 4.0 equiv.) in acetonitrile (3.9 mL) was stirred at 40° C. for 16 hours. The reaction mixture was quenched by addition of brine and extracted with ethyl acetate (3×20 mL). The combined organic phase was dried over anhydrous magnesium sulfate and concentrated under reduced pressure to give the crude product. The crude product was purified by silica gel chromatography using hexane and ethyl acetate (0-100%) as eluent to give compound 36c (0.30 g, 0.66 mmol, 60%) as a yellow solid. $^1$H NMR (500 MHz, Chloroform-d) δ 8.34 (d, J=5.3 Hz, 1H), 7.80 (s, 1H), 7.50-7.46 (m, 2H), 7.37-7.33 (m, 3H), 6.84 (d, J=5.2 Hz, 1H), 4.95-4.84 (m, 1H), 4.33 (s, 2H), 2.89-2.78 (m, 2H), 2.62 (s, 3H), 2.20 (dq, J=12.0, 2.3 Hz, 2H), 1.90 (tt, J=12.3, 6.1 Hz, 2H), 1.51 (s, 10H). $^{13}$C NMR (125 MHz, Chloroform-d) δ 172.8, 158.0, 157.1, 154.6, 144.7, 136.6, 134.3, 128.7, 128.7, 128.1, 124.1, 117.2, 80.2, 54.4, 43.4(br), 33.6, 28.5, 14.2. HRMS (ESI-TOF) m/z [M+Na]+ calcd. for $C_{24}H_{29}N_5NaO_2S^+$ 474.1934, found 474.1933.

d. Preparation of Compound 36d:

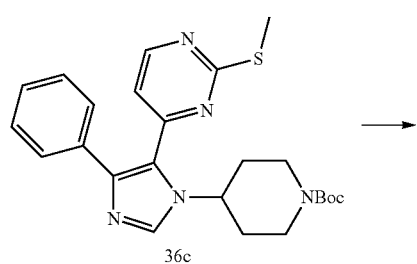

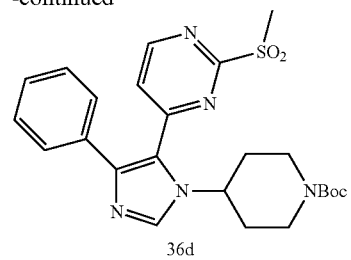

A solution of oxone (1.1 mmol, 2.4 equiv.) in water (8.5 mL) was added dropwise to a solution of compound 36c (0.45 mmol, 1.0 equiv.) in THF (6.0 mL) at −10° C. The reaction mixture was stirred at room temperature for 16 hours, and then quenched by water and extracted with DCM (3×30 mL). The combined organic phase was washed with brine and concentrated under reduced pressure to give compound 36d (0.21 g, 0.43 mmol, 95%) as a yellow solid. $^1$H NMR (400 MHz, Chloroform-d) δ 8.54 (d, J=5.4 Hz, 1H), 7.86 (s, 1H), 7.49-7.45 (m, 2H), 7.40 (ddt, J=4.2, 3.0, 1.6 Hz, 3H), 7.31 (d, J=5.4 Hz, 1H), 5.09 (tt, J=12.0, 3.7 Hz, 1H), 4.37-4.24 (m, 2H), 3.38 (s, 3H), 2.95 (s, 2H), 2.32-2.21 (m, 2H), 1.88-1.82 (m, 2H), 1.48 (s, 9H). $^{13}$C NMR (100 MHz, Chloroform-d) δ 166.1, 159.6, 157.2, 154.7, 147.6, 138.2, 134.0, 129.1, 128.8, 122.8, 80.0, 55.5, 43.3(br), 39.2, 33.7(br), 28.5.

e. Preparation of Compound 36e:

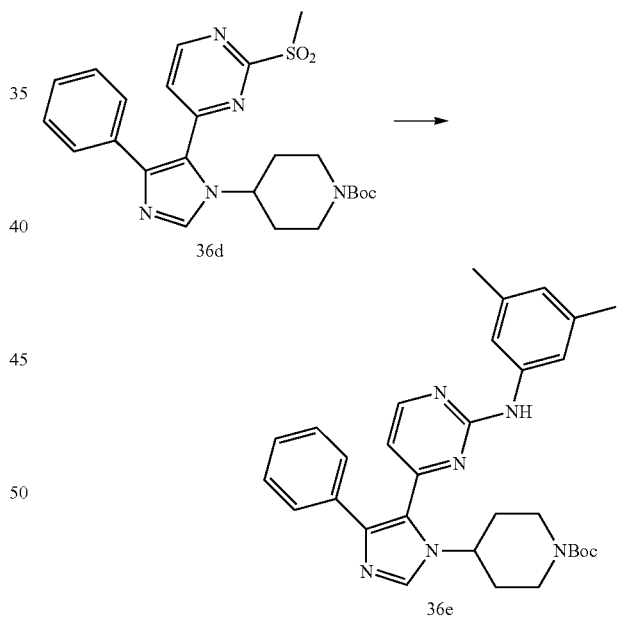

A mixture of compound 36d (0.26 mmol, 1.0 equiv.) and 3,5-dimethylaniline (1.3 mmol, 5.0 equiv.) were heated in a sealed tube at 130° C. for 16 hours behind a blast shield. The crude product was obtained as a brown oil, which was purified by silica gel chromatography using hexane and ethyl acetate (0-100%) as eluent to give compound 36e (64 mg, 0.13 mmol, 50%) as a yellow solid. 1H NMR (400 MHz, Chloroform-d) δ 8.24 (d, J=5.1 Hz, 1H), 7.73 (s, 1H), 7.55-7.51 (m, 2H), 7.34-7.30 (m, 3H), 7.22-7.18 (m, 2H), 7.09 (s, 1H), 6.75 (d, J=2.1 Hz, 1H), 6.59 (d, J=5.1 Hz, 1H), 4.83 (tt, J=12.1, 3.7 Hz, 1H), 2.44 (t, J=12.5 Hz, 2H), 2.32

(s, 6H), 2.07 (s, 2H), 1.79 (tt, J=12.8, 6.4 Hz, 2H), 1.46 (s, 9H). $^{13}$C NMR (125 MHz, Chloroform-d) δ 160.5, 158.7, 158.3, 154.6, 143.5, 138.9, 138.6, 136.0, 134.4, 128.6, 128.5, 127.8, 125.3, 118.4, 113.7, 80.1, 53.8, 43.1(br), 33.5, 28.5, 21.5.

Example 37. Synthesis of Compound 37

Example 38. Synthesis of Compound 38

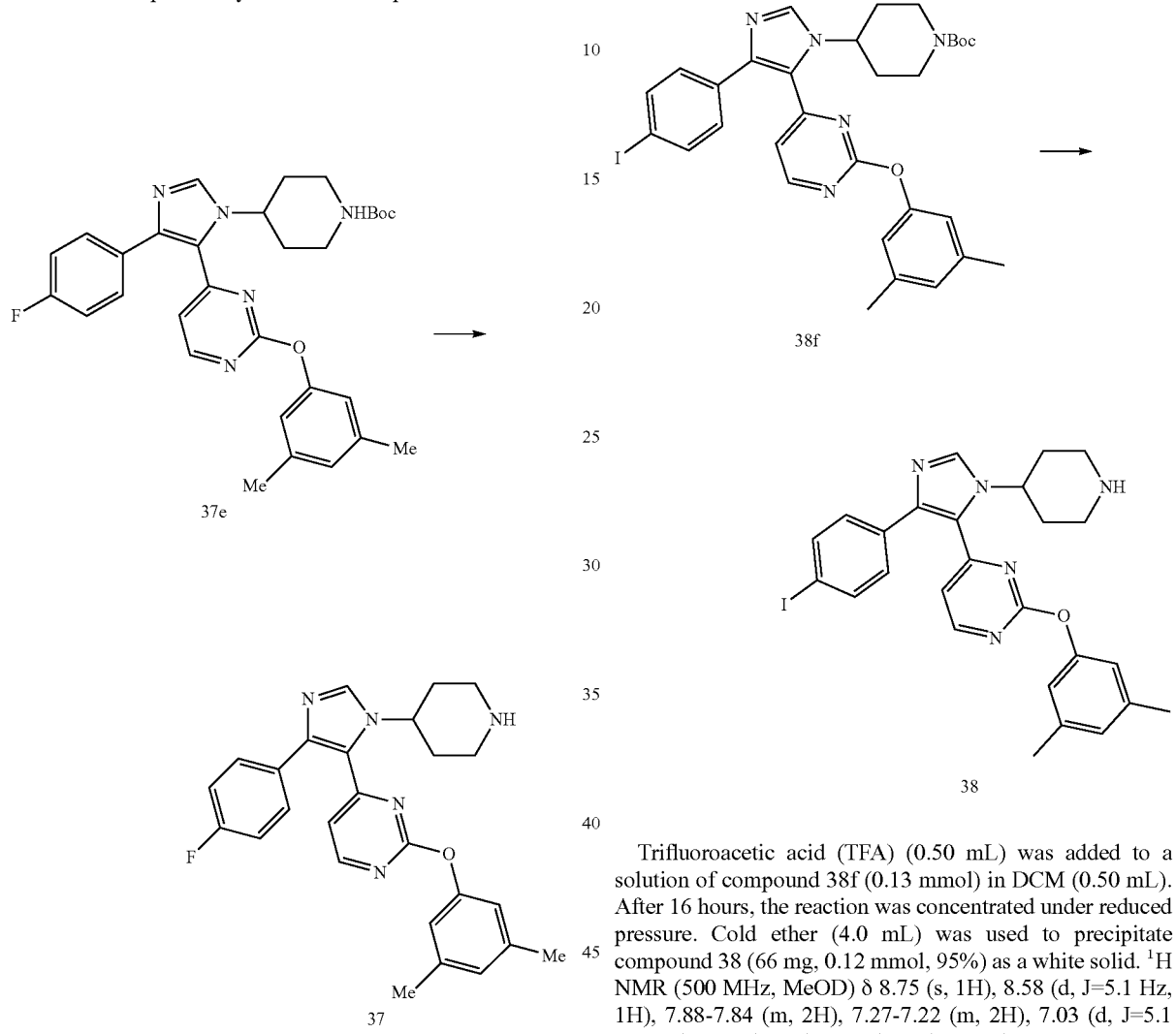

Trifluoroacetic acid (TFA) (0.50 mL) was added to a solution of compound 37e (0.13 mmol) in DCM (0.50 mL). After 16 hours, the reaction was concentrated under reduced pressure. Cold ether (4.0 mL) was used to precipitate compound 37 (40 mg, 0.09 mmol, 70%) as a white solid. $^1$H NMR (400 MHz, methanol-d4) δ 8.41 (d, J=5.2 Hz, 1H), 8.37 (s, 1H), 7.40-7.33 (m, 2H), 7.10 (t, J=8.8 Hz, 2H), 6.87 (s, 1H), 6.85 (d, J=5.2 Hz, 1H), 6.83 (s, 2H), 4.64 (ddd, J=11.9, 7.9, 3.9 Hz, 1H), 3.29-3.25 (m, 2H), 2.61 (td, J=13.1, 3.0 Hz, 2H), 2.26 (s, 6H), 2.15-2.08 (m, 2H), 1.99 (qd, J=13.1, 4.1 Hz, 2H). $^{13}$C NMR (125 MHz, methanol-d4) δ165.1, 164.5 (d, J=248.7 Hz), 162.5, 160.9 (d, J=36.4 Hz), 160.6, 157.6, 152.9, 139.7, 139.0, 136.2, 130.9 (d, J=8.9 Hz), 127.0, 126.4, 125.0, 119.0, 116.7, 115.9 (d, J=22.7 Hz), 115.7, 115.4, 52.4, 43.1, 29.5, 19.9. HRMS: calcd: 444.2200, found: 444.2207.

Trifluoroacetic acid (TFA) (0.50 mL) was added to a solution of compound 38f (0.13 mmol) in DCM (0.50 mL). After 16 hours, the reaction was concentrated under reduced pressure. Cold ether (4.0 mL) was used to precipitate compound 38 (66 mg, 0.12 mmol, 95%) as a white solid. $^1$H NMR (500 MHz, MeOD) δ 8.75 (s, 1H), 8.58 (d, J=5.1 Hz, 1H), 7.88-7.84 (m, 2H), 7.27-7.22 (m, 2H), 7.03 (d, J=5.1 Hz, 1H), 6.99 (s, 1H), 6.94 (s, 2H), 4.76 (tt, J=11.9, 4.0 Hz, 1H), 3.39 (dt, J=13.0, 2.5 Hz, 2H), 2.75 (td, J=13.1, 3.0 Hz, 2H), 2.37 (s, 6H), 2.27-2.21 (m, 2H), 2.15 (td, J=12.8, 4.1 Hz, 2H).

The intermediate compound 38f was prepared as follows.
a. Preparation of Compound 36f:

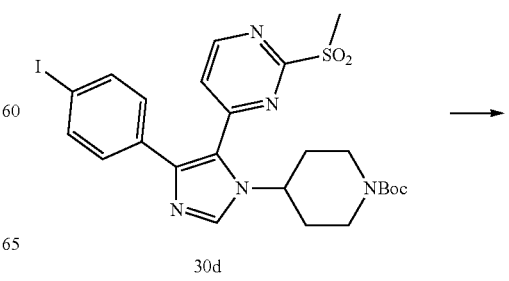

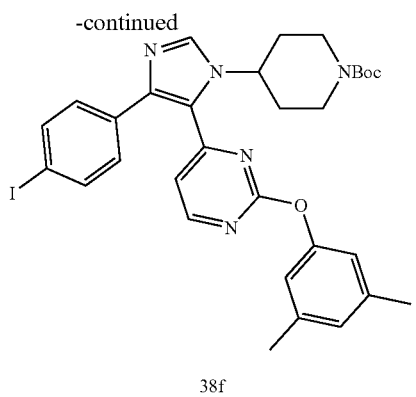

38f 3,5-Dimethylphenol (0.64 mmol) in anhydrous THF (1.5 mL) was dropwise added to a suspension of NaH (60% in mineral oil, 0.64 mmol) in THF (2 mL) at −10° C. The mixture was stirred for 10 min, followed by the addition of 30d (0.16 mmol) in THF (1.5 mL). The reaction was stirred at room temperature for 16 h, quenched by water and extracted with ethyl acetate (3×20 mL). The crude product was purified by silica gel chromatography using hexane and ethyl acetate (0-100%) as eluent to give compound 38f (53 mg, 0.08 mmol, 50%) as a white solid. $^1$H NMR (400 MHz, CDCl$_3$) δ 8.40 (d, J=5.2 Hz, 1H), 7.70 (d, J=2.7 Hz, 2H), 7.68 (d, J=1.9 Hz, 1H), 7.24-7.19 (m, 2H), 6.90 (s, 1H), 6.87 (d, J=5.2 Hz, 1H), 6.84 (s, 2H), 4.71-4.58 (m, 1H), 2.47 (t, J=11.4 Hz, 2H), 2.34 (s, 6H), 1.89 (d, J=12.3 Hz, 2H), 1.68 (tt, J=16.6, 8.5 Hz, 2H), 1.47 (s, 10H).

Example 39. Synthesis of Compound 39

Trifluoroacetic acid (TFA) (0.50 mL) was added to a solution of compound 39e (0.13 mmol) in DCM (0.50 mL). After 16 hours, the reaction was concentrated under reduced pressure. Cold ether (4.0 mL) was used to precipitate compound 39 (31 mg, 0.07 mmol, 50%) as a white solid. $^1$H NMR (500 MHz, methanol-d4) δ 8.55 (d, J=5.1 Hz, 1H), 7.50-7.46 (m, 2H), 7.32 (d, J=8.2 Hz, 2H), 7.25-7.19 (m, 4H), 6.98 (d, J=5.1 Hz, 1H), 4.77 (tt, J=11.6, 4.1 Hz, 1H), 3.44-3.36 (m, 2H), 2.76 (td, J=13.0, 3.2 Hz, 2H), 2.42 (s, 3H), 2.23-2.09 (m, 4H). $^{13}$C NMR (125 MHz, methanol-d4) δ 165.3, 164.6, (d, J=249.3 Hz), 162.6, 161.2, 161.0, (d, J=35.5 Hz), 157.7, 150.7, 138.2, 136.1, 135.4, 131.0 (d, J=9.0 Hz), 130.9, 130.0, 125.8, 125.0, 121.3, 116.8, 115.9 (d, J=21.8 Hz), 115.8, 52.5, 43.0, 29.4, 19.5. HRMS: calcd: 430.2043, found: 430.2041.

Example 40. Synthesis of Compound 40

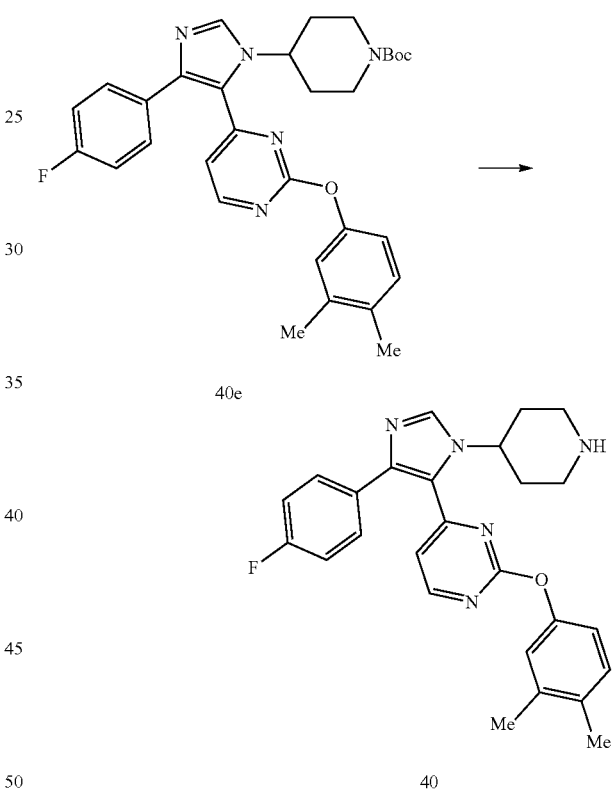

Trifluoroacetic acid (TFA) (0.50 mL) was added to a solution of compound 40e (0.13 mmol) in DCM (0.50 mL). After 16 hours, the reaction was concentrated under reduced pressure. Cold ether (4.0 mL) was used to precipitate compound 40 (31 mg, 0.07 mmol, 50%) as a white solid. $^1$H NMR (400 MHz, methanol-d4) δ 8.53 (d, J=5.1 Hz, 1H), 8.51 (s, 1H), 7.51-7.45 (m, 2H), 7.26 (d, J=8.2 Hz, 1H), 7.24-7.19 (m, 2H), 7.12 (d, J=2.5 Hz, 1H), 7.04 (dd, J=8.1, 2.5 Hz, 1H), 6.96 (d, J=5.1 Hz, 1H), 4.78 (dq, J=11.9, 4.0 Hz, 1H), 3.42-3.33 (m, 2H), 2.73 (td, J=13.0, 3.1 Hz, 2H), 2.33 (s, 6H), 2.25-2.16 (m, 2H), 2.10 (qd, J=12.9, 3.9 Hz, 2H). $^{13}$C NMR (125 MHz, methanol-d4) δ 165.3, 164.6 (d, J=248.9 Hz), 162.6, 160.8, (d, J=35.1 Hz) 157.1, 150.8, 138.3, 137.9, 136.0, 134.0, 131.1, 131.0 (d, J=8.6 Hz), 130.3, 129.8, 125.5, 125.1, 122.3, 118.6, 116.8, 115.9 (d, J=22.1 Hz), 115.8, 52.6, 43.0, 29.4, 18.5, 17.8. HRMS: calcd: 444.2200, found: 444.2226.

Example 41. Synthesis of Compound 41

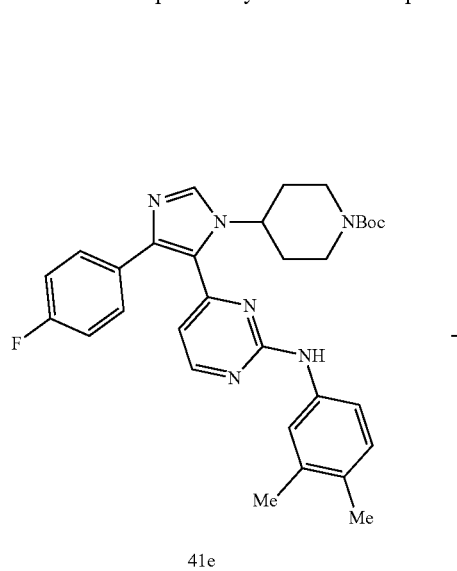

41e

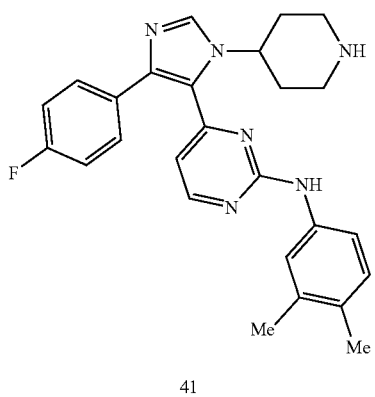

41

Trifluoroacetic acid (TFA) (0.50 mL) was added to a solution of compound 41e (0.13 mmol) in DCM (0.50 mL). After 16 hours, the reaction was concentrated under reduced pressure. Cold ether (4.0 mL) was used to precipitate compound 41 (31 mg, 0.07 mmol, 50%) as a white solid. $^1$H NMR (500 MHz, methanol-d4) δ 8.28 (d, J=5.0 Hz, 1H), 8.23 (s, 0.5H), 7.55-7.46 (m, 2H), 7.35 (dq, J=4.7, 2.4 Hz, 2H), 7.22-7.09 (m, 3H), 6.52 (d, J=5.1 Hz, 1H), 5.00 (ddt, J=12.1, 8.3, 3.8 Hz, 1H), 3.42-3.34 (m, 2H), 2.76-2.67 (m, 2H), 2.39 (dt, J=13.3, 2.7 Hz, 2H), 2.28 (d, J=3.6 Hz, 6H), 2.15 (qd, J=13.2, 4.2 Hz, 2H). $^{13}$C NMR (125 MHz, methanol-d4) δ 163.9, 161.9, 161.7, 161.4, 160.8, 158.5, 157.0, 139.9, 137.0, 136.6, 135.8, 131.6, 130.5, 130.4, 129.4, 125.4, 122.8, 119.0, 117.9, 115.4, 115.2, 112.4, 51.6, 43.1, 29.7, 18.6, 17.8. HRMS: calcd: 443.2359, found: 443.2345.

Example 42 Synthesis of Compound 42

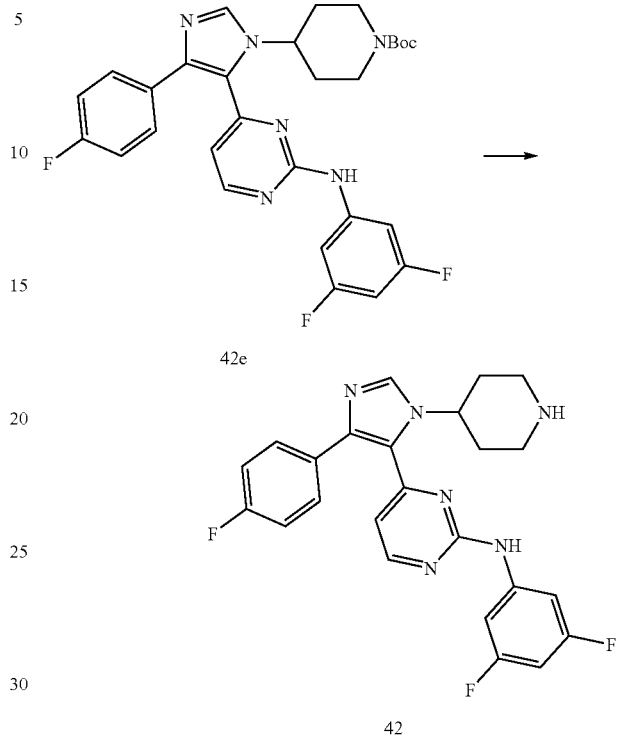

42e

42

Trifluoroacetic acid (TFA) (0.50 mL) was added to a solution of compound 42e (0.13 mmol) in DCM (0.50 mL). After 16 hours, the reaction was concentrated under reduced pressure. Cold ether (4.0 mL) was used to precipitate compound 42 (31 mg, 0.07 mmol, 56%) as a white solid. $^1$H NMR (400 MHz, methanol-d4) δ 8.46 (d, J=4.9 Hz, 1H), 7.40-7.32 (m, 1H), 7.14-7.03 (m, 1H), 6.99-6.82 (m, 2H), 3.44-3.36 (m, 2H), 2.88 (td, J=13.1, 3.0 Hz, 1H), 2.21 (d, J=13.4 Hz, 1H), 2.10 (qd, J=13.0, 4.1 Hz, 2H), 1.19 (s, 1H), 0.84-0.73 (m, 1H). $^{13}$C NMR (125 MHz, methanol-d4) δ 163.3 (dd, JC-F=248.8, 15.2 Hz), 161.1 (d, JC-F=35.2 Hz), 160.6, 158.6, 154.7 (d, J C-F=13.4 Hz), 136.5, 130.7 (d, JC-F=8.5 Hz), 117.7, 115.6 (d, JC-F=22.1 Hz), 105.8 (t, JC-F=22.1, 21.5 Hz), 100.9 (t, JC-F=26.1 Hz), 51.9, 43.2, 29.7. HRMS: calcd: 451.1680, found: 452.2210.

Example 43. Synthesis of Compound 43

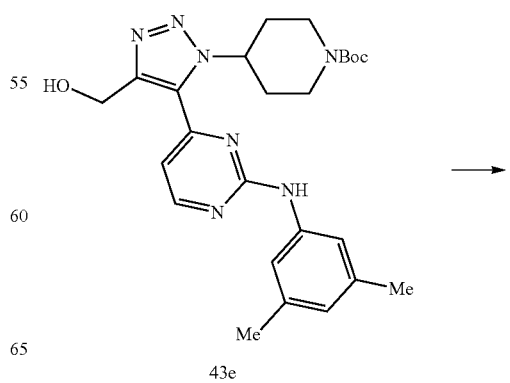

43e

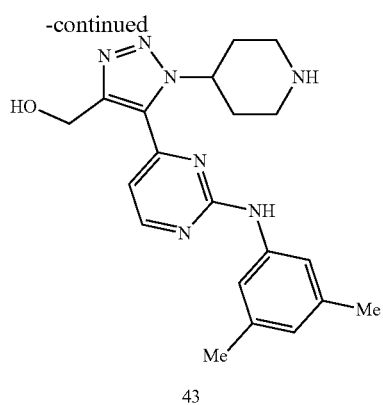

43

Trifluoroacetic acid (TFA) (0.50 mL) was added to a solution of compound 42e (0.13 mmol) in DCM (0.50 mL). After 16 hours, the reaction was concentrated under reduced pressure. Cold ether (4.0 mL) was used to precipitate compound 42 (31 mg, 0.07 mmol, 56%) as a white solid. $^1$H NMR (500 MHz, MeOD) δ 8.60 (d, J=5.0 Hz, 1H), 7.31 (d, J=5.0 Hz, 1H), 7.19 (s, 1H), 6.79 (s, 2H), 5.36 (tt, J=10.8, 4.2 Hz, 1H), 4.79 (s, 2H), 3.44 (d, J=13.2 Hz, 2H), 2.91— 2.75 (m, 2H), 2.48-2.32 (m, 4H), 2.31 (s, 6H). $^{13}$C NMR (126 MHz, MeOD) δ 160.8, 159.6, 154.3, 146.1, 139.1, 138.1, 132.6, 124.9, 119.3, 111.6, 54.4, 54.1, 42.7, 28.8, 20.1. IR (NaCl, thin film, cm-1): 2932, 2859, 1679, 1627, 1595, 1463, 1403, 1190, 1139, 1076. HRMS (ESI): calcd for C20H25N7NaO+, (M+Na)+402.2013, found 402.2022.

Example 44. Synthesis of Compound 44

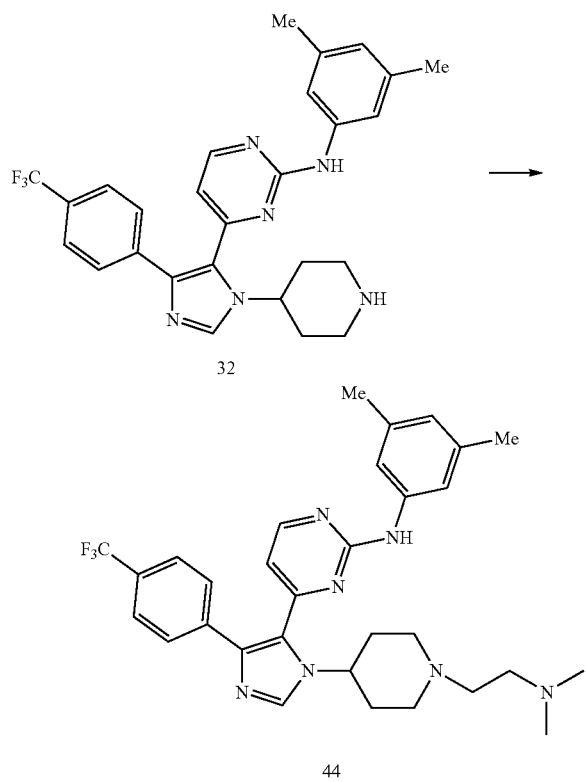

Compound 32 (0.11 mmol, 1.0 equiv.), 2-Chloro-N,N-dimethylethylamine hydrochloride (0.17 mmol, 1.5 equiv.), NaI (0.17 mmol, 1.5 equiv.) and K$_2$CO$_3$ (0.77 mmol, 7.0 equiv.) were dissolved in methyl ethyl ketone (0.37 mL). The reaction was stirred at room temperature for 16 hours then quenched by water and extracted with ethyl acetate (3×20 mL). The combined organic phase was dried over anhydrous magnesium sulfate and concentrated under reduced pressure to give the crude product, which was purified by neutral alumina chromatography using hexane and ethyl acetate (0-100%) as eluent to give the desired product 44 (25 mg, 0.044 mmol, 40%). $^1$H NMR (500 MHz, CDCl$_3$) δ 8.31 (d, J=5.4 Hz, 1H), 7.79 (s, 1H), 7.64 (d, J=8.0 Hz, 2H), 7.56 (d, J=8.0 Hz, 2H), 7.22 (s, 2H), 7.07 (s, 1H), 6.75 (s, 1H), 6.58 (d, J=4.9 Hz, 1H), 4.57 (tt, J=10.6, 4.9 Hz, 1H), 2.95 (d, J=11.4 Hz, 2H), 2.39 (h, J=7.1 Hz, 4H), 2.32 (s, 6H), 2.24 (s, 6H), 2.02 (q, J=6.1, 3.4 Hz, 4H), 1.82 (td, J=11.6, 3.0 Hz, 2H). $^{13}$C NMR (125 MHz, MeOD) δ 162.2, 160.0, 159.1, 140.8, 139.3, 138.0, 129.9, 126.5, 126.5, 125.8, 119.9, 114.1, 57.4, 56.4, 55.3, 54.0, 45.8, 45.7, 33.8, 21.6. $^{19}$F NMR (470 MHz, CDCl$_3$) δ −62.45. HRMS (ESI-TOF) m/z [M+H]+ calcd. for C$_{31}$H$_{37}$F$_3$N$_7^+$ 564.3057, found 564.3047.

Example 45. Synthesis of Compound 45

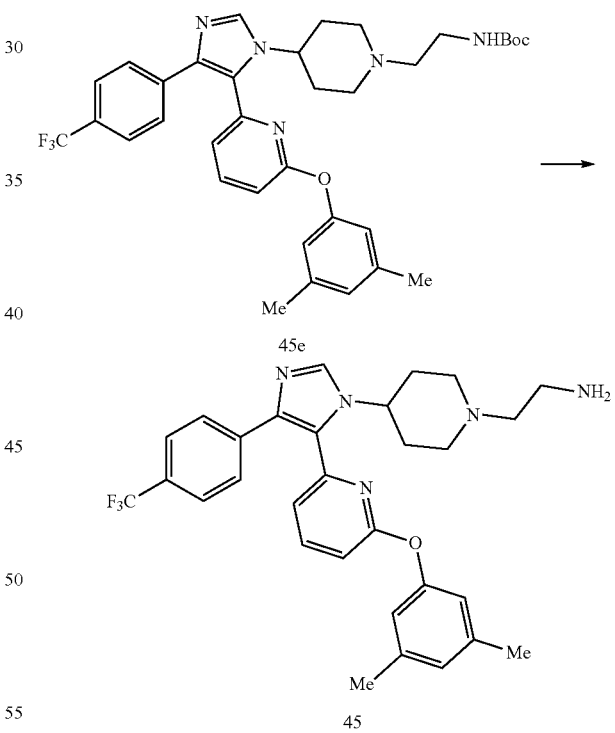

TFA (0.50 mL) was added to a solution of compound 45e (0.10 mmol) in DCM (0.50 mL). After 16 hours, the reaction was concentrated under reduced pressure. Cold ether (3 mL) was used to precipitate compound 45 (99 mg, 0.10 mmol, 96%). $^1$H NMR (500 MHz, MeOD) δ9.04 (s, 1H), 7.82 (t, J=7.8 Hz, 1H), 7.74 (d, J=8.0 Hz, 2H), 7.57 (d, J=8.0 Hz, 2H), 7.11 (d, J=8.3 Hz, 1H), 7.04 (d, J=7.3 Hz, 1H), 6.91 (s, 1H), 6.83 (s, 2H), 4.53 (tt, J=12.0, 4.2 Hz, 1H), 3.43 (d, J=12.4 Hz, 2H), 3.34 (t, J=6.5 Hz, 2H), 3.24 (t, J=6.6 Hz, 2H), 2.68 (t, J=12.4 Hz, 2H), 2.35 (dd, J=13.4, 9.6 Hz, 2H), 2.30 (s, 6H), 2.18 (dd, J=13.9, 3.8 Hz, 2H). $^{13}$C NMR (100 MHz, MeOD) δ 165.6, 154.9, 144.5, 142.5, 141.0, 130.4, 128.0, 127.2 (d, J=3.9 Hz), 122.5, 120.5, 114.2, 54.3, 53.1, 35.6, 30.9, 21.4. $^{19}$F NMR (470 MHz, MeOD) δ −64.40, −77.20. HRMS (ESI-TOF) m/z [M+H]+ calcd. for $C_{30}H_{32}F_3N_5O^+$ 536.2632, found 536.2627.

The intermediate compound 45e was prepared as follows.

a. Preparation of Compound 45a:

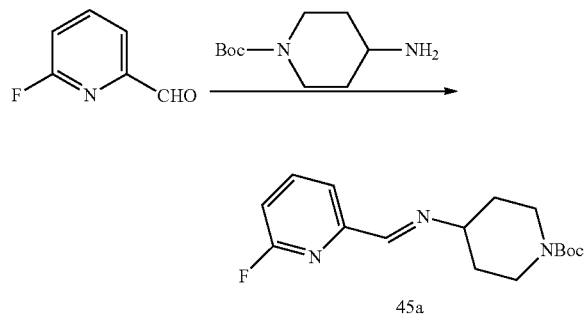

45a

Commercially available 6-fluoropicolinaldehyde (1.0 g, 8.0 mmol) and tert-butyl 4-aminopiperidine-1-carboxylate (1.6 g, 8.0 mmol) were dissolved in anhydrous $CH_2Cl_2$ (50 mL). $MgSO_4$ (1.9 g, 16 mmol) was added to the reaction mixture and was allowed to stir at room temperature for 18 hours. $MgSO_4$ was filtered out and the solvent was removed under reduced pressure. The crude compound thus obtained was purified via combiflash, 0-100% ethyl acetate in hexanes over 20 minutes to obtain compound 45a as white solid (1.29 g, 53%). $^1$H NMR (500 MHz, Chloroform-d) δ 8.31 (s, 1H), 7.93-7.89 (m, 2H), 7.85 (q, J=7.8 Hz, 1H), 7.01-6.96 (m, 2H), 4.09 (s, 2H), 3.49 (p, J=7.1, 6.6 Hz, 1H), 3.02 (s, 2H), 1.75 (dt, J=9.4, 5.8 Hz, 4H), 1.49 (s, 9H); $^{13}$C NMR (126 MHz, Chloroform-d) δ 164.2, 162.3, 159.0, 154.9, 153.2 (d, J=12.4 Hz), 141.4 (d, J=7.6 Hz), 118.5 (d, J=4.0 Hz), 110.9, 110.6, 79.5, 66.9, 32.9, 28.4; $^{19}$F NMR (470 MHz, Chloroform-d) δ −67.71 (d, J=7.7 Hz).

b. Preparation of Compound 45b:

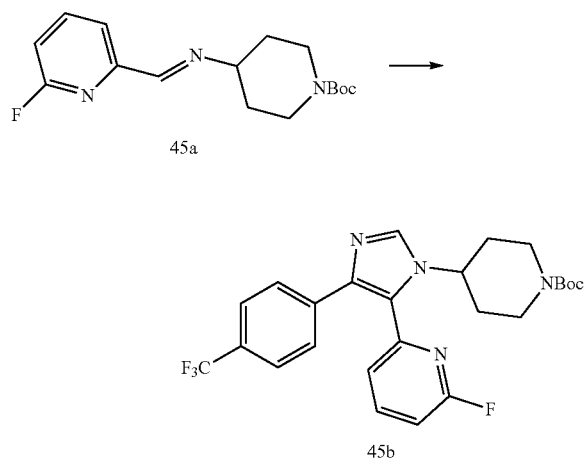

To a solution of isonitrile 32b (400 mg, 1.18 mmol) and imine 45a (362 mg, 1.18 mmol) in $CH_3CN$ (10 mL) was added $K_2CO_3$ (652 mg, 4.72 mmol). The resulting reaction mixture was heated to 48° C. in an oil-bath with stirring for 16 hours. Reaction was diluted with 25 mL $H_2O$ and the crude compound was extracted with ethyl acetate (10 mL×3). The combine organic layer was dried over $MgSO_4$ and concentrated in vacuo. The crude compound was purified via combiflash, 0-100% ethyl acetate in hexanes over 20 minutes to provide compound 45b as pale yellow solid (466 mg, 61%). $^1$H NMR (500 MHz, Chloroform-d) δ 7.93 (s, 1H), 7.77 (q, J=7.9 Hz, 1H), 7.58-7.52 (m, 5H), 7.14 (d, J=7.4 Hz, 1H), 6.97 (d, J=8.2 Hz, 1H), 4.55 (t, J=12.0 Hz, 1H), 4.28 (s, 2H), 2.76 (s, 2H), 2.14 (d, J=11.7 Hz, 2H), 1.85 (qd, J=12.3, 4.0 Hz, 3H), 1.47 (s, 9H). NMR (125 MHz, Chloroform-d) δ 164.2, 162.3, 154.5, 141.9 (d, J=7.9 Hz), 135.3, 128.1, 125.4 (d, J=3.7 Hz), 123.6 (d, J=4.2 Hz), 109.1, 108.8, 80.1, 54.2, 33.3, 28.4. $^{19}$F NMR (470 MHz, Chloroform-d) δ −62.59, −64.97 (d, J=5.7 Hz).

c. Preparation of Compound 45c:

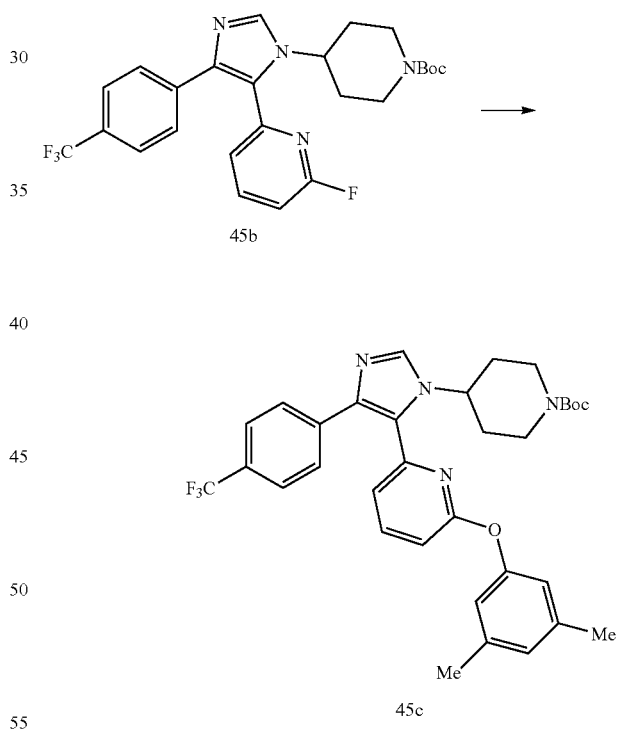

To a solution of compound 45b (450 mg, 0.92 mmol) and 2,6-dimethylphenol (225 mg, 1.84 mmol) in DMSO (4 mL) in a vacuum dried sealed tube was added $K_2CO_3$ (509 mg, 3.68 mmol). The resulting reaction mixture was heated to 150° C. in an oil-bath with stirring for 24 hours. After cooling, the crude reaction mixture was diluted with $H_2O$ (20 mL) and brine (10 mL). The crude compound was extracted with ethyl acetate (10 mL×3) and the combined organic layers were dried over MgSO4 and the solvent was removed in vacuo. The crude compound was purified via combiflash, 0-100% ethyl acetate in hexanes over 20 minutes to provide compound 45c as white solid (501 mg, 92%). $^1$H NMR (500 MHz, Chloroform-d) δ 7.94 (s, 1H), 7.68-7.54 (m, 6H), 6.94 (t, J=6.6 Hz, 2H), 6.87 (s, 1H), 6.78 (s, 2H), 4.34 (t, J=11.9 Hz, 1H), 4.07 (brs, 1H), 2.43 (d, J=12.2 Hz, 2H), 2.32 (s, 6H), 1.84 (d, J=11.9 Hz, 2H), 1.66 (q, J=11.7 Hz, 2H), 1.47 (s, 9H). $^{13}$C NMR (125 MHz, Chloroform-d) δ 154.4, 153.5, 140.2, 139.5, 134.3, 128.3, 126.9, 125.5, 125.4, 120.6, 119.4, 111.3, 80.1, 54.3, 28.4, 21.3.

d. Preparation of Compound 45d:

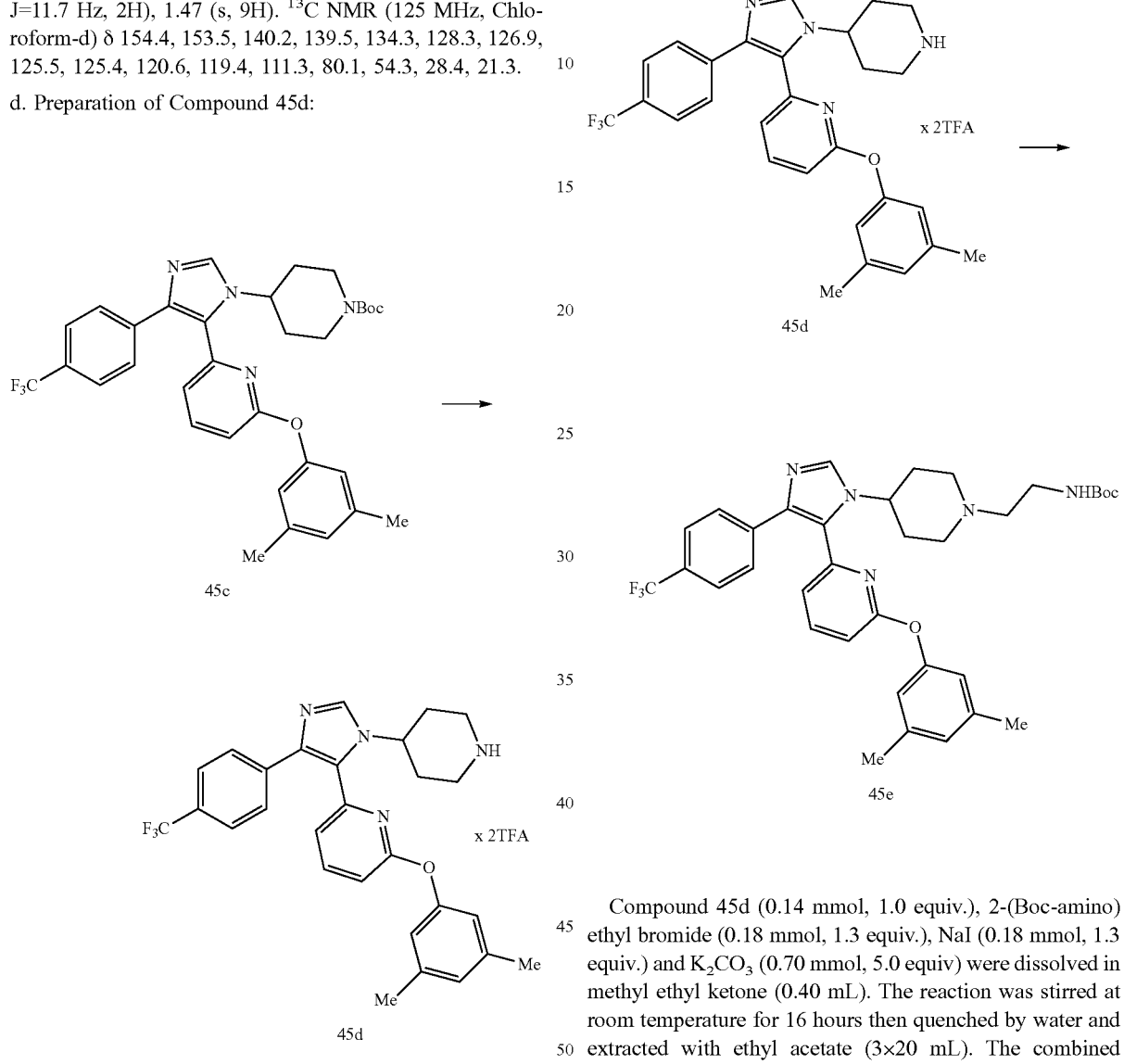

Compound 45c (480 mg, 0.81 mmol) was dissolved in CH$_2$Cl$_2$ (5 mL) and trifluoroacetic acid (5 mL) was added to it. The resulting reaction mixture was stirred at room temperature for 1 hour. The solvent was evaporated, and the crude compound was triturated with diethyl ether. Compound 45d was obtained as a white solid (510 mg, 87%). $^1$H NMR (500 MHz, DMSO-d$_6$) δ8.80 (d, J=10.3 Hz, 1H), 8.42 (d, J=10.4 Hz, 1H), 8.18 (s, 1H), 7.98-7.91 (m, 1H), 7.68 (d, J=8.4 Hz, 2H), 7.55 (d, J=8.2 Hz, 2H), 7.18 (dd, J=7.7, 2.1 Hz, 2H), 6.84 (s, 1H), 6.80 (s, 2H), 4.18 (tt, J=10.8, 4.8 Hz, 1H), 3.27 (d, J=12.6 Hz, 2H), 2.80 (q, J=10.9 Hz, 2H), 2.22 (s, 6H), 2.07-1.93 (m, 4H). $^{13}$C NMR (125 MHz, DMSO-d$_6$) δ 163.3, 153.4, 146.2, 141.3, 139.0, 135.4, 127.9, 127.3, 126.3, 125.4, 121.3, 118.9, 112.0, 50.6, 42.5, 39.5, 29.5, 20.8. $^{19}$F NMR (470 MHz, DMSO-d6) δ −63.07, −76.55.

e. Preparation of Compound 45e:

Compound 45d (0.14 mmol, 1.0 equiv.), 2-(Boc-amino)ethyl bromide (0.18 mmol, 1.3 equiv.), NaI (0.18 mmol, 1.3 equiv.) and K$_2$CO$_3$ (0.70 mmol, 5.0 equiv) were dissolved in methyl ethyl ketone (0.40 mL). The reaction was stirred at room temperature for 16 hours then quenched by water and extracted with ethyl acetate (3×20 mL). The combined organic phase was dried over anhydrous magnesium sulfate and concentrated under reduced pressure to give the crude product, which was purified by silica gel chromatography using DCM and methanol (0-20%) as eluent to give compound 45e (65 mg, 0.074 mmol, 73%). $^1$H NMR (500 MHz, CDCl$_3$) δ 7.69 (s, 1H), 7.60 (t, J=7.7 Hz, 1H), 7.57 (d, J=8.2 Hz, 2H), 7.52 (d, J=8.1 Hz, 2H), 6.93 (d, J=7.4 Hz, 1H), 6.89 (d, J=8.2 Hz, 1H), 6.83 (s, 1H), 6.78 (s, 2H), 4.93 (s, 1H), 4.20-4.08 (m, 1H), 3.20 (t, J=6.0 Hz, 2H), 2.80 (d, J=11.1 Hz, 2H), 2.40 (t, J=6.1 Hz, 2H), 2.31 (s, 6H), 1.86-1.81 (m, 4H), 1.73 (td, J=11.1, 5.9 Hz, 2H), 1.46 (s, 9H). $^{13}$C NMR (125 MHz, CDCl$_3$) δ 163.9, 156.1, 153.9, 148.1, 140.0, 139.4, 139.2, 138.5, 135.2, 128.1, 126.8, 125.3 (q, J=3.7 Hz), 120.8, 119.5, 110.7, 57.2, 53.6, 52.8, 37.6, 33.5, 28.6, 21.5. $^{19}$F NMR (376 MHz, CDCl$_3$) δ −62.44.

Example 46. Synthesis of Compound 46

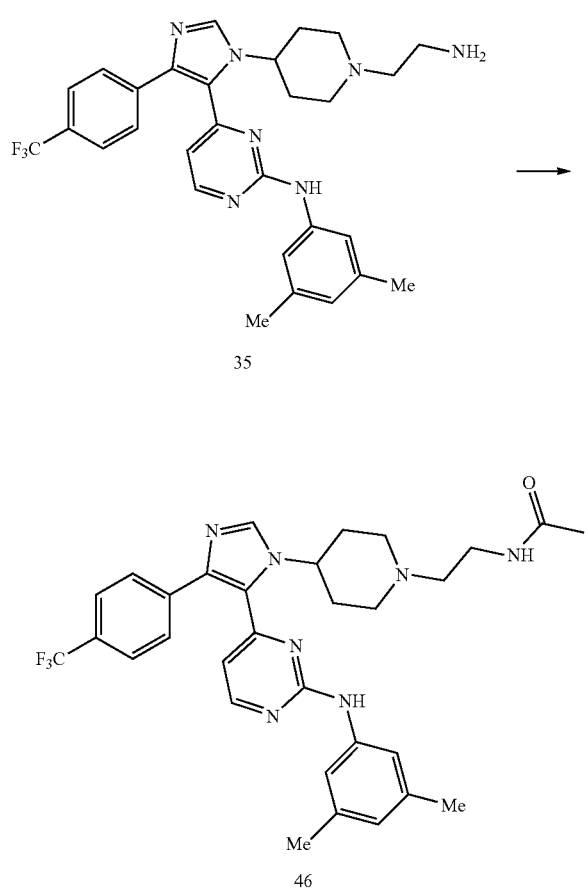

Compound 35 (0.071 mmol, 1.0 equiv.) was dissolved in DCM (0.70 mL), triethylamine (0.14 mmol, 2.0 equiv.) was added dropwise followed by acetic anhydride (0.35 mmol, 5.0 equiv.). The reaction was stirred at room temperature for 16 hours and then quenched by water and extracted by ethyl acetate (3×20 mL). The combined organic phase was dried over anhydrous magnesium sulfate and concentrated under reduced pressure to give the crude product, which was purified by silica gel chromatography using DCM and methanol (0-20%) as eluent to give compound 46 (40 mg, 0.070 mmol, 95%). $^1$H NMR (500 MHz, CDCl$_3$) δ 8.31 (d, J=5.0 Hz, 1H), 7.80 (s, 1H), 7.65 (d, J=8.1 Hz, 2H), 7.56 (d, J=8.2 Hz, 2H), 7.20 (s, 2H), 6.74 (s, 1H), 6.57 (d, J=5.2 Hz, 1H), 5.94 (d, J=5.3 Hz, 1H), 4.60 (tt, J=12.2, 4.1 Hz, 1H), 3.30 (q, J=5.7 Hz, 2H), 2.90-2.84 (m, 2H), 2.39 (t, J=6.1 Hz, 2H), 2.30 (s, 5H), 2.08-2.01 (m, 2H), 2.00 (s, 3H), 1.92 (qd, J=12.1, 3.5 Hz, 2H), 1.79 (t, J=11.6 Hz, 2H). $^{13}$C NMR (125 MHz, CDCl$_3$) δ 170.2, 160.7, 158.8, 158.4, 141.4, 138.8, 138.7, 138.0, 136.2, 128.5, 126.1, 125.5 (dd, J=8.6, 4.5 Hz), 118.4, 113.7, 56.5, 53.9, 52.6, 36.4, 33.6, 23.5, 21.6. $^{19}$F NMR (470 MHz, CDCl$_3$) δ −62.45. Final compound failed to ionize by ESI-MS.

Example 47. Synthesis of Compound 47

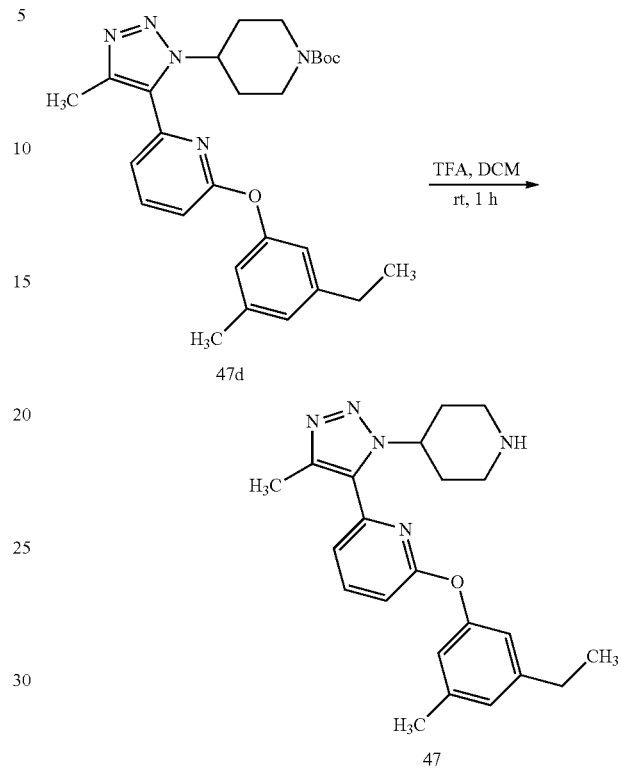

General procedure V was used and product 47 (16.8 mg, 95%) was isolated as a white solid. Analysis by $^{19}$F NMR with 2,2,2-trifluoroethanol as the internal standard indicated formation of a bis-TFA salt. $^1$H NMR (500 MHz, MeOD) δ 8.02 (apparent t, J=7.9 Hz, 1H), 7.39 (d, J=7.4 Hz, 1H), 7.12 (d, J=8.3 Hz, 1H), 6.96 (s, 1H), 6.84 (s, 2H), 4.94-4.84 (m, 1H), 3.38-3.33 (m, 2H), 2.70 (apparent t, J=11.6 Hz, 2H), 2.64 (q, J=7.9 Hz, 2H), 2.46 (s, 3H), 2.36 (s, 3H), 2.32-2.21 (m, 2H), 2.03 (apparent dd, J=14.2, 4.0 Hz, 2H), 1.22 (t, J=7.6 Hz, 3H). $^{13}$C{$^1$H} NMR (126 MHz, MeOD) δ 163.7, 154.0, 146.1, 144.2, 141.5, 140.9, 139.7, 132.1, 125.1, 119.2, 118.9, 117.9, 111.7, 53.6, 42.7, 28.6, 28.2, 20.0, 14.7, 10.2. IR (NaCl, thin film, cm$^{-1}$): 2969, 2929, 2852, 1688, 1678, 1590, 1573, 1454, 1432, 1330, 1298, 1248, 1202, 1135. HRMS (ESI-TOF) m/z [M+H]$^+$ calcd for C$_{22}$H$_{28}$N$_5$O$^+$ 378.2288, found 378.2281.

The intermediate Compound 47d was prepared as follows.

a. Preparation of Compound 47a

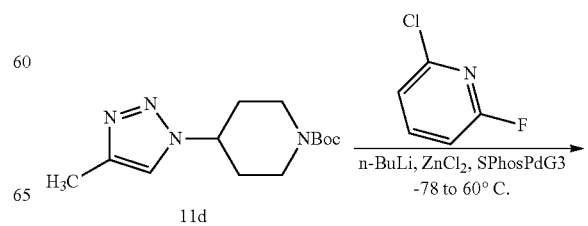

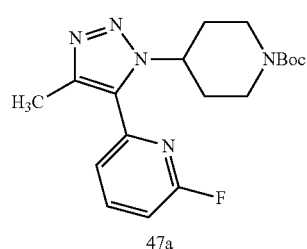

47a

To a solution of triazole (Preparative Example 4, 77.6 mg, 0.292 mmol) in DME (2 mL) cooled in a dry ice/acetone bath was added n-BuLi (0.13 mL, 2.5 M in hexanes, 0.32 mmol). After 15 minutes, a freshly prepared solution of $ZnCl_2$ (67.1 mg, 0.493 mmol) in THF (2 mL) was added and the reaction was warmed to room temperature. After 10 minutes, a solution of 2-chloro-6-fluoropyridine (77.5 mg, 0.589 mmol) and SPhosPdG3 (9.3 mg, 12 μmol) in DME (2 mL) was added and the reaction was heated to 60° C. After 4 hours, the reaction was cooled to room temperature and quenched by the addition of saturated aqueous $NH_4Cl$. The reaction mixture was extracted with EtOAc. The combined organic phases were washed with brine, dried ($Na_2SO_4$), filtered, and concentrated under reduced pressure. Final purification by column chromatography (40-80% EtOAc in Hexanes) afforded compound 47a (91.8 mg, 87%). 1H NMR (500 MHz, $CDCl_3$) δ 7.98 (apparent q, J=7.9 Hz, 1H), 7.37 (d, J=7.4 Hz, 1H), 7.01 (dd, J=8.4, 2.8 Hz, 1H), 4.98 (tt, J=11.3, 4.1 Hz, 1H), 4.26 (br, 2H), 2.89 (br, 2H), 2.47 (s, 3H), 2.24 (br, 2H), 2.11 (apparent d, J=12.1 Hz, 2H), 1.48 (s, 9H). $^{13}C\{^{1}H\}$ NMR (126 MHz, $CDCl_3$) δ 163.1 (d, $J_{C-F}$=241.9 Hz), 154.6, 146.1 (d, $J_{C-F}$=14.4 Hz), 142.3, 142.1 (d, $J_{C-F}$=8.0 Hz), 130.7, 121.5 (d, $J_{C-F}$=4.2 Hz), 109.2 (d, $J_{C-F}$=36.7 Hz), 79.8, 57.3, 43.5 (br), 32.1, 28.4, 11.8. $^{19}F$ NMR (471 MHz, $CDCl_3$) δ −64.83 (d, J=8.1 Hz). IR (NaCl, thin film, $cm^{-1}$): 2976, 2932, 2864, 1692, 1601, 1575, 1474, 1425, 1366, 1332, 1246, 1166. HRMS (ESI-TOF) m/z $[M+Na]^+$ calcd for $C_{18}H_{24}FN_5NaO_2^+$ 384.1806, found 384.1819.

b. Preparation of Compound 47b:

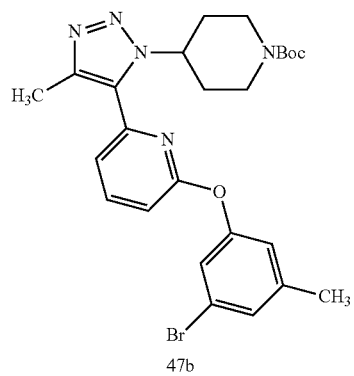

47b

To a solution of pyridine 47a (80.9 mg, 0.224 mmol) and 3-bromo-5-methylphenol (54.2 mg, 0.290 mmol) in DMF (1.1 mL) was added solid $K_2CO_3$ (55.0 mg, 0.399 mmol). The reaction was sealed under air and heated to 80° C. After 24 hours, the reaction was cooled to room temperature, quenched by addition of water, and extracted with EtOAc. The combined organic phases were washed with water, brine, dried ($Na_2SO_4$), filtered, and concentrated under reduced pressure. Final purification by column chromatography (0 to 60% EtOAc in hexanes) afforded bromide 47b (102 mg, 87%) as a white solid. $^1H$ NMR (500 MHz, $CDCl_3$) δ 7.87 (apparent t, J=7.9 Hz, 1H), 7.22-7.18 (m, 2H), 7.12 (s, 1H), 7.00 (d, J=8.3 Hz, 1H), 6.90 (s, 1H), 4.65 (tt, J=11.2, 4.1 Hz, 1H), 4.04 (br, 2H), 2.60-2.48 (m, 2H), 2.46 (s, 3H), 2.34 (s, 3H), 2.13-1.98 (m, 2H), 1.79-1.70 (m, 2H), 1.47 (s, 9H). $^{13}C\{^{1}H\}$ NMR (126 MHz, $CDCl_3$) δ 163.1, 154.6, 154.1, 145.4, 142.0, 141.5, 140.5, 131.3, 128.9, 122.2, 122.1, 121.3, 119.0, 111.3, 79.7, 56.8, 42.4 (br), 31.9, 28.4, 21.2, 12.0. IR (NaCl, thin film, $cm^{-1}$): 2976, 2929, 2863, 1693, 1595, 1568, 1471, 1454, 1426, 1366, 1331, 1300, 1275, 1165, 1153. HRMS (ESI-TOF) m/z $[M+Na]^+$ calcd for $C_{25}H_{30}BrN_5NaO_3^+$ 550.1424, found 550.1415.

c. Preparation of Compound 47d

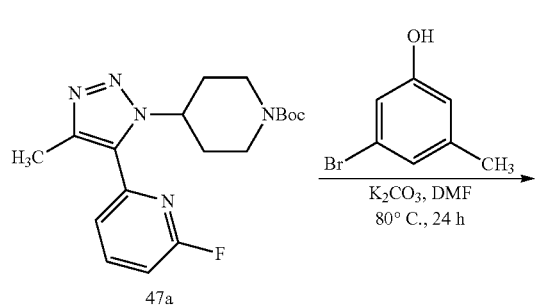

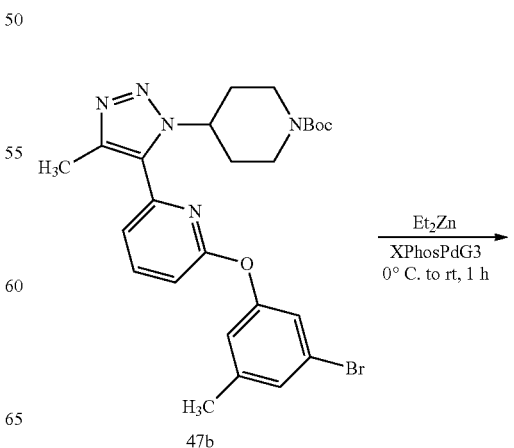

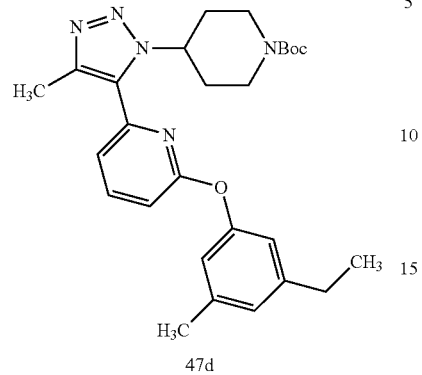

47d

To a solution of bromide 47b (52.9 mg, 0.100 mmol) and XPhosPdG3 (6.9 mg, 8.2 μmol) in THF (5 mL) at 0° C., was added Et$_2$Zn (0.20 mL, 1 M in hexanes, 0.20 mmol) dropwise. The reaction was warmed to room temperature. After 1 hour, the reaction was quench by addition of saturated aqueous NH$_4$Cl and extracted with EtOAc. The combined organic phases were washed with brine, dried (Na$_2$SO$_4$), filtered, and concentrated under reduced pressure. Final purification by column chromatography (30-100% MTBE in hexanes) afforded compound 47d (39.8 mg, 83%). $^1$H NMR (500 MHz, CDCl$_3$) δ 7.85 (apparent t, J=7.8 Hz, 1H), 7.17 (d, J=7.4 Hz, 1H), 6.99 (d, J=8.3 Hz, 1H), 6.90 (s, 1H), 6.79 (s, 2H), 4.72 (tt, J=11.1, 4.0 Hz, 1H), 4.00 (br, 2H), 2.62 (q, J=7.6 Hz, 2H), 2.49 (s, 3H), 2.46-2.36 (m, 2H), 2.34 (s, 3H), 2.03 (apparent q, J=12.5, 11.2 Hz, 2H), 1.77-1.68 (m, 2H), 1.48 (s, 9H), 1.22 (t, J=7.6 Hz, 3H). $^{13}$C{$^1$H} NMR (126 MHz, CDCl$_3$) δ 163.6, 154.6, 153.6, 146.0, 145.4, 141.9, 140.2, 139.5, 131.4, 125.6, 119.5, 118.3, 118.2, 111.2, 79.6, 56.8, 43.0 (br), 31.9, 28.7, 28.4, 21.4, 15.4, 12.1. IR (NaCl, thin film, cm$^{-1}$): 2966, 2932, 1692, 1572, 1425, 1302, 1245, 1164. HRMS (ESI-TOF) m/z [M+Na]$^+$ calcd for C$_{27}$H$_{35}$N$_5$NaO$_3^+$ 500.2632, found 500.2641.

Example 48. Synthesis of Compound 48

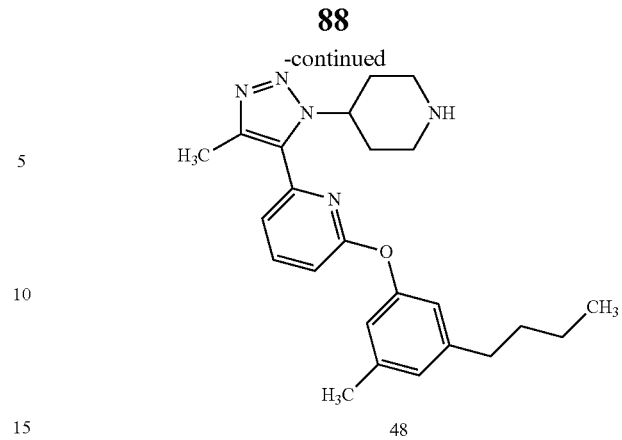

48

General procedure V was used and product 48 (27.7 mg, quant.) was isolated as a white solid. Analysis by $^{19}$F NMR with 2,2,2-trifluoroethanol as the internal standard indicated formation of a bis-TFA salt. $^1$H NMR (500 MHz, MeOD) δ 8.02 (apparent t, J=7.9 Hz, 1H), 7.38 (d, J=7.4 Hz, 1H), 7.12 (d, J=8.3 Hz, 1H), 6.93 (s, 1H), 6.85 (s, 1H), 6.79 (s, 1H), 4.90-4.83 (m, 1H), 3.38-3.33 (m, 2H), 2.72 (apparent td, J=12.6, 3.1 Hz, 2H), 2.60 (t, J=7.7 Hz, 2H), 2.46 (s, 3H), 2.36 (s, 3H), 2.31-2.20 (m, 2H), 2.06-1.98 (m, 2H), 1.57 (pent, J=7.6 Hz, 2H), 1.32 (hex, J=7.5 Hz, 2H), 0.89 (t, J=7.4 Hz, 3H). $^{13}$C{$^1$H} NMR (126 MHz, MeOD) δ 163.8, 154.0, 144.7, 144.1, 141.4, 140.9, 139.6, 132.2, 125.7, 119.1, 118.9, 118.6, 111.7, 53.6, 42.7, 34.9, 33.4, 28.6, 21.8, 20.0, 12.8, 10.1. IR (NaCl, thin film, cm$^{-1}$): 2959, 2930, 2744, 2529, 1678, 1591, 1573, 1454, 1431, 1311, 1298, 1248, 1202, 1137. HRMS (ESI-TOF) m/z [M+H]$^+$ calcd for C$_{24}$H$_{32}$N$_5$O$^+$ 406.2601, found 406.2616.

The intermediate Compound 48a was prepared as follows.

a. Preparation of Compound 48a

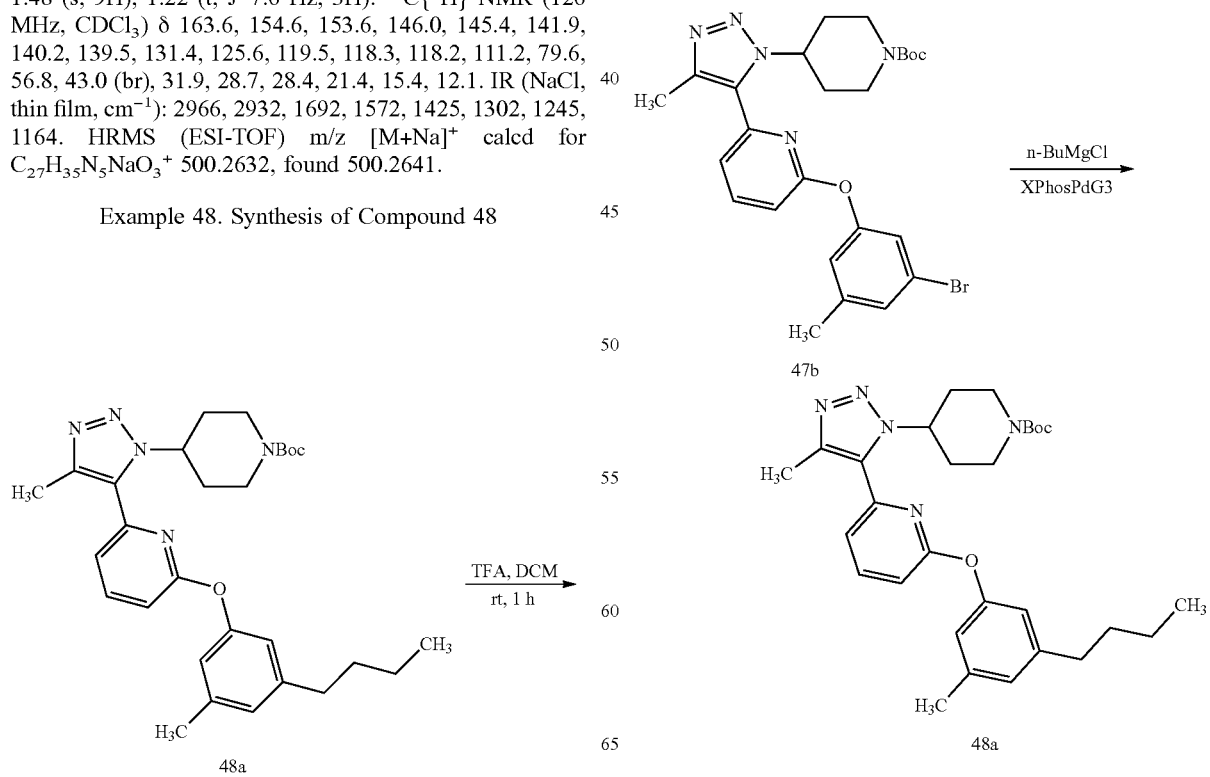

To a solution of bromide 47b (50.9 mg, 96.4 µmol) and XPhosPdG3 (5.6 mg, 6.6 µmol) in THF (5 mL) cooled in a brine bath was added n-butylmagnesium chloride (0.10 mL, 2.0 M in THF, 0.19 mmol) dropwise. After 30 minutes, the reaction was quenched by addition of H$_2$O and extracted with EtOAc. The combined organic phases were washed with brine, dried (Na$_2$SO$_4$), filtered, and concentrated under reduced pressure. Final purification by column chromatography (10-50% IPA in hexanes) afforded compound 48a (29.3 mg, 60%) as a white solid. $^1$H NMR (500 MHz, CDCl$_3$) δ 7.84 (apparent t, J=7.8 Hz, 1H), 7.17 (d, J=7.4 Hz, 1H), 6.98 (d, J=8.3 Hz, 1H), 6.88 (s, 1H), 6.78 (s, 1H), 6.77 (s, 1H), 4.71 (tt, J=11.3, 4.1 Hz, 1H), 4.01 (br, 2H), 2.57 (t, J=7.8 Hz, 2H), 2.48 (s, 3H), 2.42 (br, 2H), 2.33 (s, 3H), 2.11-1.98 (m, 2H), 1.72 (apparent d, J=11.4 Hz, 2H), 1.57 (pent, J=7.7 Hz, 2H), 1.48 (s, 9H), 1.34 (hept J=7.4 Hz, 2H), 0.91 (t, J=7.3 Hz, 3H). $^{13}$C {$^1$H} NMR (126 MHz, CDCl$_3$) δ 163.6, 154.5, 153.5, 145.3, 144.7, 141.9, 140.2, 139.4, 131.4, 126.1, 119.4, 118.7, 118.3, 111.2, 79.6, 56.8, 43.1 (br), 35.4, 33.4, 31.9, 28.4, 22.3, 21.4, 13.9, 12.1. IR (NaCl, thin film, cm$^{-1}$): 2959, 2929, 2860, 1692, 1589, 1572, 1468, 1453, 1426, 1365, 1301, 1246, 1166, 1152. HRMS (ESI-TOF) m/z [M+Na]$^+$ calcd for C$_{29}$H$_{39}$N$_5$NaO$_3$$^+$ 528.2945, found 528.2943.

Example 49. Synthesis of Compound 49

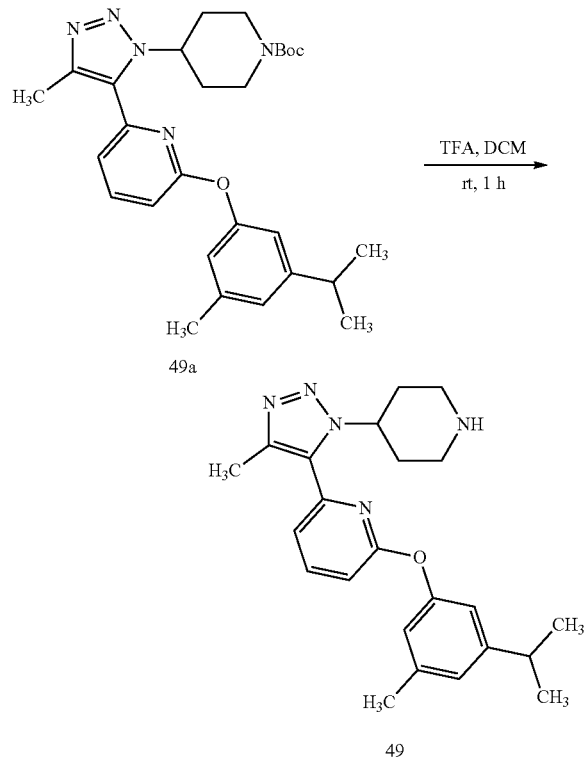

49

General procedure V was used and product 49 (21.9 mg, 98%) was isolated as a white solid. Analysis by $^{19}$F NMR with 2,2,2-trifluoroethanol as the internal standard indicated formation of a bis-TFA salt. $^1$H NMR (500 MHz, MeOD) δ 8.02 (apparent t, J=7.9 Hz, 1H), 7.39 (d, J=7.4 Hz, 1H), 7.11 (d, J=8.3 Hz, 1H), 6.99 (s, 1H), 6.85 (apparent s, 2H), 4.90-4.84 (m, 1H), 3.39-3.34 (m, 2H), 2.89 (hept, J=6.9 Hz, 1H), 2.71 (apparent t, J=11.5 Hz, 2H), 2.46 (s, 3H), 2.38 (s, 3H), 2.32-2.21 (m, 2H), 2.05 (apparent dd, J=14.2, 4.0 Hz, 2H), 1.23 (d, J=6.9 Hz, 6H). $^{13}$C{$^1$H} NMR (126 MHz, MeOD) δ 163.7, 154.0, 150.9, 144.2, 141.5, 140.9, 139.6, 132.2, 123.6, 119.1, 118.9, 116.6, 111.6, 53.5, 42.7, 33.8, 28.6, 22.9, 20.1, 10.1. IR (NaCl, thin film, cm$^{-1}$): 2962, 2929, 2858, 1677, 1591, 1573, 1460, 1431, 1200, 1176, 1141. HRMS (ESI-TOF) m/z [M+Na]$^+$ calcd for C$_{23}$H$_{29}$N$_5$NaO$^+$ 414.2264, found 414.2252.

The intermediate Compound 49a was prepared as follows.

a. Preparation of Compound 49a

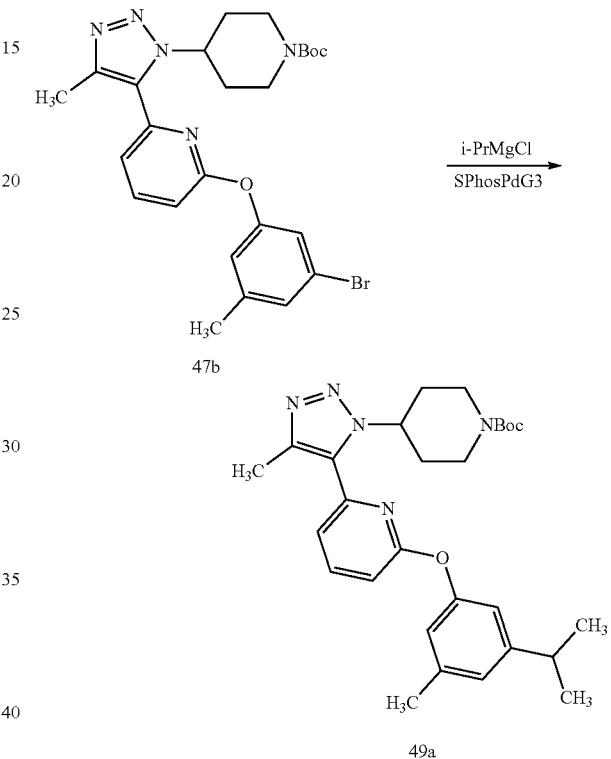

To a solution of bromide 47b (52.7 mg, 99.8 µmol) and SPhosPdG3 (4.8 mg, 6.2 µmol) in THF (5 mL) cooled in an ice bath was added isopropylmagnesium chloride (0.10 mL, 2.0 M in THF, 0.20 mmol) dropwise. After 3 hours, the reaction was quenched by addition of H$_2$O and extracted with EtOAc. The combined organic phases were washed with brine, dried (Na$_2$SO$_4$), filtered, and concentrated under reduced pressure. Final purification by column chromatography (10-40% EtOAc in hexanes) afforded product 49a (18.8 mg, 38%) as a white solid. $^1$H NMR (500 MHz, CDCl$_3$) δ 7.85 (apparent t, J=8.0 Hz, 1H), 7.18 (d, J=7.3 Hz, 1H), 6.98 (d, J=8.3 Hz, 1H), 6.93 (s, 1H), 6.82 (s, 1H), 6.79 (s, 1H), 4.74 (tt, J=11.3, 4.1 Hz, 1H), 4.01 (br, 2H), 2.88 (hept, J=6.9 Hz, 1H), 2.49 (s, 3H), 2.45-2.36 (m, 2H), 2.34 (s, 3H), 2.03 (apparent qd, J=12.0, 3.4 Hz, 2H), 1.77-1.71 (m, 2H), 1.48 (s, 9H), 1.23 (d, J=6.9 Hz, 6H). $^{13}$C{$^1$H} NMR (126 MHz, CDCl$_3$) δ 163.5, 154.6, 153.6, 150.8, 145.4, 141.9, 140.2, 139.4, 131.3, 124.1, 119.6, 118.3, 116.8, 111.1, 79.6, 56.8, 42.7 (br), 34.0, 31.9, 28.4, 23.9, 21.5, 12.2. IR (NaCl, thin film, cm$^{-1}$): 2962, 2929, 2867, 1693, 1589, 1572, 1453, 1426, 1365, 1301, 1246, 1166, 1152. HRMS (ESI-TOF) m/z [M+Na]$^+$ calcd for C$_{28}$H$_{37}$N$_5$NaO$_3$$^+$ 514.2789, found 514.2801.

Example 50. Synthesis of Compound 50

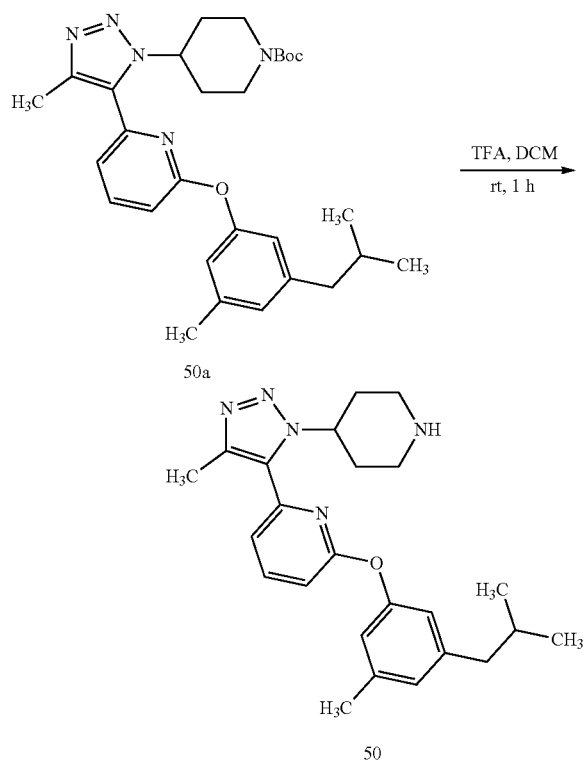

General procedure V was used and product 50 (48.6 mg, quant.) was isolated as a white solid. Analysis by $^{19}$F NMR with 2,2,2-trifluoroethanol as the internal standard indicated formation of a bis-TFA salt. $^1$H NMR (500 MHz, MeOD) δ 8.01 (apparent t, J=7.8 Hz, 1H), 7.38 (d, J=7.3 Hz, 1H), 7.11 (d, J=8.2 Hz, 1H), 6.90 (s, 1H), 6.86 (s, 1H), 6.76 (s, 1H), 4.86 (tt, J=10.8, 4.1 Hz, 1H), 3.39-3.34 (m, 2H), 2.75 (apparent td, J=12.6, 3.1 Hz, 2H), 2.46 (d, J=7.2 Hz, 2H), 2.45 (s, 3H), 2.36 (s, 3H), 2.32-2.20 (m, 2H), 2.06-1.98 (m, 2H), 1.82 (nonet, J=6.8 Hz, 1H), 0.87 (d, J=6.9 Hz, 6H). $^{13}$C{$^1$H} NMR (126 MHz, MeOD) δ 163.8, 153.9, 144.1, 143.5, 141.4, 140.9, 139.4, 132.2, 126.4, 119.3, 119.2, 118.9, 111.6, 53.6, 44.7, 42.7, 30.0, 28.5, 21.2, 20.0, 10.1. IR (NaCl, thin film, cm$^{-1}$): 2962, 2927, 2850, 1677, 1591, 1573, 1454, 1431, 1299, 1249, 1202, 1177, 1137. HRMS (ESI-TOF) m/z [M+H]$^+$ calcd for $C_{24}H_{32}N_5O^+$ 406.2601, found 406.2595.

The intermediate Compound 50a was prepared as follows.

a. Preparation of Compound 50a

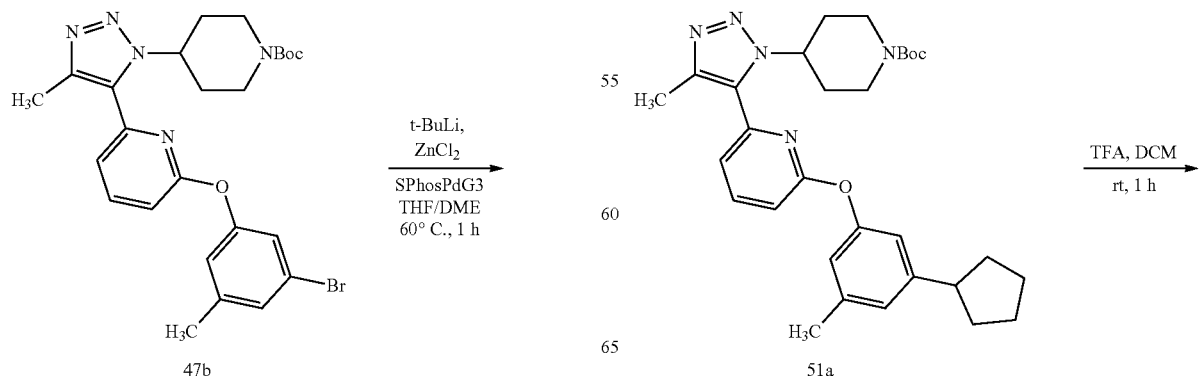

To a solution of ZnCl$_2$ (76.4 mg, 0.562 mmol) in THF (2 mL) in an ice bath, was added t-BuLi. After 10 minutes, a solution of bromide 47b (58.9 mg, 0.112 mmol) and SPhos-sPdG3 (4.8 mg, 6.2 μmol) in DME (2 mL) was added. The reaction was removed from the ice bath and heated to 60° C. After 1 hour, the reaction was quenched by addition of saturated aqueous NH$_4$Cl. The reaction mixture was extracted with EtOAc. The combined organic layers were washed with brine, dried (Na$_2$SO$_4$), filtered, and concentrated under reduced pressure. Final purification by column chromatography (20-60% EtOAc in hexanes) afforded compound 50a (38.6 mg, 68%) as a white solid. $^1$H NMR (500 MHz, CDCl$_3$) δ 7.84 (apparent t, J=7.8 Hz, 1H), 7.16 (d, J=7.4 Hz, 1H), 6.98 (d, J=8.3 Hz, 1H), 6.84 (s, 1H), 6.79 (s, 1H), 6.73 (s, 1H), 4.71 (tt, J=11.3, 4.0 Hz, 1H), 4.01 (br, 2H), 2.51-2.37 (m, 2H), 2.48 (s, 3H), 2.43 (d, J=7.1 Hz, 2H), 2.34 (s, 3H), 2.10-1.96 (m, 2H), 1.83 (hept, J=6.7 Hz, 1H), 1.73 (d, J=11.3 Hz, 2H), 1.48 (s, 9H), 0.89 (d, J=6.7 Hz, 6H). $^{13}$C{$^1$H} NMR (126 MHz, CDCl$_3$) δ 163.6, 154.6, 153.4, 145.4, 143.5, 141.9, 140.2, 139.2, 131.4, 126.8, 119.4, 119.4, 118.3, 111.1, 79.6, 56.8, 45.2, 42.4 (br), 31.9, 30.1, 28.4, 22.3, 21.4, 12.0. IR (NaCl, thin film, cm$^{-1}$): 2956, 2928, 2867, 1693, 1590, 1572, 1453, 1425, 1365, 1301, 1246, 1165, 1152. HRMS (ESI-TOF) m/z [M+Na]$^+$ calcd for $C_{29}H_{39}N_5NaO_3^+$ 528.2945, found 528.2951.

Example 51. Synthesis of Compound 51

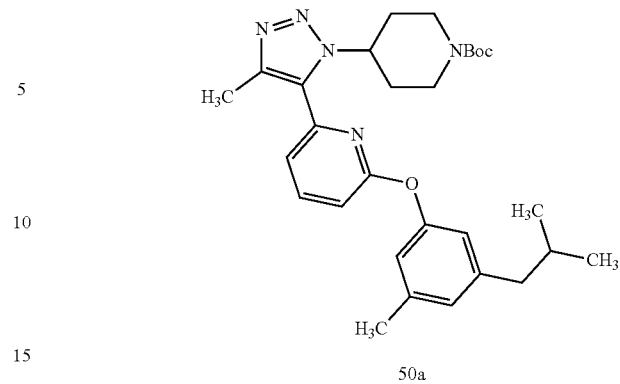

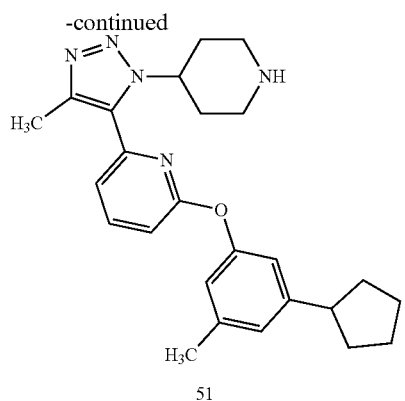

General procedure V was used and product 51 (21.6 mg, 77%) was isolated as a white solid. Analysis by $^{19}$F NMR with 2,2,2-trifluoroethanol as the internal standard indicated formation of a bis-TFA salt. $^1$H NMR (500 MHz, MeOD) δ 8.02 (apparent t, J=7.8 Hz, 1H), 7.39 (d, J=7.4 Hz, 1H), 7.11 (d, J=8.3 Hz, 1H), 7.00 (s, 1H), 6.86 (s, 1H), 6.84 (s, 1H), 4.90-4.85 (m, 1H), 3.37-3.33 (m, 2H), 2.99 (pent, J=8.7, 8.1 Hz, 1H), 2.69 (apparent td, J=12.7, 3.1 Hz, 2H), 2.46 (s, 3H), 2.37 (s, 3H), 2.31-2.22 (m, 2H), 2.09-2.00 (m, 4H), 1.86-1.77 (m, 2H), 1.75-1.66 (m, 2H), 1.61-1.50 (m, 2H). $^{13}$C{$^1$H} NMR (126 MHz, MeOD) δ 163.7, 153.9, 148.4, 144.1, 141.5, 140.9, 139.5, 132.1, 124.3, 119.1, 118.9, 117.2, 111.6, 53.6, 45.7, 42.7, 34.3, 28.6, 25.0, 20.1, 10.2. IR (NaCl, thin film, cm$^{-1}$): 2956, 2868, 1678, 1591, 1573, 1454, 1431, 1298, 1249, 1202, 1137. HRMS (ESI-TOF) m/z [M+H]$^+$ calcd for C$_{25}$H$_{32}$N$_5$O$^+$ 418.2601, found 418.2609.

The intermediate Compound 51a was prepared as follows.

a. Preparation of Compound 51a

To a solution of bromide 47b (32.8 mg, 62.1 μmol) and XYhOsPdG3 (2.0 mg, 24 μmol) in THF (0.60 mL) at room temperature was added cyclopentylmagnesium bromide (60 μL, 2.0 M in Et$_2$O, 120 μmol). The reaction was heated to 60° C. After 1 hour, the reaction was cooled to room temperature and quenched by addition of saturated aqueous NH$_4$Cl. The reaction mixture was extracted with EtOAc. The combined organic phases were washed with brine, dried (Na$_2$SO$_4$), filtered, and concentrated under reduced pressure. Final purification by column chromatography (30-90% EtOAc in hexanes) afforded product 51a (29.1 mg, 91%) as a white solid. $^1$H NMR (500 MHz, CDCl$_3$) δ 7.84 (apparent t, J=7.8 Hz, 1H), 7.18 (d, J=7.4 Hz, 1H), 6.98 (d, J=8.3 Hz, 1H), 6.94 (s, 1H), 6.83 (s, 1H), 6.78 (s, 1H), 4.74 (tt, J=11.1, 4.0 Hz, 1H), 4.01 (br, 2H), 2.95 (p, J=8.7 Hz, 1H), 2.49 (s, 3H), 2.44-2.35 (m, 2H), 2.34 (s, 3H), 2.09-1.96 (m, 4H), 1.84-1.76 (m, 2H), 1.75-1.65 (m, 4H), 1.62-1.52 (m, 2H), 1.48 (s, 9H). $^{13}$C{$^1$H} NMR (126 MHz, CDCl$_3$) δ 163.5, 154.5, 153.5, 148.5, 145.4, 141.9, 140.2, 139.3, 131.3, 124.8, 119.6, 118.3, 117.5, 111.1, 79.6, 56.8, 45.8, 43.0 (br), 34.6, 31.9, 28.4, 25.4, 21.4, 12.2. IR (NaCl, thin film, cm$^{-1}$): 2954, 2867, 1693, 1590, 1572, 1471, 1453, 1426, 1302, 1246, 1166, 1153. HRMS (ESI-TOF) m/z [M+Na]$^+$ calcd for C$_{30}$H$_{39}$N$_5$NaO$_3^+$ 540.2945, found 540.2956.

Example 52. Synthesis of Compound 52

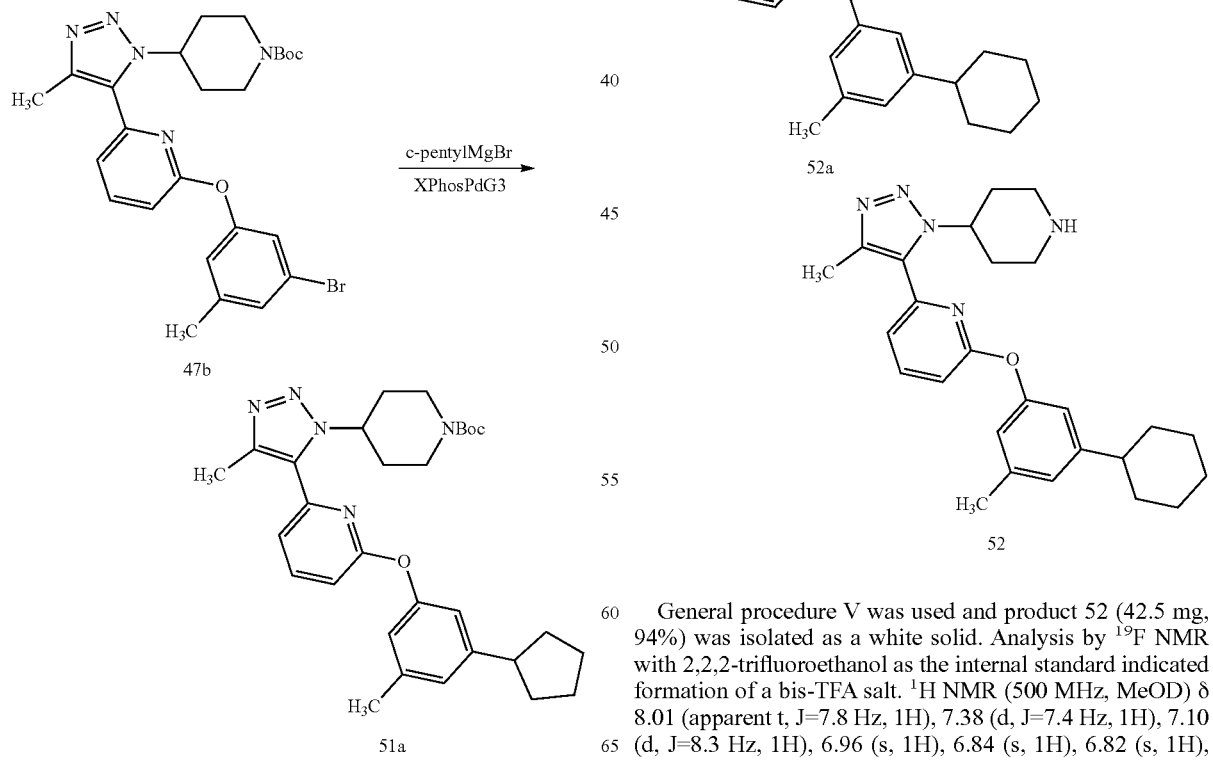

General procedure V was used and product 52 (42.5 mg, 94%) was isolated as a white solid. Analysis by $^{19}$F NMR with 2,2,2-trifluoroethanol as the internal standard indicated formation of a bis-TFA salt. $^1$H NMR (500 MHz, MeOD) δ 8.01 (apparent t, J=7.8 Hz, 1H), 7.38 (d, J=7.4 Hz, 1H), 7.10 (d, J=8.3 Hz, 1H), 6.96 (s, 1H), 6.84 (s, 1H), 6.82 (s, 1H), 4.88 (tt, J=10.6, 4.1 Hz, 1H), 3.37-3.33 (m, 2H), 2.69 (apparent td, J=12.6, 3.1 Hz, 2H), 2.53-2.47 (m, 1H), 2.46 (s, 3H), 2.36 (s, 3H), 2.31-2.21 (m, 2H), 2.04 (apparent dd, J=14.2, 4.0 Hz, 2H), 1.82 (apparent d, J=6.7 Hz, 4H), 1.74 (d, J=12.5 Hz, 1H), 1.41 (t, J=10.1 Hz, 4H), 1.33-1.20 (m, 1H). $^{13}$C{$^1$H} NMR (126 MHz, MeOD) δ 163.7, 153.9, 150.0, 144.1, 141.5, 140.9, 139.5, 132.2, 124.1, 119.1, 118.9, 117.0, 111.7, 53.6, 44.3, 42.6, 34.2, 28.6, 26.5, 25.7, 20.1, 10.2. IR (NaCl, thin film, cm$^{-1}$): 2927, 2852, 2746, 1675, 1613, 1590, 1573, 1470, 1453, 1430, 1298, 1248, 1201, 1139.

The intermediate Compound 52a was prepared as follows.
a. Preparation of Compound 52a MHz, CDCl$_3$) δ 163.5, 154.5, 153.5, 150.0, 145.3, 141.9, 140.2, 139.3, 131.3, 124.5, 119.6, 118.3, 117.2, 111.2, 79.6, 56.8, 44.4, 43.0 (br), 34.3, 31.9, 28.4, 26.8, 26.1, 21.4, 12.2. IR (NaCl, thin film, cm$^{-1}$): 2974, 2927, 2852, 1693, 1589, 1573, 1470, 1452, 1426, 1365, 1331, 1303, 1276, 1246, 1166, 1152. HRMS (ESI-TOF) m/z [M+Na]$^+$ calcd for C$_{31}$H$_{41}$N$_5$NaO$_3^+$ 554.3102, found 554.3112.

Example 53. Synthesis of Compound 53

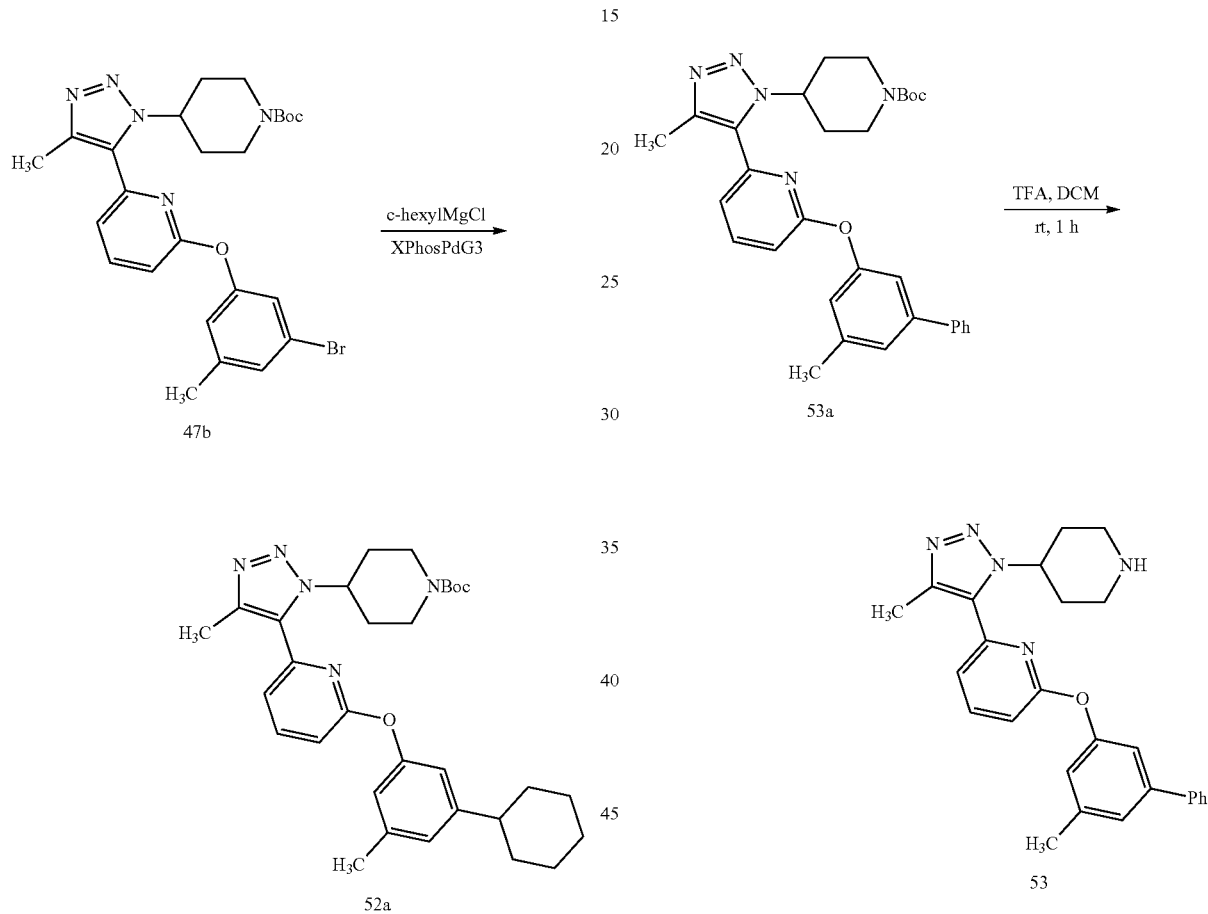

To a solution of bromide 47b (49.3 mg, 93.4 μmol) and XPhosPdG3 (4.3 mg, 5.1 μmol) in THF (5 mL) cooled in an ice bath was added cyclohexylmagnesium chloride (0.19 mL, 1.0 M in 2-methyltetrahydrofuran, 0.19 mmol). After 30 minutes, the reaction was quenched by addition of saturated aqueous NH$_4$Cl and extracted with EtOAc. The combined organic phases were washed with brine, dried (Na$_2$SO$_4$), filtered, and concentrated under reduced pressure. Final purification by column chromatography (0-50% IPA in hexanes) afforded product 52a (41.1 mg, 83%) as a white solid. $^1$H NMR (500 MHz, CDCl$_3$) δ 7.84 (apparent t, J=7.8 Hz, 1H), 7.17 (d, J=7.4 Hz, 1H), 6.98 (d, J=8.3 Hz, 1H), 6.91 (s, 1H), 6.80 (s, 1H), 6.78 (s, 1H), 4.74 (tt, J=11.3, 4.0 Hz, 1H), 4.00 (br, 2H), 2.50 (s, 3H), 2.48-2.43 (m, 1H), 2.42-2.35 (m, 2H), 2.33 (s, 3H), 2.02 (apparent qd, J=12.0, 4.2 Hz, 2H), 1.87-1.80 (m, 4H), 1.76-1.68 (m, 3H), 1.48 (s, 9H), 1.42-1.34 (m, 4H), 1.29-1.17 (m, 1H). $^{13}$C {$^1$H} NMR (126

General procedure V was used and product 53 (53.7 mg, quant.) was isolated as a white solid. Analysis by $^{19}$F NMR with 2,2,2-trifluoroethanol as the internal standard indicated formation of a bis-TFA salt. $^1$H NMR (500 MHz, MeOD) δ 8.04 (apparent t, J=7.9 Hz, 1H), 7.62 (d, J=7.7 Hz, 2H), 7.44 (apparent t, J=7.6 Hz, 2H), 7.40 (d, J=7.5 Hz, 1H), 7.39 (s, 1H), 7.35 (t, J=7.3 Hz, 1H), 7.28 (s, 1H), 7.18 (d, J=8.3 Hz, 1H), 7.02 (s, 1H), 4.88 (tt, J=10.7, 4.2 Hz, 1H), 3.27 (apparent d, J=13.1 Hz, 2H), 2.63 (apparent td, J=12.6, 3.1 Hz, 2H), 2.44 (apparent s, 6H), 2.29-2.18 (m, 2H), 2.00 (apparent dd, J=14.2, 4.0 Hz, 2H). $^{13}$C{$^1$H} NMR (126 MHz, MeOD) δ 163.6, 154.5, 144.2, 142.7, 141.5, 141.0, 140.5, 139.8, 132.2, 128.8, 127.6, 126.5, 124.0, 120.9, 119.1, 117.0, 111.8, 53.5, 42.5, 28.5, 20.1, 10.1. IR (NaCl, thin film, cm$^{-1}$): 2977, 2850, 2743, 1678, 1592, 1572, 1455, 1431, 1319, 1296, 1247, 1201, 1142. HRMS (ESI-TOF) m/z [M+H]$^+$ calcd for C$_{26}$H$_{28}$N$_5$O$^+$ 426.2288, found 426.2292.

97

The intermediate Compound 53a was prepared as follows.

a. Preparation of Compound 53a

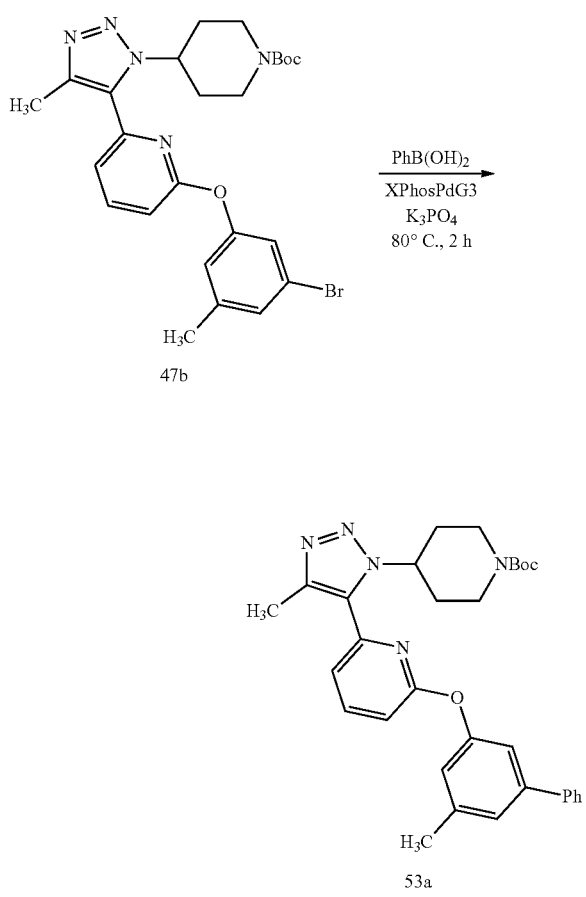

To a solution of bromide 47b (51.9 mg, 98.2 µmol), phenyl boronic acid (31.1 mg, 255 µmol), and XPhosPdG3 (9.0 mg, 10.6 µmol) in THF (0.5 mL) was added K₃PO₄ (80.3 mg, 0.378 mmol). The reaction was heated to 80° C. After 2 h, the reaction was cooled to rt, filtered through celite with EtOAc, and concentrated under reduced pressure. Final purification by column chromatography (50-100% EtOAc in hexanes) afforded compound 53a (46.8 mg, 91%). $^1$H NMR (500 MHz, CDCl₃) δ 7.87 (apparent t, J=7.8 Hz, 1H), 7.56-7.53 (m, 2H), 7.43 (apparent t, J=7.5 Hz, 2H), 7.35 (t, J=7.3 Hz, 1H), 7.29 (s, 1H), 7.22-7.16 (m, 2H), 7.04 (d, J=8.3 Hz, 1H), 6.97 (s, 1H), 4.72 (tt, J=10.9, 4.0 Hz, 1H), 3.95 (br, 2H), 2.48 (s, 3H), 2.44 (s, 3H), 2.40-2.29 (m, 2H), 2.02 (apparent qd, J=12.2, 4.2 Hz, 2H), 1.75-1.67 (m, 2H), 1.46 (s, 9H). $^{13}$C{$^1$H} NMR (126 MHz, CDCl₃) δ 163.5, 154.5, 154.0, 145.4, 142.9, 142.0, 140.3, 140.2, 140.1, 131.3, 128.9, 127.7, 127.0, 124.8, 121.1, 118.6, 117.6, 111.3, 79.6, 56.8, 43.0 (br), 31.9, 28.4, 21.5, 12.1. IR (NaCl, thin film, cm$^{-1}$): 2974, 2928, 2862, 1691, 1590, 1571, 1426, 1245, 1166, 1151. HRMS (ESI-TOF) m/z [M+Na]$^+$ calcd for C₃₁H₃₅N₅NaO₃$^+$ 548.2632, found 548.2655.

98

Example 54. Synthesis of Compound 54

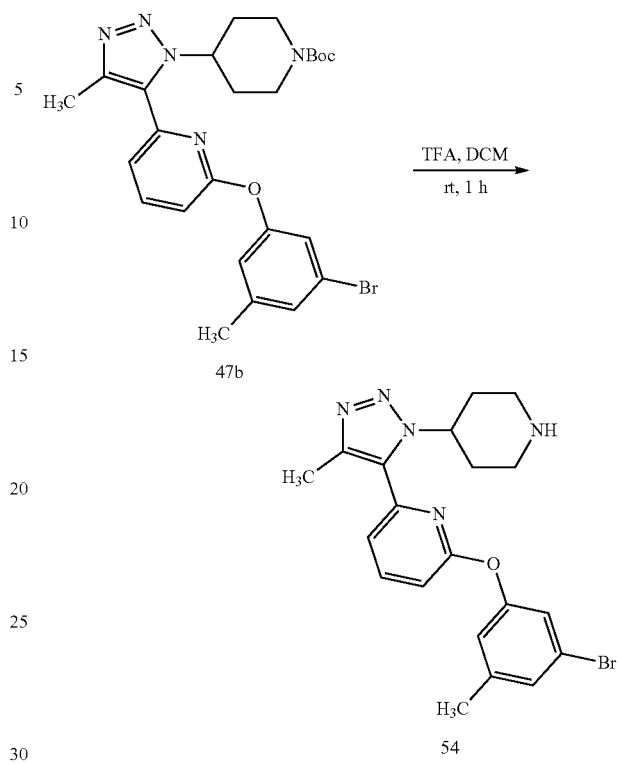

General procedure V was used and product 54 (50.2 mg, 99%) was isolated as a white solid. Analysis by $^{19}$F NMR with 2,2,2-trifluoroethanol as the internal standard indicated formation of a bis-TFA salt. $^1$H NMR (500 MHz, MeOD) δ 8.05 (apparent t, J=7.9 Hz, 1H), 7.42 (d, J=7.4 Hz, 1H), 7.30 (s, 1H), 7.24 (s, 1H), 7.17 (d, J=8.3 Hz, 1H), 7.03 (s, 1H), 4.87 (tt, J=10.4, 4.0 Hz, 1H), 3.42 (apparent dt, J=13.2, 4.1 Hz, 2H), 2.81 (apparent td, J=12.6, 3.2 Hz, 2H), 2.45 (s, 3H), 2.36 (s, 3H), 2.35-2.26 (m, 2H), 2.05 (apparent dd, J=14.2, 4.0 Hz, 2H). $^{13}$C{$^1$H} NMR (126 MHz, MeOD) δ 163.2, 154.5, 144.1, 142.1, 141.6, 141.2, 132.1, 128.5, 121.9, 121.7, 121.3, 119.5, 111.9, 53.5, 42.7, 28.6, 19.7, 10.0. IR (NaCl, thin film, cm$^{-1}$): 2990, 2743, 1678, 1596, 1568, 1455, 1430, 1416, 1298, 1257, 1201, 1143. HRMS (ESI-TOF) m/z [M+H]$^+$ calcd for C₂₀H₂₃BrN₅O$^+$ 428.1080, found 450.0900.

Example 55. Synthesis of Compound 55

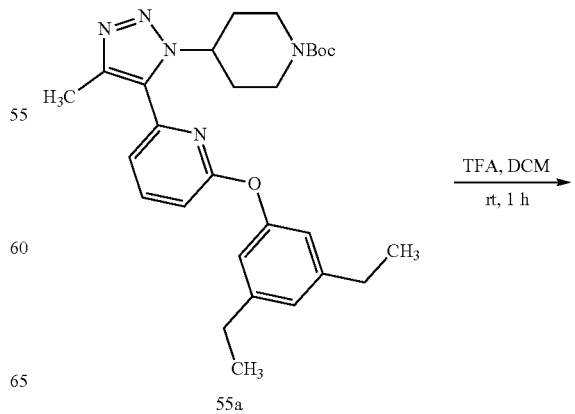

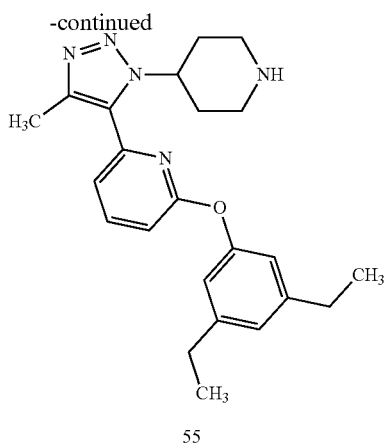

55

General procedure V was used and product 55 (17.9 mg, quant.) was isolated as a white solid. Analysis by $^{19}$F NMR with 2,2,2-trifluoroethanol as the internal standard indicated formation of a bis-TFA salt. $^1$H NMR (500 MHz, MeOD) δ 8.02 (dd, J=8.3, 7.4 Hz, 1H), 7.39 (dd, J=7.5, 0.7 Hz, 1H), 7.12 (dd, J=8.3, 0.7 Hz, 1H), 6.98 (t, J=1.5 Hz, 1H), 6.86 (d, J=1.5 Hz, 2H), 4.93-4.83 (m, 1H), 3.37-3.33 (m, 2H), 2.71 (apparent dd, J=12.7, 3.1 Hz, 2H), 2.66 (q, J=7.6 Hz, 4H), 2.46 (s, 3H), 2.32-2.20 (m, 2H), 2.04 (apparent dd, J=14.1, 3.3 Hz, 2H), 1.24 (t, J=7.6 Hz, 6H). $^{13}$C{$^1$H} NMR (126 MHz, MeOD) δ 163.7, 154.1, 146.2, 144.2, 141.5, 140.9, 132.1, 123.9, 118.9, 118.0, 111.6, 53.5, 42.7, 28.6, 28.3, 14.7, 10.2. IR (NaCl, thin film, cm$^{-1}$): 2966, 2930, 2854, 1683, 1590, 1573, 1456, 1431, 1298, 1248, 1202, 1178, 1135. HRMS (ESI-TOF) m/z [M+H]$^+$ calcd for C$_{23}$H$_{30}$N$_5$O$^+$ 392.2445, found 392.2432.

The intermediate Compound 55a was prepared as follows.

a. Preparation of Compound 47c

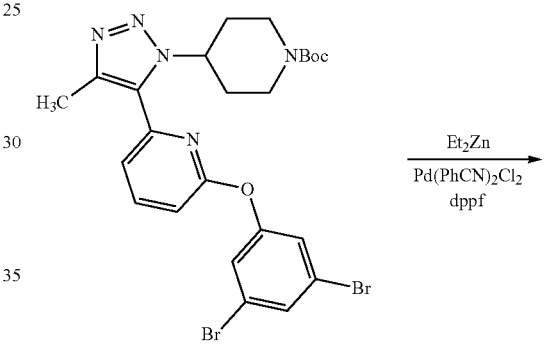

To a solution of pyridine 47a (1.07 g, 2.97 mmol) and 3,5-dibromophenol (1.07 g, 4.23 mmol) in DMF (5 mL) was added solid K$_2$CO$_3$ (637 mg, 4.62 mmol) at room temperature. The reaction was sealed under air and heated to 90° C. After 48 hours, the reaction was cooled to room temperature, quenched by addition of H$_2$O, and extracted with DCM. The combined organic phases were dried (Na$_2$SO$_4$), filtered, and concentrated under reduced pressure. Initial purification by column chromatography (5-30% IPA in hexanes followed by 30% IPA in DCM). Final purification by recrystallization (DCM/hexanes, ca. 1:10) afforded bromide 47c (1.22 g, 69%) as a white solid. $^1$H NMR (500 MHz, CDCl$_3$) δ 7.91 (apparent t, J=7.9 Hz, 1H), 7.55 (s, 1H), 7.29 (s, 2H), 7.24 (d, J=7.4 Hz, 1H), 7.04 (d, J=8.3 Hz, 1H), 4.63 (tt, J=10.8, 4.0 Hz, 1H), 4.09 (br, 2H), 2.63-2.49 (m, 2H), 2.47 (s, 3H), 2.10 (apparent qd, J=12.0, 4.3 Hz, 2H), 1.83-1.74 (m, 2H), 1.48 (s, 9H). $^{13}$C{$^1$H} NMR (126 MHz, CDCl$_3$) δ 162.6, 154.6, 154.6, 145.5, 142.1, 140.9, 131.2, 130.8, 124.1, 123.1, 119.6, 111.5, 79.8, 56.9, 43.0 (br), 31.9, 28.5, 11.9. IR (NaCl, thin film, cm$^{-1}$): 3073, 2929, 2862, 1691, 1566, 1566, 1418, 1298, 1244, 1165. HRMS (ESI-TOF) m/z [M+Na]$^+$ calcd for C$_{24}$H$_{27}$Br$_2$N$_5$NaO$_3^+$ 614.0373, found 614.0357.

b. Preparation of Compound 55a

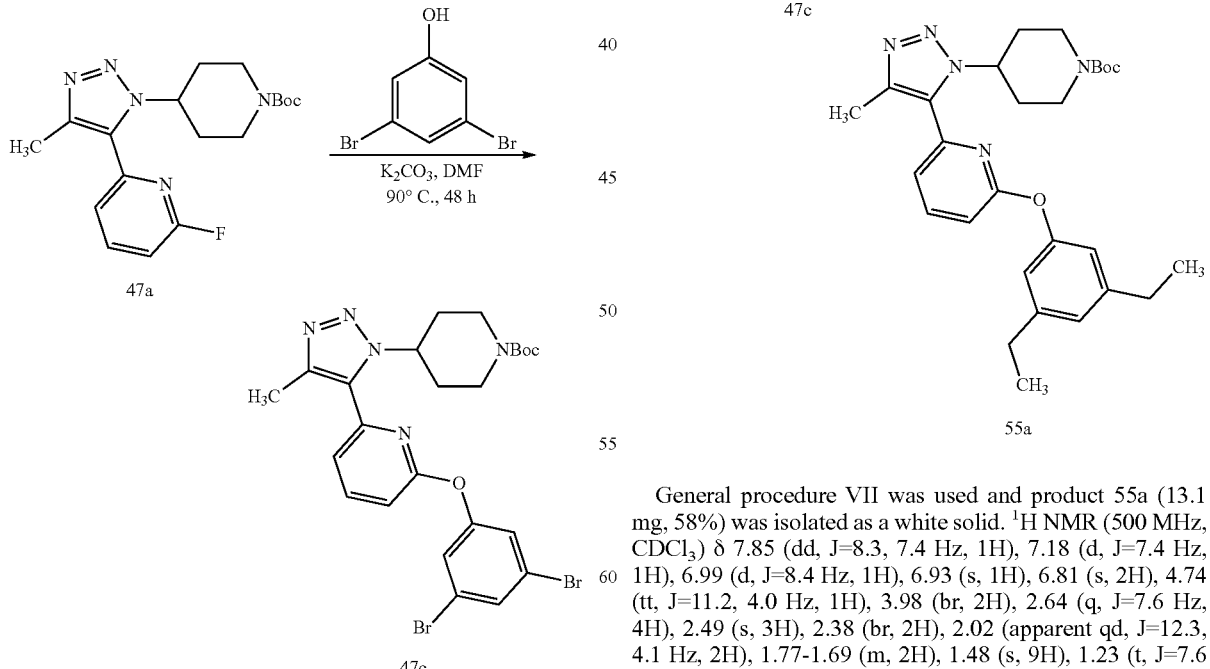

General procedure VII was used and product 55a (13.1 mg, 58%) was isolated as a white solid. $^1$H NMR (500 MHz, CDCl$_3$) δ 7.85 (dd, J=8.3, 7.4 Hz, 1H), 7.18 (d, J=7.4 Hz, 1H), 6.99 (d, J=8.4 Hz, 1H), 6.93 (s, 1H), 6.81 (s, 2H), 4.74 (tt, J=11.2, 4.0 Hz, 1H), 3.98 (br, 2H), 2.64 (q, J=7.6 Hz, 4H), 2.49 (s, 3H), 2.38 (br, 2H), 2.02 (apparent qd, J=12.3, 4.1 Hz, 2H), 1.77-1.69 (m, 2H), 1.48 (s, 9H), 1.23 (t, J=7.6 Hz, 6H). $^{13}$C{$^1$H} NMR (126 MHz, CDCl$_3$) δ163.5, 154.6, 153.6, 146.0, 145.4, 141.9, 140.2, 131.3, 124.4, 118.4, 118.3, 111.1, 79.6, 56.8, 43.0 (br), 31.9, 28.7, 28.4, 15.4, 12.2. IR (NaCl, thin film, cm$^{-1}$): 2966, 2931, 2862, 1693, 1589, 1572, 1452, 1426, 1365, 1331, 1302, 1276, 1246, 1166, 1152. HRMS (ESI-TOF) m/z [M+Na]$^+$ calcd for $C_{28}H_{37}N_5NaO_3^+$ 514.2789, found 514.2798.

Example 56. Synthesis of Compound 56

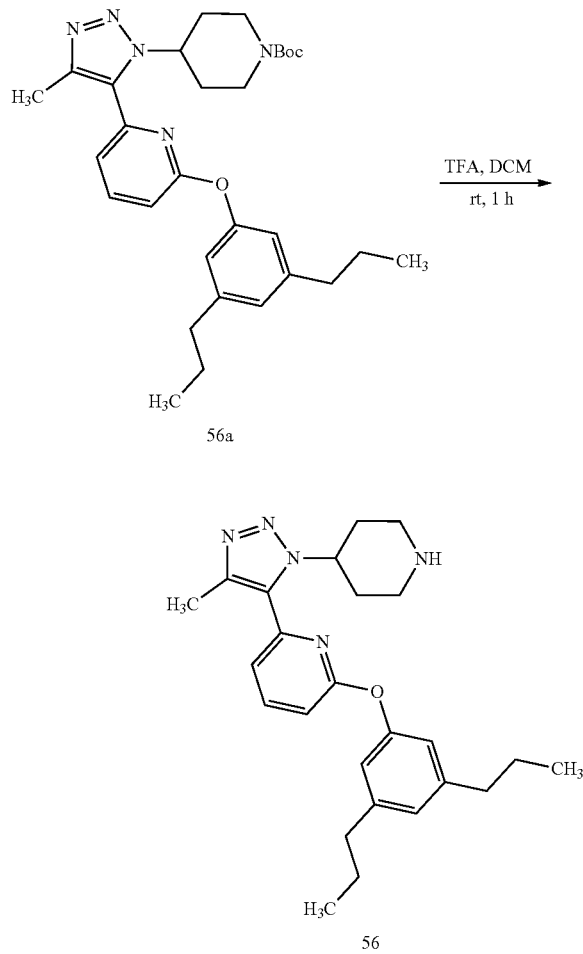

General procedure V was used and product 56 (35.4 mg, quant.) was isolated as a white solid. Analysis by $^{19}$F NMR with 2,2,2-trifluoroethanol as the internal standard indicated formation of a bis-TFA salt. $^1$H NMR (500 MHz, MeOD) δ 8.02 (dd, J=8.4, 7.4 Hz, 1H), 7.38 (dd, J=7.5, 0.7 Hz, 1H), 7.11 (dd, J=8.4, 0.7 Hz, 1H), 6.94 (t, J=1.5 Hz, 1H), 6.84 (d, J=1.5 Hz, 2H), 4.87 (tt, J=10.7, 4.1 Hz, 1H), 3.38-3.33 (m, 2H), 2.74 (apparent td, J=12.7, 3.2 Hz, 2H), 2.60 (t, J=7.4 Hz, 4H), 2.45 (s, 3H), 2.31-2.20 (m, 2H), 2.03 (apparent dd, J=14.1, 3.6 Hz, 2H), 1.63 (hex, J=7.4 Hz, 4H), 0.94 (t, J=7.4 Hz, 6H). $^{13}$C {$^1$H} NMR (126 MHz, MeOD) δ 163.8, 153.9, 144.5, 144.2, 141.5, 140.9, 132.2, 125.2, 118.9, 118.7, 111.6, 53.6, 42.7, 37.4, 28.6, 24.3, 12.7, 10.1. IR (NaCl, thin film, cm$^{-1}$): 2961, 2931, 2871, 1677, 1591, 1573, 1453, 1431, 1298, 1248, 1202, 1177, 1136. HRMS (ESI-TOF) m/z [M+H]$^+$ calcd for $C_{25}H_{34}N_5O^+$ 420.2758, found 420.2767.

The intermediate Compound 56a was prepared as follows.

a. Preparation of Compound 56a

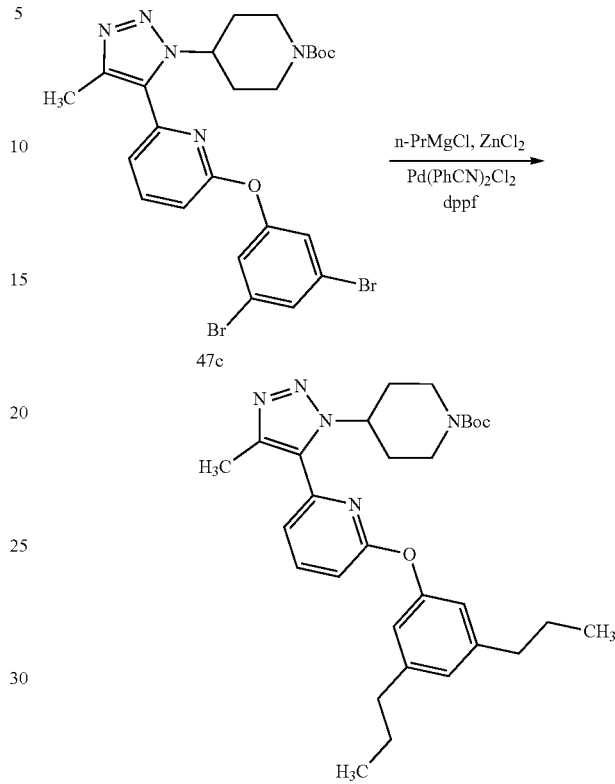

General procedure VII—

To a solution of ZnCl$_2$ (54.3 mg, 0.399 mmol) in THF (3 mL) at room temperature was added n-propylmagnesium chloride (0.10 mL, 2.0 M in Et$_2$O, 0.20 mmol). After 10 minutes, a solution of Pd(PhCN)$_2$Cl$_2$ (1.6 mg, 4.1 μmol), dppf (3.3 mg, 6.0 μmol), and bromide 47c (52.3 mg, 88.2 μmol) in THF (4 mL) was added. The reaction was heated to 50° C. After 20 hours, the reaction was cooled to room temperature and quenched by addition of saturated aqueous NH$_4$Cl. The reaction mixture was extracted with EtOAc. The combined organic phases were washed with brine, dried (Na$_2$SO$_4$), filtered, and concentrated under reduced pressure. Final purification by column chromatography (40% EtOAc in hexanes) afforded product 56a (45.5 mg, 99%) as a white solid. $^1$H NMR (500 MHz, CDCl$_3$) δ 7.84 (dd, J=8.3, 7.4 Hz, 1H), 7.17 (d, J=7.4 Hz, 1H), 6.98 (d, J=8.2 Hz, 1H), 6.88 (t, J=1.5 Hz, 1H), 6.79 (d, J=1.5 Hz, 2H), 4.73 (tt, J=11.2, 4.0 Hz, 1H), 3.99 (br, 2H), 2.56 (t, 4H), 2.49 (s, 3H), 2.40 (br, 2H), 2.02 (apparent qd, J=12.3, 4.2 Hz, 2H), 1.77-1.70 (m, 2H), 1.62 (hex, J=7.4 Hz, 4H), 1.48 (s, 9H), 0.94 (t, J=7.3 Hz, 6H). $^{13}$C {$^1$H} NMR (126 MHz, CDCl$_3$) δ 163.6, 154.5, 153.5, 145.4, 144.4, 141.9, 140.2, 131.3, 125.5, 118.9, 118.3, 111.1, 79.6, 56.8, 43.1 (br), 37.9, 31.9, 28.4, 24.4, 13.9, 12.1. IR (NaCl, thin film, cm$^{-1}$): 2960, 2931, 2870, 1695, 1589, 1572, 1468, 1452, 1427, 1302, 1246, 1166, 1152. HRMS (ESI-TOF) m/z [M+Na]$^+$ calcd for $C_{30}H_{41}N_5NaO_3^+$ 542.3102, found 542.3114.

Example 57. Synthesis of Compound 57

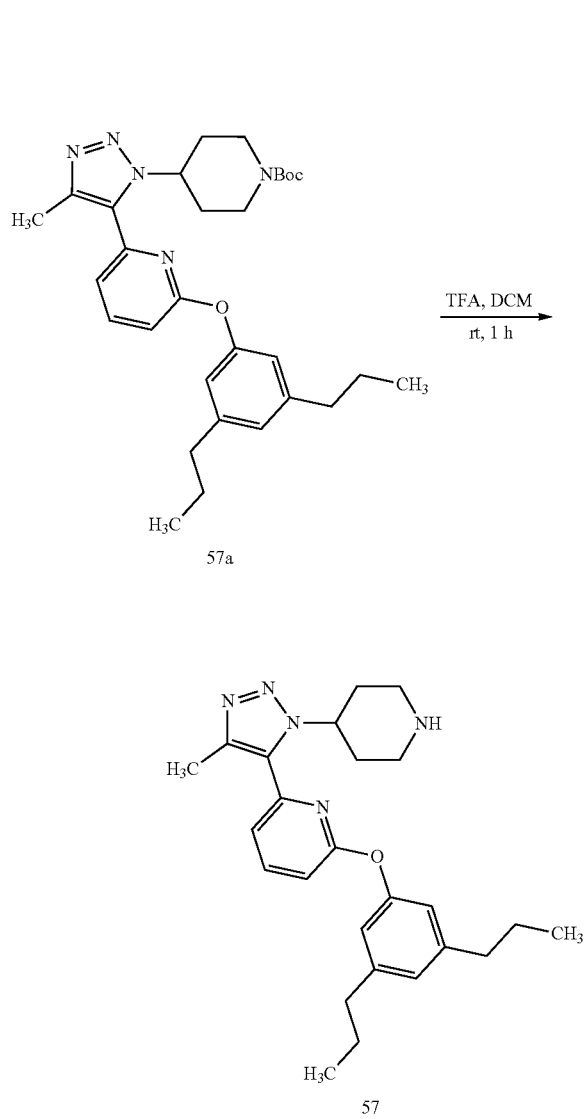

General procedure V was used and product 57 (44.0 mg, quant.) was isolated as a white solid. Analysis by $^{19}$F NMR with 2,2,2-trifluoroethanol as the internal standard indicated formation of a bis-TFA salt. $^1$H NMR (400 MHz, MeOD) δ 8.02 (apparent t, J=7.9 Hz, 1H), 7.38 (d, J=7.4 Hz, 1H), 7.11 (d, J=8.3 Hz, 1H), 6.93 (s, 1H), 6.82 (s, 2H), 4.85 (tt, J=10.6, 4.1 Hz, 1H), 3.40-3.33 (m, 2H), 2.75 (apparent td, J=12.6, 3.1 Hz, 2H), 2.62 (t, J=7.6 Hz, 4H), 2.45 (s, 3H), 2.33-2.18 (m, 2H), 2.08-1.97 (m, 2H), 1.59 (pent, J=7.5 Hz, 4H), 1.34 (hex, J=7.3 Hz, 4H), 0.91 (t, J=7.3 Hz, 6H). $^{13}$C{$^1$H} NMR (126 MHz, MeOD) δ 163.8, 154.0, 144.7, 144.1, 141.4, 140.9, 132.2, 125.1, 118.9, 118.6, 111.6, 53.6, 42.7, 35.0, 33.4, 28.6, 21.9, 12.8, 10.1. IR (NaCl, thin film, cm$^{-1}$): 2958, 2931, 2859, 2741, 1677, 1591, 1573, 1455, 1431, 1298, 1249, 1202, 1177, 1136. HRMS (ESI-TOF) m/z [M+H]$^+$ calcd for C$_{27}$H$_{38}$N$_5$O$^+$ 448.3071, found 448.3081.

The intermediate Compound 57a was prepared as follows.

a. Preparation of Compound 57a

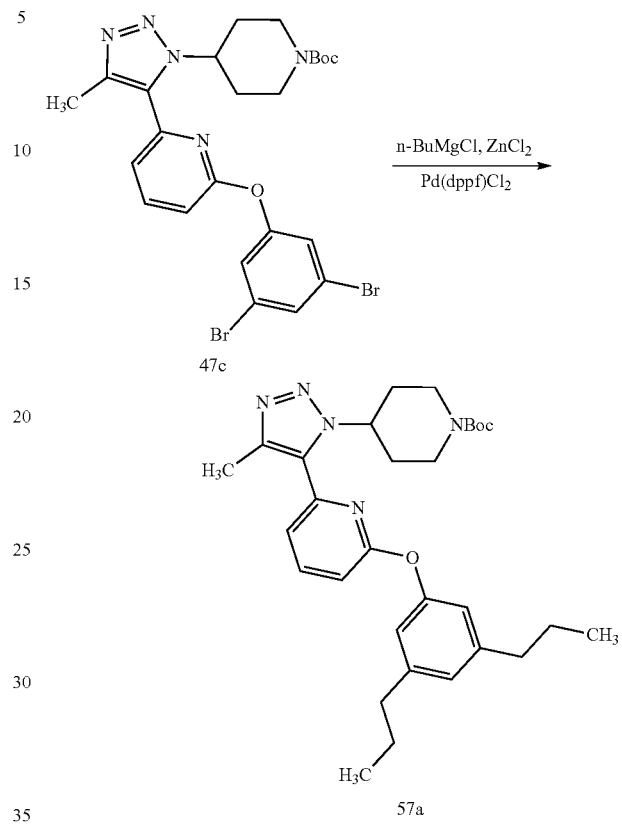

General procedure VIII—

To a solution of ZnCl$_2$ (74.6 mg, 0.549 mmol) in THF (2 mL) was added n-butylmagnesium chloride (0.10 mL, 2.0 M in THF, 0.20 mmol) at room temperature. After 5 minutes, the reaction was cooled in an ice bath. A solution of bromide 47c (48.6 mg, 82.0 µmol) in THF (2 mL) was added followed by Pd(dppf)Cl$_2$ (10.4 mg, 12.7 µmol). The reaction was removed from the ice bath and heated to 50° C. After 18 hours, the reaction was cooled to room temperature and quenched by addition of saturated aqueous NH$_4$Cl. The reaction mixture was extracted with EtOAc. The combined organic phases were washed with brine, dried (Na$_2$SO$_4$), filtered, and concentrated under reduced pressure. Final purification by column chromatography (30% EtOAc in hexanes) afforded product 57a (40.3 mg, 90%) as a white solid. $^1$H NMR (500 MHz, CDCl$_3$) δ 7.84 (dd, J=8.3, 7.4 Hz, 1H), 7.17 (dd, J=7.4, 0.7 Hz, 1H), 6.98 (dd, J=8.3, 0.7 Hz, 1H), 6.88 (t, J=1.6 Hz, 1H), 6.79 (d, J=1.5 Hz, 2H), 4.73 (tt, J=11.3, 4.0 Hz, 1H), 4.01 (br, 2H), 2.58 (t, J=7.8 Hz, 4H), 2.49 (s, 3H), 2.40 (br, 2H), 2.03 (apparent qd, J=12.3, 11.7, 3.3 Hz, 2H), 1.77-1.70 (m, 2H), 1.58 (p, J=7.6 Hz, 4H), 1.48 (s, 9H), 1.35 (hex, J=7.4 Hz, 4H), 0.92 (t, J=7.4 Hz, 6H). $^{13}$C{$^1$H} NMR (126 MHz, CDCl$_3$) δ 163.6, 154.5, 153.5, 145.4, 144.6, 141.9, 140.2, 131.3, 125.5, 118.8, 118.3, 111.1, 79.6, 56.8, 43.2 (br), 35.5, 33.5, 31.9, 28.4, 22.4, 13.9, 12.1. IR (NaCl, thin film, cm$^{-1}$): 2957, 2930, 2859, 1695, 1589, 1572, 1468, 1453, 1426, 1302, 1247, 1166, 1152. HRMS (ESI-TOF) m/z [M+Na]$^+$ calcd for C$_{32}$H$_{45}$N$_5$NaO$_3$$^+$ 570.3415, found 570.3410.

Example 58. Synthesis of Compound 58

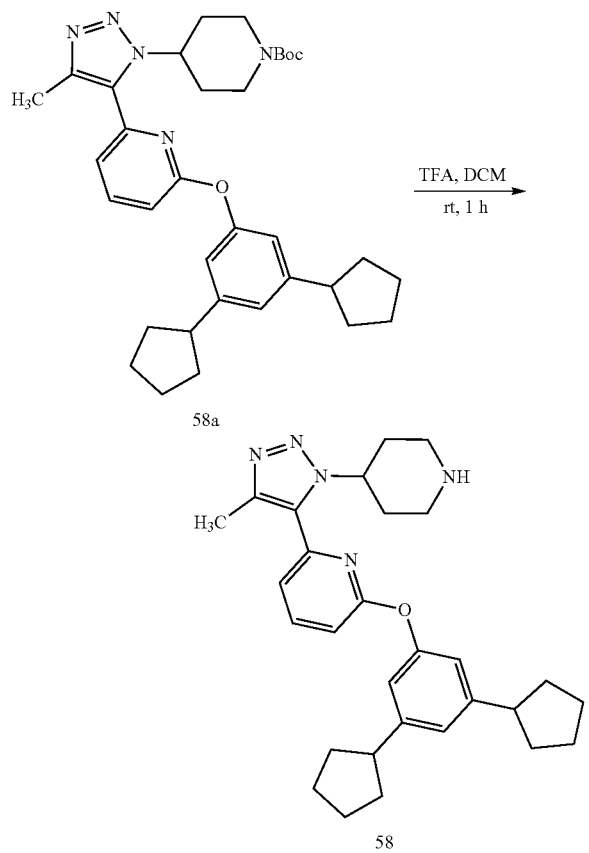

General procedure V was used and product 58 (17.6 mg, quant.) was isolated as a white solid. Analysis by $^{19}$F NMR with 2,2,2-trifluoroethanol as the internal standard indicated formation of a tris-TFA salt. $^1$H NMR (500 MHz, MeOD) δ 8.02 (dd, J=8.3, 7.4 Hz, 1H), 7.39 (dd, J=7.4, 0.7 Hz, 1H), 7.10 (dd, J=8.2, 0.7 Hz, 1H), 7.06 (t, J=1.7 Hz, 1H), 6.89 (d, J=1.5 Hz, 2H), 4.90-4.83 (m, 1H), 3.37-3.33 (m, 2H), 3.02 (tt, J=9.9, 7.5 Hz, 2H), 2.70 (apparent td, J=12.7, 3.2 Hz, 2H), 2.46 (s, 3H), 2.32-2.21 (m, 2H), 2.12-2.02 (m, 6H), 1.87-1.77 (m, 4H), 1.76-1.66 (m, 4H), 1.62-1.53 (m, 4H). $^{13}$C{$^1$H} NMR (126 MHz, MeOD) δ 163.7, 153.8, 148.3, 144.1, 141.5, 140.9, 132.2, 122.5, 118.9, 117.2, 111.6, 53.6, 45.8, 42.7, 34.3, 28.7, 25.0, 10.1. IR (NaCl, thin film, cm$^{-1}$): 2953, 2866, 1677, 1590, 1572, 1455, 1430, 1298, 1248, 1201, 1176, 1137. HRMS (ESI-TOF) m/z [M+H]$^+$ calcd for $C_{29}H_{38}N_5O^+$ 472.3071, found 472.3059.

The intermediate Compound 58a was prepared as follows.

a. Preparation of Compound 58a

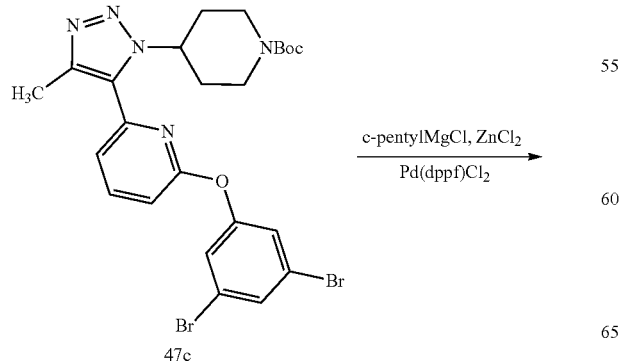

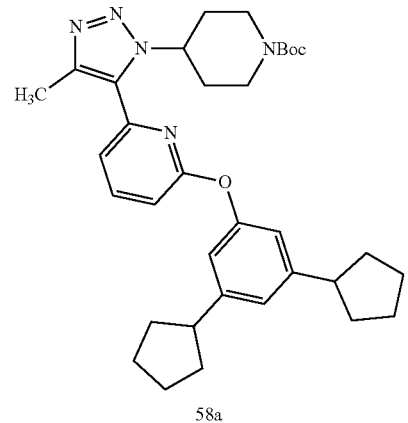

General procedure VIII was used and product 58a (35.3 mg, 82%) was isolated as a white solid. $^1$H NMR (500 MHz, CDCl$_3$) δ 7.85 (dd, J=8.3, 7.4 Hz, 1H), 7.18 (dd, J=7.5, 0.7 Hz, 1H), 7.01 (t, J=1.6 Hz, 1H), 6.98 (dd, J=8.4, 0.7 Hz, 1H), 6.85 (d, J=1.6 Hz, 2H), 4.76 (tt, J=11.2, 4.0 Hz, 1H), 4.18-3.75 (m, 2H), 2.96 (tt, J=10.0, 7.4 Hz, 2H), 2.51 (s, 3H), 2.36-2.24 (m, 2H), 2.10-1.91 (m, 6H), 1.84-1.75 (m, 4H), 1.74-1.62 (m, 6H), 1.61-1.51 (m, 4H), 1.47 (s, 9H). $^{13}$C{$^1$H} NMR (126 MHz, CDCl$_3$) δ 163.5, 154.5, 153.4, 148.2, 145.3, 142.0, 140.2, 131.1, 123.0, 118.2, 117.7, 111.1, 79.5, 56.8, 46.0, 42.9 (br), 34.6, 31.9, 28.4, 25.4, 12.3. IR (NaCl, thin film, cm$^{-1}$): 2954, 2867, 1694, 1589, 1572, 1469, 1452, 1426, 1303, 1246, 1166, 1152. HRMS (ESI-TOF) m/z [M+Na]$^+$ calcd for $C_{34}H_{45}N_5NaO_3^+$ 594.3415, found 594.3405.

Example 59. Synthesis of Compound 59

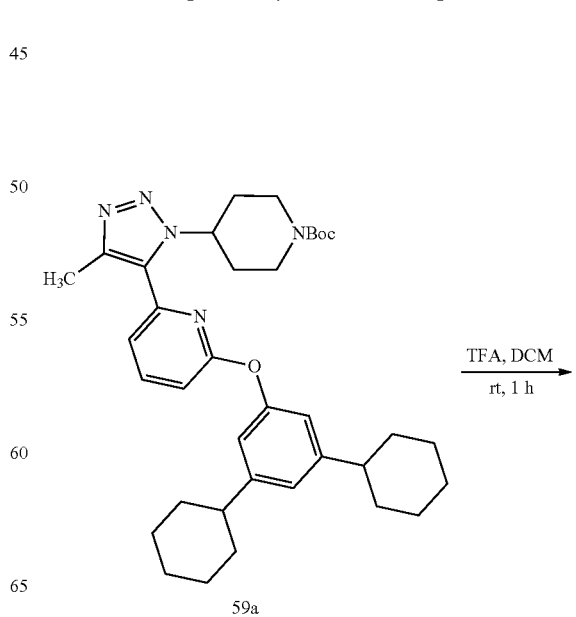

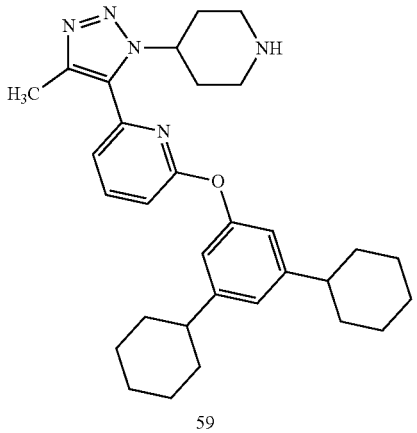

59

General procedure V was used and product 59 (28.1 mg, 86%) was isolated as a white solid. Analysis by $^{19}$F NMR with 2,2,2-trifluoroethanol as the internal standard indicated formation of a tris-TFA salt. $^1$H NMR (500 MHz, MeOD) δ 8.01 (dd, J=8.3, 7.4 Hz, 1H), 7.39 (d, J=7.1 Hz, 1H), 7.08 (d, J=8.3 Hz, 1H), 6.99 (t, J=1.6 Hz, 1H), 6.86 (d, J=1.5 Hz, 2H), 4.87 (tt, J=10.6, 4.2 Hz, 1H), 3.36-3.30 (m, 2H), 2.72 (apparent td, J=12.8, 3.0 Hz, 2H), 2.58-2.50 (m, 2H), 2.46 (s, 3H), 2.32-2.22 (m, 2H), 2.10 (apparent dd, J=14.1, 3.2 Hz, 2H), 1.85 (apparent d, J=8.8 Hz, 8H), 1.75 (d, J=12.8 Hz, 2H), 1.51-1.37 (m, 8H), 1.36-1.25 (m, 2H). $^{13}$C{$^1$H} NMR (126 MHz, MeOD) δ 163.6, 153.8, 149.9, 144.2, 141.5, 140.9, 132.3, 121.8, 119.0, 116.9, 111.6, 53.6, 44.4, 42.6, 34.3, 28.7, 26.5, 25.7, 10.1. IR (NaCl, thin film, cm$^{-1}$): 2926, 2852, 1677, 1590, 1572, 1449, 1430, 1310, 1248, 1201, 1180, 1139. HRMS (ESI-TOF) m/z [M+H]$^+$ calcd for C$_{31}$H$_{42}$N$_5$O$^+$ 500.3384, found 500.3393.

The intermediate Compound 59a was prepared as follows.

a. Preparation of Compound 58a

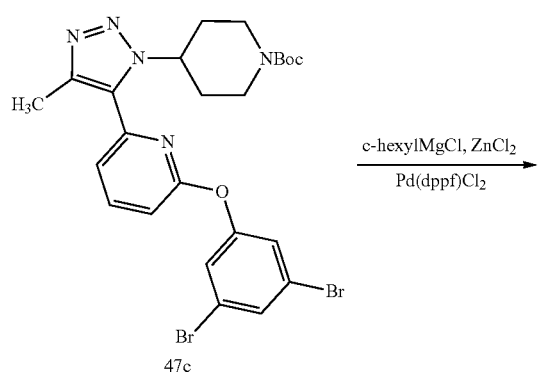

47c

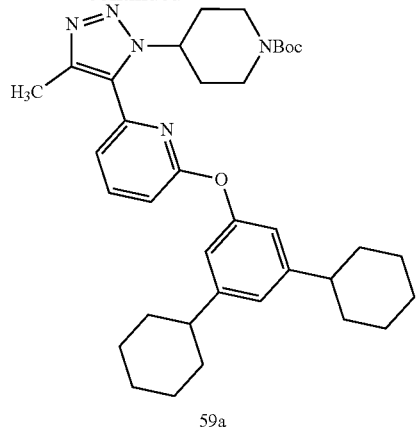

59a

General procedure VIII was used and product 59a (30.2 mg, 60%) was isolated as a white solid. $^1$H NMR (500 MHz, CDCl$_3$) δ 7.84 (dd, J=8.3, 7.5 Hz, 1H), 7.18 (d, J=7.4 Hz, 1H), 6.97 (d, J=8.3 Hz, 1H), 6.95 (t, J=1.6 Hz, 1H), 6.82 (d, J=1.5 Hz, 2H), 4.76 (tt, J=11.2, 4.0 Hz, 1H), 4.11-3.81 (m, 2H), 2.51 (s, 3H), 2.49-2.45 (m, 2H), 2.33-2.24 (m, 2H), 2.00 (apparent qd, J=12.2, 4.1 Hz, 2H), 1.88-1.81 (m, 8H), 1.74 (apparent d, J=12.5 Hz, 4H), 1.47 (s, 9H), 1.44-1.32 (m, 8H), 1.30-1.17 (m, 2H). $^{13}$C{$^1$H} NMR (126 MHz, CDCl$_3$) δ 163.4, 154.4, 153.4, 149.8, 145.4, 141.9, 140.2, 131.2, 122.4, 118.2, 117.4, 111.1, 79.5, 56.9, 44.6, 42.9 (br), 34.4, 31.9, 28.4, 26.8, 26.1, 12.3. IR (NaCl, thin film, cm$^{-1}$): 2926, 2851, 1694, 1589, 1572, 1449, 1426, 1304, 1246, 1166, 1152. HRMS (ESI-TOF) m/z [M+Na]$^+$ calcd for C$_{36}$H$_{49}$N$_5$NaO$_3{}^+$ 622.3728, found 622.3719.

Example 60. Synthesis of Compound 60

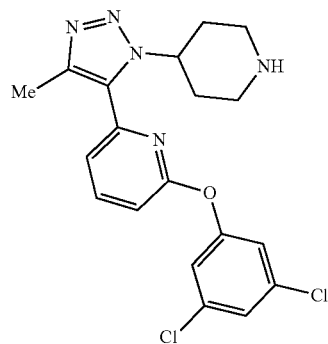 [SMILES: Cc1nnn(C2CCNCC2)c1-c1cccc(Oc2cc(Cl)cc(Cl)c2)n1]

Compound 60 was prepared using procedures similar to those described herein for the preparation of other Examples.

Example 61. Synthesis of Compound 61

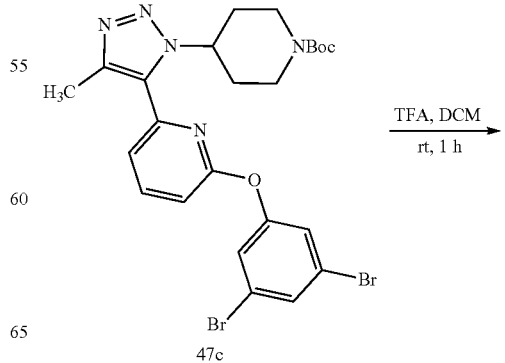

47c

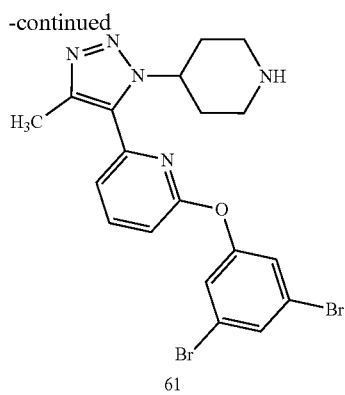

61

General procedure V was used and product 61 (33.0 mg, quant.) was isolated as a white solid. Analysis by $^{19}$F NMR with 2,2,2-trifluoroethanol as the internal standard indicated formation of a bis-TFA salt. $^1$H NMR (500 MHz, MeOD) δ 8.09 (dd, J=8.3, 7.4 Hz, 1H), 7.68 (t, J=1.7 Hz, 1H), 7.48 (d, J=1.7 Hz, 2H), 7.46 (dd, J=7.5, 0.7 Hz, 1H), 7.22 (dd, J=8.4, 0.7 Hz, 1H), 4.89-4.83 (m, 1H), 3.47 (apparent dt, J=13.1, 3.6 Hz, 2H), 2.90 (apparent td, J=12.8, 3.0 Hz, 2H), 2.44 (s, 3H), 2.40-2.28 (m, 2H), 2.08 (apparent dd, J=14.5, 4.0 Hz, 2H). $^{13}$C{$^1$H} NMR (126 MHz, MeOD) δ 162.8, 155.1, 144.2, 141.8, 141.5, 132.1, 130.4, 124.2, 122.7, 120.2, 112.0, 53.3, 42.6, 28.6, 10.0. IR (NaCl, thin film, cm$^{-1}$): 2923, 2851, 1676, 1568, 1419, 1246, 1203, 1135. HRMS (ESI-TOF) m/z [M+Na]$^+$ calcd for C$_{19}$H$_{19}$Br$_2$N$_5$NaO$^+$ 513.9849, found 513.9851.

Example 62. Synthesis of Compound 62

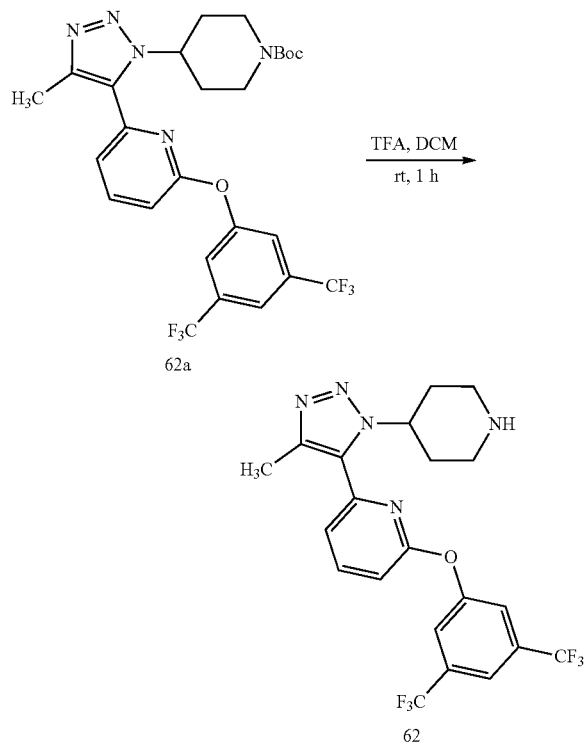

General procedure V was used and product 62 (25.5 mg, quant.) was isolated as a white solid. Integration of the $^{19}$F NMR indicated formation of a bis-TFA salt. $^1$H NMR (500 MHz, MeOD) δ 8.13 (dd, J=8.3, 7.4 Hz, 1H), 7.91 (apparent s, 3H), 7.49 (dd, J=7.5, 0.7 Hz, 1H), 7.31 (dd, J=8.4, 0.7 Hz, 1H), 4.80 (tt, J=10.3, 4.2 Hz, 1H), 3.39 (apparent dt, J=13.8, 4.4 Hz, 2H), 2.85 (apparent td, J=12.9, 3.1 Hz, 2H), 2.41 (s, 3H), 2.36-2.22 (m, 2H), 2.06-1.94 (m, 2H). $^{13}$C{$^1$H} NMR (126 MHz, MeOD) δ 162.6, 154.8, 144.2, 141.8, 141.7, 132.8 (q, J$_{C-F}$=33.9 Hz), 132.1, 124.1 (q, J$_{C-F}$=273.4 Hz), 122.6 (q, J$_{C-F}$=4.0 Hz), 120.6, 118.22 (hept, J$_{C-F}$=3.9 Hz), 112.2, 53.0, 42.2, 28.5, 9.8. $^{19}$F NMR (471 MHz, MeOD) δ −64.2 (s, 6F, ArCF$_3$), −77.5 (s, 6F, TFA). IR (NaCl, thin film, cm$^{-1}$): 2990, 2850, 1676, 1597, 1577, 1370, 1280, 1175, 1135. HRMS (ESI-TOF) m/z [M+H]$^+$ calcd for C$_{21}$H$_{20}$F$_6$N$_5$O$^+$ 472.1567, found 472.1572.

The intermediate Compound 62a was prepared as follows.

a. Preparation of Compound 62a

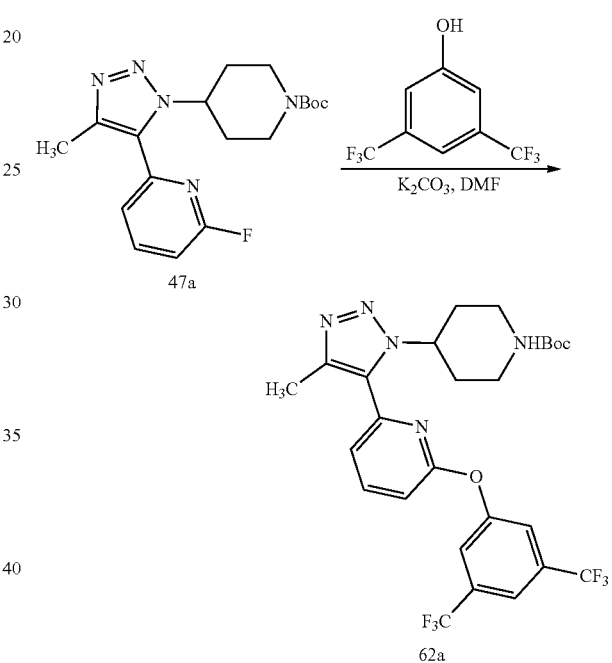

To a solution of pyridine 47a (33.2 mg, 92.0 μmol) and 3,5-bis(trifluoromethyl)phenol (21 μL, 138 μmol) in DMF (0.5 mL) was added solid K$_2$CO$_3$ (36.4 mg, 264 μmol) at room temperature. The reaction was sealed under air and heated to 130° C. After 18 hours, the reaction was cooled to room temperature and quenched by addition of H$_2$O. The reaction mixture was extracted with EtOAc. The combined organic phases were washed with H$_2$O, brine, dried (Na$_2$SO$_4$), filtered, and concentrated under reduced pressure. Final purification by column chromatography (30-50% EtOAc in hexanes) afforded product 62a (32.3 mg, 61%). $^1$H NMR (500 MHz, CDCl$_3$) δ 7.97 (dd, J=8.3, 7.5 Hz, 1H), 7.77 (s, 1H), 7.67 (s, 2H), 7.28 (d, J=7.5 Hz, 1H), 7.12 (d, J=8.3 Hz, 1H), 4.52 (tt, J=11.1, 4.0 Hz, 1H), 4.01 (br, 2H), 2.47 (s, 3H), 2.37 (ddd, J=13.6, 12.0, 2.9 Hz, 2H), 2.07 (apparent qd, J=12.2, 4.3 Hz, 2H), 1.69 (apparent d, J=12.9 Hz, 2H), 1.47 (s, 9H). $^{13}$C{$^1$H} NMR (126 MHz, CDCl$_3$) δ 162.2, 154.5, 154.2, 145.6, 142.3, 141.1, 133.3 (q, J$_{C-F}$=33.8 Hz), 130.9, 122.8 (q, J$_{C-F}$=273.5 Hz), 122.3 (d, J$_{C-F}$=4.0 Hz), 120.1, 118.7 (hept, J$_{C-F}$=4.0 Hz), 111.6, 79.8, 56.8, 42.6 (br), 31.8, 28.3, 11.9. $^{19}$F NMR (471 MHz, CDCl$_3$) δ −62.8. IR (NaCl, thin film, cm$^{-1}$): 2924, 2851, 1693, 1457, 1428, 1368, 1278, 1245, 1175, 1141. HRMS (ESI-TOF) m/z [M+Na]+ calcd for $C_{26}H_{27}F_6N_5NaO_3^+$ 594.1910, found 594.1919.

Example 63. Synthesis of Compound 63

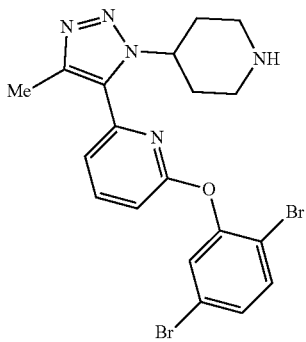 [SMILES: Cc1nnn(C2CCNCC2)c1-c1cccc(Oc2cc(Br)ccc2Br)n1]

Compound 63 was prepared using procedures similar to those described herein for the preparation of other Examples.

Example 64. Synthesis of Compound 64

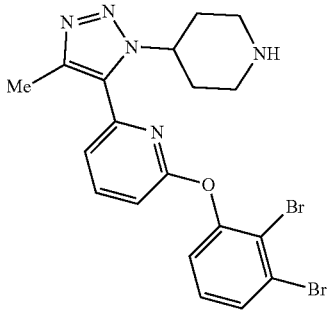 [SMILES: Cc1nnn(C2CCNCC2)c1-c1cccc(Oc2cccc(Br)c2Br)n1]

Compound 64 was prepared using procedures similar to those described herein for the preparation of other Examples.

Example 65. Synthesis of Compound 65

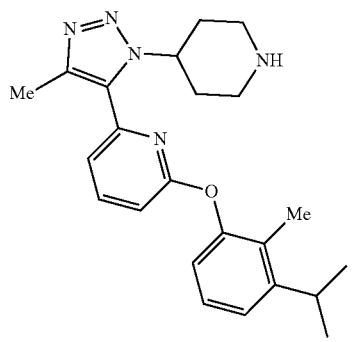 [SMILES: Cc1nnn(C2CCNCC2)c1-c1cccc(Oc2cccc(C(C)C)c2C)n1]

Compound 65 was prepared using procedures similar to those described herein for the preparation of other Examples.

Example 66. Synthesis of Compound 66

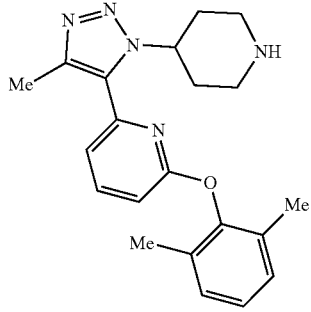 [SMILES: Cc1cccc(C)c1Oc1cccc(-c2c(C)nnn2C2CCNCC2)n1]

Compound 66 was prepared using procedures similar to those described herein for the preparation of other Examples.

Example 67. Synthesis of Compound 67

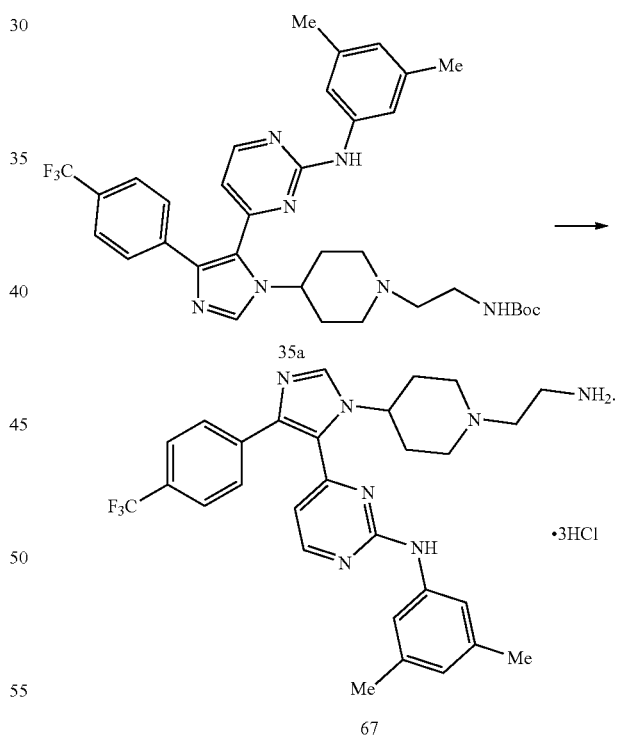

Compound 35a (0.030 mmol) was added in 4M anhydrous HCl in dioxane (0.5 mL) and dioxane (0.5 mL). After 16 hours, the solvent was removed and cold ether was used to precipitate out the desired product (16 mg, 0.025 mmol, 83%). $^1$H NMR (500 MHz, MeOD) δ 8.80-8.75 (m, 1H), 8.38 (d, J=5.2 Hz, 1H), 7.76 (d, J=8.2 Hz, 2H), 7.69 (d, J=8.1 Hz, 2H), 7.24 (s, 2H), 6.76 (s, 1H), 6.61 (d, J=5.3 Hz, 1H), 4.94 (td, J=10.7, 4.9 Hz, 1H), 3.40 (d, J=12.0 Hz, 2H), 3.26 (dd, J=6.4, 2.3 Hz, 2H), 3.08 (d, J=6.6 Hz, 2H), 2.58 (d, J=15.1 Hz, 2H), 2.36 (d, J=6.7 Hz, 4H), 2.29 (s, 6H). $^{19}$F NMR (470 MHz, MeOD) δ −64.47.

Example 68. Synthesis of Compound 68

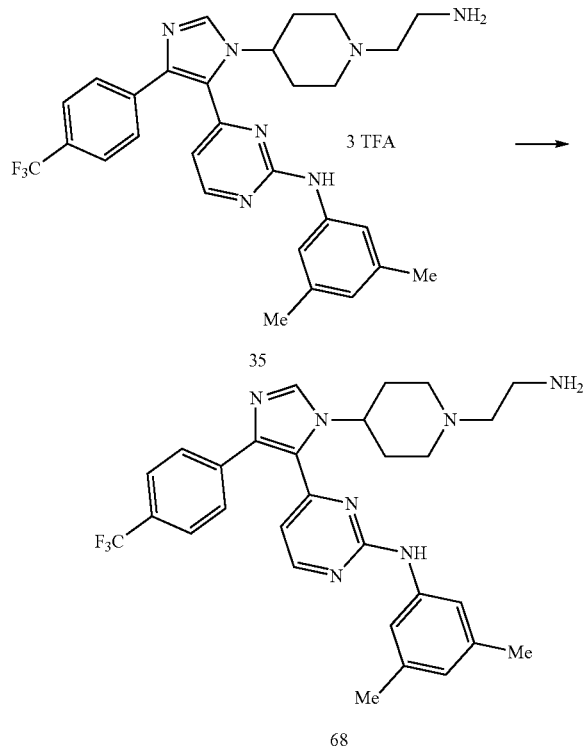

DCM (0.5 mL) was added to compound 35 (0.030 mmol) and Amberlyst A21 resin (0.20 g). After 16 hours, the resin was filtered out and DCM was removed under reduced pressure to give compound 68 (11 mg). $^1$H NMR (500 MHz, MeOD) δ 8.93 (s, 1H), 8.39 (d, J=5.1 Hz, 1H), 7.78 (d, J=8.3 Hz, 2H), 7.70 (d, J=8.2 Hz, 2H), 7.24 (d, J=1.6 Hz, 2H), 6.77 (s, 1H), 6.61 (d, J=5.0 Hz, 1H), 5.02-4.96 (m, 1H), 3.55 (d, J=12.3 Hz, 2H), 3.36 (t, J=6.3 Hz, 2H), 3.26 (t, J=6.5 Hz, 2H), 2.78 (s, 2H), 2.46 (h, J=3.6 Hz, 4H), 2.29 (s, 6H). $^{19}$F NMR (470 MHz, MeOD) δ −64.50.

Example 69. Synthesis of Compound 69

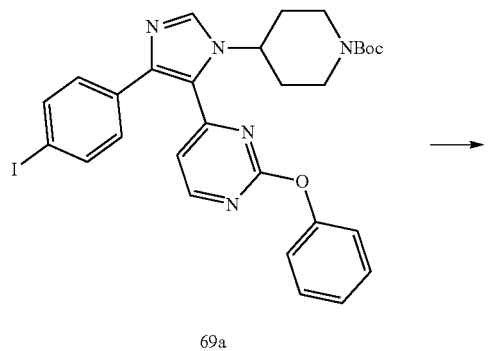

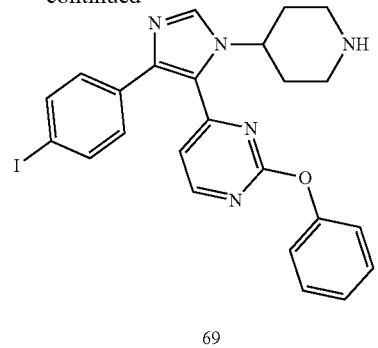

Trifluoroacetic acid (TFA) (0.50 mL) was added to a solution of compound 38a (0.13 mmol) in DCM (0.50 mL). After 16 hours, the reaction was concentrated under reduced pressure. Cold ether (4.0 mL) was used to precipitate compound 69 (63 mg, 0.12 mmol, 95%) as a white solid. $^1$H NMR (500 MHz, MeOD) δ 8.62 (s, 1H), 8.58 (d, J=5.1 Hz, 1H), 7.83 (d, J=8.2 Hz, 2H), 7.50 (t, J=7.9 Hz, 2H), 7.32 (dd, J=8.1, 2.6 Hz, 3H), 7.21 (d, J=8.3 Hz, 2H), 7.01 (d, J=5.1 Hz, 1H), 4.72 (tt, J=11.8, 4.1 Hz, 1H), 3.39-3.35 (m, 2H), 2.75 (td, J=13.1, 3.1 Hz, 2H), 2.19-2.15 (m, 2H), 2.12-2.03 (m, 2H).

The intermediate compound 69a was prepared as follows.

a. Preparation of Compound 69a:

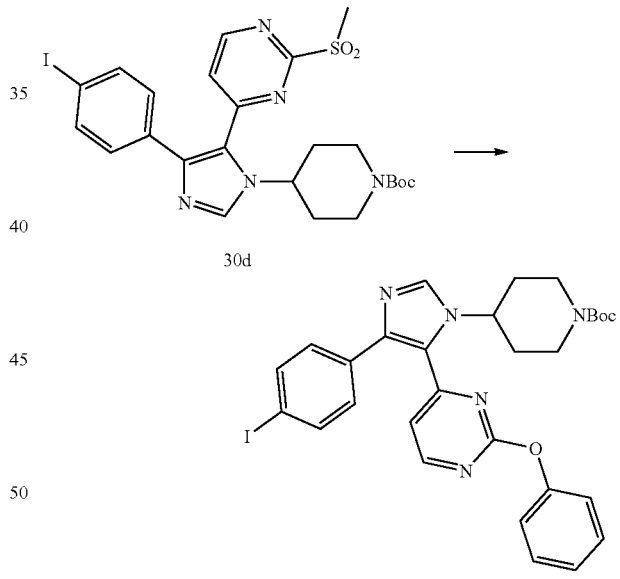

Phenol (0.64 mmol) in anhydrous THF (1.5 mL) was dropwise added to a suspension of NaH (60% in mineral oil, 0.64 mmol) in THF (2 mL) at −10° C. The mixture was stirred for 10 min, followed by the addition of 30d (0.16 mmol) in THF (1.5 mL). The reaction was stirred at room temperature for 16 h, quenched by water and extracted with ethyl acetate (3×20 mL). The crude product was purified by silica gel chromatography using hexane and ethyl acetate (0-100%) as eluent to give compound 69a (52 mg, 0.08 mmol, 52%) as a white solid. $^1$H NMR (500 MHz, CDCl$_3$) δ 8.41 (d, J=5.1 Hz, 1H), 7.68 (d, J=5.9 Hz, 2H), 7.66 (s, 1H), 7.44 (t, J=7.9 Hz, 2H), 7.28 (d, J=7.4 Hz, 1H), 7.25-7.22 (m, 2H), 7.19 (d, J=8.2 Hz, 2H), 6.88 (d, J=5.1 Hz, 1H), 4.58 (tt, J=12.0, 3.8 Hz, 1H), 2.45 (s, 2H), 1.89-1.79 (m, 2H), 1.66 (qd, J=12.4, 4.4 Hz, 2H), 1.46 (s, 9H). $^{13}$C NMR (126 MHz, CDCl$_3$) δ 165.45, 160.14, 159.81, 154.53, 152.96, 143.81, 137.87, 136.87, 133.79, 130.48, 129.84, 125.74, 124.14, 121.99, 116.76, 94.02, 80.15, 54.11, 43.05 (br), 33.39, 28.52.

Example 70. Synthesis of Compound 70

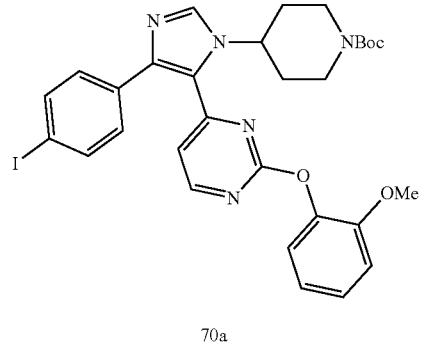

70a

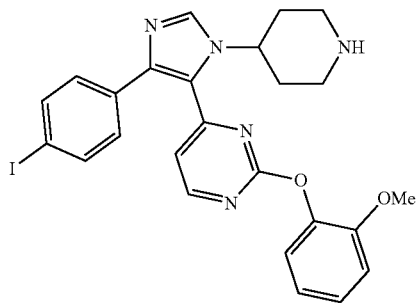

70

Trifluoroacetic acid (TFA) (0.50 mL) was added to a solution of compound 70a (0.13 mmol) in DCM (0.50 mL). After 16 hours, the reaction was concentrated under reduced pressure. Cold ether (4.0 mL) was used to precipitate compound 70 (64 mg, 0.12 mmol, 96%) as a white solid. $^1$H NMR (500 MHz, MeOD) δ 8.92 (s, 1H), 8.58 (d, J=5.1 Hz, 1H), 7.85 (d, J=8.0 Hz, 2H), 7.29 (d, J=8.0 Hz, 2H), 7.17 (d, J=8.0 Hz, 3H), 7.06 (t, J=7.7 Hz, 1H), 7.01 (d, J=5.0 Hz, 1H), 4.75 (p, J=7.9 Hz, 1H), 3.76 (s, 3H), 3.48-3.38 (m, 2H), 2.91-2.79 (m, 2H), 2.15 (dt, J=9.8, 4.8 Hz, 4H). $^{13}$C NMR (126 MHz, MeOD) δ 166.36, 162.32, 158.24, 152.98, 143.20, 139.70, 138.42, 137.46, 131.60, 129.60, 128.16, 126.72, 123.64, 122.36, 118.42, 114.58, 96.97, 56.67, 54.25, 44.45, 30.62.

The intermediate compound 70a was prepared as follows.
a. Preparation of Compound 70a:

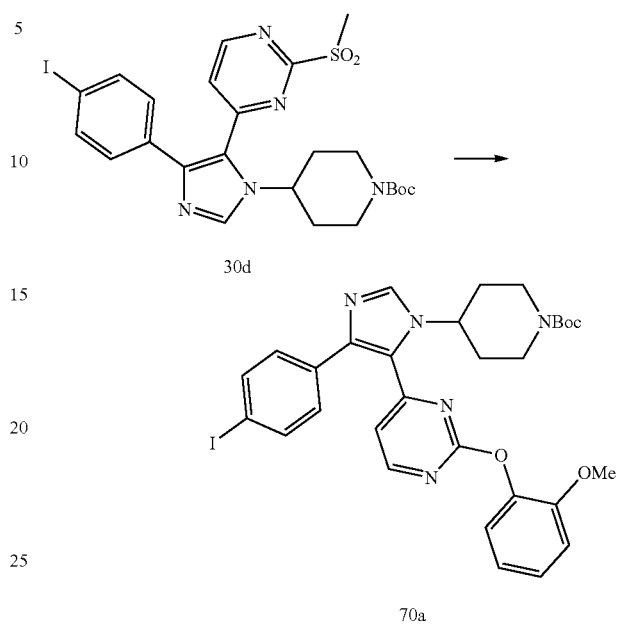

Catechol (0.80 mmol) in anhydrous THF (1.5 mL) was dropwise added to a suspension of NaH (60% in mineral oil, 0.80 mmol) in THF (2 mL) at −10° C. The mixture was stirred for 10 min, followed by the addition of MeI (0.80 mmol). After 30 min, 30d (0.16 mmol) in THF (1.5 mL) was dropwise added to the system. The reaction was stirred at room temperature for 16 h, quenched by water and extracted with ethyl acetate (3×20 mL). The crude product was purified by silica gel chromatography using hexane and ethyl acetate (0-100%) as eluent to give compound 70a (26 mg, 0.04 mmol, 25%) as a white solid. $^1$H NMR (500 MHz, CDCl$_3$) δ 8.39 (d, J=5.1 Hz, 1H), 7.69 (s, 1H), 7.66 (d, J=8.1 Hz, 2H), 7.22 (d, J=8.0 Hz, 2H), 7.17 (d, J=8.1 Hz, 2H), 7.02 (dd, J=8.3, 6.0 Hz, 2H), 6.86 (d, J=5.1 Hz, 1H), 4.61 (tt, J=12.0, 3.9 Hz, 1H), 3.75 (s, 3H), 2.54 (s, 2H), 1.89-1.81 (m, 2H), 1.67 (qd, J=12.3, 4.4 Hz, 2H), 1.46 (s, 9H). $^{13}$C NMR (126 MHz, CDCl$_3$) δ 165.34, 159.99, 159.82, 154.57, 151.66, 143.30, 142.13, 137.82, 136.62, 133.75, 130.36, 126.68, 124.33, 122.91, 121.28, 116.70, 113.25, 93.88, 80.13, 56.22, 54.07, 43.12(br), 33.34, 28.52.

Example 71. Synthesis of Compound 71

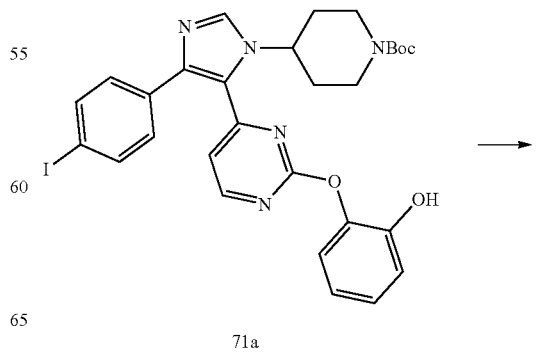

71a

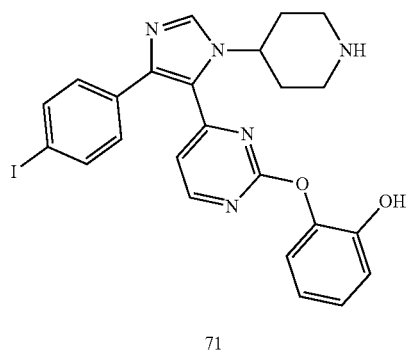

71

Trifluoroacetic acid (TFA) (0.50 mL) was added to a solution of compound 70a (0.13 mmol) in DCM (0.50 mL). After 16 hours, the reaction was concentrated under reduced pressure. Cold ether (4.0 mL) was used to precipitate compound 71 (64 mg, 0.12 mmol, 96%) as a white solid. $^1$H NMR (500 MHz, MeOD) δ 8.61 (s, 1H), 8.56 (d, J=5.0 Hz, 1H), 7.81 (d, J=8.0 Hz, 2H), 7.23 (dd, J=7.9, 1.8 Hz, 1H), 7.17 (dd, J=10.3, 7.9 Hz, 3H), 7.01-6.97 (m, 2H), 6.94 (t, J=7.8 Hz, 1H), 4.78 (tt, J=10.3, 4.7 Hz, 1H), 3.42 (dt, J=13.6, 3.2 Hz, 3H), 2.88 (td, J=12.9, 3.9 Hz, 2H), 2.13 (t, J=5.4 Hz, 4H). $^{13}$C NMR (126 MHz, MeOD) δ 166.39, 162.03, 158.99, 150.51, 142.27, 139.49, 137.71, 131.63, 131.20, 127.98, 126.41, 123.97, 121.32, 118.45, 118.27, 96.27, 53.57, 44.51, 30.71.

The intermediate Compound 71a was prepared as follows.

a. Preparation of Compound 71a:

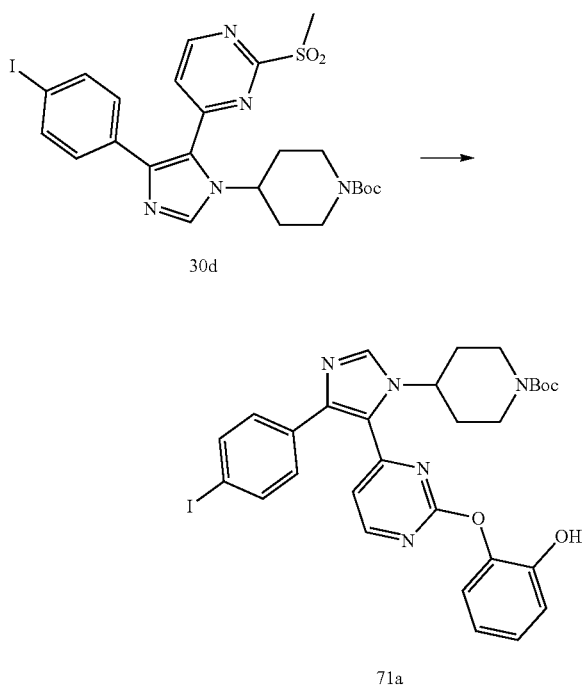 [SMILES: CC(C)(C)OC(=O)N1CCC(n2cnc(-c3ccc(I)cc3)c2-c2ccnc(S(C)(=O)=O)n2)CC1 ; CC(C)(C)OC(=O)N1CCC(n2cnc(-c3ccc(I)cc3)c2-c2ccnc(Oc3ccccc3O)n2)CC1]

Catechol (0.80 mmol) in anhydrous THF (1.5 mL) was dropwise added to a suspension of NaH (60% in mineral oil, 0.64 mmol) in THF (2 mL) at −10° C. The mixture was stirred for 10 min, followed by the addition of 30d (0.16 mmol) in THF (1.5 mL). The reaction was stirred at room temperature for 16 h, quenched by water and extracted with ethyl acetate (3×20 mL). The crude product was purified by silica gel chromatography using hexane and ethyl acetate (0-100%) as eluent to give compound 71a (25 mg, 0.04 mmol, 25%) as a white solid. $^1$H NMR (500 MHz, CDCl$_3$) δ 8.36 (d, J=5.2 Hz, 1H), 7.73 (s, 1H), 7.61 (d, J=8.1 Hz, 2H), 7.19 (dd, J=8.0, 1.5 Hz, 1H), 7.12 (dd, J=8.3, 2.3 Hz, 3H), 7.02 (dd, J=8.2, 1.5 Hz, 1H), 6.93 (td, J=7.7, 1.5 Hz, 1H), 6.85 (d, J=5.0 Hz, 1H), 4.56 (tt, J=12.0, 4.0 Hz, 1H), 4.06 (s, 3H), 2.49 (s, 2H), 1.78 (dd, J=12.3, 3.6 Hz, 2H), 1.63 (tt, J=12.4, 6.2 Hz, 2H), 1.46 (s, 10H). $^{13}$C NMR (126 MHz, CDCl$_3$) δ 164.99, 159.99, 159.94, 154.62, 148.53, 143.81, 140.85, 137.88, 137.12, 133.44, 130.46, 126.98, 124.03, 123.03, 120.77, 118.01, 116.99, 94.17, 80.23, 54.08, 42.95, 33.33, 28.54.

Example 72. Synthesis of Compound 72

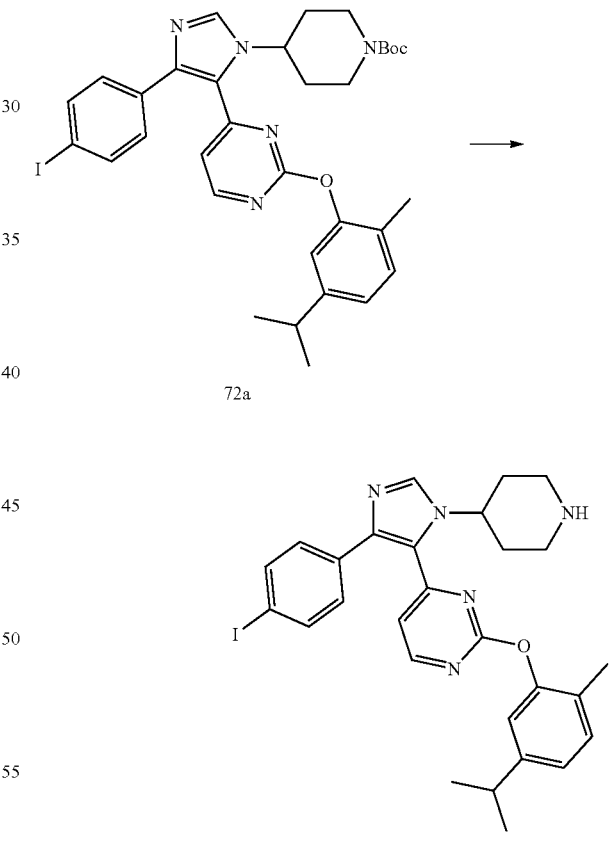

Trifluoroacetic acid (TFA) (0.50 mL) was added to a solution of compound 72a (0.13 mmol) in DCM (0.50 mL). After 16 hours, the reaction was concentrated under reduced pressure. Cold ether (4.0 mL) was used to precipitate compound 72 (70 mg, 0.12 mmol, 96%) as a white solid. $^1$H NMR (500 MHz, MeOD) δ 8.74 (s, 1H), 8.56 (d, J=5.1 Hz, 1H), 7.83 (d, J=8.0 Hz, 2H), 7.27 (d, J=7.8 Hz, 1H), 7.20 (d, J=8.0 Hz, 2H), 7.13 (dd, J=7.9, 1.7 Hz, 1H), 7.10 (d, J=1.7 Hz, 1H), 7.02 (d, J=5.1 Hz, 1H), 4.81-4.71 (m, 1H), 3.46-3.39 (m, 2H), 2.92 (h, J=7.0 Hz, 1H), 2.74 (td, J=13.0, 3.3 Hz, 2H), 2.21 (d, J=11.6 Hz, 3H), 2.19 (s, 4H), 2.14 (td, J=13.0, 4.2 Hz, 2H), 1.24 (d, J=6.9 Hz, 6H). $^{13}$C NMR (126 MHz, MeOD) δ 166.32, 162.32, 158.95, 152.52, 150.00, 139.58, 137.73, 132.50, 131.69, 130.76, 128.60, 126.45, 125.08, 121.37, 118.24, 96.56, 53.95, 44.51, 34.79, 30.78, 24.37, 16.14.

The intermediate Compound 72a was prepared as follows.

a. Preparation of Compound 72a:

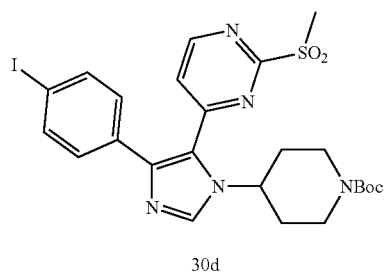

30d

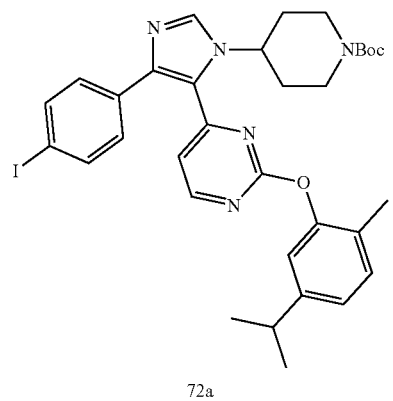

72a

Carvacrol (0.64 mmol) in anhydrous THF (1.5 mL) was dropwise added to a suspension of NaH (60% in mineral oil, 0.64 mmol) in THF (2 mL) at −10° C. The mixture was stirred for 10 min, followed by the addition of 30d (0.16 mmol) in THF (1.5 mL). The reaction was stirred at room temperature for 16 h, quenched by water and extracted with ethyl acetate (3×20 mL). The crude product was purified by silica gel chromatography using hexane and ethyl acetate (0-100%) as eluent to give compound 72a (67 mg, 0.10 mmol, 62%) as a white solid. $^1$H NMR (500 MHz, CDCl$_3$) δ 8.39 (d, J=5.1 Hz, 1H), 7.71 (s, 1H), 7.68 (d, J=8.1 Hz, 2H), 7.20 (dd, J=8.2, 3.0 Hz, 3H), 7.07 (dd, J=7.9, 1.7 Hz, 1H), 7.03 (d, J=1.7 Hz, 1H), 6.86 (d, J=5.1 Hz, 1H), 4.65 (tt, J=12.0, 3.8 Hz, 1H), 2.90 (p, J=6.9 Hz, 1H), 2.41 (q, J=10.3, 7.3 Hz, 2H), 2.16 (s, 3H), 1.90-1.82 (m, 2H), 1.67 (qd, J=12.0, 4.2 Hz, 2H), 1.46 (s, 10H), 1.23 (d, J=6.9 Hz, 7H). $^{13}$C NMR (126 MHz, CDCl$_3$) δ 165.16, 160.11, 159.94, 154.55, 151.29, 148.50, 143.86, 137.90, 136.82, 133.82, 131.32, 130.52, 124.11, 124.04, 120.31, 116.35, 94.07, 80.14, 54.17, 43.03, 33.69, 33.39, 28.52, 24.05, 16.33.

Example 73. Synthesis of Compound 73

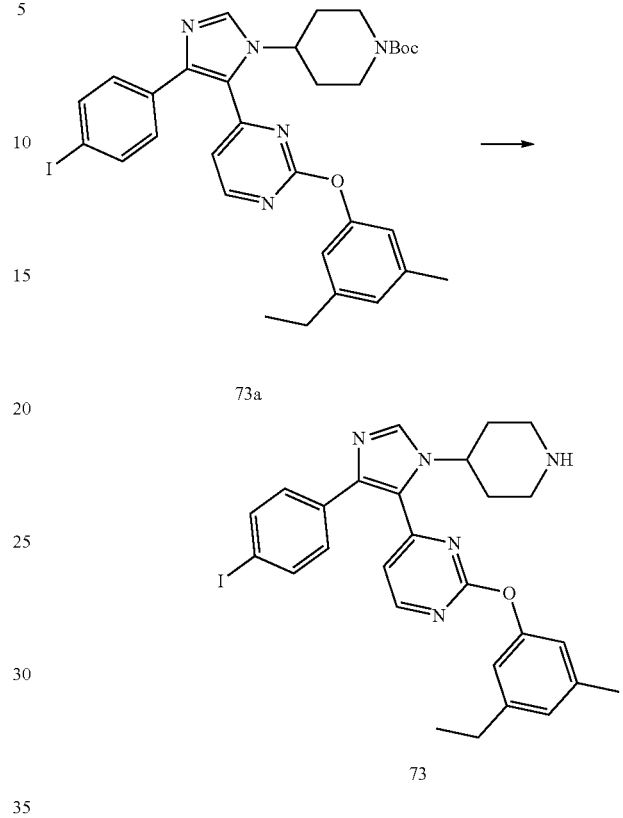

Trifluoroacetic acid (TFA) (0.50 mL) was added to a solution of compound 73a (0.13 mmol) in DCM (0.50 mL). After 16 hours, the reaction was concentrated under reduced pressure. Cold ether (4.0 mL) was used to precipitate compound 73 (68 mg, 0.12 mmol, 96%) as a white solid. $^1$H NMR (500 MHz, MeOD) δ 8.95 (s, 1H), 8.58 (d, J=5.1 Hz, 1H), 7.88-7.83 (m, 2H), 7.25-7.22 (m, 2H), 7.02 (d, J=5.1 Hz, 1H), 7.00 (s, 1H), 6.94 (s, 2H), 4.77 (tt, J=11.8, 4.0 Hz, 1H), 3.38 (dt, J=13.0, 2.5 Hz, 2H), 2.75 (td, J=13.1, 3.1 Hz, 2H), 2.65 (q, J=7.6 Hz, 2H), 2.37 (s, 3H), 2.29-2.22 (m, 2H), 2.18 (td, J=12.7, 4.0 Hz, 2H), 1.23 (t, J=7.6 Hz, 3H). 13C NMR (126 MHz, MeOD) δ 165.22, 161.05, 156.82, 152.85, 146.26, 139.82, 138.32, 137.01, 136.10, 130.34, 128.14, 125.82, 125.45, 119.12, 117.86, 117.02, 95.66, 52.96, 42.99, 29.42, 28.21, 20.00, 14.61.

The intermediate Compound 21a was prepared as follows.

a. Preparation of Compound 73a:

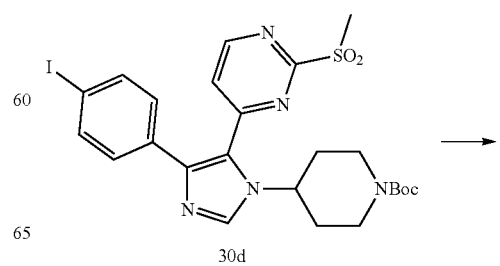

30d

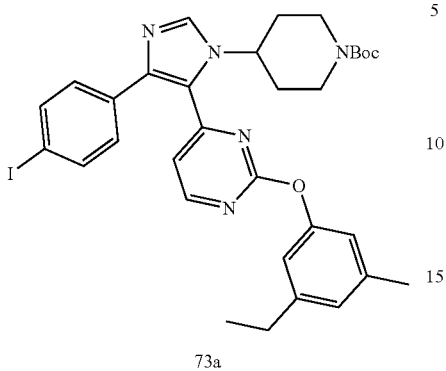

73a

3-Ethyl-5-methylphenol (0.64 mmol) in anhydrous THF (1.5 mL) was dropwise added to a suspension of NaH (60% in mineral oil, 0.64 mmol) in THF (2 mL) at −10° C. The mixture was stirred for 10 min, followed by the addition of 30d (0.16 mmol) in THF (1.5 mL). The reaction was stirred at room temperature for 16 h, quenched by water and extracted with ethyl acetate (3×20 mL). The crude product was purified by silica gel chromatography using hexane and ethyl acetate (0-100%) as eluent to give compound 73a (55 mg, 0.08 mmol, 52%) as a white solid. $^1$H NMR (500 MHz, CDCl$_3$) δ 8.39 (dd, J=5.2, 1.1 Hz, 1H), 7.70 (s, 1H), 7.69-7.65 (m, 2H), 7.21 (d, J=8.1 Hz, 2H), 6.92 (s, 1H), 6.87 (s, 1H), 6.86 (s, 2H), 4.66 (tt, J=12.0, 3.8 Hz, 1H), 2.63 (q, J=7.6 Hz, 2H), 2.43 (q, J=13.1, 12.4 Hz, 2H), 2.34 (s, 3H), 1.91-1.85 (m, 2H), 1.72-1.63 (m, 2H), 1.48-1.43 (m, 9H), 1.22 (t, J=7.5 Hz, 3H). $^{13}$C NMR (126 MHz, CDCl$_3$) δ 165.51, 159.97, 159.81, 154.59, 152.89, 146.09, 143.90, 139.63, 137.86, 136.79, 133.90, 130.52, 126.24, 124.14, 119.78, 118.38, 116.42, 94.02, 80.08, 54.17, 43.01, 33.37, 28.75, 28.50, 21.49, 15.47.

Example 74. Synthesis of Compound 74

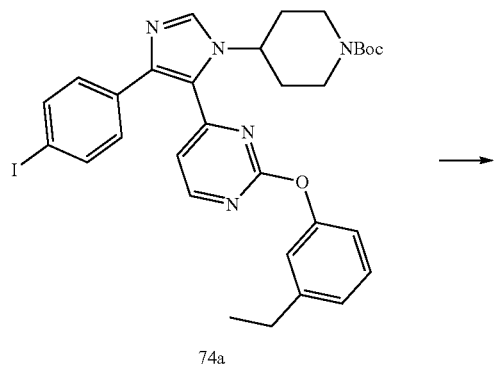

74a

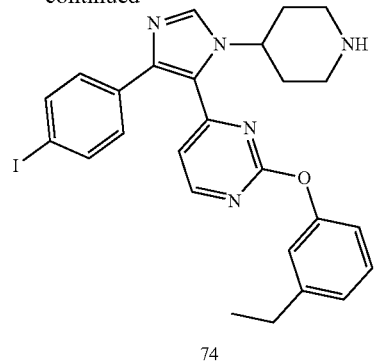

74

Trifluoroacetic acid (TFA) (0.50 mL) was added to a solution of compound 74a (0.13 mmol) in DCM (0.50 mL). After 16 hours, the reaction was concentrated under reduced pressure. Cold ether (4.0 mL) was used to precipitate compound 74 (66 mg, 0.12 mmol, 96%) as a white solid. $^1$H NMR (500 MHz, MeOD) δ 8.56 (d, J=5.1 Hz, 1H), 8.45 (s, 1H), 7.83 (d, J=8.1 Hz, 2H), 7.41 (t, J=7.8 Hz, 1H), 7.26-7.16 (m, 5H), 7.13 (dd, J=8.0, 2.3 Hz, 1H), 7.01 (d, J=5.1 Hz, 1H), 4.78-4.68 (m, 1H), 3.88 (q, J=9.2 Hz, 12H), 3.42-3.35 (m, 2H), 2.82-2.69 (m, 5H), 2.25-2.21 (m, 1H), 2.20 (s, 1H), 2.21-2.11 (m, 1H), 2.10 (d, J=4.0 Hz, 1H), 2.07 (dd, J=13.2, 4.1 Hz, 1H), 1.28 (t, J=7.6 Hz, 3H).

The intermediate Compound 74a was prepared as follows.

a. Preparation of Compound 74a:

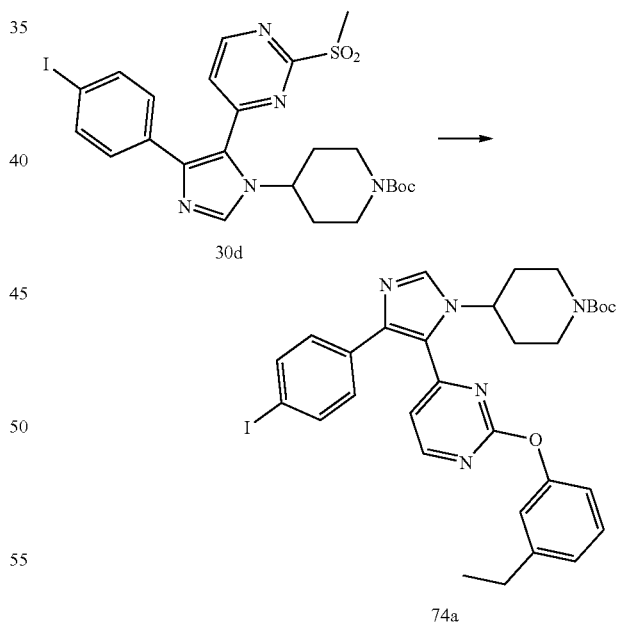

3-Ethylphenol (0.64 mmol) in anhydrous THF (1.5 mL) was dropwise added to a suspension of NaH (60% in mineral oil, 0.64 mmol) in THF (2 mL) at −10° C. The mixture was stirred for 10 min, followed by the addition of 30d (0.16 mmol) in THF (1.5 mL). The reaction was stirred at room temperature for 16 h, quenched by water and extracted with ethyl acetate (3×20 mL). The crude product was purified by silica gel chromatography using hexane and ethyl acetate (0-100%) as eluent to give compound 74a (63 mg, 0.08 mmol, 60%) as a white solid.

Example 75. Synthesis of Compound 75

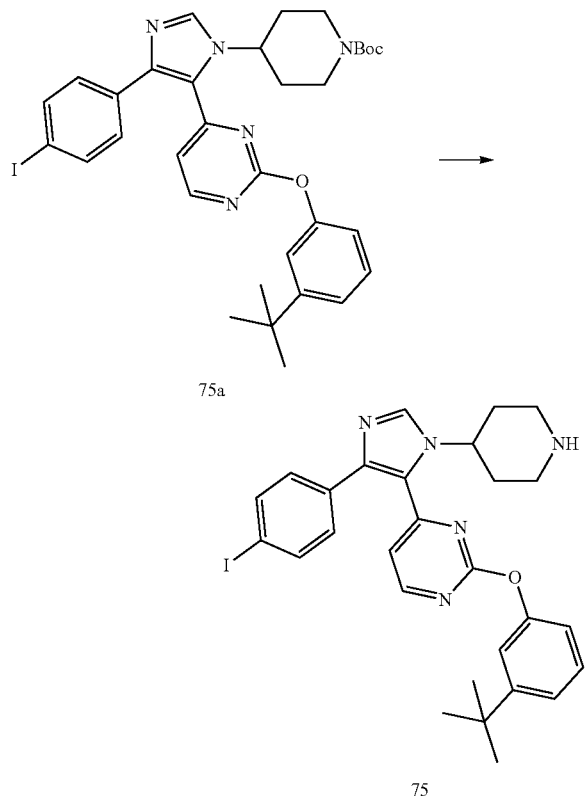

75a

75

Trifluoroacetic acid (TFA) (0.50 mL) was added to a solution of compound 74a (0.13 mmol) in DCM (0.50 mL). After 16 hours, the reaction was concentrated under reduced pressure. Cold ether (4.0 mL) was used to precipitate compound 75 (70 mg, 0.12 mmol, 96%) as a white solid. $^1$H NMR (500 MHz, MeOD) δ 8.58-8.55 (m, 2H), 7.84 (d, J=7.9 Hz, 2H), 7.43 (t, J=7.8 Hz, 1H), 7.39 (dd, J=8.0, 1.5 Hz, 1H), 7.35 (t, J=1.9 Hz, 1H), 7.24 (d, J=8.0 Hz, 2H), 7.13 (dd, J=7.9, 2.1 Hz, 1H), 7.02 (d, J=5.1 Hz, 1H), 4.79 (tt, J=12.0, 4.0 Hz, 1H), 3.44-3.37 (m, 2H), 2.81 (td, J=13.1, 2.8 Hz, 2H), 2.30-2.24 (m, 2H), 2.12 (qd, J=13.1, 4.2 Hz, 2H), 1.36 (s, 8H).

The intermediate Compound 75a was prepared as follows.

a. Preparation of Compound 75a:

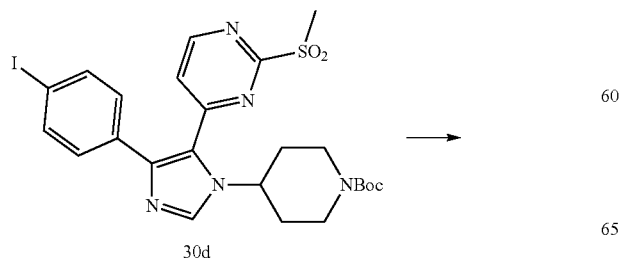

30d

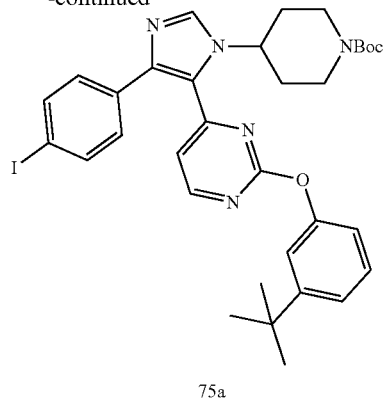

75a

3-Tert-butylphenol (0.64 mmol) in anhydrous THF (1.5 mL) was dropwise added to a suspension of NaH (60% in mineral oil, 0.64 mmol) in THF (2 mL) at −10° C. The mixture was stirred for 10 min, followed by the addition of 30d (0.16 mmol) in THF (1.5 mL). The reaction was stirred at room temperature for 16 hours, quenched by water and extracted with ethyl acetate (3×20 mL). The crude product was purified by silica gel chromatography using hexane and ethyl acetate (0-100%) as eluent to give compound 75a (48 mg, 0.07 mmol, 44%) as a white solid. $^1$H NMR (500 MHz, CDCl$_3$) δ 8.41 (d, J=5.2 Hz, 1H), 7.70 (s, 1H), 7.69 (d, J=8.6 Hz, 3H), 7.36 (t, J=7.9 Hz, 1H), 7.31-7.28 (m, 1H), 7.22 (d, J=8.0 Hz, 2H), 7.09-7.05 (m, 1H), 6.88 (d, J=5.2 Hz, 1H), 4.66 (tt, J=12.1, 3.8 Hz, 1H), 4.06 (s, 3H), 2.34 (t, J=13.1 Hz, 2H), 1.89-1.83 (m, 2H), 1.71-1.60 (m, 2H), 1.45 (s, 11H), 1.32 (s, 10H).

Example 76. Synthesis of Compound 76

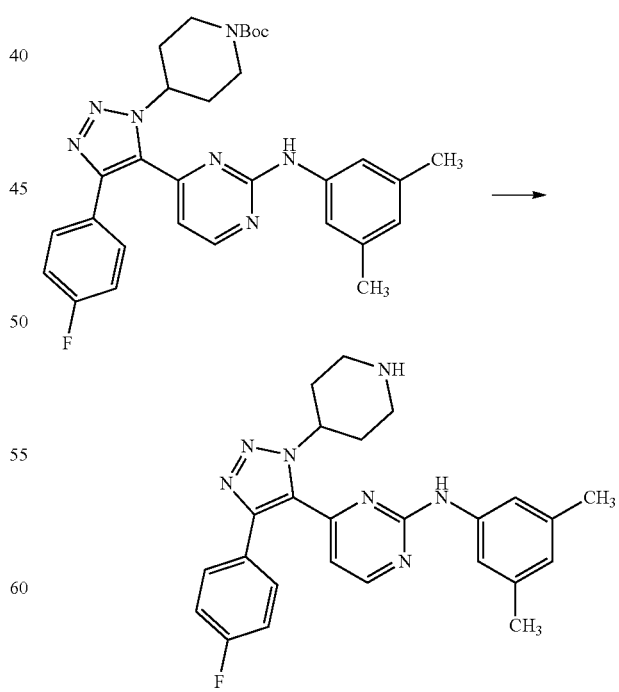

76

To a solution of tert-butyl 4-(5-(2-((3,5-dimethylphenyl)amino)pyrimidin-4-yl)-4-(4-fluorophenyl)-1H-1,2,3-triazol-1-yl)piperidine-1-carboxylate (18 mg, 32 µmol) in DCM (0.5 mL) at room temperature was added TFA (0.5 mL). After 1 hour, the product was concentrated under reduced pressure. This afforded Compound 76 quantitatively as a yellow solid. The ratio of TFA and amine was determined by $^{19}$F NMR. $^1$H NMR (500 MHz, MeOD) δ 8.44 (d, J=5.0 Hz, 1H), 7.60 (apparent dd, J=8.8, 5.3 Hz, 2H), 7.27-7.18 (m, 4H), 6.79 (s, 1H), 6.68 (d, J=5.0 Hz, 1H), 5.16 (tt, J=10.7, 4.3 Hz, 1H), 3.52-3.45 (m, 2H), 2.96-2.86 (m, 2H), 2.55-2.36 (m, 4H), 2.31 (s, 6H). $^{13}$C NMR (126 MHz, MeOD) δ 163.2 (d, $J_{C-F}$=247.6 Hz), 160.8, 159.0, 155.2, 145.4, 139.0, 138.2, 130.9, 130.1 (d, $J_{C-F}$=8.4 Hz), 126.2, 124.9, 118.9, 115.5 (d, $J_{C-F}$=22.1 Hz), 112.0, 54.0, 42.7, 28.8, 20.1. $^{19}$F NMR (376 MHz, MeOD) δ −77.5 (9H), −114.3 (1H). IR (NaCl, thin film, cm$^{-1}$): 2916, 2850, 1676, 1624, 1592, 1510, 1457, 1198, 1186, 1160, 1143. HRMS (ESI): Calculated for $C_{25}H_{26}FN_7Na^+$, (M+Na)$^+$ 466.2126, found 466.2117. HPLC Purity: 96.3%.

The intermediate tert-butyl 4-(5-(2-((3,5-dimethylphenyl)amino)pyrimidin-4-yl)-4-(4-fluorophenyl)-1H-1,2,3-triazol-1-yl)piperidine-1-carboxylate was prepared as follows.

a. Preparation of tert-butyl 4-(4-(4-fluorophenyl)-1H-1,2,3-triazol-1-yl)piperidine-1-carboxylate

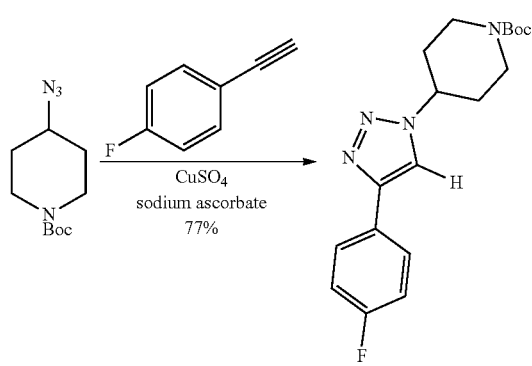

The azide (3.9 mmol) was dissolved in t-BuOH/H$_2$O (1:1, 10 mL). A separate vial was charged with alkyne (660 mg, 4.8 mmol), copper sulfate pentahydrate (40 mg, 0.16 mmol), and sodium ascorbate (170 mg, 0.84 mmol). The solution of azide was transferred into the vial containing alkyne by pipette and sealed under air. After 18 hours at room temperature, the reaction mixture was diluted with water and extracted with ethyl acetate. The combined organic phases were washed with brine, dried over anhydrous magnesium sulfate, filtered, and concentrated under reduced pressure to afford the triazole (1.10 g, 77%) as a white solid. $^1$H NMR (500 MHz, CDCl$_3$) δ 7.81 (apparent dd, J=8.8, 5.3 Hz, 2H), 7.75 (s, 1H), 7.13 (apparent t, J=8.7 Hz, 2H), 4.67 (tt, J=11.6, 4.1 Hz, 1H), 4.30 (br, 2H), 2.97 (br, 2H), 2.28-2.22 (m, 2H), 2.00 (qd, J=12.2, 4.4 Hz, 2H), 1.50 (s, 9H). $^{13}$C NMR (126 MHz, CDCl$_3$) δ 162.7 (d, $J_{C-F}$=247.4 Hz), 154.5, 146.8, 127.4 (d, $J_{C-F}$=8.1 Hz), 126.8 (d, $J_{C-F}$=3.2 Hz), 117.1, 115.9 (d, $J_{C-F}$=21.6 Hz), 80.2, 58.3, 42.7 (br), 32.5, 28.4. $^{19}$F NMR (376 MHz, CDCl$_3$) δ −113.5. IR (NaCl, thin film, cm$^{-1}$): 2974, 1689, 1496, 1424, 1244, 1166. HRMS (ESI): Calculated for $C_{18}H_{23}FN_4NaO_2^+$, (M+Na)$^+$ 369.1697, found 369.1682.

b. Preparation of tert-butyl 4-(4-(4-fluorophenyl)-5-(2-(methylthio)pyrimidin-4-yl)-1H-1,2,3-triazol-1-yl)piperidine-1-carboxylate

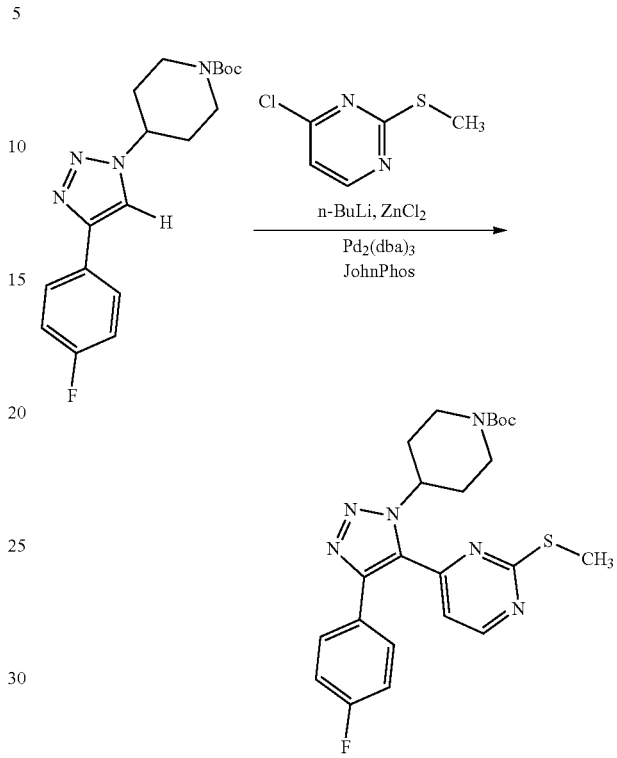

A solution of tert-butyl 4-(4-(4-fluorophenyl)-1H-1,2,3-triazol-1-yl)piperidine-1-carboxylate (170 mg, 0.50 mmol) in THF (8 mL) was cooled in a dry ice/acetone bath. Then n-BuLi (0.26 mL, 2.5 M in hexanes, 0.65 mmol) was added dropwise. After 10 minutes, a freshly prepared solution of ZnCl$_2$ (110 mg, 0.78 mmol) in THF (1 mL) was added dropwise. After 10 minutes, a freshly prepared solution of SPhos Pd G3 (17 mg, 22 µmol) in THF (1 mL) was added followed by addition of chloro-pyrimidine (0.12 mL, 1.0 mmol). The reaction was heated to 60° C. After 1.5 hours, the reaction mixture was diluted with water and extracted with ethyl acetate. The combined organic phases were washed with brine, dried over anhydrous magnesium sulfate, filtered, and concentrated under reduced pressure. Final purification by column chromatography (0-50% EtOAc in Hexanes) yielded the product as a white solid (210 mg, 88%). $^1$H NMR (400 MHz, CDCl$_3$) δ 8.50 (d, J=5.1 Hz, 1H), 7.50 (apparent dd, J=8.6, 5.4 Hz, 2H), 7.09 (apparent t, J=8.7 Hz, 2H), 6.86 (d, J=5.1 Hz, 1H), 4.96 (tt, J=11.4, 4.0 Hz, 1H), 4.30 (br, 2H), 2.89 (br, 2H), 2.61 (s, 3H), 2.42-2.28 (m, 2H), 2.23-2.06 (m, 2H), 1.50 (s, 9H). 13C NMR (101 MHz, CDCl$_3$) δ 173.9, 163.1 (d, $J_{C-F}$=248.9 Hz), 158.0, 155.3, 154.6, 146.3, 130.3 (d, $J_{C-F}$=8.3 Hz), 129.3, 126.4 (d, $J_{C-F}$=3.3 Hz), 116.5, 116.0 (d, $J_{C-F}$=21.8 Hz), 80.0, 57.8, 43.0 (br), 32.3, 28.4, 14.1. $^{19}$F NMR (376 MHz, CDCl$_3$) δ −112.2. IR (NaCl, thin film, cm$^{-1}$): 2976, 2930, 2863, 1692, 1550, 1506, 1420, 1349, 1243, 1158, 997, 913, 841, 732. HRMS (ESI): Calculated for $C_{23}H_{27}FN_6NaO_2S^+$, (M+Na)$^+$ 493.1792, found 493.1774.

c. Preparation of tert-butyl 4-(4-(4-fluorophenyl)-5-(2-(methylsulfonyl)pyrimidin-4-yl)-1H-1,2,3-triazol-1-yl)piperidine-1-carboxylate

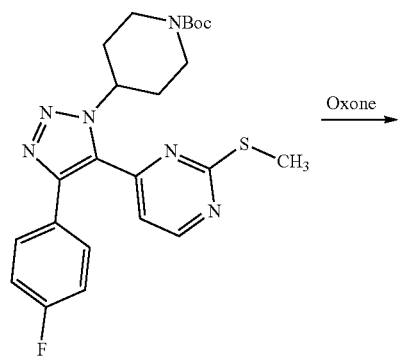

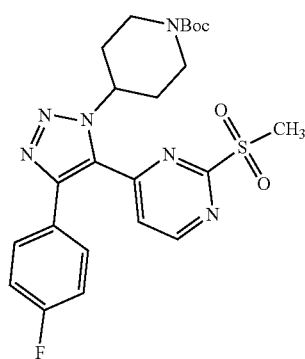

To a solution of tert-butyl 4-(4-(4-fluorophenyl)-5-(2-(methylthio)pyrimidin-4-yl)-1H-1,2,3-triazol-1-yl)piperidine-1-carboxylate (350 mg, 0.74 mmol) in THF (10 mL) cooled in an ice bath, a solution of Oxone (690 mg, 2.3 mmol) in water (3 mL) was added dropwise. The reaction was sealed under air and warmed to room temperature. After 20 hours, the reaction was diluted with ice water and extracted with ethyl acetate. The combined organic phases were washed with brine, dried over anhydrous magnesium sulfate, filtered, and concentrated under reduced pressure. This afforded the sulfone (330 mg, 66%) as a white solid. $^1$H NMR (400 MHz, CDCl$_3$) δ 8.80 (d, J=5.3 Hz, 1H), 7.50 (apparent dd, J=8.8, 5.2 Hz, 2H), 7.41 (d, J=5.3 Hz, 1H), 7.15 (apparent t, J=8.6 Hz, 2H), 5.15 (tt, J=10.6, 4.6 Hz, 1H), 4.33 (br, 2H), 3.41 (s, 3H), 2.97 (br, 2H), 2.44-2.16 (m, 4H), 1.48 (s, 9H). $^{13}$C NMR (126 MHz, CDCl$_3$) δ 166.6, 163.4 (d, $J_{C-F}$=250.2 Hz), 158.9, 157.0, 154.6, 147.7, 130.6 (d, $J_{C-F}$=8.3 Hz), 128.0, 126.0 (d, $J_{C-F}$=3.3 Hz), 122.8, 116.4 (d, $J_{C-F}$=21.8 Hz), 79.9, 59.2, 43.3 (br), 39.1, 32.4, 28.4. $^{19}$F NMR (376 MHz, CDCl$_3$) δ −110.9. IR (NaCl, thin film, cm$^{-1}$): 2977, 2929, 1685, 1578, 1507, 1420, 1324, 1244, 1159, 1135, 843. HRMS (ESI): Calculated for C$_{23}$H$_{27}$FN$_6$NaO$_4$S$^+$, (M+Na)$^+$ 525.1691, found 525.1688.

d. Preparation of tert-butyl 4-(5-(2-((3,5-dimethylphenyl)amino)pyrimidin-4-yl)-4-(4-fluorophenyl)-1H-1,2,3-triazol-1-yl)piperidine-1-carboxylate

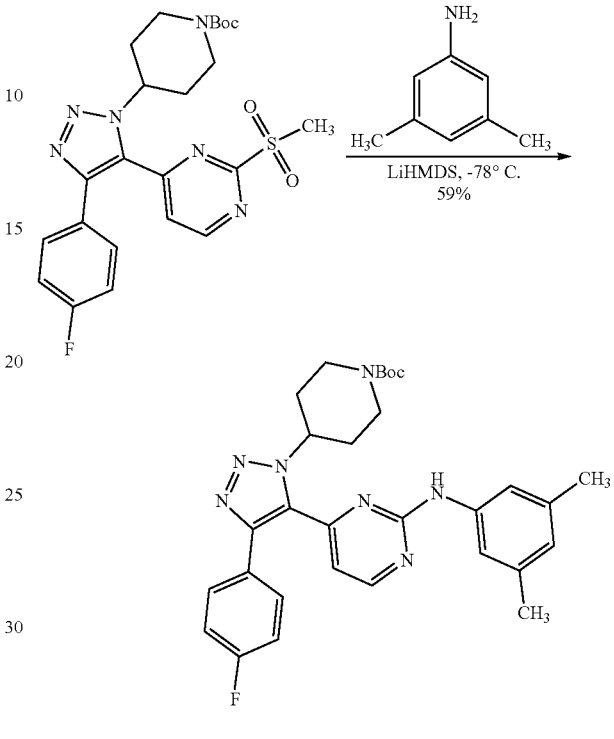

To a vial containing tert-butyl 4-(4-(4-fluorophenyl)-5-(2-(methylsulfonyl)pyrimidin-4-yl)-1H-1,2,3-triazol-1-yl)piperidine-1-carboxylate (85 mg, 0.170 mmol), 2,5-dimethylaniline (0.21 mL, 1.7 mmol) was added neat. The vial was sealed under air and heated to 100° C. After 3 hours, the reaction mixture was cooled to room temperature diluted with THF (0.5 mL) and then Boc$_2$O (0.10 mL, 0.44 mmol) was added. After an additional 2 hours at room temperature, the reaction was concentrated under reduced pressure. Purification by column chromatography (0-60% IPA in hexanes with 1% TEA) yielded semi-pure material. The purified material was recrystallized in DCM and hexanes to afford the desired product (54 mg, 59%) as a white solid. $^1$H NMR (500 MHz, CDCl$_3$) δ 8.41 (d, J=5.0 Hz, 1H), 7.59 (apparent dd, J=8.7, 5.4 Hz, 2H), 7.36 (s, 1H), 7.20 (s, 2H), 7.10 (apparent t, J=8.7 Hz, 2H), 6.80 (s, 1H), 6.61 (d, J=5.0 Hz, 1H), 4.93 (tt, J=11.4, 4.0 Hz, 1H), 4.16 (br, 2H), 2.58 (br, 2H), 2.33 (s, 6H), 2.32-2.19 (m, 2H), 2.09-2.02 (m, 2H), 1.49 (s, 9H). $^{13}$C NMR (126 MHz, CDCl$_3$) δ 163.0 (d, $J_{C-F}$=248.4 Hz), 160.7, 159.3, 156.0, 154.5, 145.7, 138.7, 138.3, 130.2 (d, $J_{C-F}$=8.2 Hz), 130.0, 126.6 (d, $J_{C-F}$=3.1 Hz), 125.7, 118.4, 115.8 (d, $J_{C-F}$=21.7 Hz), 112.9, 79.9, 57.3, 42.7 (br), 32.2, 28.4, 21.4. $^{19}$F NMR (376 MHz, CDCl$_3$) δ −112.7. IR (NaCl, thin film, cm$^{-1}$): 2974, 1691, 1536, 1430, 1160. HRMS (ESI): Calculated for C$_{30}$H$_{34}$FN$_7$NaO$_2$$^+$, (M+Na)$^+$ 566.2650, found 566.2643.

Compounds of the invention can be prepared using a procedure similar to that described in (Divakaran, A. et al. J. Med. Chem. 2018, 61, 9316-9334.

The biological activity of a compound can be evaluated using the procedures described in Examples 77-93.

Example 77. Fluorescence Spectroscopy

Fluorescence spectra were obtained at room temperature using an Agilent Cary Eclipse fluorescence spectrophotometer in quartz cuvettes or white 96-well plates (Costar, Corning, NY). Each measurement was done in triplicate. Sample stock solutions were prepared in HPLC grade DMSO. DNA stock solutions were prepared in Tris buffer (50 mM NaCl, 2 mM Tris, pH 7.5).

Example 78. General Procedure for Multiwell DNAse I Assay

A reaction mixture (total volume of 100 µL) containing 4 (4 µM) and QIII (8 µM) was prepared in 9:1 Tris buffer (10 mM Tris-HCl, 0.25 mM $MgCl_2$, 0.1 mM $CaCl_2$, pH 7.5): DMSO. Tris buffer was prepared using nuclease-free water. The reaction mixtures were prepared in white 96-well plates (Costar, Corning, NY) and incubated at room temperature for 2 min. Varying concentrations of DNAse I prepared in Tris buffer (10 mM Tris-HCl, 0.25 mM $MgCl_2$, 0.1 mM $CaCl_2$, pH 7.5) were added to the reaction mixture and incubated at room temperature for 10 min. Fluorescence spectra were obtained using Agilent Cary Eclipse fluorescence spectrophotometer, $\lambda_{ex}$=445 nm. NIR emission intensity at 785 nm was detected.

Example 79. Lineweaver-Burk Plot

The assay was performed in multiwell plates as described in the general procedure above using a reaction mixture (100 µL) prepared from a starting solution of 4/QIII (4 and 81.1M, respectively, see General Procedure) diluted with buffer to obtain varying substrate concentrations of QIII (0, 0.25, 0.5, 1, 1.5, 2, 4 and 8 µM). DNAse I (4 U/mL) was added and mixtures were incubated at room temperature for 10 min. followed by fluorescence measurements. The initial digestion rates ($V_0$) were measured from time curves of digestion reactions.

Example 80. Detection of DNAse I in Human Serum

Human serum from human male AB plasma was purchased from Sigma-Aldrich. DNAse I assay was performed as previously described. Different concentrations of DNAse I were prepared in human serum and added to reaction mixtures.

Example 81. Determination of $IC_{50}$ Values of DNAse I Inhibitors

DNAse I assay was performed as previously described in the presence of DNAse I (4 U) and various concentrations of the inhibitor. Stock solutions of the inhibitors were prepared in Tris buffer (10 mM Tris-HCl, pH 7.5). The $IC_{50}$ values were calculated by plotting log[inhibitor] versus NIR emission intensity of 4. The dose-response curves were analyzed by nonlinear regression using GraphPad Prism 8.0 (GraphPad Software, Inc., La Jolla, CA, USA).

Example 82. Protein Expression $His_6$ BRD4 D1 were expressed and purified as reported by A. K. Urick, et al., *ACS Chem. Biol.* 2015, 10, 2246-2256.

Example 83. $His_9$ BRD4 D1 Expression

The $His_6$ BRD4 D1 insert was modified by addition of three histidines to the hexahistidine tag via site-directed mutagenesis by standard procedures (A. K. Urick, et al., *ACS Chem. Biol.* 2015, 10, 2246-2256). The resulting gene was co-transformed with pRARE (Novagen) into BL21 (DE3) *E. coli* (N. K. Mishra, et al., *ACS Chem. Biol.* 2014, 9, 2755-2760). Cells were grown on Luria-Bertani (LB) agar plates containing kanamycin (100 mg/mL) at 37° C. for 12 hours. Individual colonies were picked and grown for 12 hours in 5 mL of LB containing kanamycin (100 mg/mL). The primary culture was used to inoculate 1 L of LB media containing kanamycin (100 mg/mL) and the culture was grown by shaking at 220 RPM at 37° C. until an OD600 of 0.6-0.8 was reached.

Example 84. BRD4 D2 Expression

The pET-28a(+) plasmid containing the second bromodomain of BRD4 (residues 333-460) was purchased from GenScript. The *E. coli* strain BL21 Star (DE3) was transformed with the plasmid containing the desired insert and plated onto an agar plate containing the appropriate antibiotics. The plate was incubated overnight at 37° C. A 5 mL LB culture containing antibiotics, chloramphenicol (35 mg/L) and kanamycin (100 mg/L), was inoculated using a single colony form this plate and grown overnight at 37° C. and shaking at 215 rpm. The primary culture was used to inoculate 1 L of LB media containing chloramphenicol (35 mg/L) and kanamycin (100 mg/L) at 37° C. at 215 rpm until the optical density at 600 nm had reached 0.6-0.8. An equilibration time of 30 minutes at 20° C. and 215 rpm was followed by the addition of 1 mM IPTG to induce protein expression. The culture was shaken for 16-20 hours at 20° C. and 220 rpm. Cells were pelleted by centrifugation at 8,000 g and stored at −20° C. until purification.

Example 85. BRD2 D1 Expression

The pET28a(+) plasmid containing the first bromodomain of BRD2 (Residues 71-194) was purchased from GenScript. The *E. coli* strain BL21(DE3)-RIL were transformed with the BRD2 D1 plasmid and plated onto an agar plates containing kanamycin (100 mg/L) and chloramphenicol (35 mg/L). The plate was incubated overnight at 37° C. A 5 mL LB culture containing kanamycin (100 mg/L) and chloramphenicol (35 mg/L) was inoculated using a single colony from this plate and grown overnight at 25° C. and shaking at 220 rpm. The primary culture was used to inoculate 1 L of LB media containing chloramphenicol (35 mg/L) and kanamycin (100 mg/L) until the optical density at 600 nm had reached 0.6-0.8. At this point, an equilibration time of 30 minutes at 20° C. and 220 rpm was followed by the addition of 1 mM IPTG to induce protein expression. The culture was shaken for 16-20 hours at 20° C. and 220 rpm. Cells were pelleted by centrifugation at 8,000 g and stored at −20° C. until purification.

Example 86. Fluorescence Anisotropy

Fluorescence-anisotropy experiments were carried out in 50 mM HEPES, 100 mM NaCl, and 4 mM CHAPS at pH=7.4 in 384-well plates (Corning 4511). 10 µM Fl-JQ1 stock in DMSO were diluted to 15 nM (A. Divakaran, et al., *J. Med. Chem.* 2018, 61, 9316-9334). A Tecan Infinity 500 was used with an excitation wavelength at 485 nm and emission at 535 nm. Protein was serially diluted across the plate, after 30 min, anisotropy values were measured and fit using equation 1 in GraphPad Prism for direct binding experiment. B and c are the maximum and minimum anisotropy values; a is the concentration of Fl-JQ1 (15 nM); x is the concentration of protein; and y is the observed anisotropy value in equation 1.

$$y = c + (b-c)\frac{(Kd + a + x) - \sqrt{(Kd + a + x)^2 - 4ax}}{2a} \quad \text{equation 1}$$

The protein concentrations of the competition experiments were determined from the direct-binding experiments at which the Fl-JQ1 is 80% bound. Using a 10 mM stock solution in DMSO, inhibitors were serially diluted from 50 µM to subnanomolar concentrations. The concentrations of protein, tracer, and other components were kept constant. Anisotropy values were fit using GraphPad Prism's [inhibitor] versus response (four parameters) function. The $IC_{50}$ values are reported as the mean±SEM, as determined from three independent experiments. Direct binding with Fl-JQ1 and self-competition experiments with (+)-JQ1 were carried out before competition experiments to check protein quality and assay stability. This experimental protocol was used to determine $IC_{50}$ values for inhibitors against BRD4-D1 and BRD4-D2. Data for representative compounds is provided in the following table.

| Example | $IC_{50}$ BRD4-D1 (µM) | $IC_{50}$ BRD4-D2 (µM) |
| --- | --- | --- |
| *(structure)* | 3.01 | 5.87 |
| *(structure)* | 9.7 ± 1.8 | |
| *(structure)* | 12 ± 1.1 | |
| *(structure)* | 3.6 ± 0.05 | |
| *(structure)* | 97 ± 2.6 | |
| *(structure)* | >100 | |

-continued
| Example | IC$_{50}$ BRD4-D1 (μM) | IC$_{50}$ BRD4-D2 (μM) |
|---|---|---|
| 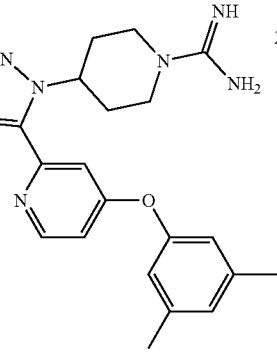 | >100 2·TFA | |
| 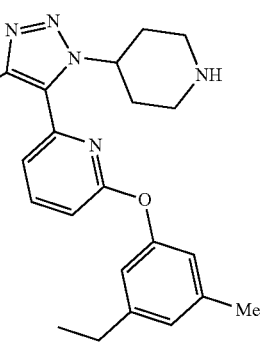 | 1.57 ± 0.1 | 3.92 |
| 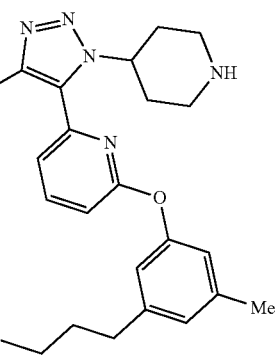 | 2.40 ± 0.3 | — |
| 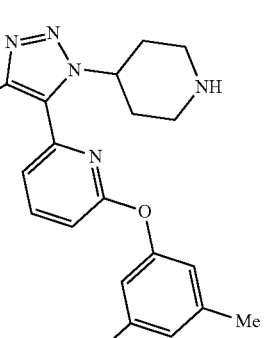 | 3.23 ± 0.5 | 4.76 |
-continued
| Example | IC$_{50}$ BRD4-D1 (μM) | IC$_{50}$ BRD4-D2 (μM) |
|---|---|---|
| 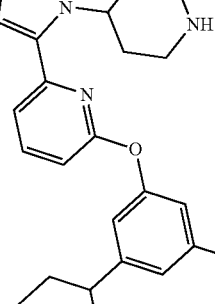 | 3.21 ± 0.3 | 7.35 |
| 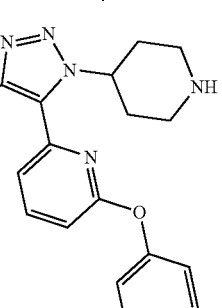 | 4.44 | 7.35 |
| 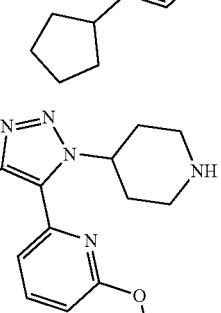 | 4.75 ± 0.4 | — |
| 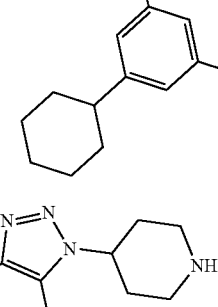 | 2.78 ± 0.3 | 6.39 |

| Example | IC$_{50}$ BRD4-D1 (µM) | IC$_{50}$ BRD4-D2 (µM) |
|---|---|---|
| 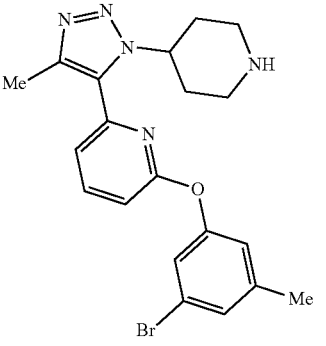 [SMILES: Cc1cc(Br)cc(Oc2cccc(-c3c(C)nnn3C3CCNCC3)n2)c1] | 1.43 ± 0.2 | 2.56 |
| 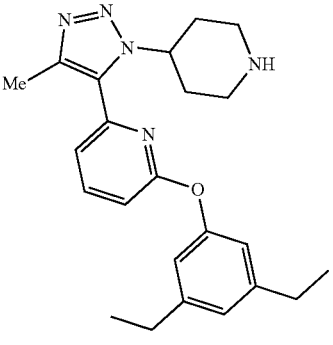 [SMILES: CCc1cc(CC)cc(Oc2cccc(-c3c(C)nnn3C3CCNCC3)n2)c1] | 1.50 ± 0.2 | 3.60 |
| 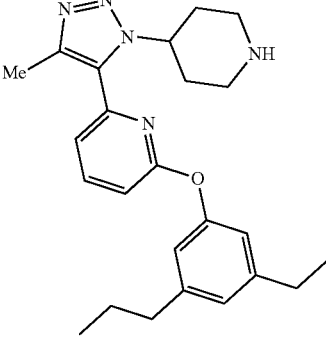 | 2.60 ± 0.1 | 14.4* |
| 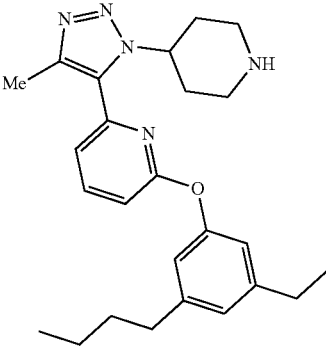 | 8.61 | 27.7* |
| Example | IC$_{50}$ BRD4-D1 (µM) | IC$_{50}$ BRD4-D2 (µM) |
|---|---|---|
| 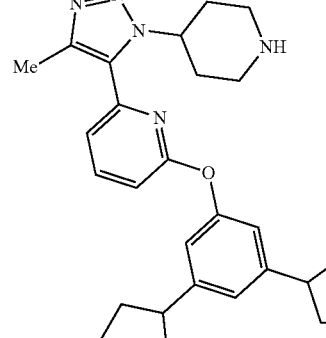 | 21.8 ± 3 | 53.8 |
| 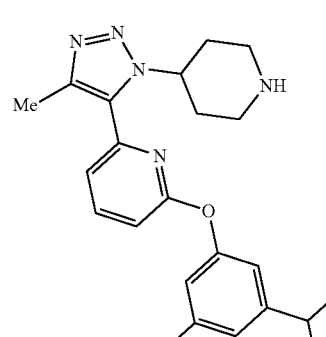 | 62.6 | >100 |
| 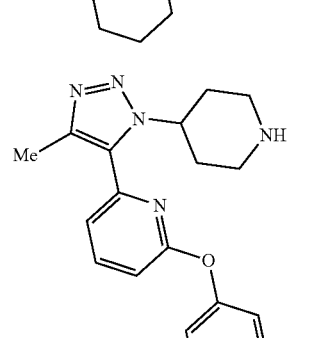 | 1.14 | 2.28 |
| 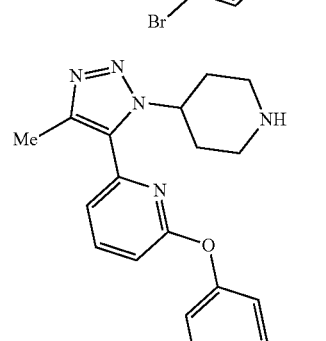 | 14.3 ± 2 | 45.6 |

| Example | IC₅₀ BRD4-D1 (μM) | IC₅₀ BRD4-D2 (μM) |
|---|---|---|
| [structure: 4-iodophenyl imidazole piperidine pyrimidine-O-phenyl] | | 2.4 ± 0.06 |
| [structure: with 2-methoxyphenyl] | | 3.2 ± 0.6 |
| [structure: with 2-hydroxyphenyl] | | 3.0 ± 0.1 |
| [structure: with 2-methyl-5-isopropylphenyl] | | 0.036 ± 0.005 |
| [structure: with 3-ethyl-5-methylphenyl] | | 0.055 ± 0.004 |
| [structure: with 3-ethylphenyl] | | 0.20 ± 0.003 |
| [structure: with 3-tert-butylphenyl] | | 0.11 ± 0.025 |

*IC₅₀ values were determined by fluorescence anisotropy. Data represents the mean and standard deviation of three independent trials.

Example 87. General Procedure for AlphaScreen Assay with His₉-BRD4 D1

AlphaScreen assay procedure for BRD4 D1 was adapted from the manufacturers protocol (PerkinElmer, USA). Nickel chelate (Ni-NTA) acceptor beads and streptavidin donor beads were purchased from PerkinElmer (Cat. #: 6760619M). The biotinylated histone H4 KAc5,8,12,16 peptide was purchased from EpiCypher, with the sequence: Ac-SGRGK(Ac)GGK(Ac)GLGK(Ac)GGAK(Ac)RHRKVLR-Peg (Biot)

All reagents were diluted in the assay buffer (50 mM HEPES-Na⁺ (ChemImpex), 100 mM NaCl (SigmaAldrich), 0.05% CHAPS (RPI), 0.1% BSA (SigmaAldrich), pH=7.4). Final assay concentrations (after the addition of all assay components) of 7.5-60 nM for His₉-tagged BRD4 D1 and 25-100 nM for the biotinylated peptide were used. 3-fold serial dilutions were prepared with varying concentrations of the compounds and a fixed protein concentration, keeping the final DMSO concentration at 0.1%. For each plate, (+)-JQ1 was run in duplicate as a positive control. 5 µL of these solutions were added to a 384-well plate (ProxiPlate-384, PerkinElmer). The plate was sealed and kept at room temperature for 30 minutes, followed by the addition of 5 µL of the biotinylated peptide. 5 µL of nickel chelate acceptor beads was added to each well under low light conditions (<100 lux), to a final concentration of 20 µg/mL, and the plate was incubated at room temperature in the dark for 30 minutes. This was followed by the addition of 5 µL (20 µg/mL final concentration) of streptavidin donor beads in low light conditions. After incubation for 30 minutes in the dark, the plate was read in AlphaScreen mode using a PerkinElmer EnSpire plate reader. Each compound was run in duplicate. The data was normalized against DMSO negative control signal to obtain the % normalized AlphaScreen signal and $IC_{50}$ values were calculated in GraphPad Prism 5 using [inhibitor] versus response (four parameters) function.

Example 88. P38 Assay p38 activity was evaluated in an competitive inhibition assay based on phage display by Eurofins DiscoverX (Fremont California).

Data for representative compounds of the invention from Examples 86, 87, and 88 is provided in the following table.

| Example | BRD4 D1 $IC_{50}$ by $FA^a$(µM) | BRD4 D1 $IC_{50}$ by AlphaScreen$^b$(µM) | p38α $K_d^c$(nM) |
|---|---|---|---|
| | | >100 | |
| | | >100 | |
| | | >100 | |

| Example | BRD4 D1 IC$_{50}$ by FA$^a$(μM) | BRD4 D1 IC$_{50}$ by AlphaScreen$^b$(μM) | p38α K$_d^c$(nM) |
|---|---|---|---|
| | >100 | | |
| 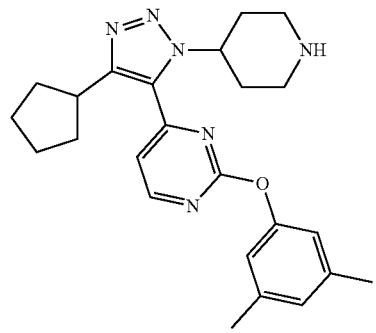 [SMILES: Cc1cc(C)cc(Oc2nccc(-c3c(C4CCCC4)nnn3C3CCNCC3)n2)c1] | | | |
| 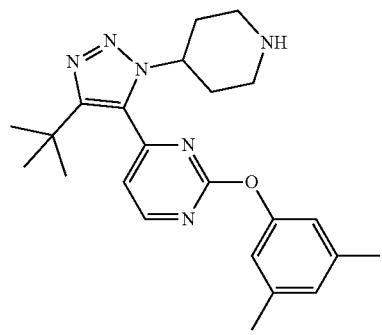 [SMILES: Cc1cc(C)cc(Oc2nccc(-c3c(C(C)(C)C)nnn3C3CCNCC3)n2)c1] | >100 | | |
| 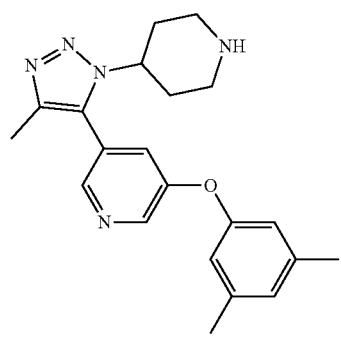 | >100 | | |
| 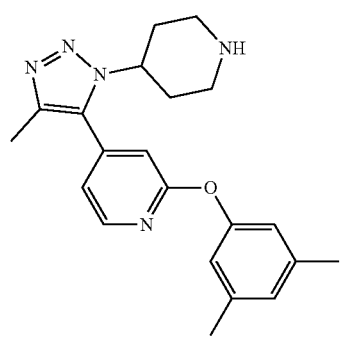 | 97 ± 2.6 | | |

-continued
| Example | BRD4 D1 IC$_{50}$ by FA$^a$(μM) | BRD4 D1 IC$_{50}$ by AlphaScreen$^b$(μM) | p38α K$_d^c$(nM) |
|---|---|---|---|
| 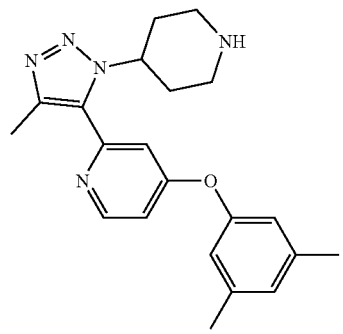 | >100 | | |
| 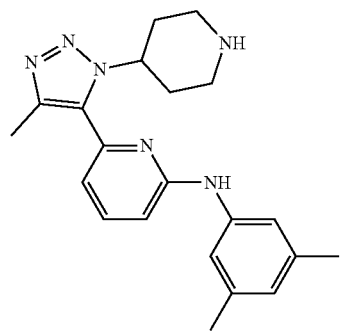 | 4.5 ± 0.35 | | >25 |
| 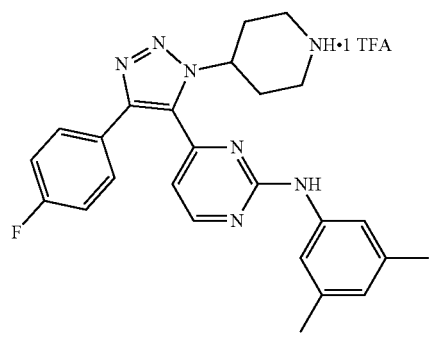 | >100 | | 120 ± 51 |
| 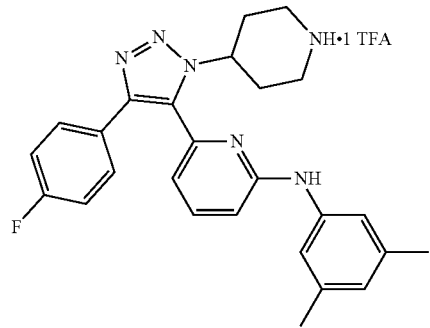 | | | 6500 ± 6300 |

| Example | BRD4 D1 IC$_{50}$ by FA$^a$(μM) | BRD4 D1 IC$_{50}$ by AlphaScreen$^b$(μM) | p38α K$_d^c$(nM) |
|---|---|---|---|
| | | | 5000 ± 6100 |
| 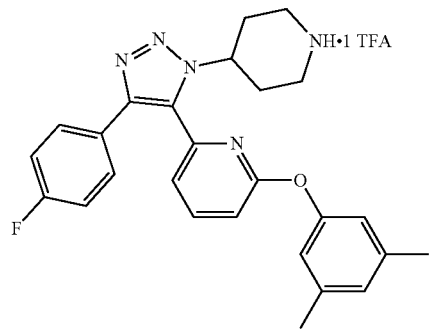 | | | |
| 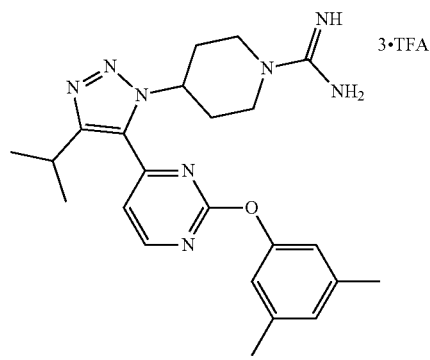 [SMILES: Cc1cc(C)cc(Oc2nccc(-c3c(C(C)C)nnn3C3CCN(C(=N)N)CC3)n2)c1] | | >100 | |
| 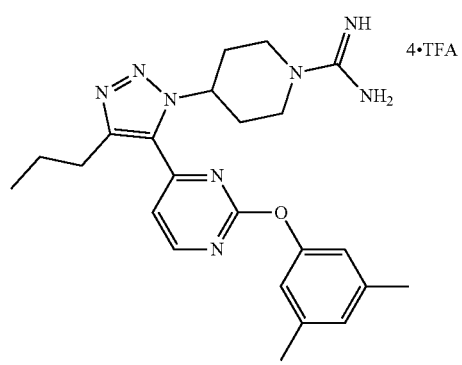 [SMILES: CCCc1nnn(C2CCN(C(=N)N)CC2)c1-c1ccnc(Oc2cc(C)cc(C)c2)n1] | | >100 | |
| 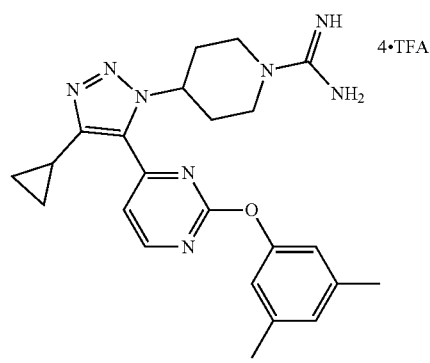 [SMILES: Cc1cc(C)cc(Oc2nccc(-c3c(C4CC4)nnn3C3CCN(C(=N)N)CC3)n2)c1] | | 61 ± 8.1 | |

| Example | BRD4 D1 IC$_{50}$ by FA$^a$(μM) | BRD4 D1 IC$_{50}$ by AlphaScreen$^b$(μM) | p38α K$_d^c$(nM) |
|---|---|---|---|
| 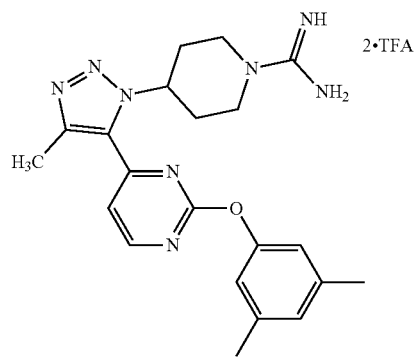 | 9.7 ± 1.8 | | |
| 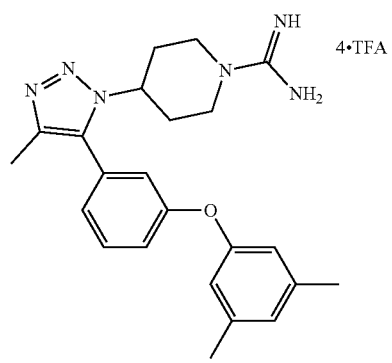 | 12 ± 1.1 | | |
| 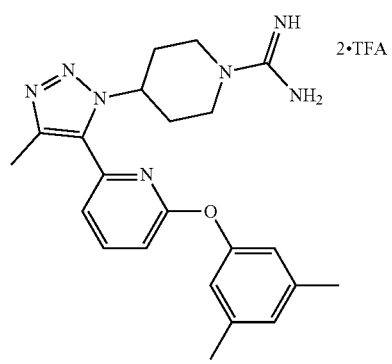 | 3.6 ± 0.05 | | |
| 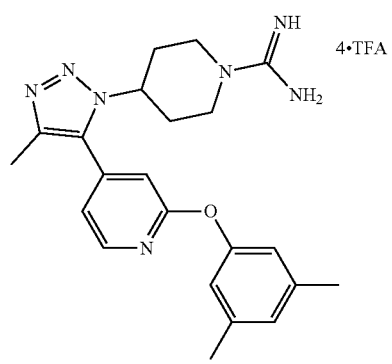 | 97 ± 2.6 | | |

| Example | BRD4 D1 IC$_{50}$ by FA$^a$(μM) | BRD4 D1 IC$_{50}$ by AlphaScreen$^b$(μM) | p38α K$_d^c$(nM) |
|---|---|---|---|
| 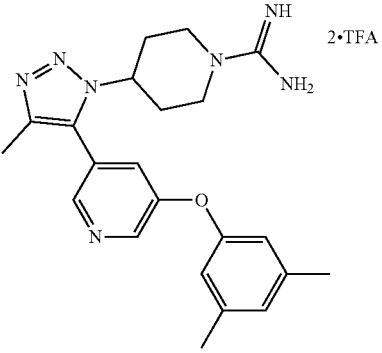 2·TFA | >100 | | |
| 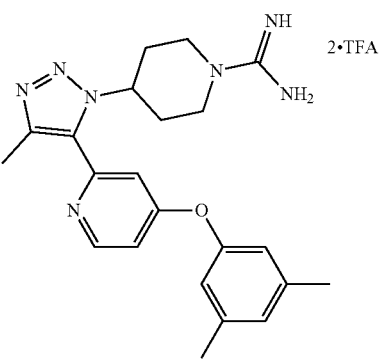 2·TFA | >100 | | |
| 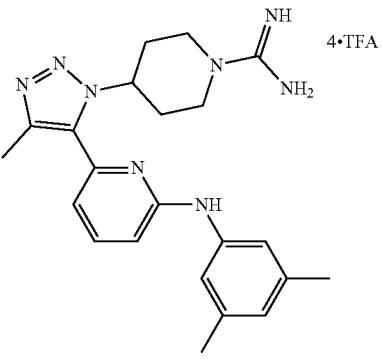 4·TFA | 4.5 ± 0.35 | | |
| 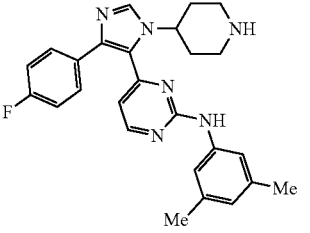 [SMILES: Cc1cc(C)cc(Nc2nccc(-c3c(-c4ccc(F)cc4)ncn3C3CCNCC3)n2)c1] | 11 ± 0.8 | 3.8 | 0.47 |
| 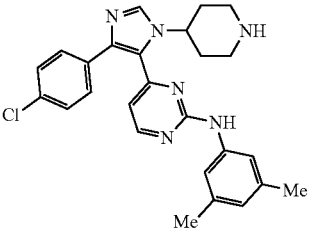 [SMILES: Cc1cc(C)cc(Nc2nccc(-c3c(-c4ccc(Cl)cc4)ncn3C3CCNCC3)n2)c1] | 0.61 ± 0.2 | | |

-continued

| Example | BRD4 D1 IC$_{50}$ by FA$^a$(μM) | BRD4 D1 IC$_{50}$ by AlphaScreen$^b$(μM) | p38α K$_d$$^c$(nM) |
| --- | --- | --- | --- |
| [4-bromophenyl imidazole piperidine pyrimidine 3,5-dimethylaniline structure] | 0.20 ± 0.02 | 0.44 | |
| [4-iodophenyl imidazole piperidine pyrimidine 3,5-dimethylaniline structure] | 0.079 ± 0.01 | 0.25 | |
| [4-methylphenyl imidazole piperidine pyrimidine 3,5-dimethylaniline structure] | 1.2 ± 0.2 | 1.1 | — |
| [4-trifluoromethylphenyl imidazole piperidine pyrimidine 3,5-dimethylaniline structure] | 0.31 ± 0.06 | 0.64 | 260 |
| [4-methoxyphenyl imidazole piperidine pyrimidine 3,5-dimethylaniline structure] | 9.4 ± 0.4 | 3.9 | |
| [4-chlorophenyl imidazole piperidine-guanidine pyrimidine 3,5-dimethylaniline structure] | 1.6 | 1.4 | |

-continued
| Example | BRD4 D1 IC$_{50}$ by FA$^a$(μM) | BRD4 D1 IC$_{50}$ by AlphaScreen$^b$(μM) | p38α K$_d^c$(nM) |
|---|---|---|---|
| 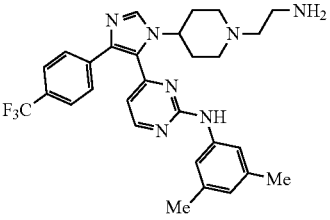 [SMILES: Cc1cc(C)cc(Nc2nccc(-c3c(-c4ccc(C(F)(F)F)cc4)ncn3C3CCN(CCN)CC3)n2)c1] | 0.13 ± 0.01 | 0.29 | 1900 |
| 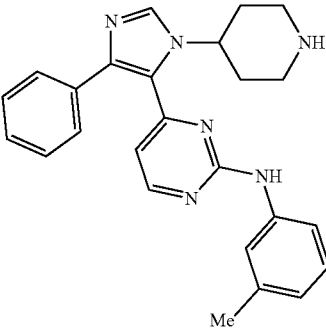 | 4.5 ± 0.2 | 2.6 | |
| 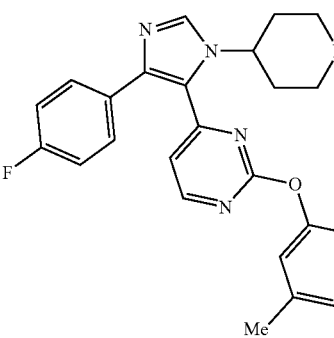 | 3.7 ± 1 | | |
| 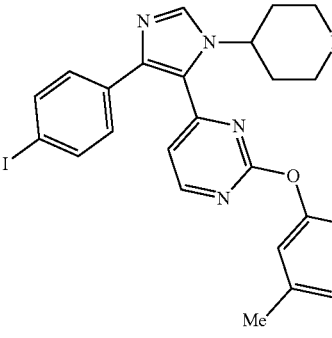 | 0.19 ± 0.02 | 0.17 | |
| 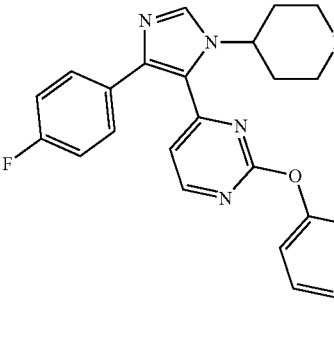 | 24 ± 0.8 | | |

| Example | BRD4 D1 IC$_{50}$ by FA$^a$(μM) | BRD4 D1 IC$_{50}$ by AlphaScreen$^b$(μM) | p38α K$_d^c$(nM) |
|---|---|---|---|
| 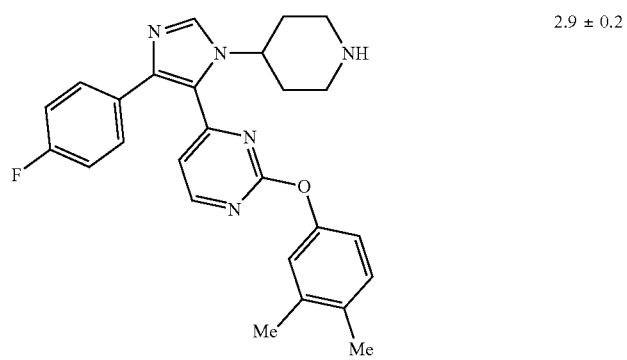 | | 2.9 ± 0.2 | |
| 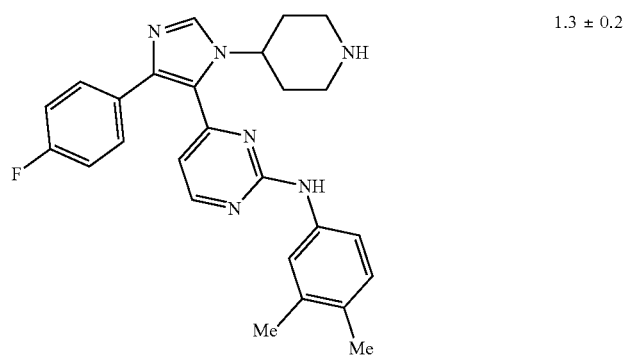 | | 1.3 ± 0.2 | |
| 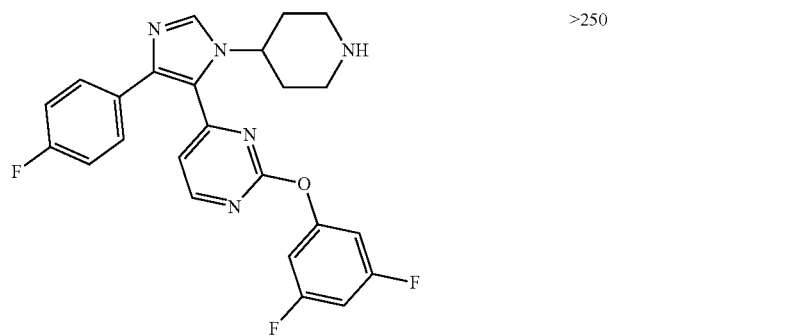 | | >250 | |
| 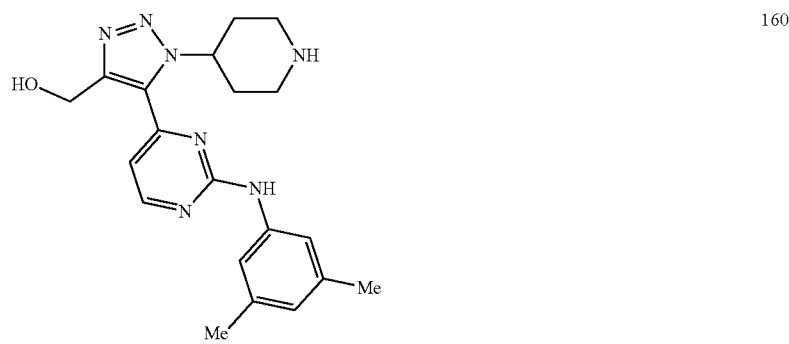 | | | 160 |

| Example | BRD4 D1 IC$_{50}$ by FA$^a$(μM) | BRD4 D1 IC$_{50}$ by AlphaScreen$^b$(μM) | p38α K$_d^c$(nM) |
|---|---|---|---|
| 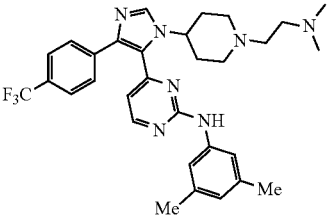 [SMILES: Cc1cc(C)cc(Nc2nccc(-c3c(-c4ccc(C(F)(F)F)cc4)ncn3C3CCN(CCN(C)C)CC3)n2)c1] | 0.15 ± 0.03 | 0.20 | — |
| 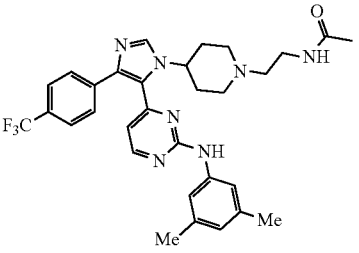 [SMILES: CC(=O)NCCN1CCC(n2cnc(-c3ccc(C(F)(F)F)cc3)c2-c2ccnc(Nc3cc(C)cc(C)c3)n2)CC1] | 0.42 ± 0.01 | 1.5 | — |
| 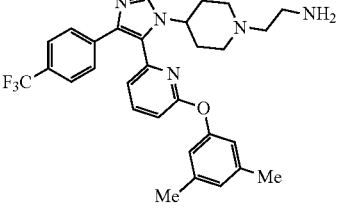 | 1.1 ± 0.01 | 1.3 | >30,000 |
| 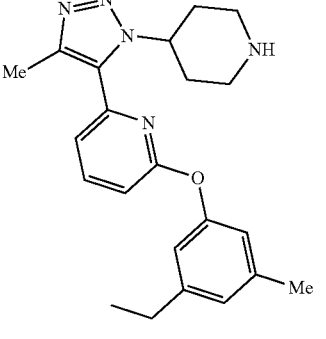 | 1.57 ± 0.1 | 3.92 | |
| | 2.40 ± 0.3 | | |

-continued
| Example | BRD4 D1 IC$_{50}$ by FA$^a$(μM) | BRD4 D1 IC$_{50}$ by AlphaScreen$^b$(μM) | p38α K$_d{}^c$(nM) |
|---|---|---|---|
| 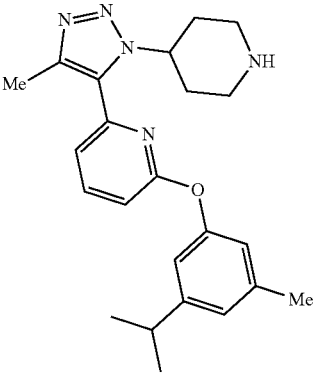 [SMILES: Cc1cc(Oc2cccc(-c3c(C)nnn3C3CCNCC3)n2)cc(C(C)C)c1] | 3.23 ± 0.5 | 4.76 | |
| 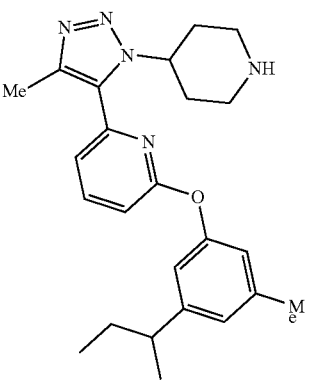 [SMILES: CCC(C)c1cc(C)cc(Oc2cccc(-c3c(C)nnn3C3CCNCC3)n2)c1] | 3.21 ± 0.3 | 7.35 | |
| 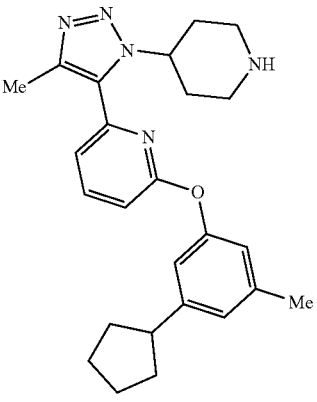 [SMILES: Cc1cc(Oc2cccc(-c3c(C)nnn3C3CCNCC3)n2)cc(C2CCCC2)c1] | 4.44 | | |
| 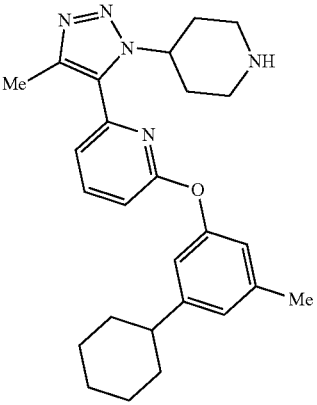 [SMILES: Cc1cc(Oc2cccc(-c3c(C)nnn3C3CCNCC3)n2)cc(C2CCCCC2)c1] | 4.75 ± 0.4 | | |

| Example | BRD4 D1 IC$_{50}$ by FA$^a$(μM) | BRD4 D1 IC$_{50}$ by AlphaScreen$^b$(μM) | p38α K$_d^c$(nM) |
| --- | --- | --- | --- |
| | 2.78 ± 0.3 | 6.39 | |
| 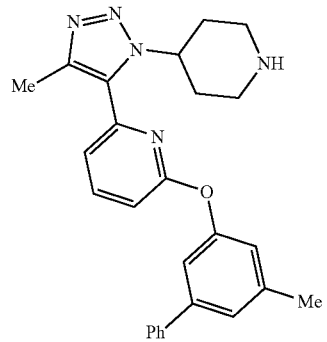 [SMILES: Cc1cc(Oc2cccc(-c3c(C)nnn3C3CCNCC3)n2)cc(-c2ccccc2)c1] | 1.43 ± 0.2 | 2.56 | |
| 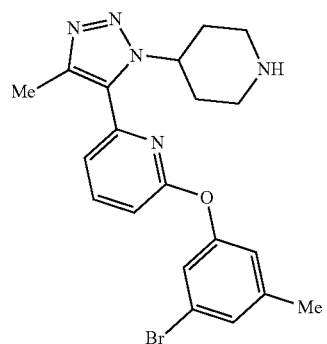 [SMILES: Cc1cc(Br)cc(Oc2cccc(-c3c(C)nnn3C3CCNCC3)n2)c1] | 1.50 ± 0.2 | 3.60 | |
| 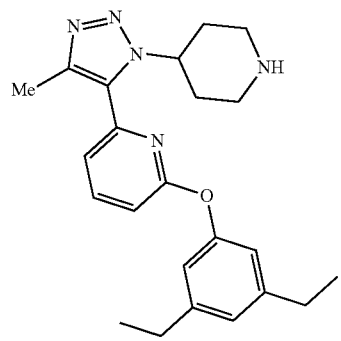 [SMILES: CCc1cc(CC)cc(Oc2cccc(-c3c(C)nnn3C3CCNCC3)n2)c1] | 2.60 ± 0.1 | 14.4 | |
| 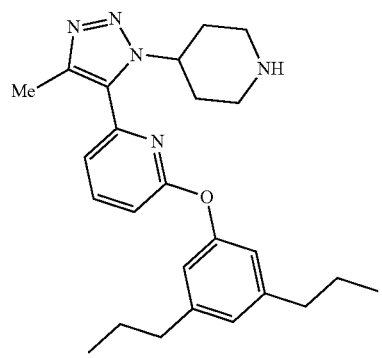 [SMILES: CCCc1cc(CCC)cc(Oc2cccc(-c3c(C)nnn3C3CCNCC3)n2)c1] | | | |

-continued
| Example | BRD4 D1 IC$_{50}$ by FA$^a$(μM) | BRD4 D1 IC$_{50}$ by AlphaScreen$^b$(μM) | p38α K$_d^c$(nM) |
|---|---|---|---|
| 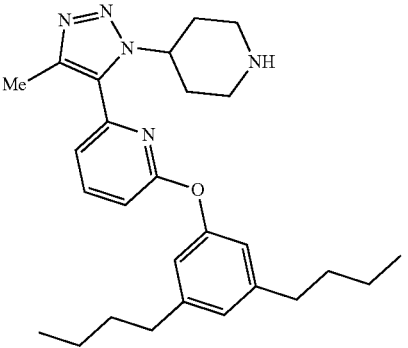 [SMILES: CCCCc1cc(CCCC)cc(Oc2cccc(-c3c(C)nnn3C3CCNCC3)n2)c1] | 8.61 | 27.7 | |
| 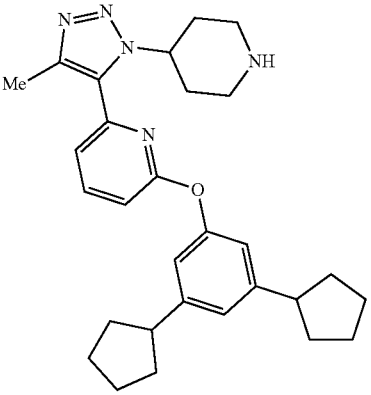 [SMILES: Cc1nnn(C2CCNCC2)c1-c1cccc(Oc2cc(C3CCCC3)cc(C3CCCC3)c2)n1] | 21.8 ± 3 | 53.8 | |
| 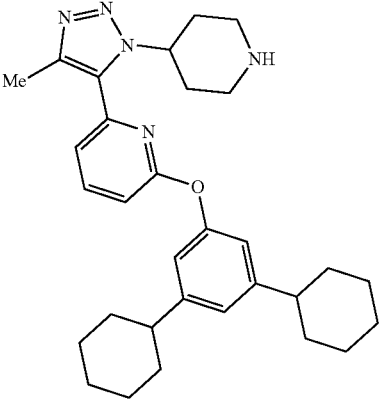 [SMILES: Cc1nnn(C2CCNCC2)c1-c1cccc(Oc2cc(C3CCCCC3)cc(C3CCCCC3)c2)n1] | 62.6 | >100 | |
| 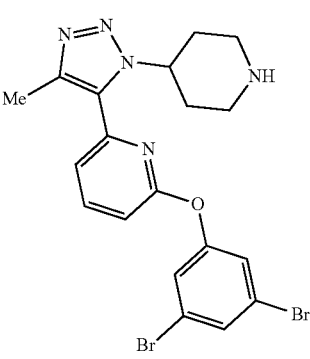 | 1.14 | 2.28 | |

| Example | BRD4 D1 IC$_{50}$ by FA$^a$(μM) | BRD4 D1 IC$_{50}$ by AlphaScreen$^b$(μM) | p38α K$_d$$^c$(nM) |
|---|---|---|---|
| | 14.3 ± 2 | 45.6 | |
| 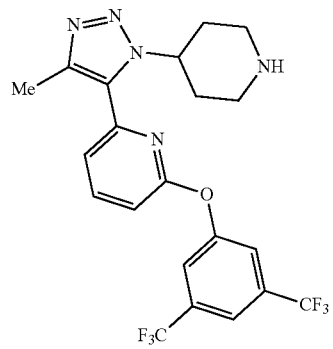 [SMILES: Cc1nnn(C2CCNCC2)c1-c1cccc(Oc2cc(C(F)(F)F)cc(C(F)(F)F)c2)n1] | 2.4 ± 0.06 | | |
| 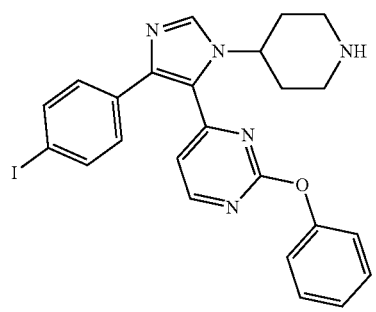 [SMILES: Ic1ccc(-c2ncn(C3CCNCC3)c2-c2ccnc(Oc3ccccc3)n2)cc1] | 3.2 ± 0.06 | | |
| 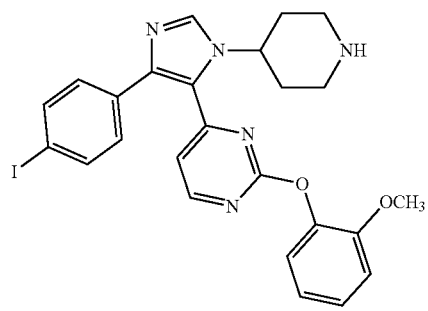 [SMILES: COc1ccccc1Oc1nccc(-c2c(-c3ccc(I)cc3)ncn2C2CCNCC2)n1] | 3.0 ± 0.1 | | |
| 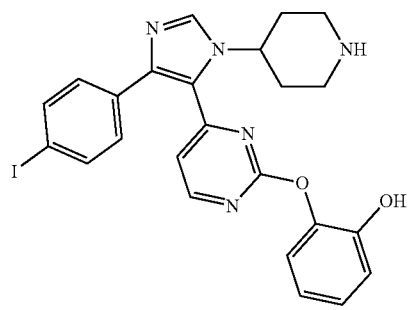 [SMILES: Oc1ccccc1Oc1nccc(-c2c(-c3ccc(I)cc3)ncn2C2CCNCC2)n1] | | | |

-continued

| Example | BRD4 D1 IC$_{50}$ by FA$^a$(μM) | BRD4 D1 IC$_{50}$ by AlphaScreen$^b$(μM) | p38α K$_d{}^c$(nM) |
|---|---|---|---|
| 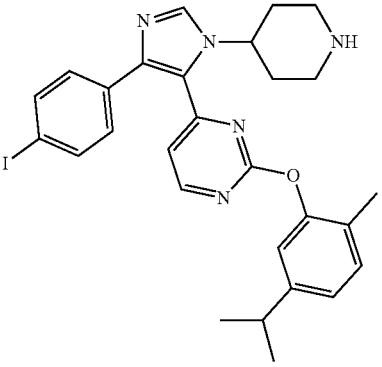 [SMILES: Cc1ccc(C(C)C)cc1Oc1nccc(-c2c(-c3ccc(I)cc3)ncn2C2CCNCC2)n1] | 0.036 ± 0.005 | | |
| 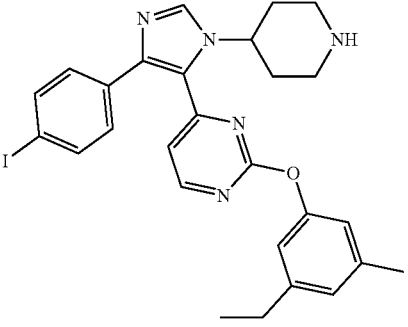 [SMILES: CCc1cc(C)cc(Oc2nccc(-c3c(-c4ccc(I)cc4)ncn3C3CCNCC3)n2)c1] | 0.055 ± 0.004 | | |
| 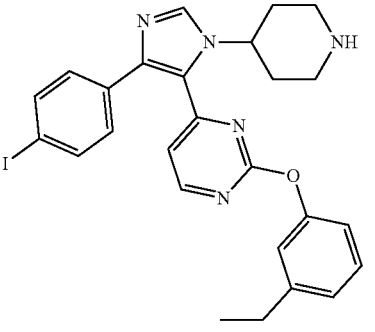 [SMILES: CCc1cccc(Oc2nccc(-c3c(-c4ccc(I)cc4)ncn3C3CCNCC3)n2)c1] | 0.20 ± 0.003 | | |
| 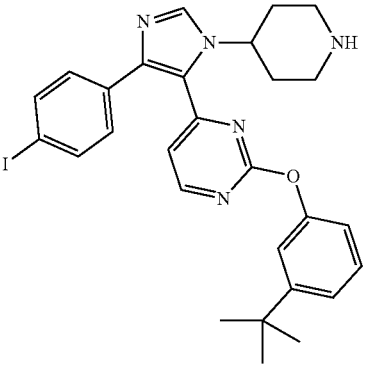 [SMILES: CC(C)(C)c1cccc(Oc2nccc(-c3c(-c4ccc(I)cc4)ncn3C3CCNCC3)n2)c1] | 0.11 ± 0.025 | | |

$^a$Data represents the mean and SEM of three biological replicates.
$^b$Data represents the mean of two technical replicates except (+)-JQ1.
$^†$Data represents the mean and standard deviation of six biological replicates.
$^c$K$_d$ values were determined by KINOMEscan. Data represents the mean of two biological replicates.

Example 89. Crystallization Conditions and X-Ray Data Collection Methods

Compound 44 (20 μM) was co-crystalized with BRD D1 (300-400 μM, in 10 mM HEPES, 100 mM NaCl, pH 7.4) in 200 mM NaI, 100 mM Bis-Tris propane, 20% (v/v) PEG 3350, 10% (v/v) ethylene glycol at pH 8.5 using the hanging drop method. Harvestable crystals grew in 1-2 days at ambient temperature. Crystals were harvested, cryoprotected in ethylene glycol and flash frozen. Data was collected at Advanced Photon Source with the NECAT 24-IDE beamline. Phaser-MR17 (P. Emsley, et al., *Acta Crystallogr. Sect. D Biol. Crystallogr.* 2010, 66, 213-221) was used to solve the structure via molecular replacement using PDB ID 3MXF as a reference. Phenix18 and Coot were used for structure refinement.

Example 90. Cell Culture

MM.1S cells were grown in a humidified 5% $CO_2$ environment at 37° C. Cells were cultured in standard tissue culture flasks using RPMI 1640 media (Corning) supplemented with 10% fetal-bovine serum (FBS, Cellgro), penicillin/streptomycin (50 μg/mL each, Cellgro). The mixed suspension/adherent cells were sub-cultured at a 1:8 dilution by decanting suspended cells and dissociating adherent cells from plates in 0.25% trypsin/EDTA (Gibco) with 2 minute incubation times. Cell-line authenticity was verified using the short-tandem-repeat (STR)-profiling service provided by ATCC.

Example 91

Thermal Stability Profiling (A. Divakaran, et al., *J. Med Chem.* 2018, 61, 9316-9334; and R. Jafari, et al., *Nat. Protoc.* 2014, 9, 2100-2122).

Approximately $3 \times 10^6$ MM.1S cells were treated with the desired amounts of compound in serum supplemented RPMI-1640 media, with DMSO concentrations normalized to 0.05% for all samples. Dosed cells in microcentrifuge tubes were incubated at 37° C. for 1 h. with mild intermittent agitation. Upon completion of the incubation period, cells were pelleted at 300×g. and rinsed in PBS, before being re-suspended in 100 μL PBS supplemented with 1× cOmplete Mini Protease (Roche). Re-suspended cells were thermally denatured at 48° C. for 3 min in a heat block and subsequently equilibrated at room temperature for a further 3 min. Cells were lysed over three freeze-thaw cycles and centrifuged (15 min at 15,000×g.), before soluble protein concentrations of supernatants were determined using the BCA protein assay kit (Pierce). Samples were normalized to the lowest total soluble-protein concentration and analyzed by western blot.

Example 92. Western Blotting

MM.1S cells were seeded in 24-well plates at a density of $2 \times 10^6$ cells per well and treated with compounds for 8 h, with DMSO concentrations normalized to 0.05%. Cells were harvested by low-speed centrifugation at 500×g. for 5 minutes. and washed twice with ice-cold PBS. Cells were lysed in 100 μL of RIPA buffer (ThermoFisher Scientific) supplemented with 1× cOmplete Mini Protease (Roche). After high-speed centrifugation (15 minutes at 15,000×g.), protein concentrations were determined by a Bradford assay (ThermoFisher Scientific) and normalized by total protein content. Normalized samples were mixed with 4× NuPAGE LDS loading buffer (Invitrogen) and 10× reducing agent (Invitrogen), and heated at 95° C. for 5 minutes. This was followed by separation on 8-12% SDS-PAGE using Tris/Glycine/SDS buffer (BioRad). Proteins were transferred to PVDF membranes for 7 minutes on a BioRad Trans-Blot Turbo. Membranes were incubated subsequently with TBS-TWEEN20 (TBS-T) containing 5% nonfat dry milk for 16 hours at 4° C. with primary antibodies (c-Myc, Cell Signaling Technology, #5605, diluted 1:500 in TBS-T containing 5% nonfat dry milk; BRD4, Cell Signaling Technology, #13440, diluted 1:1000 in TBS-T containing 5% nonfat dry milk; β-actin, Invitrogen # MA5-11869, diluted 1:1000 in TBS-T containing 5% nonfat dry milk). After the membranes were washed five times with TBS-T, they were incubated with 1000-fold-diluted HRP-, or Alexa Fluor 680-conjugated secondary antibodies from Invitrogen (goat anti-rabbit-IgG, #G-31460 and goat anti-mouse-IgG, #G-21040/A 21057; in TBS-T containing 5% nonfat dry milk) for 4 hours at room temperature. Membranes were washed three times in TBS-T and treated with SuperSignal West Dura substrates (ThermoFisher Scientific) for 1 min. and imaged using a LiCor Odessey Fc. Experiments were performed in biological triplicate and densitometry was processed using ImageJ.

Example 93. Viability Assays

MM. 1S cells were seeded in 96-well plates at approximately 20 000 cells per well (0.05 mL) and dosed with increasing compound concentrations in the presence of 0.05% DMSO with three technical replicates per concentration (100 μL final volume). After incubation for 69 hours at 37° C., 10 μL of Alamar Blue reagent (Invitrogen) was added to each well and the plates were incubated a further 3 hours at 37° C. Fluorescence was determined using a Synergy plate reader (BioTek, Ex.: 560 nm, Em.: 590 nm) and dose-response data were normalized to untreated and blank wells containing 0.05% DMSO in cell culture media. Data analysis was performed using GraphPad Prism as previously reported (A. Divakaran, et al., *J. Med. Chem.* 2018, 61, 9316-9334).

Example 94

The following illustrate representative pharmaceutical dosage forms, containing a compound of formula I ('Compound X'), for therapeutic or prophylactic use in humans.

| (i) Tablet 1 | mg/tablet |
|---|---|
| Compound X= | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X= | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X= | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| Compound X = (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/ml) | mg/ml |
|---|---|
| Compound X = (free acid form) | 10.0 |
| Monobasic sodium phosphate | 0.3 |
| Dibasic sodium phosphate | 1.1 |
| Polyethylene glycol 400 | 200.0 |
| 1.0N Sodium hydroxide solution (pH adjustment to 7.0-7.5) | q.s. |
| Water for injection | q.s. ad 1 mL |

| (vi) Aerosol | mg/can |
|---|---|
| Compound X= | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:
1. A compound of formula (Ic):

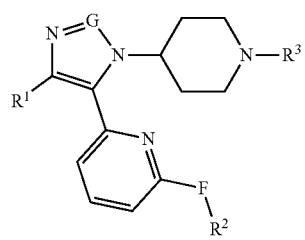

(Ic)

or a pharmaceutically acceptable salt thereof, wherein:
$R^1$ is selected from H, halo, aryl, $(C_1-C_6)$alkyl, $(C_3-C_6)$cycloalkyl, $(C_1-C_6)$alkoxy, $(C_2-C_6)$alkenyl, and $(C_2-C_6)$alkynyl, wherein any $(C_1-C_6)$alkyl, $(C_3-C_6)$cycloalkyl, $(C_1-C_6)$alkoxy, $(C_2-C_6)$alkenyl, and $(C_2-C_6)$alkynyl of $R^1$ is optionally substituted with one or more groups independently selected from the group consisting of halo, oxo, —OH, cyano, $(C_3-C_6)$cycloalkyl, and $(C_1-C_6)$alkoxy; and wherein any aryl of $R^1$ is optionally substituted with one or more groups independently selected from the group consisting of halo, —OH, cyano, $(C_1-C_6)$alkyl, $(C_3-C_6)$cycloalkyl, $(C_1-C_6)$alkoxy, $(C_2-C_6)$alkenyl, $(C_2-C_6)$alkynyl, $(C_1-C_6)$alkanoyl, $(C_1-C_6)$alkoxycarbonyl, $(C_1-C_6)$alkylthio and $(C_2-C_6)$alkanoyloxy, wherein any $(C_1-C_6)$alkyl, $(C_3-C_6)$cycloalkyl, $(C_1-C_6)$alkoxy, $(C_2-C_6)$alkenyl, $(C_2-C_6)$alkynyl, $(C_1-C_6)$alkanoyl, $(C_1-C_6)$alkoxycarbonyl, $(C_1-C_6)$alkylthio and $(C_2-C_6)$alkanoyloxy group on an aryl of $R^1$ is optionally substituted with one or more groups independently selected from the group consisting of halo and —OH;

$R^2$ is aryl that is optionally substituted with one or more groups independently selected from the group consisting of halo, —OH, cyano, $(C_1-C_6)$alkyl, $(C_3-C_6)$cycloalkyl, and $(C_1-C_6)$alkoxy, wherein any $(C_1-C_6)$alkyl, $(C_3-C_6)$cycloalkyl, and $(C_1-C_6)$alkoxy of $R^2$ is optionally substituted with one or more groups independently selected from the group consisting of halo, and $(C_1-C_6)$alkoxy;

$R^3$ is selected from the group consisting of H, —C(=N($R^a$))$NR^aR^b$, and $(C_1-C_6)$alkyl that is optionally substituted with one or more groups independently selected from the group consisting of halo, —OH, cyano, $(C_3-C_6)$cycloalkyl, $(C_1-C_6)$alkoxy, —C(=N($R^a$))$NR^aR^b$, and —$NR^aR^b$;

each $R^a$ and $R^b$ is independently selected from the group consisting of H, $(C_1-C_6)$alkyl, $(C_1-C_6)$alkanoyl, and $(C_3-C_6)$cycloalkyl; or $R^a$ and $R^b$ together with the nitrogen to which they are attached form a 4-6 membered ring heterocycle;

F is O, S, or $NR^c$;
G is CH or N; and
$R^c$ is H or $(C_1-C_6)$alkyl.

2. A compound of formula (Ig):

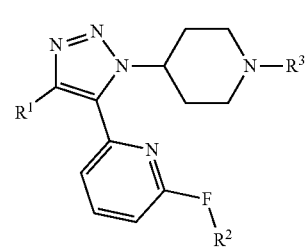

(Ig)

or a pharmaceutically acceptable salt thereof, wherein:
$R^1$ is selected from H, halo, aryl, $(C_1-C_6)$alkyl, $(C_3-C_6)$cycloalkyl, $(C_1-C_6)$alkoxy, $(C_2-C_6)$alkenyl, and $(C_2-C_6)$alkynyl, wherein any $(C_1-C_6)$alkyl, $(C_3-C_6)$cycloalkyl, $(C_1-C_6)$alkoxy, $(C_2-C_6)$alkenyl, and $(C_2-C_6)$alkynyl of $R^1$ is optionally substituted with one or more groups independently selected from the group consisting of halo, oxo, —OH, cyano, $(C_3-C_6)$cycloalkyl, and $(C_1-C_6)$alkoxy; and wherein any aryl of $R^1$ is optionally substituted with one or more groups independently selected from the group consisting of halo, —OH, cyano, (C₁-C₆)alkyl, (C₃-C₆)cycloalkyl, (C₁-C₆)alkoxy, (C₂-C₆)alkenyl, (C₂-C₆)alkynyl, (C₁-C₆)alkanoyl, (C₁-C₆)alkoxycarbonyl, (C₁-C₆)alkylthio and (C₂-C₆)alkanoyloxy, wherein any (C₁-C₆)alkyl, (C₃-C₆)cycloalkyl, (C₁-C₆)alkoxy, (C₂-C₆)alkenyl, (C₂-C₆)alkynyl, (C₁-C₆)alkanoyl, (C₁-C₆)alkoxycarbonyl, (C₁-C₆)alkylthio and (C₂-C₆)alkanoyloxy group on an aryl of R¹ is optionally substituted with one or more groups independently selected from the group consisting of halo and —OH;

R² is aryl that is optionally substituted with one or more groups independently selected from the group consisting of halo, —OH, cyano, (C₁-C₆)alkyl, (C₃-C₆)cycloalkyl, and (C₁-C₆)alkoxy, wherein any (C₁-C₆)alkyl, (C₃-C₆)cycloalkyl, and (C₁-C₆)alkoxy of R² is optionally substituted with one or more groups independently selected from the group consisting of halo, and (C₁-C₆)alkoxy;

R³ is selected from the group consisting of H, —C(=N(Rᵃ))NRᵃRᵇ, and (C₁-C₆)alkyl that is optionally substituted with one or more groups independently selected from the group consisting of halo, —OH, cyano, (C₃-C₆)cycloalkyl, (C₁-C₆)alkoxy, —C(=N(Rᵃ))NRᵃRᵇ, and —NRᵃRᵇ;

each Rᵃ and Rᵇ is independently selected from the group consisting of H, (C₁-C₆)alkyl, (C₁-C₆)alkanoyl, and (C₃-C₆)cycloalkyl; or Rᵃ and Rᵇ together with the nitrogen to which they are attached form a 4-6 membered ring heterocycle;

F is O, S, or NRᶜ; and

Rᶜ is H or (C₁-C₆)alkyl.

3. A compound of formula (Ig):

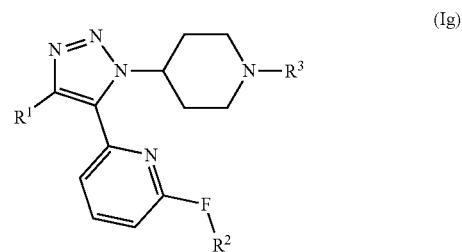

(Ig)

or a pharmaceutically acceptable salt thereof, wherein:
R¹ is (C₁-C₆)alkyl optionally substituted with —OH;
F is O;
R² is aryl that is optionally substituted with one or more groups independently selected from the group consisting of halo, —OH, cyano, (C₁-C₆)alkyl, (C₃-C₆)cycloalkyl, and (C₁-C₆)alkoxy, wherein any (C₁-C₆)alkyl, (C₃-C₆)cycloalkyl, and (C₁-C₆)alkoxy of R² is optionally substituted with one or more groups independently selected from the group consisting of halo, and (C₁-C₆)alkoxy;
R³ is selected from the group consisting of H, —C(=N(Rᵃ))NRᵃRᵇ, and (C₁-C₆)alkyl that is optionally substituted with one or more groups independently selected from the group consisting of halo, —OH, cyano, (C₃-C₆)cycloalkyl, (C₁-C₆)alkoxy, —C(=N(Rᵃ))NRᵃRᵇ, and —NRᵃRᵇ; and
each Rᵃ and Rᵇ is independently selected from the group consisting of H, (C₁-C₆)alkyl, (C₁-C₆)alkanoyl, and (C₃-C₆)cycloalkyl; or Rᵃ and Rᵇ together with the nitrogen to which they are attached form a 4-6 membered ring heterocycle.

* * * * *